US009174972B2

(12) United States Patent
Abraham et al.

(10) Patent No.: US 9,174,972 B2
(45) Date of Patent: **\*Nov. 3, 2015**

(54) COGNITION ENHANCING COMPOUNDS AND COMPOSITIONS, METHODS OF MAKING, AND METHODS OF TREATING

(71) Applicant: NeuroSolis, Inc., Madison, WI (US)

(72) Inventors: Brent D. Abraham, Verona, WI (US); Richard R. Copp, Oregon, WI (US); James G. Farnham, Madison, WI (US); Seth A. Hanson, Madison, WI (US); Michael L. Hendrickson, Madison, WI (US); Jeffrey C. Ockuly, Madison, WI (US); Trevor M. Twose, Fitchburg, WI (US); Melinda L. Verdone, Waunakee, WI (US)

(73) Assignee: NeuroSolis, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/791,251

(22) Filed: Mar. 8, 2013

(65) Prior Publication Data

US 2013/0274299 A1 Oct. 17, 2013

Related U.S. Application Data

(63) Continuation of application No. PCT/US2011/050899, filed on Sep. 8, 2011.

(60) Provisional application No. 61/403,001, filed on Sep. 8, 2010.

(51) Int. Cl.
*C07D 413/04* (2006.01)
*C07D 403/04* (2006.01)
*C07D 417/04* (2006.01)

(52) U.S. Cl.
CPC ............ *C07D 413/04* (2013.01); *C07D 403/04* (2013.01); *C07D 417/04* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 3,062,804 | A | 11/1962 | Albertson |
| 4,870,081 | A | 9/1989 | Orlek et al. |
| 5,043,343 | A | 8/1991 | Wyman |
| 5,134,146 | A | 7/1992 | Showell et al. |
| 5,175,166 | A | 12/1992 | Dunbar et al. |
| 5,328,924 | A | 7/1994 | Sauerberg et al. |
| 5,403,845 | A | 4/1995 | Dunbar et al. |
| 5,470,856 | A | 11/1995 | Plate |
| 5,817,875 | A | 10/1998 | Karimian et al. |
| 6,171,520 | B1 | 1/2001 | Imai et al. |
| 2005/0277654 | A1 | 12/2005 | Maynard et al. |
| 2007/0082940 | A1 | 4/2007 | Skolnick et al. |
| 2009/0036461 | A1 | 2/2009 | Hamprecht et al. |
| 2011/0263613 | A1* | 10/2011 | Hendrickson et al. ........ 514/256 |

FOREIGN PATENT DOCUMENTS

| | | | |
|---|---|---|---|
| WO | WO9211261 | * | 7/1992 |
| WO | WO 92/21339 A1 | | 12/1992 |
| WO | WO 2010/102218 A1 | | 9/2010 |
| WO | WO 2011/085406 A1 | | 7/2011 |

OTHER PUBLICATIONS

Kushner et al., Pharmacological uses and perspectives of heavy water and deuterated compounds. Canadian Journal of Physiology and Pharmacology 1999, 77, 79-88.*
CAPLUS printout of "US Patent Application Publication No. 2011/0263613, published on Oct. 27, 2011, filed on Jan. 11, 2011, and claimed priority to U.S. Appl. No. 61/294,100, filed Jan. 11, 2010".*
International Search Report and Written Opinion, International Application No. PCT/US2011/050899 (published as WO 2012/033956) (Jan. 25, 2012).
Peng et al., "The Predicted 3D Structures of the Human M1 Muscarinic Acetylcholine Receptor with Agonist or Antagonist Bound," *ChemMedChem*, 1:878-890 (2005).
Suzuki et al., "Synthesis of (1-Azabicyclo[3.3.0]ocianyl)metyl-Substituted Aromatic Heterocycles and Their Muscarinic Activity," *Chem. Pharm. Bull.*, 47(6):876-879 (1999).
Anonymous, "Precision Deuterium Chemistry Backgrounder," web publication, Concert Pharmaceuticals, Inc., Lexington, MA, (6 pages) (2009).
Baker et al., "Muscarinic Agonists for the Central Nervous System," in *Drug Design for Neuroscience*, pp. 61-85, Raven Press (1993).
Dunbar et al., "Design, Synthesis, and Neurochemical Evaluation of 5-(3-Alkyl-1,2,4-oxadiazol-5-yl)-1,4,5,6-tetrahydropyrimidines as $M_1$ Muscarinic Receptor Agonists," *J. Med. Chem.*, 36(7):842-847 (Apr. 1, 1993).
Foster et al., "Deuterium Isotope Effects in the Metabolism of Drugs and Xenobiotics: Implications for Drug Design," in *Advances in Drug Research*, vol. 14, pp. 1-40, Academic Press (Jan. 1, 1985).
International Search Report and Written Opinion, International Application No. PCT/US2010/026380 (published as Publication No. WO 2010/102218 A1 ), Jun. 16, 2010 (10 pages).
International Search Report and Written Opinion, International Application No. PCT/US2011/020902 (published as Publication No. WO 2011/085406 A1 ), Mar. 23, 2011 (21 pages).

(Continued)

*Primary Examiner* — Michael Barker
*Assistant Examiner* — Po-Chih Chen
(74) *Attorney, Agent, or Firm* — Perkins Coie LLP

(57) ABSTRACT

The invention relates generally to muscarinic agonists, which are useful for stimulating muscarine receptors, and treating cognitive disorders. Included among the muscarinic agonists disclosed herein are oxadiazole derivatives, compositions, and preparations thereof. Methods of synthesizing oxadiazole compounds also are provided. This disclosure also relates in part to compositions for enhancing cognitive function in subjects such as humans, the compositions comprising a muscarinic agonist or a pharmaceutically suitable form thereof. This disclosure relates in part to methods of treating animals such as humans by administering such compositions.

10 Claims, 21 Drawing Sheets

(56) References Cited

OTHER PUBLICATIONS

MacLeod et al., "Synthesis and Muscarinic Activities of 1,2,4-Thiadiazoles," *J. Med. Chem.*, 33(7):2052-2059 (1990).

Macor et al., "Synthesis and Use of 5-Vinyl-1,2,4-oxadiazoles as Michael Acceptors. A Rapid Synthesis of the Potent Muscarinic Agonist L-670,548," *J. Org. Chem.*, 61(10):3228-3229 (Jan. 1, 1996).

Messer et al., "Development of CDD-0102 as a Selective $M_1$ Agonist for the Treatment of Alzheimer's Disease," *Drug Development Research*, 57(4):200-213 (Dec. 1, 2002).

Messer et al., "Synthesis and Biological Characterization of 1,4,5,6-Tetrahydropyrimidine and 2-Amino-3,4,5,6-tetrahydropyridine Derivatives as Selective m1 Agonists," *J. Med. Chem.*, 40(8):1230-1246 (Apr. 1, 1997).

Street et al., "Synthesis and Biological Activity of 1,2,4-Oxadiazole Derivatives: Highly Potent and Efficacioua Agonists for Cortical Muscarinic Receptors," *J. Med. Chem.*, 33(10):2690-2697 (1990).

Supplementary European Search Report, European Application No. EP 10 74 9400, Sep. 18, 2012 (23 pages).

Supplementary European Search Report, European Application No. EP 11 73 2334, May 3, 2013 (8 pages).

Zhang et al., "Development of 5-(3-alkenyl-1,2,4-oxadiazol-5-yl)-1,4,5,6-tetrahydropyrimidine derivatives as selective muscarinic agonists for the treatment of Alzheimer's disease," *Life Sciences*, 60(13/14):1163, Abstract of Poster Presentation (Feb. 1, 1997).

\* cited by examiner

| Dose and route | Relative Hippocampal Inositol Phosphate Concentration |
|---|---|
| Control | 100 |
| MCD-386 30 mg/kg sc | 171 |

*FIG. 10B*

COGNITION ENHANCING COMPOUNDS AND COMPOSITIONS, METHODS OF MAKING, AND METHODS OF TREATING

PRIORITY DATA & INCORPORATION BY REFERENCE

This application is a continuation of International Application No. PCT/US2011/050899, filed Sep. 8, 2011, which claims the benefit of U.S. Provisional Patent Application No. 61/403,001, filed Sep. 8, 2010, entitled "Cognition Enhancing Compounds and Compositions, Methods of Making, and Methods of Treating," each of which application is incorporated herein by reference in its entirety.

STATEMENT REGARDING FEDERALLY SPONSORED RESEARCH OR DEVELOPMENT

This invention was made with United States government support awarded by the following agency: National Institute of Mental Health, Grant R44MH067430. The United States government has certain rights in this invention.

FIELD

This disclosure relates generally to muscarinic agonists, which are useful for stimulating muscarinic receptors and treating cognitive disorders. Included among the muscarinic agonists disclosed herein are oxadiazole derivatives, compositions and preparations thereof. Methods of synthesizing oxadiazole compounds also are provided. This disclosure also relates in part to compositions for enhancing cognitive function in subjects such as humans, the compositions comprising a muscarinic agonist or a pharmaceutically suitable form thereof. This disclosure relates in part to methods of treating animals such as humans by administering such compositions. Other aspects of the disclosure will become apparent to those skilled in the art.

BACKGROUND

Recent research efforts have focused on treating patients suffering from cognitive deficits with agonists that may activate muscarinic cholinergic receptors. Molecular biological studies have identified and characterized five subtypes of muscarinic receptors ($M_1$, $M_2$ ... $M_5$), each with a unique amino acid sequence, tissue-specific expression, ligand binding profile and associated biochemical response. The use of muscarinic receptor agonists for treating cognitive defects, however, may be hindered by the undesirable cholinergic side effects produced by their administration, including diaphoresis (excessive sweating), hypersalivation (excessive salivation), flushing (reddening of the skin, especially in the cheeks and neck), gastro-intestinal tract upsets, such as increased stomach acid, nausea, vomiting and diarrhea, breathing difficulties, tachycardia (slow heart beat), dizziness, syncope (fainting), headache, convulsions, and somnolence (sleepiness).

BRIEF DESCRIPTION OF THE FIGURES

FIG. 4A compares Compound 3 (a racemic mixture of 3-methyl-5-(piperidin-3-yl)-1,2,4-oxadiazole) (♦), 3a (the D-tartrate salt of S-(+)-3-methyl-5-(piperidin-3-yl)-1,2,4-oxadiazole) (■), and 3b (the L-tartrate salt of R-(−)-3-methyl-5-(piperidin-3-yl)-1,2,4-oxadiazole) (▲); FIG. 4B compares compounds 7 (3-D3-methyl-5-(piperidin-3-yl)-1,2,4-oxadiazole) ( ), 7a (the D-tartrate salt of S-(+)-3-D3-methyl-5-(piperidin-3-yl)-1,2,4-oxadiazole) ( ), and 7b (the L-tartrate salt of R-(−)-3-D3-methyl-5-(piperidin-3-yl)-1,2,4-oxadiazole) ( ).

FIG. 10B shows the increase in hippocampal inositol phosphate signaling involved in disease-modification caused by MCD-386 in normal rats.

FIG. 15 shows an ORTEP drawing of compound 106a.

DETAILED DESCRIPTION

I. Definitions

Figure 1:
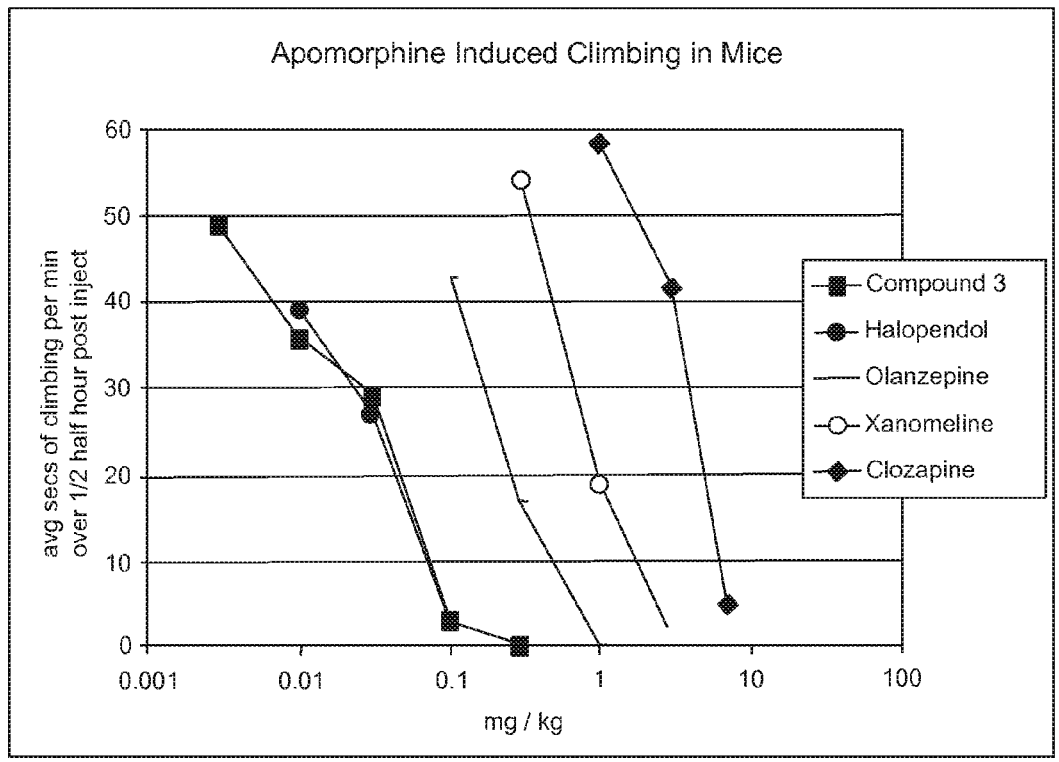
FIG. 1 is a graph showing the activity of a Compound 3 (a racemic mixture of 3-methyl-5-(piperidin-3-yl)-1,2,4-oxadiazole) described herein. In the apomorphine induced climbing model of psychosis in comparison to known antipsychotic agents and the muscarinic agonist xanomeline.

The following terms, which are used in this disclosure, are defined as follows:

A receptor subtype "selective" agonist is a full or partial agonist which is more potent or more efficacious at one or more of the muscarinic M1, M2, M3, M4 or M5 receptor subtypes than at the others. Thus, an M1 selective agonist or an M1/M4 selective agonist is more potent or more efficacious at M1 or M1 and M4 receptor subtypes respectively than at the others.

The terms "sustained release" and "controlled release" are used interchangeably in this disclosure and are defined for purposes of this disclosure as the release of the compositions described herein from the dosage form at such a rate that blood (e.g., plasma or serum) concentrations are maintained within the desired therapeutic range longer than would be observed for the same dose of drug given by the same route of administration in a formulation that provides substantially immediate release, it will be apparent mat different time periods will be relevant for different routes and means of administration. In some embodiments the period over which extended release is observed is about one or two hours. In other embodiments, the period over which the extended release is observed is for about three, foot, five, or six hours. In still other embodiments, the extended release is observed for about eight, ten, twelve, sixteen, twenty or twenty four hours. Where physical means of administering the compositions described herein are employed, e.g., via an iontophoretic patch or an apparatus that provides metered doses, sustained or controlled release may be extended from hours to once daily, or longer on the order of days, or even weeks to months, depending upon the device employed and its ability to be replenished and/or replaced with a supply of the drug for administration.

The term "pulsed release" means as a series of releases of a drug (e.g., any of the compositions described herein) from a dosage to that acts to provide a sustained or controlled release. Embodiments of the compositions and dosage form a described herein can provide pulsed release.

The term "immediate release" means a release of a composition described herein from a dosage form in a relatively brief period of time. In such "immediate release" formulations, the purpose of the excipients is to bind together the drug in a stable, mechanically robust dosage form, such as a tablet, that rapidly disintegrates on ingestion, providing little or no restraint on the release of the drug. Use dosage form will not generally contain excipients intended to slow down the release of the compound. Highly soluble compounds in rapidly disintegrating immediate release dosage forms, might release the compound in only seconds to minutes after making contact with the fluid in the stomach, although it may take longer (e.g., up to 60 minutes) with other compounds/formulations.

The terms "cognitive enhancement" or "cognition-enhancing" refer to an enhancement of one or more of an subjects' characteristics selected from the group consisting of: improved memory of places; improved memory of people; improved memory of information; improved memory offsets; improved memory of how to operate and use tools; improved ability to analyze information; improved ability to deduce or reason; improved ability to synthesize conclusions; improved ability to think strategically; improved ability to make plans and decisions; improved ability to execute on plans and decisions; improved ability to perform activities of daily living; improved ability to be employed; enhanced activity of neuronal mechanisms responsible for effective memory and cognition (including muscarinic functions); reduced pathogenetic mechanisms leading to loss of memory and cognitive function; reduced loss of neurons or neuronal activity that lead to loss of cognitive and memory function; improved scores on neuropyschological tests such as ADAS-Cog or MMSE and others, improved scores on clinical assessments of the activities of daily living such as ADCS-ADL; increased α-secretase activity as compared to similarly situated subjects (e.g., humans with Alzheimer's disease) mat are not administered a muscarinic agonist described herein, reduced Aβ production as compared to similarly situated subjects that are not administered a muscarinic agonist described herein, increased sAPPα production as compared to similarly situated subjects that are not administered a muscarinic agonist described herein, and/or reduced Tail pathology and/or apoptosis as compared to similarly situated subject that are not administered a muscarinic agonist described herein; as well as other effects.

The term "disease-modifying" effect or action refers to an inhibition, amelioration, reversal, improvement or other alteration of the disease process of a subject or an effect on the underlying pathophysiology or neurobiology of the disease. Tins might comprise

- The halting or slowing down of disease progression as measured by cognitive and functional measurement tools and if these results are linked to an effect on the underlying disease process
- The halting or slowing down of neuron death or the halting of slowing down of neuronal dysfunction
- A reduction in the accumulation of amyloid plaques, fibrils or aggregates, or of oligomers or dimers of A-beta, or a reduction, in the concentration of A-beta in the brain or cerebrospinal fluid, or the rate of production of A-beta in the brain
- A reduction in the apoptosis or programmed death of neurons
- A reduction in the production of neurofibrillary tangles
- A reduction in the concentration of Tau protein or phosphorylation of Tau protein
- Partially or completely restoring lost cholinergic neuronal function
- Imposing pharmacological control of cholinergic neuronal function
- Correcting an imbalance of cholinergic function relative to other neurotransmitters Such a disease-modifying effect might be evident by the stabilization of an accepted primary or secondary endpoint or co-primary endpoint for several years, for two years, for 18 months, or for 12 months, such as cognitive function and/or memory of the patient, as evidenced by halting or reducing the rate of deterioration of a standard measure of cognitive function, or improvement in a standard measure of cognition and/or memory, such as Mini-Mental Score, or ADAS-COG, NTB, or by halting or reducing the rate of deterioration in a standard test of activities of daily living, such as ADL, IADL, ADCS-ADL or DAD, or changes in an assessment of quality of life using ADRQL or QOL-AD, or a global assessment, such as CIBIC-plus or ADCS-CGIC, or of a test of the overall clinical condition, such as CDR.

These and any other measures of disease modifying activity discussed herein might be established by comparing relevant parameters, which might include slope analysis or assessment of the time to an event, in groups of patients against matched groups of unaffected individuals in randomized, blinded, placebo-controlled clinical trials. The investigational drag might be compared with an active control drug, a hybrid trial design might be used, initially placebo-controlled and then progressing to a comparative effectiveness design, with placebo patients switching to test article, or a three arm trial comparing test article, placebo and active control might be used.

Disease-modifying activity might be evidenced by an MRI or emission tomographic or other imaging endpoint, or of an adequately qualified and validated, biomarker endpoint, such as:

- Halting or a reduction in the rate of shrinking of the brain, as evidenced by an imaging technique, such as volumetric MRI or CAT
- Halting or reducing the rate of shrinking or atrophy of a key part of the brain, known to be affected by AD, such as the hippocampus, the entorrhinal complex or the parahippocampal cortex, as evidenced by an imaging technique, such as volumetric MRI or CAT
- Halting or reducing the rate of deterioration in a test of brain function, using a metabolic marker, such as glucose uptake, or FDG imaging or functional MRI, PET or other imaging technique with a suitable metabolic tracer
- Stabilizing or reducing the rate of accumulation or a reduction in the amounts of amyloid plaque or A-beta containing deposits in the brain as measured using a suitable A-beta binding tracer such as the Pittsburg compound
- Reducing the concentration of A-beta in blood plasma or serum, or in the cerebrospinal fluid (CSF), as measured following lumbar puncture or a different method of accessing CSF, or a reduction in the rate of turnover of A-beta in the CSF, using suitable radioisotope pulse-chase experiments
- Reducing the concentration of Tau protein or phosphorylated Tau in the CSF, or a Change in the ratio of Tau or phosphorylated Tau to A-beta or another comparative marker substance, in the CSF
- A change in any diagnostic, staging, monitoring or other marker substance in any part of the body that has been validated for Alzheimer's disease Disease-modifying activity might be evidenced by a beneficial effect on outcomes, such as reduction in the development of any of the following, or an increase in the time after diagnosis, relative to the disease-population average and adjusted for disease stage or other demographic factor, of the time

- To progress to a later stage of disease as measured by a standard method
- To loss of the ability to live an independent life
- To becoming bed-ridden
- To exhibiting behavioral disturbances, such as agitation, verbal outbursts, or aggression, psychosis, or other disorders characteristic of the later stages of Alzheimer's disease, measured using a scale such as BEHAVE-AD or BRSD
- To loss of physical functions such as being able to swallow
- To contracting pneumonia or other medical complications of Alzheimer's disease, or a reduction in the number of occurrences of such complications or severity of such complications.

It might also be evidenced by an increase above the disease average of the survival time or time to death, adjusted for disease stage or other demographic factors, after diagnosis. It might be evidenced using clinical trial designs such as randomized delayed start and randomized withdrawal. It might also be evidenced by pharmacoeconomic outcomes, such as a reduction in the costs of providing care to a treated patient or group of patients, relative to the average cost of providing care to a non-affected person or a group of non-affected persons, including groups matched for other factors, such as age, gender and with similar co-morbidities.

"Treating" or "treatment" to achieve a cognition-enhancing effect as described above thus can mean the administration of compounds and compositions in an amount and for a time sufficient to achieve cognition-enhancing effects as described herein. Such treatment thus may achieve an alleviation, in whole or in part, of symptoms associated with a disorder or disease, or a slowing, inhibition or halting of further progression or worsening of those symptoms, or prevention or prophylaxis of the disease or disorder in a subject at risk for developing the disease or disorder, or an actual improvement in the disease state itself of a "subject," typically a human. For example, within the context of treating cognitive disorders such as Alzheimer's disease, successful treatment may include clinical benefit, an alleviation of symptoms, such as stabilization or improvement in cognition or memory (using well-established indices such as ADAS-COG), or a slowing or halting the progression of the disease, as measured by, a reduction in the production of the 42-amino acid peptide Aβ from the precursor APP, a reduction in the phosphorylation of the tau protein, a stabilization, reduction or halt in neuronal cell death or increased survival rate. The terra "treating" may also include the administration of compounds and compositions described herein in an amount and for a time sufficient to achieve a "disease-modifying" effect, as defined above.

As used herein, a "therapeutically effective amount" refers to an amount of a compound or composition that achieves a desired objective of "treating" as defined above. For example, a therapeutically effective amount may alleviate, in whole or in part, symptoms associated with a disorder or disease, or slow or halt further progression or worsening of those symptoms, or prevent or provide prophylaxis for the disease or disorder in a subject at risk for developing the disease or disorder, or achieve a "disease-modifying" effect in a subject mat has such a disease or disorder. Such amounts are illustrated further below.

A "subject" is any animal mat can benefit from the administration of a compound or composition as disclosed herein. In same embodiments, the subject is a mammal, for example, a human, a primate, a dog, a cat, a horse, a cow, a pig, a rodent, such as for example a rat or mouse. Typically, the mammal is a human.

Generally, reference to a certain element, such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the disclosure. Procedures for inserting such, labels into the compounds of this disclosure will be readily apparent to those skilled in the art based on the disclosures herein.

Alkyl groups include straight chairs and branched chain alkyl groups having the number of carbons indicated herein. In some embodiments an alkyl group has from 1 to 12 carbon atoms, from 1 to 10 carbons or, in some embodiments, from 1 to 8, 1 to 6, or 1, 2, 3 or 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neo-pentyl, isopentyl, and 2,2-dimethylpropyl groups. Representative substituted alkyl groups may be substituted one or more times with substituents such as those listed above, and include without limitation haloalkyl (e.g., trifluromethyl), hydroxyalkyl, thioalkyl, aminoalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3, 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, adamantyl, decalinyl, and the like. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed herein.

In general, "substituted" refers to an organic group (e.g., an alkyl or aryl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bands, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitrites (i.e., CN); and the like. Substituted also includes multiple substitution, e.g., disubstituted groups such as dialkyl, diaryl etc.

The term "leaving group" refers to an atom or group of atoms which may be replaced by another atom or group of atoms (e.g., a nucleophile, such as an amine, thiol, carbanion, and the like) during a chemical reaction. Illustrative leaving groups are well known in the art and include, but are not limited to halogen groups (e.g. I, Br. F, Cl), sulfonate groups (e.g., mesylate, tosylate, triflate), substituted alkylsulfonate groups (e.g. haloalkylsulfonate); $C_6$-aryloxy or substituted $C_6$-aryloxy groups; acyloxy groups and the like.

The term "protected" with respect to hydroxyl groups, amine groups, and carboxy groups, groups refers to forms of these functionalities that are protected from undesirable reaction by means of protecting groups. Protecting groups such as hydroxyl, amino, and carboxy protecting groups, are known to those skilled in the art and can be added or removed using well-known procedures such as those set forth in Protective Groups in Organic Synthesis, Greene, T. W.; Wuts, P. G. M., John Wiley & Sons, New York, N.Y., (3rd Edition, 1999). Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxy methyl ether, 2-methoxyethoxymethyl ether, tetrahydropyranyl ethers, 1-ethoxyethyl ether, allyl ether, benzyl ether; esters such as, but not limited to, benzoyl, formate, acetate, trichloroacetate, and trifluoroacetate.

Amino groups may be protected as substituted or unsubstituted amides, sulfonamides, carbamates, and the like, as well as Silyl, alkyl, alkenyl and aralkyl amines. Amino-protecting groups (also known as N-protecting groups) comprise acyl groups such as formyl, acetyl, propionyl, pivaloyl, t-butylacetyl, phenylacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, 4-nitrobenzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarboxyl, phenylthiocarbonyl and the like; alkyl groups such as benzyl, triphenylmethyl (trityl), p-methoxyphenyldiphenylmethyl, benzyloxymethyl and the like; and silyl groups such as trimethylsilyl and the like. Acid-stable amino protecting groups are not substantially removed by and do not substantially react with acid or interfere with synthetic reactions that take place in the presence of acid. Exemplary acid-stable protecting groups include but are not limited to fluorenylmethyloxycarbonyl. Base-stable N-protecting groups are amino-protecting groups that are sot substantially removed by and do not substantially react with base or interfere with synthetic reactions that take place in the presence of base. Typical base-stable N-protecting groups include formyl, acetyl, benzoyl, pivaloyl, t-butylacetyl, phenylsulfonyl, benzyl, t-butyloxycarbonyl (Boc), benzyloxycarbonyl (Cbz), trityl, and p-methoxyphenyldiphenylmethyl (Mmt). Suitable N-protecting groups for use herein include triphenylmethyl groups, optionally substituted with one or more $C_{1-6}$ alkoxy groups. In some embodiments, the triphenylmethyl groups are substituted with one, two or three methoxy groups, e.g., Mmt, 4,4'-dimethoxytrityl and 4,4',4"-trimethoxytrityl. Certain amino-protecting groups are both acid-stable and base-stable. Such protecting groups may be removed by alternative methods, e.g., hydrogenation. Exemplary acid-stable and base-stable amino-protecting groups include but are not limited to substituted and unsubstituted benzyl groups.

The term "protected" with respect to amine groups refers to forms of amines which are protected from undesirable reaction by means of protecting groups. Protecting groups are known to those skilled in the art and can be added or removed using well-known procedures such as those set forth in Protective Groups in Organic Synthesis, Greene, T. W.; Wuts, P. G. M., John Wiley & Sons, New York, N.Y., (3rd Edition, 1999).

As used herein, the term, "base" refers to a chemical compound that deprotonates another compound when reacted with it. Those skilled in the art will understand when a base is suitable for use in a reaction disclosed herein and can select such a base. Depending on the reaction, suitable bases for use in accordance with this disclosure may include but are not limited to, e.g., tertiary amines and basic alkali metal salts and hydrides. In some embodiments, the tertiary amines include triethylamine, N-methylmorpholine and diisopropylethylamine. In some embodiments, the basic alkali metal hydrides and salts include, e.g., sodium hydride (NaH), potassium hydride (KH), sodium carbonate ($Na_2CO_3$), potassium carbonate ($K_2CO_3$), sodium bicarbonate ($NaHCO_3$), sodium and potassium alkoxides including, but not limited to, sodium and potassium t-butoxide, propoxide, i-propoxide, ethoxide, methoxide, and the like, sodium amide ($NaNH_2$), potassium amide ($KNH_2$), and the like.

As used herein, an "acetylcholinesterase inhibitor" is any compound (or its pharmaceutically acceptable salts) that inhibits the activity of the enzyme acetylcholinesterase in hydrolyzing acetylcholine into its constituents, acetic acid and choline.

II. Compounds

Compounds that may be used in the compositions and methods disclosed herein stimulate muscarinic receptors. Included within such compound are cyclic oxadiazoles and thiadiazoles. Included within the cyclic oxadiazoles and thiadiazoles are those that are substituted in the 3 and 5 position. Included within such 3,5-substituted oxadiazoles and thiadiazoles are those which are substituted with azacycles.

A. Pyrimidinyl-Substituted Oxadiazoles and Thiadiazoles

Embodiments of this disclosure provide compounds of Formula I and pharmaceutically acceptable salts and stereoisomers thereof:

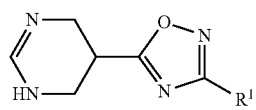

I wherein
$R^1$ is selected from the group consisting of —$CR^2R^2R^4$,

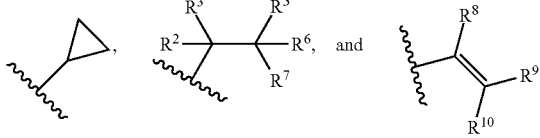

$R^2$, $R^3$, $R^4$ are independently selected from D or F; and
$R^5$, $R^6$, $R^7$, $R^8$, $R^9$, and $R^{10}$ are independently selected from H, D, F or a methyl group;
provided that not more than one of $R^5$, $R^6$, $R^7$, $R^8$, $R^9$, and $R^{10}$ is a methyl group.

In some embodiments of compounds of Formula I, $R^1$ is

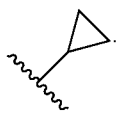 [SMILES: *C1CC1]

In some embodiments of compounds of Formula I, $R^1$ is —$CR^2R^3R^4$. In some embodiments of I, $R^2$, $R^3$, and $R^4$ are all D or all F. In others, $R^2$, $R^3$, and $R^4$ are all D.

In some embodiments of compounds of Formula I, $R^1$ is

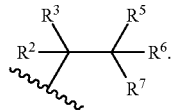

In such compounds, $R^2$, $R^3$, $R^5$, $R^6$, $R^7$ each may be D or H, including for example, when $R^2$, $R^3$, $R^5$, $R^6$, $R^7$ each are D (3-(ethyl-d5)-5-(1,4,5,6-tetrahydropyrimidin-5-yl)-1,2,4-oxidiazole), when $R^2$ is H and $R^3$, $R^5$, $R^6$, $R^7$ are each D (3-(ethyl-d4)-5-(1,4,5,6-tetrahydropyrimidin-5-yl)-1,2,4-oxadiazole), when $R^2$, $R^3$, $R^5$ and $R^6$ are each D and $R^7$ is H (3-(ethyl-d4)-5-(1,4,5,6-tetrahydropyrimidin-5-yl)-1,2,4-oxadiazole), when $R^2$ and $R^3$ are each H and $R^5$, $R^6$, $R^7$ are each D (3-(ethyl-d3)-5-(1,4,5,6-tetrahydropyrimidin-5-yl)-1,2,4-oxadiazole), when $R^2$ and $R^6$ are each H and $R^3$, $R^5$ and $R^7$ are D (3-(ethyl-d3)-5-(1,4,5,6-tetrahydropyrimidin-5-yl)-1,2,4-oxidiazole), when $R^5$ and $R^6$ are each H and $R^2$, $R^3$ and $R^7$ are D (3-(ethyl-d3)-5-(1,4,5,6-tetrahydropyrimidin-5-yl)-1,2,4-oxadiazole), when $R^5$, $R^6$ and $R^7$ are each H and $R^2$ and $R^3$ are each D (3-(ethyl-d2)-5-(1,4,5,6-tetrahydropyrimidin-5-yl)-1,2,4-oxadiazole), when $R^2$, $R^3$ and $R^5$ are each H and $R^6$ and $R^7$ are each D (3-(ethyl-d2)-5-(1,4,5,6-tetrahydropyrimidin-5-yl)-1,2,4-oxadiazole), when $R^2$, $R^5$ and $R^6$ are each H and $R^3$ and $R^7$ are each D (3-(ethyl-d2)-5-(1,4,5,6-tetrahydropyrimidin-5-yl)-1,2,4-oxadiazole), when $R^2$, $R^3$, $R^5$ and $R^6$ are each H and $R^7$ is D (3-(ethyl-d1)-5-(1,4,5,6-tetrahydropyrimidin-5-yl)-1,2,4-oxadiazole), and when $R^2$, $R^5$, $R^6$ and $R^7$ are each H and $R^3$ is D (3-(ethyl-d1)-5-(1,4,5,6-tetrahydropyrimidin-5-yl)-1,2,4-oxadiazole).

In some embodiments of compounds of Formula I, $R^2$ and $R^3$ are both D or both F. In others, $R^2$ and $R^3$ are both D.

In some embodiments of compounds of Formula I, $R^5$, $R^6$, and $R^7$ are each D or F. In others, $R^3$, $R^6$, and $R^7$ are each D. In some embodiments. $R^2$, $R^3$, $R^5$, $R^6$, and $R^7$ are each D.

In some embodiments of compounds of Formula I, $R^1$ is

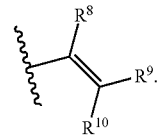

In some embodiments of compounds of Formula I, one of $R^8$, $R^9$, and $R^{10}$ is a methyl group. In others, $R^9$ is a methyl group and $R^8$ and $R^{10}$ are both H. Where one of $R^9$ and $R^{10}$ is a methyl group, it will be understood that both cis and trans geometric configurations are possible.

In all of the compounds described above, the oxygen atom may be replaced with a sulfur to form a thiodiazol.

B. Exemplary Methods of Making Pyrimidinyl-Substituted Oxadiazoles and Thiadiazoles Embodiments herein also provide methods for synthesizing oxadiazole compounds useful for the stimulation of muscarinic receptors and thus for the treatment of conditions affecting cognition and memory (e.g., Alzheimer's disease).

In accordance with one aspect of this disclosure, embodiments include methods of synthesizing compounds of Formula I and pharmaceutically-acceptable salts and stereoisomer thereof.

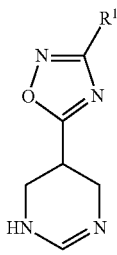

wherein
R$^1$ is selected from the group consisting of —CR$^2$R$^3$R$^4$,

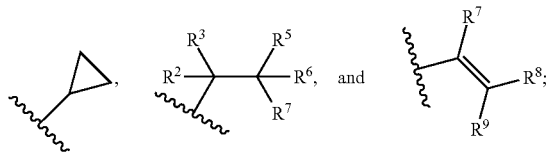

R$^2$, R$^3$, R$^4$ are independently selected from H, D or F; and R$^5$, R$^6$, R$^7$, R$^8$, R$^9$, and R$^{10}$ are independently selected from H, D, F or a methyl group: provided that not more than one of R$^4$, R$^5$, R$^6$, R$^7$, R$^8$, R$^9$, and R$^{10}$ is a methyl group.

In some embodiments of compounds of Formula I, R$^1$ is

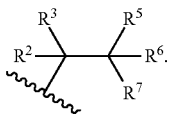

In such compounds, R$^2$, R$^3$, R$^5$, R$^6$, R$^7$ each may be D or H, including for example, when R$^2$, R$^3$, R$^5$, R$^6$, R$^7$ each are D (3-(ethyl-d5)-5-(1,4,5,6-tetrahydropyrimidin-5-yl)-1,2,4-oxidiazole), when R$^2$ is H and R$^3$, R$^5$, R$^6$, R$^7$ are each D (3-(ethyl-d4)-5-(1,4,5,6-tetrahydropyrimidin-5-yl)-1,2,4-oxadiazole), when R$^2$, R$^3$, R$^5$ and R$^6$ are each D and R$^7$ is H (3-(ethyl-d4)-5-(1,4,5,6-tetrahydropyrimidin-5-yl)-1,2,4-oxadiazole), when R$^2$ and R$^3$ are each H and R$^5$, R$^6$, R$^7$ are each D (3-(ethyl-d3)-5-(1,4,5,6-tetrahydropyrimidin-5-yl)-1,2,4-oxadiazole), when R$^2$ and R$^6$ are each H and R$^3$, R$^5$ and R$^7$ are D (3-(ethyl-d3)-5-(1,4,5,6-tetrahydropyrimidin-5-yl)-1,2,4-oxidiazole), when R$^5$ and R$^6$ are each H and R$^2$, R$^3$ and R$^7$ are D (3-(ethyl-d3)-5-(1,4,5,6-tetrahydropyrimidin-5-yl)-1,2,4-oxadiazole), when R$^5$, R$^6$ and R$^7$ are each H and R$^2$ and R$^3$ are each D (3-(ethyl-d2)-5-(1,4,5,6-tetrahydropyrimidin-5-yl)-1,2,4-oxadiazole), when R$^2$, R$^3$ and R$^5$ are each H and R$^6$ and R$^7$ are each D (3-(ethyl-d2)-5-(1,4,5,6-tetrahydropyrimidin-5-yl)-1,2,4-oxadiazole), when R$^2$, R$^5$ and R$^6$ are each H and R$^3$ and R$^7$ are each D (3-(ethyl-d2)-5-(1,4,5,6-tetrahydropyrimidin-5-yl)-1,2,4-oxadiazole), when R$^2$, R$^3$, R$^5$ and R$^6$ are each H and R$^7$ is D (3-(ethyl-d1)-5-(1,4,5,6-tetrahydropyrimidin-5-yl)-1,2,4-oxadiazole), and when R$^2$, R$^5$, R$^6$ and R$^7$ are each H and R$^3$ is D (3-(ethyl-d1)-5-(1,4,5,6-tetrahydropyrimidin-5-yl)-1,2,4-oxadiazole).

In one aspect, embodiments provide a method of synthesizing a compound of Formula I such as, e.g., 3-ethyl-5-(1,4,5,6-tetrahydropyrimidin-5-yl) 1,2,4-oxadiazole. In one embodiment, the method comprises treating a compound of Formula II or a salt thereof,

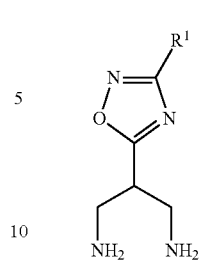

with formate ester equivalent to provide a compound of Formula I or a salt thereof.

Formate ester equivalents are well known in the art and are compounds which provide formate esters or formic acid in situ or react to give the same product as formate eaters. Thus, formate ester equivalents include, e.g., trialkylorthoformates such as triethylorthoformate, trimethylonhoformate or diethoxymethylacetate, halomethyl alkyl ethers, halomethyl allyl others, or a mixture thereof. In one embodiment, the formate ester equivalent is selected from triethylorthoformate, trimethylorthoformate or diethoxymethylacetate. In an illustrative embodiment, the formate ester equivalent is triethylorthoformate.

A variety of suitable solvents such as, but not limited to, alcohols such as methanol, ethanol, or propanol may be employed in the reaction of the compound of Formula II with a formate ester equivalent. In illustrative embodiments, ethanol is used as the solvent. In some embodiments, the formate ester equivalent may be added to a solution of the compound of Formula I in ethanol at room temperature. In other embodiments, the mixture may be heated to reflux and refluxed for a suitable period of time until the reaction is substantially complete. By "substantially" is meant all or nearly all.

In some embodiments, compound of Formula I can be prepared from compounds of Formula III. Thus, in one embodiment, the method comprises preparing a compound of Formula II by removing the base-sable N-protecting groups from a compound of Formula III,

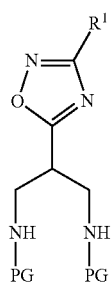

wherein each PG is independently a base-stable N-protecting group; and R$^1$ is as defined herein.

Those of skill in the art will understand that a variety base-stable N-protecting groups may be used. In some embodiments, the base-stable N-protecting groups may be selected from t-butyloxycarbonyl, benzyloxycarbonyl, or chlorobenzyloxycarbonyl. In an illustrative embodiment, the base-stable N-protecting groups are t-butyloxycarbonyl.

The base-stable N-protecting group PG may be removed by techniques known in the art. In some embodiments, where the PG is t-butyloxycarbonyl, it may be removed by exposing the compound of Formula III to an amount of acid sufficient to remove substantially all of the t-butyloxycarbonyl groups. In some embodiments, the acids used for deprotection may be selected from trifluoroacetic acid, hydrochloric acid or methanesulfonic acid. In an illustrative embodiment, the acid used to remove the base-stable N-protecting group from a compound of Formula III is hydrochloric acid. The acid salt obtained after deprotection of the compound of Formula III may be used as such for the next step. Optionally, the acid used to remove the Boc protecting group may be neutralized with a tertiary amine such as N-methylmorpholine, N-diisopropylethylamine or triethylamine, and the free base form of the compound of Formula II used in the next step.

The compound of Formula III may be prepared from the compound of Formula IV. Thus, in one embodiment, the method comprises treating a compound of Formula IV,

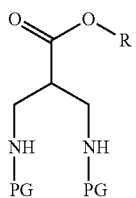

IV with amide oxime VIII,

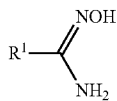

VIII in the presence of a base to give a compound of Formula III (see above); wherein R is a methyl or ethyl group and each PG is independently a base-stable N-protecting group, as described herein, and $R^1$ (of Formula III) is also as defined herein.

A variety of solvents and bases may be used for the above reaction of compound IV with amide oxime VIII. In some embodiments, the solvent is methanol, tetrahydrofuran, toluene, acetonitrile, or dimethylformamide. In some embodiments, the base is selected from NaH, KH, sodium methoxide or potassium t-butoxide. In an illustrative embodiment, the base is NaH. In some such embodiments, the base is NaH in a solvent such as THF. Alternatively, the solvent can be toluene and the base can be potassium carbonate.

The amide oxime used for reaction with compound of Formula IV may be obtained commercially (e.g. propionamidoxime, Alpha Aesar. Catalog #H50889) or may be prepared according to the procedure in Organic Process Research and Development 2006, 10, 36, by treating the appropriate nitrile with hydroxylamine in water or in an alcoholic solvent such as methanol or a mixture thereof.

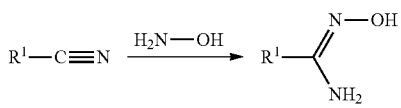

The compound of Formula IV can be prepared from the compound of Formula V. Thus, in one embodiment, the methods comprise preparing the compound of Formula IV by treating the compound of Formula V or a salt thereof,

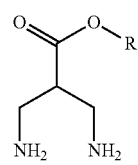

V with a reagent that attaches a base-stable N-protecting group to each amino group of Formula V, wherein R in Formula V is a methyl or ethyl group.

A variety of reagents may be used to attach base-stable N-protecting groups to each amino group of Formula V. (See, Wuts, above, and Bodanszky, M. Bodanszky, A., *The Practice of Peptide Synthesis*, Springer-Verlag. New York, 1984.) In some embodiments, the reagent for attaching an N-protecting group is selected from di-t-butyldicarbonate, t-butyloxychloroformate, benzyloxychloroformate, or chlorobenzyloxychloroformate. In an illustrative embodiment, the reagent for attaching an N-protecting group is t-butyloxychloroformate. In some embodiments, the preparation of compound IV may be carried out in the presence of a base. Typically the amount of base used will be sufficient to neutralize any acid addition salt of the reactants present and/or neutralize any acid formed during reaction (i.e., a neutralizing amount of base). It is within the skill in the art to select an amount of base necessary to effect the protection reaction. In some embodiments, the base is an alkali metal carbonate or bicarbonate, or is a tertiary amine. In an illustrative embodiment, the base is sodium bicarbonate, potassium bicarbonate, sodium carbonate, potassium carbonate, or cesium carbonate. A variety of solvents may be used for the N-protecting reaction, including, e.g., alcoholic solvents such as ethanol, or mixtures of water and dioxane.

In some embodiments, the compound of Formula V can be prepared from compound of Formula VI. Thus, in one embodiment, the method comprises preparing the compound of Formula V by removing the $R^1$ groups from the compound of Formula VI,

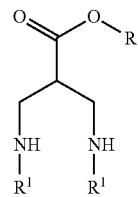

VI wherein R in Formula V is a methyl or ethyl group, and each $R^1$ is independently a substituted or unsubstituted benzyl group.

$R^1$ may easily be removed by using standard methods known in the art such as by hydrogenation in the presence of a suitable metal catalyst or by using magnesium bromide-dimethyl sulfide, ceric ammonium nitrate (CAN) or 2,3-dichlor-5,6-dicyanol,4-benzoquinone (DDQ). In an illustrative embodiment, palladium on carbon is used to catalyze the hydrogenation of the compound of Formula VI. The reaction may be conducted in presence of an acid such as acetic acid and using an alcoholic solvent such as methanol. The free amino compound of Formula V may be recovered as such or may be converted to a salt, such as the HCl salt, prior to conversion to the compound of Formula IV.

The compound of Formula VI may be prepared from compound of Formula VII. This, in one embodiment, the method comprises preparing the compound of Formula VI by treating the compound of Formula VII.

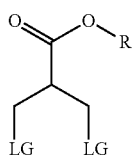

VII with a substituted or unsubstituted benzylamine in presence of base; wherein R in Formula VII is a methyl or ethyl group, and each LG is independently a leaving group. LG can be any suitable leaving group known in the art which can be substituted by a benzyl amine. In some embodiments, each LG is a halogen (e.g., Cl, Br, I) or a sulfonyl ester (mesylate, tosylate, benzenesulfonate, or triflate). In an illustrative embodiment, each LG is a bromo group. Compounds of Formula VII may be obtained from commercial sources such as Aldrich Chemical Company or Acros Organics or prepared using methods known in the art.

A variety of substituted or unsubstituted benzylamines may be used for treating the compound of Formula VII. In some embodiments, the substituents on benzylamine may be selected from halogen, nitro, carboxy, $C_1$-$C_4$ alkyl or alkoxy, such as methoxy, or dialkoxy. A base may be used to neutralize the acid formed during the reaction. In some embodiments, the base used is an organic base. In some embodiments, the base is selected from diisopropylethylamine, N-methyl morpholine, N-ethyl morpholine, triethylamine, 2,6-lutidine, N-ethylpiperidine, imidazole, and 5,6 dimethylbenzimidazole. In an illustrative embodiment, the base is diisopropylethylamine. A variety of solvents, including, but not limited to, chlorinated solvents such as chloroform may be used for the conversion of compound of Formula VII to compound of Formula VI. The compound of Formula VI may be recovered and used as such or may be converted to a salt, such as the HCl salt, prior to its conversion to a compound of Formula V.

The methods set forth above employ several intermediate compounds and reaction schemes that also are embodiments of this disclosure. Thus, for example, embodiments include compounds of Formula IX or salts thereof,

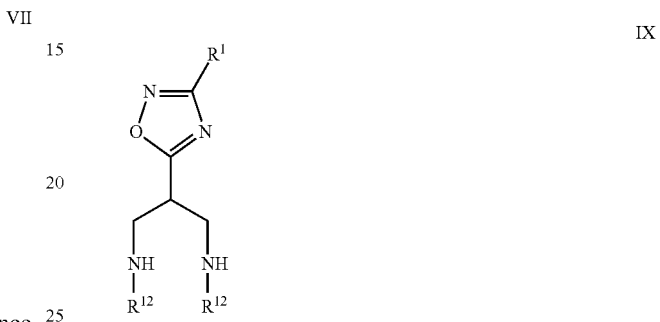

wherein each $R^{12}$ is independently —H, or an N-protecting group. The N-protecting groups may be as described hereinabove. Embodiments of reaction schemes also include schemes comprising one or more steps before the creation of Formula IX and/or one or more steps following the creation of Formula IX. The same applies mutatis mutandi to the compounds of Formulas I-VIII above, as well as to the compounds and reaction schemes provided below.

In one illustrative and non-limiting embodiment, the compound of Formula I (1) may be prepared as shown below in Scheme 1. Thus, 3-Ethyl-5-(1,4,5,6-tetrahydropyrimidin-5-yl)-1,2,4-oxadiazole can be prepared starting from dibromo compound 7. Treatment of compound 7 with excess benzylamine in presence of a base such as DIEA gives compound 6. The reaction may be carried out in any suitable solvent, such as chloroform or dichloromethane, or with non-halogenated solvents, such as alcohols, ethers or toluene, and optionally with cooling to, e.g., 0-5 C. As indicated above, this displacement may be carried out with other substituted benzyl groups under similar conditions.

Scheme 1

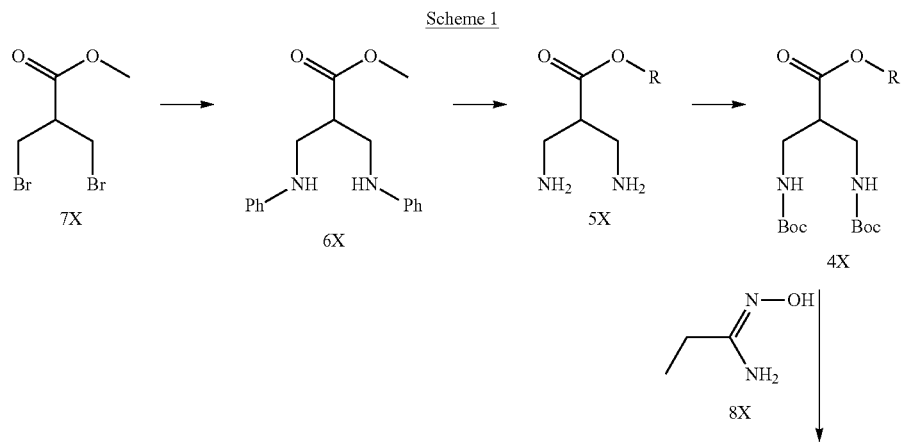

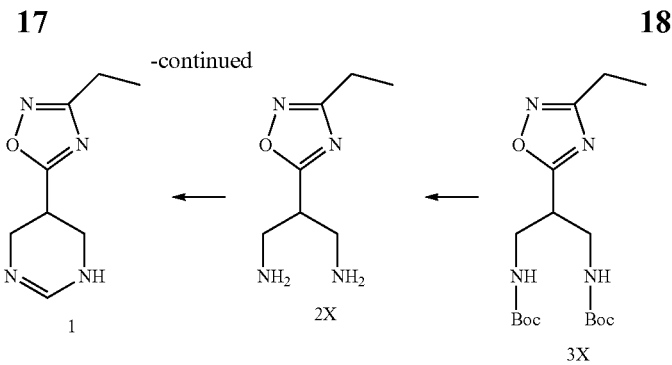

Next, the N-protecting groups of compound 6X are changed. First, the benzyl groups of compound 6X are removed by standard methods such as e.g. hydrogenation in the presence of a transition metal catalyst such as Pd, Pd(OH)$_2$ or Pt. Suitable solvents for the hydrogenation include alcohols and mixtures of alcohols and acids such as acetic acid. The hydrogenation is carried out under an atmosphere of hydrogen, optionally under pressure, to give compound 5X. The free amino groups of compound 5X may be protected with Boc groups to give compound 4X, but other suitable N-protecting groups listed above may be used. Standard conditions (di-tertbutyldicarbonate, NaHCO$_3$ ethanol) for this N-protection reaction may be used.

The N-protected compound 4X may be treated with propionamidoxime 8X in the presence of a strong base such as NaH in, e.g., THF, to give oxadiazole 3. (Propionamidoxime 8X may be synthesized by treating propionitrile with hydroxylamine in a suitable solvent.) Compound 3X may be deprotected by standard methods known in the art, for e.g., by exposure to an acid such as HCl or TFA. The free amino compound 2X or a salt thereof may be treated with a formate ester equivalent such as triethylorthoformate to give the final product, an oxadiazole compound of Formula I. Suitable solvents for the latter reaction include alcohols such as methanol or ethanol, optionally heated to reflux. Compound 1 may subsequently be recovered as the fire base.

Those skilled in the art also will appreciate that other synthetic routes may be employed. For example, as shown in Scheme 2 below, compounds of Formula I also may be prepared starting from the nitrile A1, bearing an R$^1$ group. Such nitriles are commercially available or may be made by known methods from the corresponding alcohol (e.g. by tosylation followed by displacement of the tosyl group by a cyano group). The nitrile may be converted into the N-hydroxyamidine A2 under standard conditions such as by treatment with N-hydroxylamine and sodium methoxide in methanol. The latter reaction may be carried out with cooling (e.g., an ice bath) and/or with heating up to, e.g., about 50° C.

Scheme 2

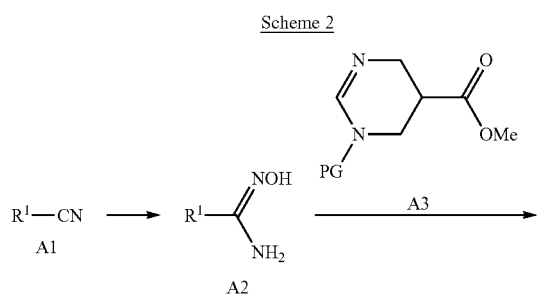

Cyclization of compound A2 with the N-protected tetrahydropyrimidine A3 under basic conditions (e.g., NaH or KH) yields the N-protected tetrahydropyrimidinyl-oxadiazole A4. The ethyl ester of compound A3 may also be used. The latter reaction may be carried out in any suitable solvent such as, e.g., THF. Any N-protecting group that can withstand the oxadiazole ring formation without destabilizing the tetrahydropyrimidine may be used, including but not limited to substituted and unsubstituted triphenylmethyl groups such as trityl, Mmt, 4,4'-dimethoxytrityl, and 4,4',4''-trimethoxytrityl. Finally, compound A4 may be N-deprotected to give the final product, a compound of Formula I. Those of skill in the art will understand that the deprotection conditions will depend on the nature of the protecting group and may readily select the appropriate conditions for the deprotection. For example, Mint groups may be removed under acidic conditions (e.g., 2 M HCl).

R$_1$ groups containing deuterium or fluorine and/or that are olefins or cyclopropyl may be installed using the above synthetic route. For example, nitrile A1 can be purchased or synthesized with deuterium or fluorine incorporated. Alternatively, compound A2 be made with a hydroxyl group in the side chain. The hydroxyl group can be replaced with fluorine using standard methods (e.g. DAST reagent).

The N-protected intermediate A3 from Scheme 2 may be made according to the procedure set forth in Scheme 3.

Scheme 3

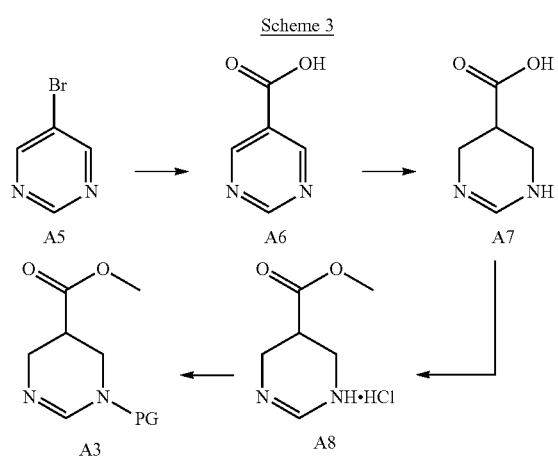

3-Bromopyrimidine (compound A5) may be carboxylated by treatment with n-butyllithium and carbon dioxide in tetrahydrofuran to give the acid A6. The latter compound may be hydrogenated using any suitable catalyst such as Pd/C in a solvent such as water to provide tetrahydropyrimidine A7. Formation of the methyl ester from A7, may be carried out using standard conditions such as HCl in methanol to give compound A8. Alternatively, ethanol in HCl could be used to generate the ethyl ester. Any suitable N-protecting group may be installed to give intermediate A3. Exemplary N-protecting groups include trityl, Mmt, 4,4'-dimethoxytrityl, and 4,4',4-trimethoxytrityl (suitable protecting conditions include the use of the corresponding chloride, and a base such as DBU in a solvent such as dichlormethane, at ambient temperature for 2-24 hours).

Where a thidiazole is desired, the oxygen in the above syntheses may be replaced with a sulfur.

C. Azacycle- and Azabicyclo-Substituted Oxadiazoles and Thiadiazoles

Yet other compounds that may be used in the compositions and methods of this disclosure include compounds of Formula I, IA, IB, X, XA or XB, which have the following structures:

I

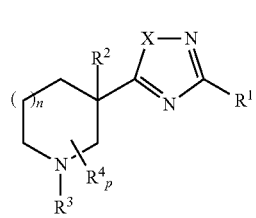

IA

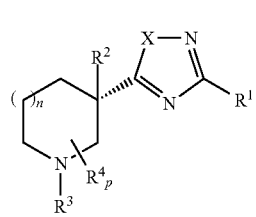

IB

X

XA

XB wherein
X is O or S;
$R^1$ is $NH_2$, or methyl, optionally substituted with 1-3 deuterium atoms; or, when X is S, $R^1$ can also be H or D;
$R^2$ is H, F, a substituted or unsubstituted C1-4 alkyl group, OH or OR wherein R is a substituted or unsubstituted C1-4 alkyl group
$R^3$ is H or, when X is S, $R^3$ can also be methyl, optionally substituted with 1-3 substituents selected from the group consisting of deuterium and fluorine;
$R^4$ is F at each occurrence;
n is 0, 1 or 2;
m is 1 or 2; and
p is 0, 1 or 2.

In some embodiments, X can be O and the compound is an oxadiazol, such a 1,2,4-oxadiazole. In other embodiments, X is S and the compound is a thiadiazole such as a 1,2,4-thiadiazole.

In some embodiments, $R^2$ is H. In others, $R^2$ is F. In others, $R^2$ is OH. In some embodiments. $R^2$ is a substituted or unsubstituted $C_{1-4}$ alkyl group. For example, the $C_{1-4}$ alkyl group may be optionally substituted with one or more halogen, including, but not limited to F or Cl. In some embodiments, $R^2$ is an $C_{1-4}$ alkyl group optionally substituted with 1-3 fluoro groups. Thus, in some embodiments, $R^2$ is methyl fluoromethyl, trifluoromethyl, ethyl 2-fluoroethyl, 2,2,2-trifluoroethyl, propyl, 3-fluoropropyl, 3,3,3-trifluoropropyl, 4-fluorobutyl, or 4-trifluorobutyl. In still other embodiments, $R^2$ is OR, in which R is as defined above. In some embodiments, R is a $C_{1-4}$ alkyl group optionally substituted with one or more halogen, including but not limited to F or Cl. In some embodiments, R is a $C_{1-4}$ alkyl group optionally substituted with 1-3 fluor groups. Thus, in some embodiments, OR is methoxy, fluoromethoxy, trifluoromethoxy, ethoxy, 2-fluoroethoxy, 2,2,2-trifluoroethoxy, propoxy, 3-fluoropropoxy, 3,3,3-trifluoropropoxy, 4-fluorobutoxy, or 4-trifluorobutoxy. In certain embodiments of the compounds disclosed herein, $R^1$ is H. In some embodiments, n is 0 or 1. In still other embodiments, p is 1 or 2. In some embodiments, p is 2 and each F is on the same carbon.

In some embodiments:
  X is O or S;
  $R^1$ is $NH_2$, or methyl optionally substituted with 1-3 deuterium atoms; or, when X is S, $R^1$ can also be H or D;
  $R^2$ is H, F or OH;
  $R^3$ is H or, when X is S, $R^3$ can also be methyl, optionally substituted with 1-3 substituents selected from the group consisting of deuterium and fluorine;
  is 0 or 1; and
  is 0.

In some embodiments, n is 0 and the cyclic amine is a pyrrolidine of Formulas I, IIA, or IIB:

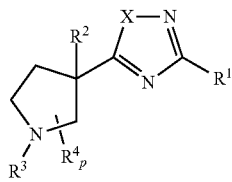

II

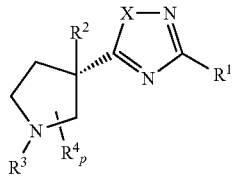

IIA

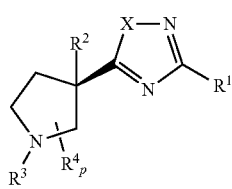

IIB

In such embodiments, the pyrrolidine of Formulas II, IIA and IIB may be optionally substituted in the 4 position with a substituted or unsubstituted $C_{1-6}$ alkyl such as methyl. For example, the $C_{1-6}$ alkyl group may be optionally substituted with one or more halogen, including, but not limited to F or Cl. In some embodiments, $R^2$ is an $C_{1-6}$ alkyl group optionally substituted with 1-3 fluoro groups. Thus, in some embodiments, $R^2$ is methyl, fluoromethyl trifluoromethyl, ethyl, 2-fluoroethyl, 2,2,2-trifluoroethyl, propyl, 3-fluoropropyl, 3,3,3-trifluoropropyl, 4-fluorobutyl, or 4-trifluorobutyl.

In some embodiments, n is 1 and the cyclic amine is a piperidine of Formula III, IIIA, or IIIB:

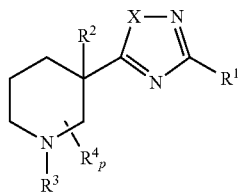

III

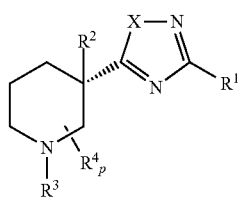

IIIA

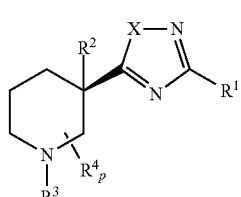

IIIB

In some embodiments, n is 2 and the cyclic amine is a azepane of Formula IV, IVA, or IVB:

IV

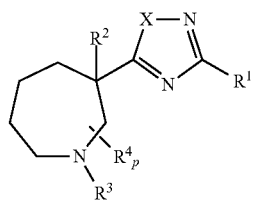

IVA

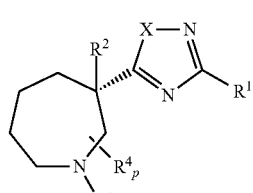

IVB

It will be understood that each variable (e.g., X, $R^1$, $R^2$, $R^3$, $R^4$ and p) of compounds of Formulas II, III, and IV may have any of the values set forth above for compounds of Formula I.

In some embodiments of the foregoing compounds, $R^1$ is $CH_3$ e.g. 3-(methyl)-5-(piperidin-3-yl)-1,2,4-oxadiazole, (R)-3-(methyl)-5-(piperidin-3-yl)-1,2,4-oxadiazole, (S)-3-(methyl)-5-(piperidin-3-yl)-1,2,4-oxadiazole, 5-(3-azabicyclo[3.1.0]hexan-1-yl)-3-(methyl)-1,2,4-oxadiazole, 5-((1S)-

3-azabicyclo[3.1.0]hexan-1-yl)-3-(methyl)-1,2,4-oxadiazole, 5-((1R)-3-azabicyclo[3.1.0]hexan-1-yl)-3-(methyl)-1,2,4-oxadiazole, 5-(3-azabicyclo[3.1.0]heptan-1-yl)-3-(methyl)-1,2,4-oxadiazole, 5-((1S)-3-azabicyclo[3.1.0]heptan-1-yl)-3-(methyl)-1,2,4-oxadiazole, and 5-((1R)-3-azabicyclo[3.1.0]heptan-1-yl)-3-(methyl)-1,2,4-oxadiazole, 3-methyl-5-(4-methylpyrrolidin-3-yl)-1,2,4-oxadiazole, 3-methyl-5-((3S,4S)-4-methylpyrrolidin-3-yl)-1,2,4-oxadiazole, 3-methyl-5-(3R,4R)-4-methylpyrrolidin-3-yl)-1,2,4-oxadiazole, 3-methyl-5-(piperidin-3-yl)-1,2,4-oxadiazole, (S)-3-methyl-5-(piperidin-3-yl)-1,2,4-oxadiazole, (R)-3-methyl-5-(piperidin-3-yl)-1,2,4-oxadiazole, 5-(3-fluoropiperidin-3-yl)-3-methyl-1,2,4-oxadiazole, (R)-5 (3-fluoropiperidin-3-yl)-3-methyl-1,2,4-oxadiazole, (S)-5-(3-fluoropiperidin-3-yl)-3-methyl-1,2,4-oxadiazole, 3-methyl-5-(piperidin-3-yl)-1,2,4-thiadiazole, (S)-3-methyl-5-(piperidin-3-yl)-1,2,4-thiadiazole, (R)-3-methyl-5-(piperidin-3-yl)-1,2,4-thiadiazole, 3-methyl-5-(pyrrolidin-3-yl)-1,2,4-oxadiazole, (S)-3-methyl-5-(pyrrolidin-3-yl)-1,2,4-oxadiazole, and (R)-3-methyl-5-pyrrolidin-3-yl)-1,2,4-oxadiazole.

In some embodiments of the foregoing compounds, $R^1$ is $CD_3$, e.g. 3-(methyl-d3)-5-(piperidin-3-yl)-1,2,4-oxadiazole, (R)-3-(methyl-d3)-5-(piperidin-3-yl)-1,2,4-oxadiazole, (S)-3-(methyl-d3)-5-(piperidin-3-yl)-1,2,4-oxadiazole, 5-(3-azabicyclo[3.1.0]hexan-1-yl)-3-(methyl-d3)-1,2,4-oxadiazole, 5-((1S)-3-azabicyclo[3.1.0]hexan-1-yl)-3-(methyl-d3)-1,2,4-oxadiazole, 5-((1R)-3-azabicyclo[3.1.0]hexan-1-yl)-3-methyl-d3)-1,2,4-oxadiazole, 5-(3-azabicyclo[3.1.0]heptan-1-yl)-3-(methyl-d3)-1,2,4-oxadiazole, 5-((1S)-3-azabicyclo[3.1.0]heptan-1-yl)-3-(methyl-d3)-1,2,4-oxadiazole, and 5-((1R)-3-azabicyclo[3.1.0]heptan-1-yl)-3-(methyl-d3)-1,2,4-oxadiazole, 3-(methyl-d3)-5-(4-methylpyrrolidin-3-yl)-1,2,4-oxadiazole, 3-(methyl-d3)-5-((3S,4S)-4-methylpyrrolidin-3-yl)-1,2,4-oxadiazole, 3-methyl-d3)-5-((3R,4R)-methylpyrrolidin-3-yl)-1,2,4-oxadiazole, 3-(methyl-d3)-5-(piperidin-3-yl)-1,2,4-oxadiazole, (S)-3-(methyl-d3)-5-(piperidin-3-yl)-1,2,4-oxadiazole, (R)-3-(methyl-d3)-5-(piperidin-3-yl)-1,2,4-oxadiazole, 5-(3-fluoropiperidin-3-yl)-3-(methyl-d3)-1,2,4-oxadiazole, (R)-5-(3-fluoropiperidin-3-yl)-3-(methyl-d3)-1,2,4-oxadiazole, (S)-5-(3-fluoropiperidin-3-yl)-3-(methyl-d3)-1,2,4-oxadiazole, 3-(methyl-d3)-5-(piperidin-3-yl)-1,2,4-thiadiazole, (S)-3-(ethyl-d3)-5-(piperidin-3-yl)-1,2,4-thiadiazole, (R)-(methyl-d3)-5-(piperidin-3-yl)-1,2,4-thiadiazole, (methyl-d3)-5-(pyrrolidin-3-yl)-1,2,4-oxadiazole, (S)-3-(methyl-d3)-5-(pyrrolidin-3-yl)-1,2,4-oxadiazole, and (R)-3-(methyl-d3)-5-(pyrrolidin-3-yl)-1,2,4-oxadiazole.

In other embodiments of the foregoing compounds, $R^1$ is $CHD_2$, e.g., 3-(methyl-d2)-5-(piperidin-3-yl)-1,2,4-oxadiazole, (R)-3-(methyl-d2)-5-(piperidin-3 yl)-1,2,4-oxadiazole, (S)-3-(methyl-d2)-5-(piperidin-3-yl)-1,2,4-oxadiazole, 5-(3-azabicyclo[3.1.0]hexan-1-yl)-3-(methyl-d2)-1,2,4-oxadiazole, 5-(1S)-3-azabicyclo[3.1.0]hexan-1-yl)-3-(methyl-d2)-1,2,4-oxadiazole, 5-((1R)-3-azabicyclo[3.1.0]hexan-1-yl)-methyl-d2)-1,2,4-oxadiazole, 5-(3-azabicyclo[3.1.0]heptan-3-(methyl-d2)-1,2,4-oxadiazole, 5-((1S)-3-azabicyclo[3.1.0]heptan-1-yl)-3-(methyl-d2)-1,2,4-oxadiazole, and 5-((1R)-3-azabicyclo[3.1.0]heptan-1-yl)-3-(methyl-d2)-1,2,4-oxadiazole, 3-(methyl-d2)-5-(4-methylpyrrolidin-3-yl)-1,2,4-oxadiazole, 3-(methyl d2)-5-((3S,4S)-4-methylpyrrolidin-3-yl)-1,2,4 oxadiazole, 3-(methyl-d2)-5-((3R,4R)-4-methylpyrrolidin-3-yd)-1,2,4-oxadiazole, 3-(methyl-d2)-5-(piperidin-3-yl)-1,2,4-oxadiazole, (S)-3-(methyl-d2)-5-(piperidin-3-yl)-1,2,4-oxadiazole, (R)-3-(methyl-d3)-5-(piperidin-3-yl)-1,2,4-oxadiazole, 5-(3-fluoropiperidin-3-yl)-3-(methyl-d2)-1,2,4-oxadiazole, (R)-5-(3-fluoropiperidin-3-yl)-3-(methyl-d2)-1,2,4-oxadiazole, (S)-5-(3-fluoropiperidin-3-yl)-3-(methyl-d2)-1,2,4-oxadiazole, 3-(methyl-d2)-5-(piperidin-3-yl)-1,2,4-thiadiazole, (S)-3-(methyl-d3)-5-(piperidin-3-yl)-1,2,4-thiadiazole, (R)-(methyl-d2)-5-(piperidin-3-yl)-1,2,4-thiadiazole, (methyl-d2)-5-(pyrrolidin-3-yl)-1,2,4-oxadiazole, (S)-3-(methyl-d2)-5-(pyrrolidin-3-yl)-1,2,4-oxadiazole, and (R)-3-(methyl-d2)-5-(pyrrolidin-3-yl)-1,2,4-oxadiazole.

In yet other embodiments of the foregoing compounds, $R^1$ is $CH_2D$, e.g., 3-(methyl-d1)-5-(piperidin-3-yl)-1,2,4-oxadiazole, (R)-3-(methyl-d1)-5-(piperidin-3-yl)-1,2,4-oxadiazole, (S)-3-(methyl-d1)-5-(piperidin-3-yl)-1,2,4-oxadiazole, 5-(3-azabicyclo[3.1.0]hexan-1-yl)-3-(methyl-d1)-1,2,4-oxadiazole, 5-((1S)-3-azabicyclo[3.1.0]hexan-1-yl)-3-(methyl-d1)-1,2,4-oxadiazole, 5-((1R)-3-azabicyclo[3.1.0]hexan-1-yl)-3-(methyl-d1)-1,2,4-oxadiazole, 5-(3-azabicyclo[3.1.0]heptan-1-yl)-3-(methyl-d1)-1,2,4-oxadiazole, 5-((1S)-3-azabicyclo[3.1.0]heptan-1-yl)-3-(methyl-d1)-1,2,4-oxadiazole, and 5-((1R)-3-azabicyclo[3.1.0]hexan-1-yl)-3-(methyl-d1)-1,2,4-oxadiazole, 3-(methyl-d1)-5-(4-methylpyrrolidin-3-yl)-1,2,4-oxadiazole, 3-(methyl-d1)-5-((3S,4S)-4-methylpyrrolidin-3-yl)-1,2,4-oxadiazole, 3-(methyl-d1)-5-((3R,4R)-4-methylpyrrolidin-3-yl)-1,2,4-oxadiazole, 3-(methyl-d1)-5-piperidin-3-yl)-1,2,4-oxadiazole, (S)-3-(methyl-d1)-5-(piperidin-3-yl)-1,2,4-oxadiazole, (R)-3-(methyl-d1)-5-piperidin-3-yl)-1,2,4-oxadiazole, 5-(3-fluoropiperidin-3-yl)-3-(methyl-d1)-1,2,4-oxadiazole, (R)-5-(3-fluoropiperidin-3-yl)-3-(methyl-d1)-1,2,4-oxadiazole, (S)-5-(3-fluoropiperidin-3-yl)-3-(methyl-d1)-1,2,4-oxadiazole, 3-(methyl-d1)-5-(piperidin-3-yl)-1,2,4-thiadiazole, (S)-3-(methyl-d1)-5-(piperidin-3-yl)-1,2,4-yl)-1,2,4-oxadiazole, (S)-3-(methyl-d1)-5-(pyrrolidin-3-yl)-1,2,4-oxadiazole, and (R)-3-(methyl-d1)-5-(pyrrolidin-3-yl)-1,2,4-oxadiazole.

In another aspect, this disclosure provides compounds of Formula XI, stereoisomers thereof or pharmaceutically acceptable salts thereof, wherein the compound has the structure:

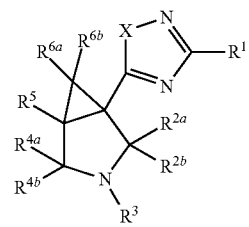

XI wherein

X is O or S;

$R^1$ is $NH_2$, a $C_{1-6}$ alkyl group or a $C_{3-6}$ cycloalkyl group, wherein the alkyl or cycloalkyl groups are optionally substituted with 1 or more deuterium atoms (D);

$R^{2a}$, $R^{2b}$, $R^{4a}$, $R^{4b}$, $R^5$, $R^{6a}$, and $R^{6b}$ are independently selected from H or D; and $R^3$ is H, D or an amino-protecting group.

In some embodiments, the compounds of Formula XI have the structure of Formula XIA or XIB:

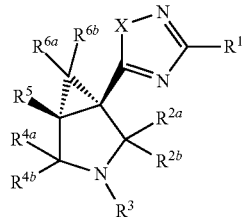

XIA

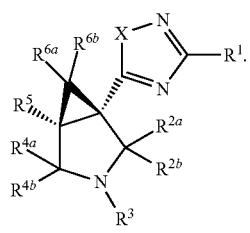

XIB

In some embodiments of compounds of Formulas XI, XIA and XIB, X is O and the compound is an oxadiazole. In other embodiments, X is S and the compound is a thiadiazole.

In some embodiments of compounds of Formulas XI, XIA and XIB, $R^1$ is a $C_{1-6}$ alkyl group or a cyclopropyl group, optionally substituted with 1, 2, 3, 4, 5, or 6 D. In some embodiments $R^1$ is $CH_3$, $CDH_2$, $CD_2H$ or $CD_3$. In other embodiments, $R^1$ is $CH_3$ or $CD_3$. In some embodiments, $R^1$ is $NH_2$ only when X is O. In some embodiments, $R^{2a}$ and $R^{2b}$ are both D. In certain embodiments, $R^3$ is H. In still other embodiments, $R^3$ is an amino-protecting group selected from benzyl, t-Butyloxycarbonyl, fluorenylmethyloxycarbonyl, and benzyloxycarbonyl. In some embodiments, $R^{4a}$ and $R^{4b}$ are both D. In certain embodiments, $R^5$ is D. In other embodiments. $R^{4a}$, $R^{4b}$, and $R^5$ are all D. In some embodiments, $R^{6a}$ and $R^{6b}$ are both D. It should be understood that each permutation of such compounds in which one or more or all of $R^{2a}$ and $R^{2b}$, $R^{4a}$ and $R^{4b}$ and $R^5$ is/are D is envisioned. For example, compounds with the following $R^{2a}$, $R^{2b}$, $R^{4a}$, $R^{4b}$ and $R^5$ groups that are D are envisioned:

$R^{2a\ or\ b}$
$R^{4a\ or\ b}$
$R^5$
$R^{2a}$, $R^{2b}$
$R^{2a}$, $R^{2b}$, $R^{4a\ or\ b}$
$R^{2a}$, $R^{2b}$, $R^{4a}$, $R^{4b}$
$R^{2a}$, $R^{2b}$, $R^{4a\ or\ b}$ and $R^5$
$R^{2a}$, $R^{2b}$, and $R^5$
$R^{2a}$, $R^{2b}$, $R^{4a}$, $R^{4b}$ and $R^5$
$R^{2a\ or\ b}$, $R^{4a}$, $R^{4b}$ and $R^5$
$R^{2a\ or\ b}$, $R^{4a\ or\ b}$ and $R^5$
$R^{2a\ or\ b}$ and $R^{4a\ or\ b}$
$R^{2a\ or\ b}$ and $R^5$
$R^{4a}$, $R^{4b}$ and $R^5$ In addition, each stereoisomer of each of the present compounds is envisioned including, without limitation, the (1R, 5R) and (1S,5S) enantiomers, such as in the compounds of Formula XIA and XIB.

In some embodiments of compounds of Formulas XI, XIA and XIB, the compound is selected from the group consisting of 5-(3-azabicyclo[3.1.0]hexan-1-yl)-3-methyl-d3-1,2,4-oxadiazole, 5-(2,2-d2-3-azabicyclo[3.1.0]hexan-1-yl)-3-methyl-1,2,4-oxadiazole, 5-(4,4-d2-3-azabicyclo[3.1.0]hexan-1-yl)-3-methyl-1,2,4-oxadiazole, 5 (2,2,4,4-d4-3-azabicyclo [3.1.0]hexan-1-yl)-3-methyl-1,2,4-oxadiazole, 5-(4,4,5-d3-3-azabicyclo[3.1.0]hexan-1-yl)-3-methyl-1,2,4-oxadiazole, and 5-(6,6-d2-3-azabicyclo[3.1.0]hexan-1-yl)-3-methyl-1,2, 4-oxadiazole.

In some embodiments of compounds of Formulas XI, XIA and XIB, the compound is selected from the group consisting of 5-((1R,5R)-3-azabicyclo[3.1.0]hexan-1-yl)-3-methyl-d3-1,2,4-oxadiazole, 5-(1R,5R)-2,2-d2-3-azabicyclo[3.1.0]hexan-1-yl)-3-methyl-1,2,4-oxadiazole, 5-((1R,5R)-4,4-d2-3-azabicyclo[3.1.0]hexan-1-yl)-3-methyl-1,2,4-oxadiazole, 5-((1R,5R)-2,2,4,4-d4-3-azabicyclo[3.1.0]hexan-1-yl)-3-methyl-1,2,4-oxadiazole, 5-((1R,5R)-4,4,5-d3-3-azabicyclo [3.1.0]hexan-1-yl)-3-methyl-1,2,4-oxadiazol, and 5-((1R, 5R)-6,6-d2-3-azabicyclo[3.1.0]hexan-1-yl)-3-methyl-1,2,4-oxadiazole, and/or 5-((1S,5S)-3-azabicyclo[3.1.0]hexan-1-yl-3-methyl-d3-1,2,4-oxadiazole, 5-((1S,5S)-2,2-d2-3-azabicyclo[3.1.0]hexan-1-yl)-3-methyl-1,2,4-oxadiazole, 5-((1S,5S)-4,4-d2-3-azabicyclo[3.1.0]hexan-1-yl)-3-methyl-1,2,4-oxadiazole, 5-(1S,5S)-2,2,4,4-d4-3-azabicyclo [3.1.0]hexan-1-yl)-3-methyl-1,2,4-oxadiazole, 5-((1S,5S)-4, 4,5-d3-3-azabicyclo[3.1.0]hexan-1-yl)-3-methyl-1,2,4-oxadiazole, and 5-((1S,5S)-6,6-d2-3-azabicyclo[3.1.0] hexan-1-yl)-3-methyl-1,2,4-oxadiazole.

In some embodiments, compounds disclosed herein are a mixture of enantiomers, e.g. a racemic mixture of compounds of Formula IA and IB (or, IIA and IIB, IIIA and IIIB, IVA and IVB, XIA and XIB or any other pair of enantiomeric compounds disclosed herein. In other embodiments, the compounds include at least 90 mol % of a single enantiomer, e.g. at least 90 mol % of compound of Formula IA or at least 90 mol % of a compound of Formula IB. Likewise, embodiments provide compounds including at least 90 mol % of a compound of any one of compounds of Formula IIA, IIB, IIA, IIIB, IVA, IVB, XIA or XIB. In still other embodiments, there are provided compounds including at least at least 91 mol %, at least 92 mol %, at least 93 mol %, at least 94 mot % at least 95 mol %, at least 96 mol %, at least 97 mol % at least 98 mol % at least 99 mol % of any one of compounds of Formula IA, IB, IIA, IIB, IIIA, IIIB, IVA, IVB, XIA or XIB.

D. Methods of Making Azacycle- and Azabicyclo-Substituted Oxadiazoles and Thiadiazoles The substituted 1,2,4-oxadiazoles and 1,2,4-thiadiazoles described herein may be synthesized by methods well known in the art. The following methods are offered by way of example and are not limiting. Those of skill in the art will understand that many similar methods may be used to produce the compounds described herein.

As shown in Scheme 4, compounds of Formula I (in which X is O and other variables are as defined herein) may be prepared from compounds A9, the 3-carboxylate or 3-alkylcarboxylate of pyrrolidin, piperidine or azepane (R' is H or $C_{1-4}$ alkyl). For example, piperidinyl compounds are conveniently prepared from commercially available ethyl nipecotate. In one step, the nitrogen of the cyclic amine is protected with a suitable N-protecting group. PG, such as an acid sensitive N-protecting group. Such protecting groups are well known in the art and include for example t-butyloxycarbonyl (Boc), benzyloxycarbonyl (Cbz) or methoxycarbonyl. Alternatively, the cyclic amino acid may be derivatized to the desired ester, followed by N-protection or vice versa. By way of example only. N-Boc-3-pyrrolidine-3-carboxylic acid in a suitable solvent (e.g., THF) may be treated with a tertiary amine, alkyl chloroformate (e.g., ethyl chloroformate), and a catalyst (e.g., DMAP) to provide the ethyl ester.

Scheme 4

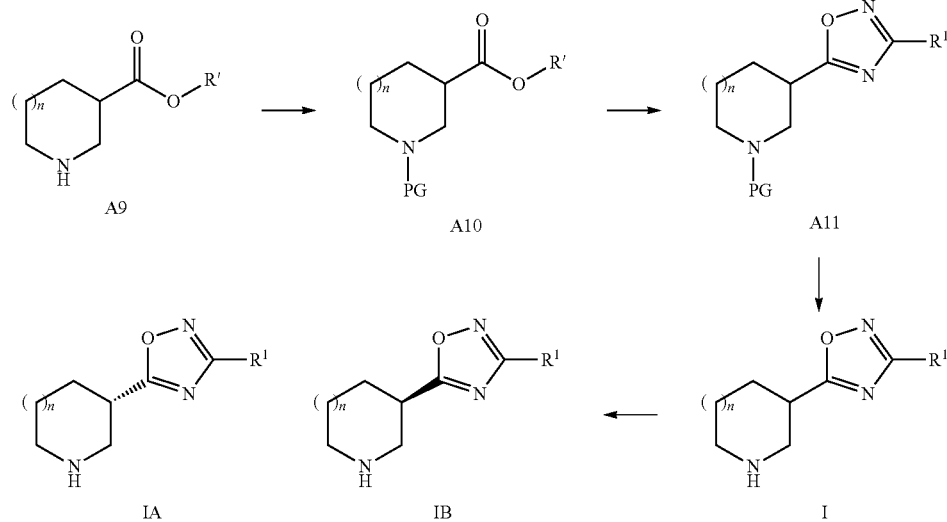

Compound A10 may be converted to the oxadiazole by treating with the appropriate amino oxime (e.g., acetamide oxime, D1-, D2-, or D3-acetamide oxime) or cyanamide and a base such as methoxide. The reaction may be performed in any suitable solvent including but not limited to THF or methyl THF, and toluene, and may optionally be heated, e.g., to reflux to improve yields and/or shorten reaction times. The N-protecting group is then removed under conditions appropriate for the selected protecting group. Thus, e.g., Boc may be removed by treatment with an acid such as HCl or TFA until starting material is consumed. Finally, the 3-position epimers may be resolved by standard techniques such as fractional crystallization with a chiral acid (e.g., D-tartrate or L-tartrate).

Scheme 5

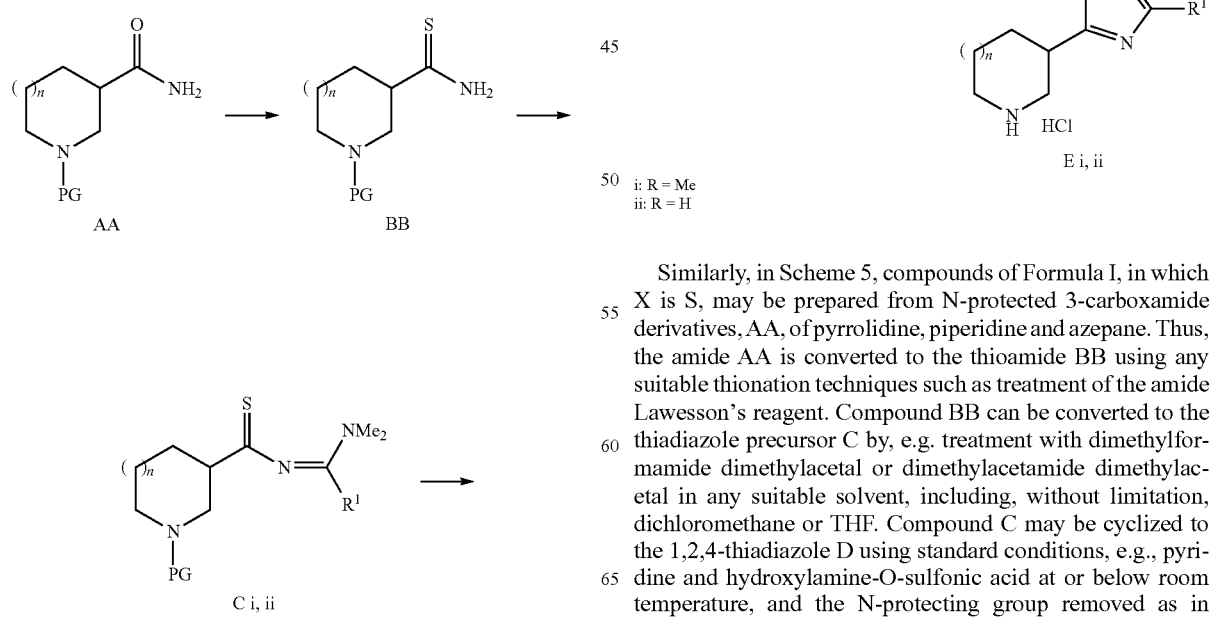

i: R = Me
ii: R = H

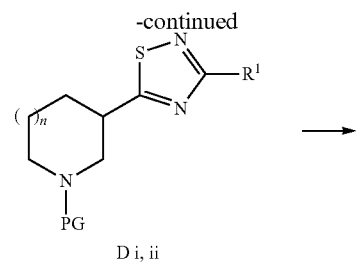

Similarly, in Scheme 5, compounds of Formula I, in which X is S, may be prepared from N-protected 3-carboxamide derivatives, AA, of pyrrolidine, piperidine and azepane. Thus, the amide AA is converted to the thioamide BB using any suitable thionation techniques such as treatment of the amide Lawesson's reagent. Compound BB can be converted to the thiadiazole precursor C by, e.g. treatment with dimethylformamide dimethylacetal or dimethylacetamide dimethylacetal in any suitable solvent, including, without limitation, dichloromethane or THF. Compound C may be cyclized to the 1,2,4-thiadiazole D using standard conditions, e.g., pyridine and hydroxylamine-O-sulfonic acid at or below room temperature, and the N-protecting group removed as in Scheme 4 above.

US 9,174,972 B2

29

Scheme 6

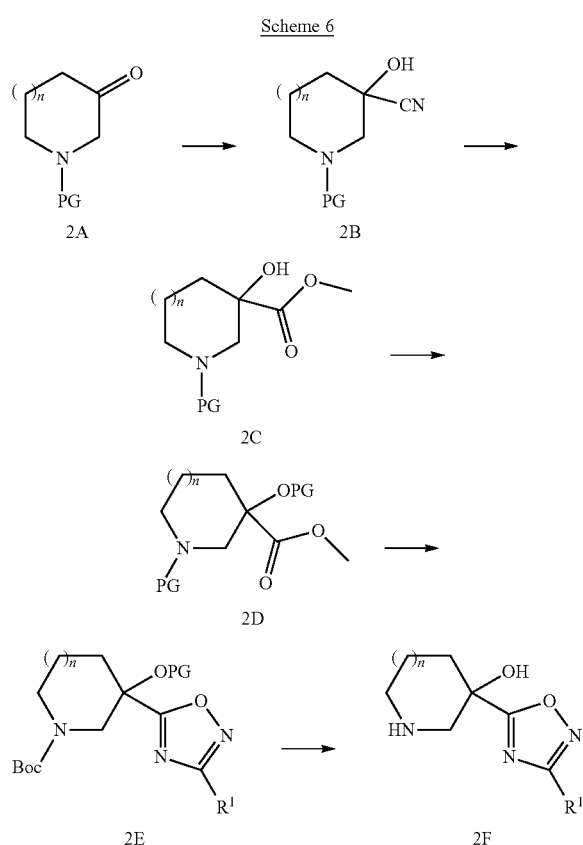

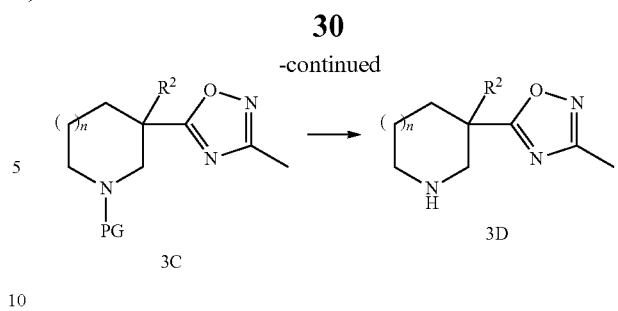

Scheme 6 shows how compounds of Formula I (in which X is O and R² is a hydroxyl group or alkoxy group) may be prepared. Cyanide addition to ketone 2A, in which N is protected by a suitable N-protecting group (e.g., Boc or Cbz), provide the hydroxy compound 2B. The cyano group may be hydrolyzed to the acid with subsequent formation of the ester under standard conditions (e.g., strong acid such as HCl and an alcohol such a methanol or ethanol). Depending on the N-protecting group used, it may need to be reinstalled (e.g., Boc) at this point. Also, the hydroxy group may be alkylated with suitable electrophiles (e.g., alkyl iodides, etc.) to give the alkoxy compound or may be protected with, e.g., THP or silyl groups, under standard conditions to give compound 2D. The oxadiazole may be formed as described in Scheme 4 to provide compound 2E, and any protecting groups removed to give the hydroxyl compound. Alternatively, where O was alkylated earlier in the synthesis, compound 2E will be a compound of Formula 7.

Scheme 7

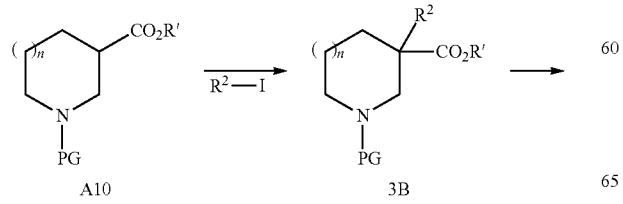

Scheme 7 illustrates preparation of compounds of Formula I (in which X is O and R² is an alkyl group) using an enolate alkylation to install R². Starting from the same ester as in Scheme 1 (PG, n, R¹ are all as described above), deprotonation with a strong base such as an alkali metal hydride (e.g., lithium diisopropylamide or lithium hexamethyldisilazide), and alkylation with an electrophilic R2 group such as an alkyl iodide provides compound 3B. The remaining steps in the process are as in Scheme 4. The same basic enolate alkylation may be used in preparing thiadiazoles. After alkylation, the ester may be converted to a primary amide using, e.g., ammonia, and the procedures of Scheme 5 used to produce the thiadiazole.

An example of the preparation of an azabicyclo-substituted oxadiazole, 5-(3-azabicyclo[4.1.0]heptan-1-yl)-3-methyl-1,2,4-oxadiazole, is provided below in the Examples.

In accordance with another aspect of this disclosure, embodiments include methods of preparing compounds of Formula XI stereoisomers thereof and pharmaceutically acceptable salts thereof. The methods include contacting a compound of Formula XX

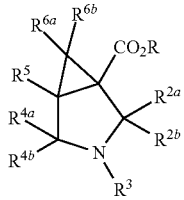

XX with N-hydroxyguanidine or the alkylamide oxime, R'—C(NOH)NH₂, wherein R' is a $C_{1-6}$ alkyl or a $C_{3-6}$ cycloalkyl group, optionally substituted with one or more D, in the presence of a suitable base to provide the compound of Formula XI,

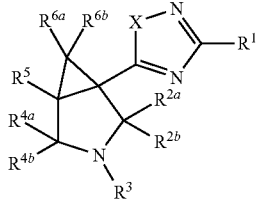

XI wherein
X is O;
R is a $C_{1-4}$ alkyl group or a benzyl group;
R¹ is a $C_{1-4}$ alkyl group or a $C_3$ cycloalkyl group, wherein the alkyl or cycloalkyl groups are optionally substituted with 1 or more D;

$R^{2a}$, $R^{2b}$, $R^{4a}$, $R^{4b}$, $R^5$, $R^{6a}$, and $R^{6b}$ are independently selected from H or D; and $R^3$ is a base-stable amino-protecting group.

In some embodiments of the methods of preparing compounds of Formula XI, the base is selected from the group consisting of sodium methoxide, potassium methoxide, potassium tert-butoxide, sodium hydride and potassium carbonate. In certain embodiments, $R^3$ is selected from the group consisting of t-butyloxycarbonyl, benzyloxycarbonyl, chlorobenzyloxycarbonyl, methoxycarbonyl and ethoxycarbonyl. Any suitable solvent may be used in the present methods, including but not limited to tetrahydrofuran, 2-methyltetrahydrofuran, toluene, $C_{1-4}$ alcohols (typically that correspond to the alkoxide base being used), e.g., methanol and t-butanol, and mixtures of any two or more thereof. During the reaction, the solvent may be heated to, e.g., reflux or a lower temperature. In some embodiments, the methods further comprising removing the base-stable protecting group to provide the compound of Formula XI wherein $R^3$ is H and has the structure of Formula XII:

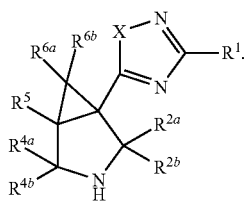

XII

The enantiomers of compounds of Formula XI may be resolved by crystallizing a salt of the compound of Formula XII and a chiral acid (i.e., fractional crystallization). For example in some embodiments of the methods, the salt of the compound of Formula XII is a tartrate salt. Thus, using L-tartaric acid provides the L-tartrate salt of the (1R,5R) enantiomer of the compound of Formula XII, while using D-tartaric acid provides the D-tartrate salt of the (1S,5S) enantiomer of the compound of Formula XII. The cystallizations may be carried out in any suitable solvent including but not limited to, alcohols (e.g., methanol, ethanol), ethers (e.g. diethyl ether, THF), acetonitrile or mixtures of any two or more thereof (e.g. methanol/diethyl ether, methanol/acetonitrile).

In an illustrative embodiment, the present methods provide compounds of Formula XI is selected from the group consisting of 5-((1R,5R)-3-azabicyclo[3.1.0]hexan-1-yl)-3-methyl-d3-1,2,4-oxadiazole, 5-((1R,5R)-2,2-d2-3-azabicyclo[3.1.0]hexan-1-yl)-3-methyl-1,2,4-oxadiazole, 5-((1R,5R)-4,4-d2-3-azabicyclo[3.1.0]hexan-1-yl)-3-methyl-1,2,4-oxadiazole, 5-((1R,5R)-2,2,4,4-d4-3-azabicyclo[3.1.0]hexan-1-yl)-3-methyl-1,2,4-oxadiazole, 5-((1R,5R)-4,4,5-d3-3-azabicyclo[3.1.0]hexan-1-yl)-3-methyl-1,2,4-oxadiazole, 5-((1R,5R)-6,6-d2-3-azabicyclo[3.1.0]hexan-1-yl)-3-methyl-1,2,4-oxadiazole, 5-((1S,5S)-3-azabicyclo[3.1.0]hexan-1-yl)-3-methyl-d3-1,2,4-oxadiazole, 5-((1S,5S)-2,2-d2-3-azabicyclo[3.1.0]hexan-1-yl)-3-methyl-1,2,4-oxadiazole, 5-((1S,1S)-4,4-d2-3-azabicyclo[3.1.0]hexan-1-yl)-3-methyl-1,2,4-oxadiazole, 5-((1S,5S)-2,2,4,4-d4-3-azabicyclo[3.1.0]hexan-1-yl)-3-methyl-1,2,4-oxadiazole, 5-((1S,5S)-4,4,5-d3-3-azabicyclo[3.1.0]hexan-1-yl)-3-methyl-1,2,4-oxadiazole, and 5-((1S,5S)-6,6-d2-3-azabicyclo[3.1.0]hexan-1-yl)-3-methyl-1,2,4-oxadiazole.

Alternatively, compounds of Formula XI wherein X is S and the compound is a thiadiazole may be prepared from compounds of Formula XX using methods dial include one or more steps as shown in Scheme 8. Variables not otherwise defined in Scheme 8 have the same definitions as described for compounds of Formula XX herein.

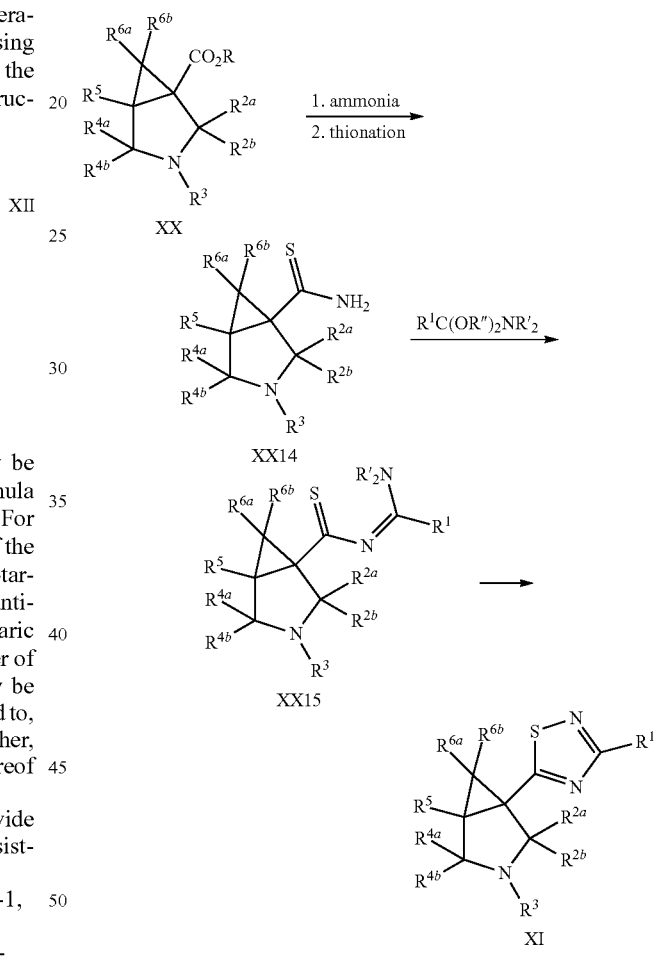

Scheme 8

The methods include contacting a compound of Formula XX with ammonia to form the primary amide, followed by a thionation agent, such as e.g., Lawesson's agent, to provide the compound of Formula XX14. Compound XX14 can be converted to the thiadiazol precursor by treatment with $R^1C(OR'')_2NR'_2$, wherein $R^1$ is a $C_{1-6}$ alkyl or a $C_{3-6}$ cycloalkyl group, optionally substituted with one or more D, and R' and R'' are independently selected from a $C_{1-4}$ alkyl group. For example, XX14 may be treated with dimethylacetamide dimethylketal or 2-d3-dimethylacetamide dimethylketal to provide compounds of Formula XX15. The latter compound may be cyclized under standard conditions, including but not limited to contacting XX15 with pyridine and hydroxylamine-O-sulfonic acid at or below room temperature.

Compounds of Formula XX may be prepared by a variety of methods. In an illustrative embodiment, compounds of Formula XX may be prepared in accordance with Scheme 9

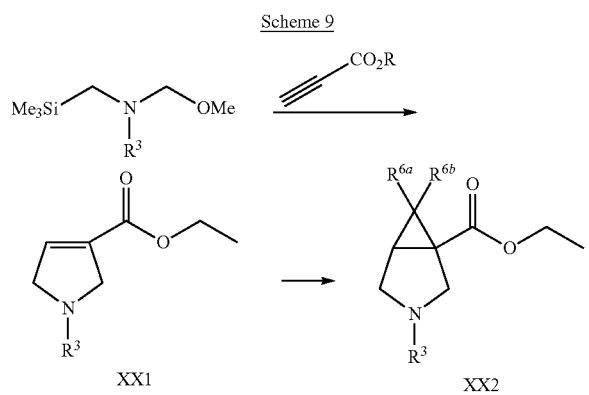

Thus, compounds of Formula XX may be prepared by one or more of the following steps:
  contacting a $C_{1-4}$ alkyl ester of propiolate with N-protected N-methoxymethyl)-N-trimethylsilylmethylamine in the presence of an effective amount of acid to provide a compound XXI:

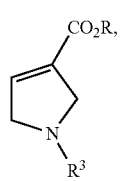

XXI wherein
  R is a $C_4$ alkyl group or a benzyl group; and
  $R^3$ is an acid-stable and a base-stable amino-protecting group;
  contacting the compound of Formula XXI with trimethylsulfoxonium iodide (TMSOI) or TMSOI-d9 in the presence of a suitable base to provide a compound of Formula XX2:

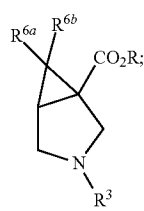

XX2 wherein $R^{6a}$ and $R^{6b}$ are independently selected from H and D;
  replacing the acid-stable and base-stable amino-protecting group of the compound of Formula XX2 with a base-stable protecting group to provide the compound of Formula XX wherein $R^{2a}$, $R^{2b}$, $R^{4a}$, $R^{4b}$, and $R^5$ are all H.
In some embodiments of methods for preparing compounds of Formula XX, in steps involving the compound XXI, R is ethyl and $R^3$ is benzyl. Formation of XXI may be carried out in any suitable solvent for such cycloadditions (see, e.g. Korean J. Med. Chem. (1994) 4(2), 119, incorporated herein by reference in its entirety). Likewise, formation of XX2 may be carried out in any suitable solvent such as, e.g., DMSO. In some embodiments involving the compound XX2, R is ethyl an $R^3$ is benzyl. In certain embodiments involving the compound XX2, the base is selected from sodium hydride, potassium hydride and potassium t-butoxide. Removal of an acid-stable and base-stable protecting group such as benzyl or benzyl derivatives may be carried out using standard hydrogenation techniques e.g., hydrogen or ammonium formate and a noble metal catalyst such as 10% Pd/C, Pt, PtO, Pd(OH)$_2$ and the like. Alcohols such as methanol and other standard solvents may be used as a solvent for such hydrogenations.

In another illustrative embodiment, the compound of Formula XX may be prepared in accordance with Scheme 10

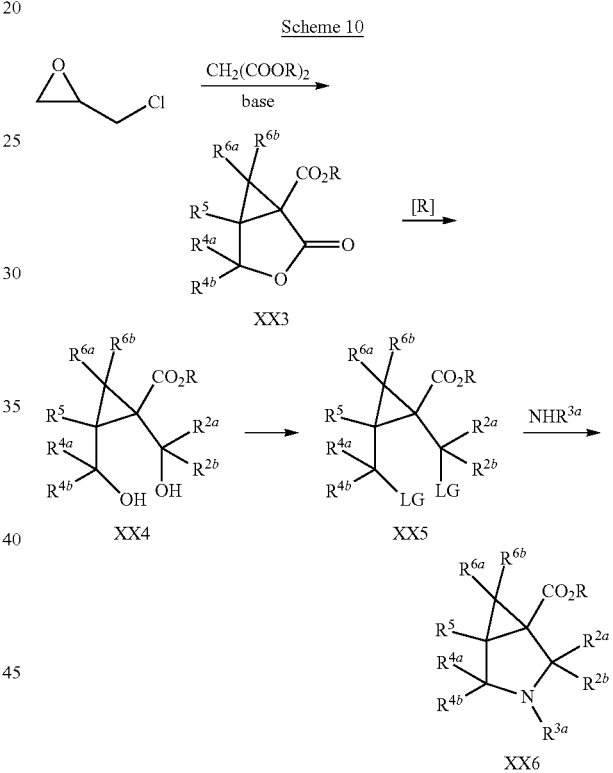

Thus, as shown in Scheme 10, compounds of Formula XX may be prepared by one or more of the following steps:
  contacting epichlorohydrin, optionally substituted with 1-5 D, with a malonate ester in the presence of an effective amount of a suitable base to provide a compound of Formula XX3:

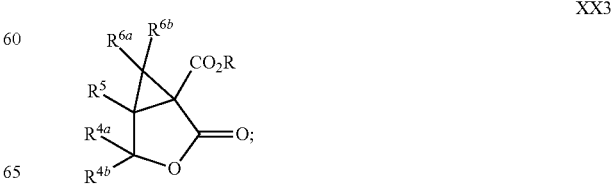

contacting the compound of Formula XX3 with a suitable reducing agent to provide a compound of Formula XX4:

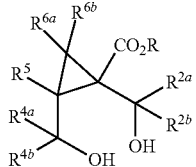

XX4 converting the hydroxyl groups of the compound of Formula XX4 into leaving groups LG to provide a compound of formula XX5

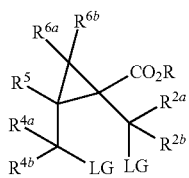

XX5 wherein LG selected from a halide or a sulfonate ester, contacting a compound of Formula XX5 with $R^{3a}NH_2$ to provide a compound of Formula XX6:

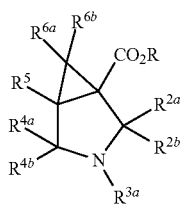

XX6 wherein $R^{3a}$ is H or a acid-stable amino-protecting group;

replacing $R^{3a}$ with a base-stable protecting group to provide a compound of Formula XX.

In some embodiments of such methods, the epichlorohydrin is a (2R)-epichlorohydrin. In certain embodiments of the methods, the epichlorohydrin is (2R)-3-d2-epichlorohydrin, (2R)-2,3-d3-epichlorohydrin, or (2R)-1-d2-epichlorhydrin. Bases that may be used in formation of the compound of Formula XX3 include, e.g., sodium methoxide or ethoxide, potassium methoxide or ethoxide, and the like. Any suitable solvent may also be used in formation of XX3 such as methanol, ethanol or other alcohols. Optionally the formation of XX3 may be carried out at or below room temperature (e.g., about 0° C.) or with heating (e.g. to reflux of the alcohol used). In some embodiments of the methods, the compound of Formula XX3 is contacted with a reducing agent selected from the group consisting of $NaBH_4$, $NaBD_4$, $KBH_4$, $KBD_4$, $LiBH_4$ and $LiBD_4$. The reduction may be carried out in any suitable solvent such as alcohols (e.g., methanol, ethanol) or aqueous alcohols. In other embodiments, the hydroxyl groups of the compound of Formula XX4 are contacted with mesyl chloride or methanesulfonic anhydride in the presence of a suitable base and converted to the mesylate leaving group. Suitable bases include TEA or other tertiary organoamines. In certain embodiments, the compound of Formula XX5 is contacted with ammonia, benzylamine, dimethoxybenzylamine or trimethoxybenzylamine.

In yet another illustrative embodiment, the compound of Formula XX may be prepared in accordance with Scheme 11.

Scheme 11

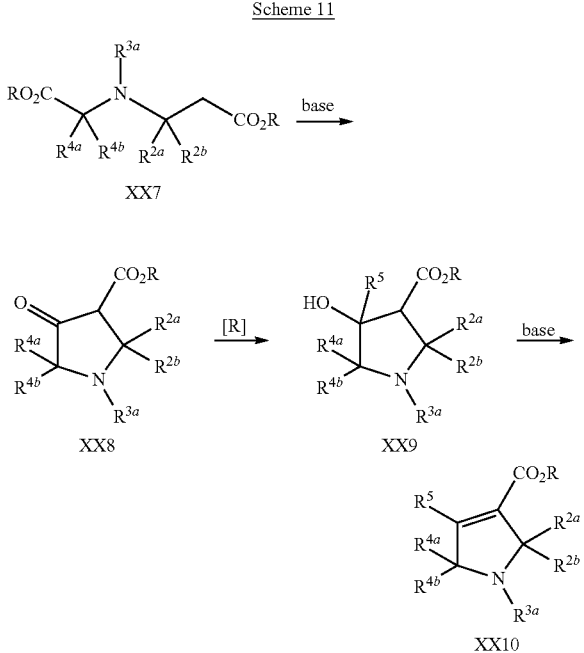

Thus, as shown in Scheme 11, compounds of Formula XX may be prepared by one or more of the following steps:

contacting a compound of Formula XX7:

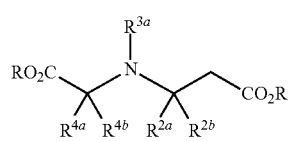

XX7 with a suitable base to provide a cyclic compound of Formula XX8:

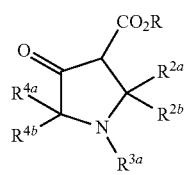

XX8

Wherein

R at each occurrence is independently a $C_{1-4}$ alkyl or benzyl group;

$R^{2a}$, $R^{2b}$, $R^{4a}$, and $R^{4b}$ are independently selected from H or D; and $R^{3a}$ is an acid-stable amino-protecting group;

contacting the compound of Formula XX8 with a suitable reducing agent to provide a compound of Formula XX9:

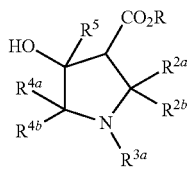

wherein $R^5$ is H or D;

converting the hydroxyl group of the compound of Formula XX9 to a leaving group and contacting the resulting compound with a suitable base to provide a compound of Formula XX10:

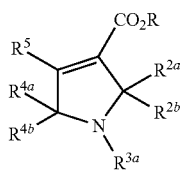

contacting the compound of Formula XX10 with trimethylsulfoxonium iodide (TMSOI) or TMSOI-d9 in the presence of a suitable base to provide a compound of Formula XX6:

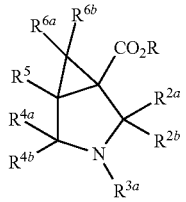

wherein $R^{3a}$ is an acid-stable and base-stable amino-protecting group; and replacing the acid-stable and base-stable amino-protecting group of the compound of Formula XX6 with a base-stable amino-protecting group to provide the compound of Formula XX.

In some embodiments of these methods, the compound of Formula XX7 is contacted with a base selected from the group consisting of potassium t-butoxide, sodium ethoxide and sodium hydride. Formation of the compound Formula XX8 may be carried out in any suitable solvent such as THF, methyl THF, alcohols such as ethanol, and mixtures thereof. In other embodiments, the compound of Formula XX8 is contacted with a reducing agent selected from the group consisting of $NaBH_4$, $NaBD_4$, $KBH_4$, $KBD_4$, $LiBH_4$ and $LiBD_4$. The reduction may be carried out in any suitable solvent such as alcohols (e.g., methanol, ethanol) or aqueous alcohols. In certain embodiments, the hydroxyl group of the compound of Formula XX9 is contacted with mesyl chloride in the presence of a suitable base and converted to the mesylate leaving group. The mesylate may then contacted with a base selected from the group consisting of 8-diazabicyclo [5.4.0]dec-7-ene (DBU), and triethylamine (TA) to provide the compound of Formula XX10. Suitable solvents for the formation of XX10 include but am not limited to dichloromethane and chloroform.

The methods may further include preparing the compound of XX7 by
contacting a $C_{1-4}$ alkyl ester of glycine, optionally deuterated with 1 or 2 D with a $C_{1-4}$ alkyl ester of acrylate to provide a compound of Formula XX7; or
contacting a $C_{1-4}$ alkyl ester of beta-alanine, optionally deuterated with 1, 2, 3, or 4 D with a $C_{1-4}$ alkyl ester of 2-oxoacetic acid to provide a compound of Formula XX7.

The present methods may further include preparing the compound of Formula XX7 by one or more of the following steps:
contacting a $C_{1-4}$ alkyl ester of glycine, with a $C_{1-4}$ alkyl ester of acrylate to provide a compound of Formula XX12:

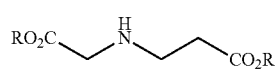

wherein R is independently at each occurrence a $C_{1-4}$ alkyl group or a benzyl group;
protecting the amino group of the compound of Formula XX12 with a base-stable amino-protecting group to provide the compound of Formula XX13;

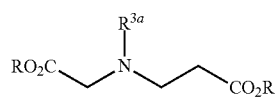

wherein $R^{3a}$ is a base-stable amino-protecting group;
contacting the compound of Formula XX13 with an alcohol having an exchangeable deuteron in the presence of a suitable base to provide the compound of Formula XX7 wherein $R^{4a}$ and $R^{4b}$ are each D.

In some embodiments of the methods, $R^{3a}$ is t-butyloxycarbonyl. In some embodiments, R is a methyl or ethyl group at each occurrence.

E. Forms of Agonist Compounds

Those of skill in the art will appreciate that muscarinic agonists, including the substituted oxadiazoles and thiadiazoles described herein, may exhibit the phenomena of tautomerism, conformational isomerism, geometric isomerism and/ or stereoisomerism. As the Formula drawings within the specification and claims can represent only one of the possible tautomeric, conformational isomeric, stereoisomeric or geometric isomeric forms, it should be understood that the invention encompasses any tautomeric, conformational isomeric, stereoisomeric and/or geometric isomeric forms of the compounds having one or more of the utilities described herein, as well as mixtures of these various different forms.

Stereoisomers (also known as optical isomers) of the compounds described herein include all chiral, diastereomeric, and racemic forms of a structure, unless the specific stereochemistry is expressly indicated. Thus, compounds disclosed herein include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all included within the scope of this disclosure.

Embodiments of this disclosure also include salts of muscarinic agonists such as the substituted oxadiazoles and thiadiazoles described herein. For example, when the compound has a basic group such as an amino group (e.g., a basic nitrogen in a tetrahydropyrimidine ring), then such compound may be employed in the form of a salt. Salts can be formed with inorganic or organic acids. Examples of suitable acids for the formation of pharmaceutically acceptable acid addition salts are hydrochloric, sulfuric, phosphoric, acetic, trifluoro acetic, benzoic, citric, malonic, salicylic malic, fumaric, oxalic, succinic, tartaric, lactic, gluconic, ascorbic, maleic, aspartic, benzenesulfonic, methane and ethanesulfonic, hydroxymethane and hydroxyethanesulfonic acids and the like. The salts will be formed in a known conventional manner and the preferred salts are organic acid or an inorganic acid addition salts. Further particulars can be had by reference to the Journal of Pharmaceutical Science, 66 (1) 1-19 (1977).

III. Combination Compositions and Co-Administrations Comprising Muscarinic Agonists and Antagonists One or more muscarinic agonists, including the substituted oxadiazoles and thiadiazoles described herein. e.g., one or more of a compound of Formulas I, IA, IB, II, IIA, IIB, III, IIIA, IIIB, IV, IVA, IVB, XI, XIA and XIB (described above in sections C and D), also may be combined in compositions with, or co-administered with, one or more muscarinic antagonists to achieve a cognition-enhancing effect or a disease-modifying effect. In some embodiments, agonists that are selective for at least M1 are employed. In some embodiments, agonists that are selective for at least M2 are employed, in some embodiments, agonists that are selective for at least M3 are employed, in some embodiments, agonists that are selective for at least M4 are employed, and in some embodiments, agonists that are selective for at least M5 are employed. In some embodiments, agonists that are selective for at least two or more receptors are employed, for example, agonists that are selective for at least M1/M2, M1/M3, M1/M4, M1/M5, M2/M3, M2/M4, M2/M5, M3/M4, M3/M5, and M4/M5. In some advantageous embodiments, at least one M1 or M1/M4 selective muscarinic agonist, or a pharmaceutically acceptable form thereof, is present in a dosage form and amount that achieves a cognition-enhancing effects or a disease-modifying effect. Included within such compound are cyclic oxadiazoles and thiadiazoles. Included within the cyclic oxadiazoles and thiadiazoles are those that are substituted in the 3 and 5 position. Included within such 3,5-substituted oxadiazoles and thiadiazoles are those which are substituted with azacycles. The dosage amounts of these agonists also can be such that, if not present in combination with, or co-administered with, the antagonist, the subject would experience one or more mild moderate and/or severe cholinergic side effects from the muscarinic agonist In some embodiments, therefore, at least one M1 or M1/M4 selective muscarinic agonist or pharmaceutically acceptable forms thereof can be combined in a dosage form with, or co-administered with, at least one muscarinic antagonist. The at least one M1 or M1/M4 selective agonist is in an amount sufficient to achieve a cognition-enhancing or disease modifying effect in a subject while causing one or more at least moderate cholinergic side effects. The at least one muscarinic antagonist is present in an amount sufficient to limit the cholinergic side effects to at most mild or moderate side effects. The terms mild, moderate and severe side effects relate to the amount of discomfort experienced by the patient, i.e., mild, moderate or severe.

In some embodiments, the antagonists are not selective for the muscarinic receptors for which the agonists are selective. In some embodiments the antagonists do not substantially cross the blood brain barrier. In some embodiments, which may provide advantageous results, the antagonists are both not selective for the muscarinic receptors for which the agonists we selective and do not substantially cross the blood brain barrier. While not wishing to be bound by any particular theory regarding specific differences in cholinergic receptor activation or inactivation, the maintenance of cognitive enhancing effects while limiting cholinergic side effects through the administration of a pharmaceutical composition (e.g. one comprising an M1 or M1/M4 selective muscarinic agonist) and a muscarinic antagonist that is not selective for the same receptor(s) as the agonist and also does not cross the blood brain barrier, may be due to the inhibitory effects of the muscarinic antagonists in the periphery of a subject, which inhibitory effects limit cholinergic side effects. Because these antagonists are not selective for the same muscarinic receptor(s) as the agonist, and do not substantially cross the blood brain barrier, they do not interfere with the action of the agonist on centrally located receptors. Use of the term "substantially" here means that most, almost all, or all of the amount of antagonist administered to the subject does not cross the blood brain barrier. For example, less than 25%, less than 20%, less than 15%, less than 10%, less than 5, less than 3%, or less than 1% of the amount of antagonist administered does not cross the blood brain barrier. The muscarinic agonist, e.g., the M1 or M1/M4 selective muscarinic agonist, is thus able to provide the intended benefit to a subject By co-administration is meant the separate administration of agonist and antagonist, e.g. in separate dosage forms such as separate pills, separate injectable solutions or separate iontophoretic patches, as opposed to administration in the same dosage form such as in a single pill, single injectable solution or single iontophoretic patch. Depending on the agonist and antagonist, their rates of metabolism and the dosage forms employed for each, the administration of the antagonist may be at the same time as the agonist, or before or after the agonist. In fact, the administration of each can be on very different schedules, but by co-administration it is meant that both the agonist and antagonist will be present in the subject at the same time at some point in the treatment of the subject.

In embodiments of such combinations or co-administrations, the muscarinic agonist may be any known agonist. Included within such agonists are cyclic oxadiazoles and thiadiazoles, including those that are substituted in the 3 and 5 position. Included within such 3,5-substituted oxadiazoles and thiadiazoles are those which are substituted with azacycles, including those described above. Advantageous embodiments may employ M1 or M1/M4 selective agonists, for example, 5-3-ethyl-1,2,4-oxadiazol-5-yl)-1,4,5,6-tetrahydropyrimidine, also known as MCD-386, which is described in the literature, including in U.S. Pat. No. 5,403,845 to Dunbar et al. MCD-386 has been found to provide disease-modifying effects when given in a sufficiently high dosage, although such dosages can produce moderate to severe cholinergic side effects in human subjects when not combined or co-administered with a muscarinic antagonist. Pharmaceutically acceptable forms of the muscarinic agonists are included within such embodiments and can include such well known forms as a salt, isomer, hydrate, clathrate, solvate or polymorph.

The muscarinic antagonists of the combination or co-administrations include but are not limited to atropine sulfate. N-methylatropine nitrate, flavoxate hydrochloride, N-methylscopolamine hydrochloride (methscopolamine), oxybutinin chloride, glycopyrrolate bromide, darifenacin hydrobromide, solifenacin succinate, propantheline bromide, trospium chloride, tolterodine tartrate, fesoterodine fumarate, methantheline bromide and combinations thereof. It may be advantageous to use these antagonists in the form of their hydrochloride salts, which are included herein. The pharmaceutically acceptable form of the muscarinic antagonists described herein include, e.g., a salt, isomer, hydrate, clathrate, solvate or polymorph of said muscarinic antagonist. Embodiments of the composition or co-administration include embodiments where the muscarinic antagonist does not substantially cross the blood-brain barrier. Embodiments of the muscarinic antagonists employed in compositions or co-administrations include hydrophilic muscarinic antagonists. In some embodiments, the muscarinic antagonists can have a hydrophilic measure of log D<1. In some embodiments, the muscarinic antagonists described herein can have a quaternary amino function or a tertiary amino function with a high pKa. Generally, compounds with a quaternary amino function will not cross the blood-brain barrier, and tertiary amines with high pKa will generally cross the blood-brain barrier less well than those with a low pK. For low blood-brain barrier penetration, the pKa is advantageously above 9.5, with better results when the pKa is above 10.5. In some embodiments, the muscarinic antagonists described herein can have an amino function with a pKa>8.4 or a pKa>9.4. Embodiments of combination pharmaceuticals discussed herein can include muscarinic antagonists with features of any or all of the embodiments discussed above. In a non-limiting example, a muscarinic antagonist employed in a combination pharmaceutical composition or co-administration with an M1 or M1/M4 selective muscarinic agonist can lack the ability to substantially cross the blood brain barrier, have a hydrophilic measure or log D<1, have a pKa>8, >9, >9.5 or >10.5, and/or have a quarternary amino function.

The muscarinic antagonists described herein can have short intermediate and long term inhibitory effects on muscarinic receptors. The duration of inhibitory effect can be modulated through, for example, dosage amount, dosage vehicle (e.g., sustained release versus immediate release formulations), and dosage frequency. Cholinergic side effects can include diaphoresis, hypersalivation, flushing, gastro-intestinal tract upsets, increased stomach acid, nausea, vomiting and diarrhea, breathing difficulties, tachycardia, dizziness syncope, headache, convulsions, somnolence and combinations thereof.

Routine experimentation will provide acceptable or optimum dosages of antagonist for the particular agonist used. The amount employed should be one that reduces or eliminates the cholinergic side effects, but does not cause unacceptable side effects associated with antagonists such as dry mouth, etc. For MCD-386, the following amounts may provide acceptable results: atropine sulfate (300-1200 microg 4-6 times/day oral; 400-600 microg 4-6×/day im), N-methylscopolamine hydrochloride (methscopolamine) (2.5-5 mg q6 hr oral), and glycopyrrolate bromide (100-200 microg 4-6 hr im or 1-2 mg bid or tid oral). Where an iontophoretic device employing a silver-silver chloride electrode system is used, then it may be advantageous to choose an antagonist that is a halide salt, advantageously a bromide or chloride, and most advantageously a chloride salt, which would be compatible with the silver-silver chloride electrode system. Acceptable results for such an iontophoretic device may be obtained using flavoxate hydrochloride, N-methylscopolamine hydrochloride (methscopolamine), and trospium chloride.

The pharmaceutical compositions or co-administrations of muscarinic agonists and antagonists can employ any of the dosages forms discussed below.

IV. Methods of Treatment

The compounds and compositions described herein may be administered to treat normal cognitive impairment that accompanies aging, or to treat disorders such as Alzheimer's disease, dementia. ADHD, autism and schizophrenia, or to treat cognitive impairment due to injury, e.g., concussions or other brain trauma. Embodiments of the compounds and compositions described herein also can be administered in an amount and for a duration sufficient to provide disease-modifying effect, such as modifying the course of Alzheimer's disease.

In addition to treating cognitive disorders, the compounds and compositions described herein may be administered to enhance cognition, to help maintain cognition, or to slow, prevent and/or reverse a decrease of cognition due to aging, trauma or a disorder such as Alzheimer's disease. Exemplary durations can be, e.g., for a day, week, month, six months, a year, or indefinitely, depending on the purpose for which the compounds are administered. Where the compounds are being administered for treating a disorder such as Alzheimer's disease, it is expected that the compounds may be administered essentially indefinitely.

While not wishing to be bound by any particular theory, the foregoing effects. i.e., cognitive enhancement, treating cognitive impairment maintaining cognition and slowing, preventing or reversing a decrease in cognition may result from treatment of symptoms related to natural aging or a medical condition such a Alzheimer's disease. Alternatively, the effects may result from disease modification caused by the administration of the compositions described herein, for example, reduced neuron loss as compared to similarly situated animals (i.e., animals having the same cognitive disorder such as Alzheimer's disease) that are not administered a composition described herein, increased α-secretase activity as compared to similarly situated animals that are not administered a composition described herein, reduced Aβ production as compared to similarly situated animals that are not administered a composition described herein, increased sAPPα production as compared to similarly situated animals that are not administered a composition described herein, and/or reduced Tau pathology and/or apoptosis as compared to similarly situated animals that are not administered a composition described herein.

Other embodiments provide methods of treating subjects suffering from a cholinergic deficit or otherwise in need of stimulation of muscarinic receptors. Thus, there are provided methods comprising administering an effective amount of a compound or composition disclosed herein to a subject in need thereof. The methods may be used with subjects suffering from presenile dementia, senile dementia, Huntington's chorea, tardive dyskinesia, hyperkinesia, mania, Tourette syndrome or Alzheimer's disease.

The compositions described herein may be co-administered with other compounds useful for treating Alzheimer's disease or symptoms associated therewith. Such compounds include but are not limited to Memantine, cholinesterase inhibitors such as donepezil, galantamine and rivastigmine, and therapeutic antibody treatments. The amount of a composition described herein and co-administered compound may be administered in the same amounts as if administered singularly, or the composition described herein and/or other compound may be administered at reduced dosage.

The compositions described herein may be administered periodically to provide a sporadic or occasional effect, or consistently to provide a relatively constant effect. Cognition-enhancing effects that may be achieved from administration of these compositions include but are not limited to improved memory of places; improved memory of people; improved memory of information; improved memory of facts; improved memory of how to operate and use tools; improved ability to analyze information; improved ability to deduce or reason; improved ability to synthesize conclusions; improved ability to think strategically; improved ability to make plans and decisions; improved ability to execute on plans and decisions; improved ability to perform activities of daily living; improved ability to be employed; enhanced activity of neuronal mechanisms responsible for effective memory and cognition (including muscarinic functions); reduced pathogenetic mechanisms leading to loss of memory and cognitive function; reduced the loss of neurons or neuronal activity that lead to loss of cognitive and memory function; improved scores on neuropyschological tests such as ADAS-Cog or MMSE; and improved scores on clinical assessments of the activities of daily living such as ADCS-ADL.

Some embodiments disclosed herein provide various methods for enhancing cognition and memory and for treating conditions and diseases characterized at least in part by a deficit of cholinergic activity in the brain of a subject or which may otherwise be ameliorated by increased cholinergic activity. Thus, compounds and compositions described herein, including the oxadiazole and thiadiazole compounds described above, can be employed in methods of enhancing cognition and/or memory comprising administering to a subject an effective amount of such compounds or compositions (including forms such as stereoisomers and acceptable salts there of). Thus, for example, embodiments of such methods can employ one or more of a compound of Formulas I, IA, IB, II, IIA, IIB, III, IIIA, IIIB, IV, IVA, IVB, XI, XIA and XIB (described above in sections C and D). The subject of such methods may be but need not be suffering from a cognitive deficit or memory loss. In some embodiments, the subject suffers from Alzheimer's disease or another form of dementia (including, but not limited to those described herein). Cognitive impairment that may be treated by methods of this disclosure include that resulting from other neurologic and psychiatric causes including but not limited to cerebrovascular disease, cerebral autosomal dominant arteriopathy, anterior communicating artery aneurysm, Lewy Body Disease, Parkinson's Disease, progressive supranuclear palsy, frontotemporal dementia, epilepsy with hippocampal atrophy, multiple sclerosis, traumatic brain injury, schizophrenia, inherited spinocerebellar ataxia, depression unresponsive to 5-hydroxytryptamine and norepinephrine reuptake inhibitors, REM and non-REM sleep disorders, alcoholism, Down Syndrome. Huntington's disease, autism, fragile X syndrome, congenital central hypoventilation syndrome (CCHS), Ret syndrome, and congenital transcarbamylase (OTC) deficiency. The cognitive impairment may also result from medical causes such as delirium, diabetes mellitus type II, hypertension, breast and lung cancer, hysterectomy or menopause resulting in estradiol levels of less than about 20 pg/mL, in children that had prenatal exposure to nicotine, in patients (including elderly persons) following anesthesia or surgery, or in fatigued persons.

The same compounds and compositions also may be employed in effective amounts to treat a subject suffering from one or more of cognitive impairment, Mild Cognitive Impairment, frontotemporal dementia, dementia with Lewy bodies, presenile dementia, senile dementia, Down's syndrome, Huntington's chorea, tardive dyskinesia, hyperkinesia, mania, and Tourette syndrome.

The same compounds and compositions also may be employed in effective amounts in methods to stimulate muscarinic receptors in a subject's brain. Such methods include administering to a subject one or more of such compounds or compositions (including, e.g. stereoisomer and pharmaceutically acceptable salt thereof) in an amount and for a duration sufficient to stimulate muscarinic receptors in the subject's brain. In some embodiments, the stimulation of the muscarinic receptors includes tonic stimulation and/or phasic stimulation. In some embodiments, the level of inositol phosphates in the subject's brain is increased relative to the levels prior to administration. For example, the level of inositol phosphate may be increased in neurons expressing muscarinic M1 receptors. In some embodiments, the subject suffers from Alzheimer's disease.

The same compounds and compositions also may be employed in effective amounts to treat psychosis. Thus, embodiments include administering to a subject suffering from psychosis, a therapeutically effective amount of the compounds and compositions described above (including, e.g., stereoisomers and pharmaceutically acceptable salt thereof). In some instances, the psychosis accompanies or results from schizophrenia or Alzheimer's disease. In some instances, the phychosis accompanies or results from depression or a form of depression such as psychotic major depression.

The same compounds and compositions also may be employed in effective amounts in methods for reducing Aβ in a subject. Thus, embodiments include administering to a subject in need thereof a therapeutically effective amount of the compounds and compositions described above (including, e.g., stereoisomers and pharmaceutically acceptable salt thereof) to achieve a reduction in Aβ. In some embodiments, the level of Aβ is reduced in neurons expressing muscarinic M1 receptors, in, e.g., the brain. Suitable subjects for methods of this disclosure include those having mutations in known genes such as presenilin and amyloid precursor protein (APP), or in other genes, which cause excessive production of Aβ or inadequate clearance of Aβ, or who have accumulations of Aβ in tissues, including fibrils, rafts or Aβ containing amyloid plaques. For examples, the subject may suffer from familial early onset forms of Alzheimer's disease caused by mutations in identified genes, or may suffer from the sporadic form of Alzheimer's disease, in which the causes of abnormalities in Aβ metabolism have as yet not been identified.

In some embodiments, methods disclosed herein include administering to a subject suffering from a neurological condition or disorder comprising a deficit impairment or imbalance in cholinergic activity, or which is ameliorated by stimulation of muscarinic receptors (e.g., M1 muscarinic receptors), an effective amount of any of the compounds disclosed herein, a stereoisomer thereof, or a pharmaceutically acceptable salt there of, or a composition comprising an effective amount of such a compound, to provide one or more biological activities of the muscarinic agonist selected from: inhibiting glycogen synthase kinase 3β activity, which is known to reduce phosphorylation of Tau protein, hypothesized to be involved in neurodegenerative disease processes, and known to decrease apoptosis, or programmed death of neurons; increasing protein kinase C (PKC) activity, known to increase the activity of alpha-secretase and decrease the activity of beta-secretase, thereby directing APP metabolism away from neurotoxic Aβ towards neuroprotective and neurotrophic sAPP-alpha; and increasing levels of inositol phosphates, known to increase the activity of PKC in neurons expressing M1 muscarinic receptors. It will be understood by those of skill in the art that the inhibition of such biological activities or increase or decrease in physiological levels of such biological markers is relative to that which exists in the subject prior to administration of compounds and compositions disclosed herein. Compounds that may be used in embodiments of methods disclosed herein include but are not limited to one or more of a compound of Formulas I, IA, IB, II, IIA, IIB, III, IIIA, IIIB, IV, IVA, IVB, XI, XIA and XIB (described above in sections C and D). Embodiments of methods disclosed herein thus provide a multi-mode therapeutic action on the disease process of, e.g. Alzheimer's disease, tauopathies, and other conditions and disorders disclosed herein.

In certain conditions and disorders, e.g., those involving a presynaptic cholinergic deficit or impairment, the effects of embodiments of compounds and compositions disclosed herein may be enhanced by administration with acetylcholine inhibitors. Thus, all the methods disclosed herein may further include administration to the subject of a therapeutically effective amount of an acetylcholine inhibitor simultaneously, sequentially, or separately with compounds in accordance with this disclosure. Acetylcholinesterase inhibitors that may be used in accordance with this disclosure as well-known in the art and include but are not limited to 1,2,3,4-tetrahydro-5-aminoacridine (tacrine) (U.S. Pat. No. 4,816,456), physostigmine (eserine), rivastigmine, monoamine acridines and their derivatives (U.S. Pat. No. 4,816,456), 1-benzyl-4-(5,6-dimethoxy-1-indanon)-2-yl)methyl piperidine (Aricept, donepezil, E2020) (U.S. Pat. No. 4,895,841), piperidine and piperazine derivatives (U.S. Pat. No. 5,041,455), piperidinyl-alkanoyl heterocyclic compounds (EP 487071), N-benzyl-piperidine derivatives (U.S. Pat. No. 5,106,856), 4-(1-benzyl:piperidyl)-substituted fused quinoline derivatives (EP 481429-A) and cyclic amide derivatives (EP 468187). Other typical acetylcholinesterase inhibitors include carbonic acid derivatives such as those described in U.S. Pat. No. 5,602,176 (e.g. exelon, ENA-713, which is (s)-[N-ethyl-3-[(1-dimethylamino)ethyl]-N methyl-phenyl-carbamate]), and phosphonate compounds such as O,O-dimethyl-(1-hydroxy-2,2,2-trichloroethyl) phosphonate (metrifonate, or trichlorfon). Benzazepinols such as galantamine are also useful acetylcholinesterase inhibitors. In practice, a therapeutically effective amount of a compound or composition described above may vary depending upon the route of administration and dosage form. Effective amounts of such compounds typically fall within the range of from about 0.001 up to about 100 mg/kg/day, typically within the range of from about 0.005 to about 50 mg/kg/day, and more typically in the range of about 0.01 up to 5 mg/kg/day. Typical ranges may be in the range of from 0.01 to 0.05 or from 0.05 to 0.10 mg/kg/day. Within such typical ranges are included 0.01 to 0.03, 0.02 to 0.04, 0.03 to 0.05, 0.04 to 0.06, 0.05 to 0.07, 0.06 to 0.08, 0.07 to 0.09, and 0.08 to 0.10 mg/kg/day. Typically, the compound or compounds of the instant invention are selected to provide a formulation that exhibits a high therapeutic index. The therapeutic index is the dose ratio between desired therapeutic effects and undesired adverse effects, or between therapeutic and toxic effects which can be expressed as the ratio between ED50 and $LD_{50}$. $ED_{50}$ is the dose therapeutically effective in 50% of the population and the $LD_{50}$ is the dose lethal to 50% of the population and the. The $ED_{50}$ and $LD_{50}$ are determined by standard pharmaceutical procedures in animal cell cultures or experimental animals.

In embodiments, the compounds described herein, e.g., one or more of a compound of Formulas I, IA, IB, II, IIA, IIB, III, IIA, IIIB, IV, IVA, or IVB, XI, XIA and XIB (descried above in sections C and D), can be administered to an animal, particularly a mammalian subject or patient such as a human, in an amount and a dosage form that will limit the maximum circulating concentration of the compound (e.g. in serum, plasma or cerebrospinal fluid) so a to avoid undesired levels of cholinergic side effects that can result from its administration. Advantageous embodiments described herein include sustained release pharmaceutical compositions and/or dosage forms (e.g. iontophoretic patches) that provide sustained release of such compounds.

Embodiments of the compositions and dosage forms described herein thus will provide sustained release such that, when compared to an equivalent amount of the compound, e.g., one or more of a compound of Formulas I, IA, IB, II, IIA, IIB, III, IIIA, IIIB, IV, IVA, IVB, XI, XIA and XIB (described above in sections C and D), administered to an animal in an immediate release dosage form, the composition or dosage form provides a serum or plasma Cmax that is reduced by at least 10%, at least 20%, at least 30%, at least 40%, at least 50%, or greater. Such compositions and dosage forms, when administered to animals capable of metabolizing the compound, also provide a serum or plasma concentration that decreases in the two hours following Cmax by less than 50%, by less than 40%, by less than 35%, by less than 30%, by less than 25%, by less than 20%, by less than 15%, and by less than 10%. Advantageously, such compositions and dosage forms also provide a serum or plasma concentration that decreases in the 4 hours following Cmax by less then 50%, by less than 40%, by less than 35%, by less than 30%, by less than 25% or by less than 20%.

Embodiments of the compositions and dosage forms described herein may be used to providing a Cmax of any of the above-described within a ng/ml range selected from the group consisting of 0.01 to 1.0, 1.0 to 5.0, 5.0 to 10.0, 10.0 to 15.0, 15.0 to 20.0, 20.0 to 25.0, 25.0 to 30, 30-40 and 40-50. Within the foregoing ranges, embodiments of the compositions and dosage forms described herein may be used to providing a Cmax of such compounds. e.g., one or more of a compound of Formulas I, IA, IB, II, IIA, IIB, III, IIA, IIIB, IV, IVA, IVB, XI, XIA and XIB (described above in sections C and D), within a ng/ml range selected from the group consisting of 0.01 to 0.05, 0.05 to 0.1, 0.1 to 0.5, 0.5 to 1, 1 to 2, 2 to 3, 3 to 5, 5 to 7, 7 to 10, 10 to 12, 12 to 15, 15 to 20 and 20 to 25. And within the foregoing ranges, embodiments of the compositions and dosage forms described herein may be used to providing a Cmax of Compound 1 within a ng/ml range selected from the group consisting of 0.01 to 0.025, 0.025 to 0.05, 0.05 to 0.075, 0.075 to 0.1, 0.1 to 0.15, 0.15 to 0.2, 0.2 to 0.25, 0.25 to 0.5, 0.5 to 0.75, 0.75 to 1.0, 1.0 to 1.5, 1.5 to 2.0, 2.0 to 2.5, 2.5 to 3.0, 3.0 to 4.0, 4.0 to 5.0, 5.0 to 6.0, 6.0 to 7.0, 7.0 to 8.0, 8.0 to 9.0, 9.0 to 10.0, 10.0 to 11.0, 11.0 to 12.0, 12.0 to 13.0, 13.0 to 14.0, 14.0 to 15.0, 15.0 to 16.0, 16.0 to 17.0, 17.0 to 18.0, 18.0 to 19.0, 19.0 to 20.0, 20.0 to 21.0, 21.0 to 22.0, 22.0 to 23.0, 23.0 to 24.0 and 24.0 to 25.0. Embodiments of the compositions and dosage forms described herein may be used to providing a Cmax of the above compounds within a ng/ml range formed by any two, three or four adjacent ranges in the foregoing sets of adjacent ranges in this paragraph. The desired Cmax chosen may depend on several factors and will be within the purview of the physician. For example, some patients may be more sensitive to the cholinergic side effects of the chosen compound and for those patients compositions providing lower Cmax values may be preferred.

In embodiments described herein in which any of the above compounds, e.g., one or more of a compound of Formulas I, IA, IB, II, IIA, IIB, III, IIIA, IIIB, IV, IVA IVB, XI, XIA and XIB (described above in sections C and D) is combined or co-administration with a muscarinic antagonist, the amount of compound may be used to provide a plasma or serum concentration within any range although the minimum Cmax of the compound likely will be one that, in the absence of the antagonist, would yield at least some cholinergic side effects, and typically at least moderate cholinergic side effects.

The desired dosage of a compound or composition disclosed herein naturally may depend on several factors and will be within the discretion of the subject's physician. For example, some patients may be more or less sensitive to the compounds disclosed herein and for those patients compositions providing higher of lower plasma or scrum values may be preferred. Also, some subjects may metabolize the compound or may metabolize it at different rates, and so dosages and/or alternative dosage forms may be required to provide the desired serum or plasma concentration. Skilled artisans will appreciate that specific dosages of such compounds and compositions may be adjusted depending on conditions of disease, the age, body weight, general health conditions, sex, and diet of the subject, dose intervals, administration routes, excretion rate, and combinations of active compounds.

As discussed in greater detail below, pharmaceutical compositions described herein may be designed to be fast-releasing compositions in which the active compound(s) are made available to the patient's system quickly, sustained-releasing in which the active compound(s) are made available to the patient's system quickly on a prolonged or controlled basis, or a combination of both so as to achieve both an immediate release of a given amount and a sustained release of a given amount of the same or different compound(s)

In another embodiment, the compounds of the disclosure can be used as markers in diagnostic imaging. For example, 11-C may be incorporated into the compounds, replacing 12-C to generate tracer compounds that can be used as markers of muscarinic receptors in the brain and the rest of the body of humans or animals that may be detected and imaged in three dimensions using positron emission tomography (PET). The replacement of non-radioactive 12-C by radioactive 11-C advantageously has little effect on the physicochemical properties of the compound, or on its pharmacokinetics, distribution, receptor binding or pharmacodynamic actions.

V. Dosage Forms

A. Exemplary Dosage Forms

The compounds and compositions described herein can be formulated into pharmaceutically acceptable compositions, which may include one or more pharmaceutically acceptable carriers. Such compositions may be prepared by mixing one or more compounds or compositions described herein, including, e.g., pharmaceutically acceptable salts thereof or stereoisomers thereof with pharmaceutically acceptable carriers, excipients, binders, diluents or the like to prevent and treat cognitive disorders associated with cholinergic deficits. The compounds and compositions may thus be used to prepare pharmaceutical compositions useful for any one of the above-described methods of treatment, e.g., Alzheimer's disease. Such compositions can be in the form of for example, granules, powders, tablets, capsules, syrup, suppositories, injections, emulsions, elixirs, suspensions or solutions. The instant compositions can be formulated for various routes of administration, for example, by oral, transdermal, parenteral, rectal, nasal, vaginal administration, or via implanted reservoir or other device such as a stent. Such implants may employ known inert materials such as silicones and biodegradable polymers. They also may be provided in combination with delivery vehicles such as in micelles or liposomes, or some other encapsulating technology. Parenteral or systemic administration includes, but is not limited to, subcutaneous, intravenous, intraperitoneally, intramuscular, intrathecal, intracranial, and intracerebroventricular injections.

The following dosage forms are given by way of example and should not be construed as limiting the embodiments of this disclosure.

For oral, buccal, and sublingual administration, powders, suspensions, granules, tablets, pills, capsules, gelcaps, and caplets are acceptable as solid dosage forms. These can be prepared, for example, by mixing one or more compounds disclosed herein, or pharmaceutically acceptable salts or stereoisomers thereof, with at least one additive such as a starch or other additive. Suitable additives are sucrose, lactose, cellulose sugar, mannitol, maltitol, dextran starch, agar, alginates, chitins, chitosans, pectins, tragacanth gum, gum arabic, gelatins, collagen, casein, albumin, synthetic or semi-synthetic polymers or glycerides. Optionally, oral dosage forms an contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable costing materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to freeze dried, rotary dried or spray dried powders, amorphous powders, granules, precipitates, or particulates. For injection, the formulations may optionally contain stabilizers, pH modifiers, surfactants, bioavailability modifiers and combinations of these.

Intrathecal administration, via bolus dosage or constant infusion, allows the local administration of a compound to a region of the spinal cord, such as the dorsal horn regions, delivering the compound directly to the subarachnoid space containing the CSF (cerebrospinal fluid). Central delivery to the spinal cord regions can also be performed by epidural injection to a region of the spinal cord exterior to the arachnoid membrane. Enhancing permeation of the active compound through meningeal membranes may be achieved by using hypertonic dosing solutions that increase permeability of meningeal membranes, or by addition of permeation enhancers, such as, but not limited to, liposomal encapsulation, surfactants, or ion-pairing agents.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Compounds and compositions described herein also may be administered to the lungs by inhalation through the nose or mouth. Suitable pharmaceutical formulations for inhalation include Aqueous and nonaqueous aerosols, solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Ordinarily, an aqueous aerosol is made by formulating an aqueous solution or suspension of the compound or composition together with conventional pharmaceutically acceptable carriers and stabilizers. The carriers and stabilizers vary with the requirements of the particular compound or composition, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g. in a fluorocarbon propellant) can also be used to deliver embodiments of the compounds and compositions disclosed herein.

Aerosols containing compounds and compositions disclosed herein may be conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols using sonic nebulizers may advantageous in some instances because nebulizers minimize exposure of the agent to shear, which can result in degradation of the compound.

For nasal administration, the compounds and compositions may be provided in a spray, nasal drops or aerosol containing an appropriate solvent(s) and optionally other compounds such as, but not limited to stabilizers, antimicrobial agents, antioxidants, pH modifiers, surfactants, bioavailability modifiers and combinations of these. For administration in the form of nasal drops, the compounds and compositions may be formulated in oily solutions or as a gel. For administration of nasal aerosol, any suitable propellant may be used including compressed air, nitrogen, carbon dioxide, or a hydrocarbon based low boiling solvent.

B. Immediate and Delayed/Sustained Release Dosages

Embodiments of the sustained release pharmaceutical compositions for the compounds and compositions described herein can offer significant advantages to both clinicians and their patients. Embodiments of the sustained release dosage forms generally control the rate of release. At the same time, embodiments of the sustained release formulations can maintain an effective concentration of the composition over time, thereby providing the recipient with a therapeutic effect over an extended duration. Embodiments of the sustained release dosage forms of the compositions described herein are thus advantageously administered to recipients in fewer doses than their immediate release counterparts and thus achieve improved therapeutic effect in the fewer doses. This can provide a significant benefit for patients whose cognition is sufficiently impaired such that compliance with self-administration schedules can present a real problem. Moreover, because of potential variations in the half-life in humans, conventional immediate release compositions may have to be administered to a patient multiple times within a 24 hour window in order to maintain adequate bioavailability of the drug to achieve therapeutic effect. Even if the patient or caregiver is diligent in administering the conventional immediate release composition, therefore, such compositions can yield a series of sub-optimal serum or plasma concentration profiles characterized by rapid increases, followed by fairly rapid decreases. Such rapid increases and decreases can provide a patient with a short window of appropriate blood concentration of the medicament for optimum therapy. Such profiles can be even worse if the patient or caregiver forgets to promptly administer a subsequent dosage.

Embodiments of a sustained release dosage form, on the other hand, may only have to be administered to a patient one to four times, at most, in a 24 hour period, or longer, in order to achieve the target organ concentration in a desired therapeutic range for a prolonged period of time.

Moreover, as discussed above, for patients who self-administer, sustained release dosage forms can result in better patient compliance and clinical outcomes due to the lower frequency of dosing (patients are less likely to miss doses), lower quantity of dosage units to be consumed, and the reduced undesired side-effects. As also mentioned above, this is particularly important in patients with cognitive deficiencies such as Alzheimer's disease who may have trouble remembering to take their medication.

Embodiments of sustained or controlled release compositions and dosage forms may be divided broadly into categories based on their routes of administration, e.g., oral dosage forms (including inhalable forms), parenteral/implantable dosage forms, and transdermal (including transmucosal) dosage forms. Within each of those categories numerous pharmaceutical compositions and dosage forms exist, and in some instances compositions or dosage form may be suitable for delivery by more than one route of administration (e.g., some dosage forms that deliver drugs by osmotic means can be used orally or subcutaneously). A variety of treatises address the delivery of pharmaceuticals including sustained release formulations and methods of their use including: *Sustained and Controlled Release Drug Delivery Systems*, Robinson. J. R., Ed. 1978, Marcel Dekker Inc. NY and *Modified Release Drug Delivery Technology*, by Michael J. Rathbone, Jonathan Hadgraf (Editor), Michael S. Roberts (Editor), Majella E. Lane (Editor), Published by Taylor & Francis, Inc.

In some embodiments, for example, the pharmaceutical composition is a dosage form selected from the group consisting of a tablet, liquid for oral administration, oral spray, intranasal spray, inhalable formulation, pill, gel, solid, capsule, multi-particulate, transdermal patch, implantable dosage, and injectable solution including intravenous drip (including in lyophilized and re-constituted form). Included within such embodiments are dosage forms that swell or unfold to a size such that the dosage form is retained in the stomach or the upper portion of the small intestine for at period of least 1 hour, at least 2 hours, at least three hours, at least 4 hours, at least 5 hours, at least 6 hours or for a period of longer than 6 hours.

1. Oral Dosage Forms

Oral dosage forms suitable for immediate or sustained delivery of the compounds and compositions described herein include without limitation, forms such as tablets, multi-particulates, beads, granules, aggregates, powders, gels, solids, semi-solids, foodstuffs, liquids, and capsules (including those containing any of the aforementioned forms). Other forms of orally administered compositions may be readily apparent to skilled artisans and are included within the scope of the term "oral dosage."

In some embodiments, the oral dosage form will be in the form of a tablet that provides a sustained release. In such embodiments a composition described herein may be combined with a variety of agents that will form a composition from which the drug is released with sustained release kinetics. For such preparations the combination may be with a variety of agents including, by way of non-limiting example, hydrophilic polymers (including polymers that form hydrogels upon hydration), and hydrophobic polymers.

A variety of compositions may be employed for the sustained release delivery from tablets, including for example tablets having a monolithic core composed of a single pharmaceutical composition. Examples of such compositions include but are not limited to, those found in U.S. Pat. Nos. 5,292,534 and 5,415,871, which teach sustained release formulations employing xanthum gum, U.S. Pat. No. 4,795,327, which discloses a method for preparing a composition comprising a medicament and a mixture of one or more nonionic cellulose ethers (methyl cellulose or hydroxypropylmethylcellulose) and an anionic surfactant, U.S. Pat. No. 4,983,398, which teaches a composition comprising one or more non-ionic cellulose ethers and an alkali metal carboxylate, U.S. Pat. Nos. 4,855,143 and 4,775,535, which teach compositions employing a cellulose ether base material, (e.g., hydroxypropylmethylcellulose) and an active therapeutic agent, U.S. Pat. No. 4,734,285, which describes a process for providing sustained release solid tablets comprising a medicament and a water-soluble hydroxypropyl methylcellulose ether, U.S. Pat. No. 7,052,706, which teaches the use of hydrophobic materials blended with medicament to produce sustained release formulations that can be tableted, and U.S. Pat. No. 4,680,323, which describes a carrier system comprising hydroxypropyl cellulose and a carboxy vinyl polymer.

Other formulations that may be employed to prepare a sustained release formulation in the form of a tablet have been described in other U.S. patents. Those patents include, but are not limited to U.S. Pat. Nos. 6,893,661, 6,875,793, 4,601,894, 4,687,757, 4,695,591, 4,994,276, 4,167,558, 4,259,314, 4,308,251, 4,389,393, 4,525,345, 4,556,678, 4,692,337, 5,073,380, 5,417,982, 4,968,509, 5,462,747, 5,439,687 and 5,264,446. Yet other sustained release tablet formulations may be readily apparent to skilled artisans and such other formulations are included within the scope of this disclosure of sustained release tablets.

In some embodiments, the oral dosage form will be in the form of a tablet for oral administration having a first layer and a second layer; where the first layer comprises a first composition comprising a composition described herein and a second layer comprises a second composition comprising a composition described herein. In such combination compositions, the first and second compositions may release at the same or at different rates when administered to a subject. In one embodiment, the first layer is a sustained release layer and the second layer is an immediate release layer. Such embodiments advantageously provide a relatively rapidly-achieved concentration, followed by a prolonged delivery. In another embodiment both layers are sustained release layers which release at different rates. In another embodiment both layers are immediate release layers which release at different rates. Yet additional layers can be added to such combination compositions to provide different release rates and combinations thereof.

Further, any of the oral dosage forms having one or more sections, compartments, layers, coatings, particles or the like, can be employed with the combination pharmaceutical compositions. e.g., of selective M1 or M1/M4 muscarinic agonist in combination with muscarinic antagonist. In a non-limiting example, in a tablet for oral administration having a first layer and a second layer, the first layer can comprise a muscarinic agonist as described herein and the second layer can comprise a muscarinic antagonist as described herein. Such combination oral dosage forms can be in any of the forms described herein.

Where tablets comprise a first layer and a second layer, the two layers may be compressed against one another so that a portion of each layer is exposed on at least one face of the tablet (e.g., as either the top or bottom of the tablet). Alternatively, the tablet may comprise the first layer within a coating of the second layer. Where it is desirable to use an immediate release formulation with a tablet having a first layer that is within the second layer, the second layer may be formulated to be the immediate release layer so that the sustained release layer (or core) is coated by the immediate release layer which coats the sustained release layer. Where it is desirable to use a combination pharmaceutical composition, e.g., of selective M1 or M1/M4 muscarinic agonist in combination with muscarinic antagonist either the agonist or antagonist can comprise the first and second layers.

In other embodiments, oral dosage form is a tablet comprising a first, second and third layers; where each layer comprises a different pharmaceutical composition that releases a composition described herein at a different rate when administered to a subject. As with the bi-layered tablets described above, the three layers may be compressed against one another so that a portion of each layer is exposed on at least one face of the tablet. Alternatively, the layers of the tablet may be arranged as approximately concentric layers, so that the first layer is within the second layer and the second layer is within the third layer. Other configurations are certainly possible, and the bi-layer and tri-layered tablets may be manufactured according to any method known to those of skill in the art.

Formulations having multiple layers that may be adapted for the sustained release delivery are described for example in U.S. Pat. Nos. 6,372,252, 6,039,974, 5,462,747, 5,407,687, 5,200,193, 4,844,907, 3,184,386, and U.S. Pat. Nos. 6,899,896 and 5,543,155, which describe coated bi-layer controlled release tablets. Other multiple-layer tablet formulations may be readily apparent to skilled artisans and are included within the scope of this disclosure of multi-layer tablet formulations.

In some embodiments the oral dosage form will be in the form of a tablet having one or more coatings that control the release of the pharmaceutical composition contained therein. In such embodiments the tablet may take a variety of forms and have a variety of characteristics. For example, coated tablets may have a monolithic core comprised of a single pharmaceutical composition of a composition described herein or the coated tablets may comprise a core of layered pharmaceutical compositions comprising one or more compositions described herein. In those embodiments where tablets comprise a coating to achieve the sustained release, the tablets comprise at least one coating applied over an amount of a composition described herein or an amount of a composition comprising a composition described herein. Multiple layers and multiple coatings obviously may be employed.

While sustained release tablets or matrices may be coated externally to control the rate at which a composition is released, it is not required that a controlled release coating form the external coating of the tablet Instead, the controlled release layer which overlies a coated amount of a composition-containing composition may be coated with an immediate release layer or another controlled release layer.

It will be appreciated that a variety of compositions may be applied to the surface of tablets that do not substantially affect their rate of drug delivery. Such compositions include pigmented coatings and the like. Where the outermost layer is an immediate release layer, it may be coated with a layer that does not significantly interfere with the immediate release.

Any of the compositions described herein thus may be administered in any suitable immediate or sustained release coated tablet form. Examples of coated pharmaceutical compositions in the form of tablets that can be adapted for the sustained release delivery include, but are not limited to, those described in the following patents: U.S. Pat. No. 5,543,155 provides a diffusion-osmotic controlled drug-release pharmaceutical composition comprising a monolithic or bi-layer core and a polymeric film-coat. In some embodiments the film coating is comprised of an ammonium methacrylate copolymer. U.S. Pat. No. 5,849,330 provides a rapid release core of active coated with slow releasing coating containing active. As such composition increase the rate of delivery of active as the drug in the rapid release core becomes available, such compositions may raise the circulating concentration of drug late in the delivery profile. Such delivery profiles may advantageously avoid situations where the circulating concentration of active falls below the desired therapeutic amount before the net dose is given. U.S. Pat. No. 6,110,500 provides coated tablet providing a release of active agent with zero-order release kinetics. U.S. Pat. No. 6,156,343 discloses a tablet comprising a mixture of a drug and a water-soluble polymer coated with a material consisting of a water-insoluble polymer and a water-soluble polymer and/or an enteric polymer. U.S. Pat. No. 6,264,985 provides a tablet having an erodible core containing at least one active substance, and a substantially erosion-resistant shell consisting of a dry-coated layer, where the shell has at least one opening. U.S. Pat. No. 6,365,185 describes a modified release drug delivery system, consisting of a solid core comprising an active agent together with a hydrogel, with the solid core being coated with a semi-permeable, self-destructing membrane which is optionally drilled to provide a release orifice, and optionally further coated with the same or different active agent material. U.S. Pat. No. 6,649,187 provides a coated composition comprising a combination of an amine drug with a polyalkylamine polymer, which can be a hydrogel, the combination of which is coated with a film-forming polymer having apertures in the coat. U.S. Pat. No. 7,125,563 describes tablets comprising a core of active combined with an extended release agent (e.g., a hydrophobic polymer such as ethyl cellulose), where the core is coated with an extended release costing of a hydrophobic polymer (e.g. a polymer comprising ethyl cellulose). Other of coated pharmaceutical compositions in the form of tablets for sustained delivery may be readily apparent to skilled artisans and are included within the scope of this disclosure of such tablets.

In some embodiments the oral dosage form will be in the form of a capsule that provides an immediate or a sustained release dosage. As a dosage form, capsules may contain any number of compositions, including beads, granules, aggregates, powders, gels, solids, semi-solids, liquids, and particles, to name a few. One such embodiment is a capsule comprising a plurality of particles that are prepared so that different groups of the particles release a composition described herein with different kinetics. The release by different groups of particles with different kinetics can be achieved by changing the composition of the particle, applying different coatings to different groups of particles, or both. In another such embodiment, a capsule comprises a plurality of particles that are prepared so that the different groups release the different parts of the combination pharmaceutical compositions. The release can be modulated for these compositions in a same manner as described above.

Particles can be of any size and shape, provided they can be loaded into a capsule suitable for oral administration. In some embodiments the particles can be spheroids, which are spherical granule having a diameter of approximately 0.5 to 2 mm. Examples of microparticles can include particles having a diameter of about 100 microns, although smaller or larger diameter particles are possible. Ranges of particulate diameters can include, for example, leas than 50 microns, 50-100 microns, 50-150 microns, 100-150 microns, 100-200 microns, 150-250 microns, and larger than 250 microns. Different particulate sizes also can be included within the same capsule to effect different release rates in the particulates Such particulates can be prepared using fluidized bed coating processes and devices (e.g. Wurster coating) as employed in the Glatt Pharmaceutical Systems GCPG-3. Possible commercial providers of microparticle compositions include Aptuit, Patheon Inc. and Eurand.

Microparticles may be incorporated into quick-dissolving films or other dosage forms designed to melt in the mouth and then be swallowed with the saliva or with a drink. Alternatively, microparticles may be packaged in unit doses in two-part capsules or in sachets, which may be opened, to enable administration by sprinkling on food, such as apple sauce. Such microparticles may be coated to mask the taste of the drug, since they directly contact the taste buds. In each case these dosage forms may improve compliance and be more convenient for patients, particularly the elderly or those who have difficulty with swallowing tablets.

Thus, embodiments of capsule dosage forms for pharmaceutical compositions of the compositions described herein may comprise more than one group of particles where each group of particles is coated with a coating that provides a different rate of release from the particle. Exemplary coatings for particles include those suitable for the preparation of coated tablets described above. In addition, the capsule itself may be coated to control its degradation.

In addition to capsules containing groups of particles that release at different rates, capsules may contain particles having a single composition that provide for immediate or sustained release.

In some embodiments the pharmaceutical compositions described herein are sustained release pharmaceutical compositions in the form a capsule containing film coated spheroids having a matrix comprising a composition described herein in admixture with non-water-swellable microcrystalline cellulose, where the film cost comprises ethylcellulose optionally combined with hydroxypropyl methylcellulose. The capsule of the composition may be comprised of any suitable polymeric material, such as gelatin.

Suitable microcrystalline cellulose can be, for example, Avicel-PH-101 (available from FMC Corporation, American Viscose Division, Avicel Sales, Marcus Hook. Pa., U.S.A.). Suitable forms of ethylcellulose can have a viscosity in the range of 5 to 100 cps at 20° C. (U.S. National Formulary XIII) (content of ethoxy groups 44 to 51% by weight), and more particularly a viscosity of 50 cps at 20° C. (content of ethoxy groups 48 to 49% by weight). One suitable form of hydroxypropyl methylcellulose is that having a viscosity in the range 3 to 100 cps at 20° C. (U.S. National Formulary XIII), and more particularly a viscosity of 6 cps at 20° C.

The film coat may comprise, for example, 80 to 100% by weight of ethylcellulose and 0 to 20% by weight of hydroxypropyl methylcellulose, and more particularly 90% by weight of ethylcellulose and 10% by weight of hydroxypropyl methylcellulose. In addition, the film cost may optionally contain up to 20% by weight of a plasticizer, for example a vegetable oil for example castor oil, or glycerol, or a glyceryl eater of a fatty acid, for example glyceryl triacetate or glyceryl monoricinoleate. The film coat may comprise 5 to 15% by weight of the coated spheroids, and preferably 9 to 10% by weight thereof.

Other pharmaceutical compositions in the form of a capsule that contains particles comprised of an active drug substance that may be adapted for delivery include, but are not limited to the compositions described in U.S. Pat. Nos. 5,670,172, 5,565,295, 4,867,985, 4,844,910, 4,309,406, and 4,138,475.

In other embodiments the pharmaceutical compositions described herein are sustained release pharmaceutical compositions in the form of capsules containing a composition comprising a composition described herein and a polymer that provides sustained release such as a hydrogel. In still other embodiments, the capsule may contain a tablet and smaller particles or granules wherein both the tablet and the particles and granules each contain a composition described herein.

Exemplary pharmaceutical compositions in the form of a capsule that can be adapted to provide for the sustained release include, but are not limited to those described below.

U.S. Pat. No. 7,022,342 describes a pharmaceutical composition in the form of a capsule comprising a plurality of particles (pellets). The particles have a core of active in combination with microcrystalline cellulose and ethylcellulose and are coated with a mixture comprising ethylcellulose, hydroxypropyl methylcellulose, acetyl tributyl citrate and talc. U.S. Pat. Nos. 4,140,755, 4,167,558 and 4,424,235 disclose sustained release pharmaceutical formulations that freely float in the gastric fluid for an extended period of time during which substantially all of the active substance is released therefrom. U.S. Pat. No. 4,126,672 discloses uncoated sustained release pharmaceutical capsules comprising a mixture of one or several active substances and at least one hydrophilic colloidal substance, which in contact with water forms gel, where hydroxypropyl-methylcelluose is preferably used as a hydrocolloid substance. U.S. Pat. No. 5,198,229 discloses floating capsules having a part containing the active substance, a part containing air or some other gas, providing buoyancy, and two separate parts containing inert material which swells upon contact with fluid. The capsule floats in the stomach and is retained them as it dispenses drug. Other pharmaceutical compositions in the form of a capsule that can be adapted to provide for the sustained release may be readily apparent to skilled artisans and are included within the scope of this disclosure of such capsules.

Capsules are well known in the art and may be formed from any suitable material. For example, capsules may be prepared from polymer-based materials including, but not limited to, such as, for example, hydroxypropyl methylcellulose, gelatin and starch.

As mentioned above, some embodiments of this disclosure are directed to sustained release dosage forms comprising a water swellable composition. For example, in some embodiments the entire core of a pharmaceutical composition formed as a tablet will be comprise of a pharmaceutical composition that swells upon hydration. In other embodiments, only a portion of a tablet's core will comprise a composition that swells upon hydration. Upon ingestion, such tablets hydrate and expand in the stomach providing a controlled release of the drug contained in the pharmaceutical composition. Tablets comprising components that swell upon hydrating can advantageously be coated or covered with a membrane that acts to control the release of a composition described herein, e.g., being of either limited permeability to or being impermeable for some time to the composition. Coatings may also be applied to regulate the rate at which the contents of the tablet are hydrated.

Exemplary formulations that may be adapted for the delivery include, but are not limited to, those found in the following disclosures. U.S. Pat. No. 6,733,784 describes an expanding tablet that can be adapted to deliver the compositions described herein. The tablet comprises a drug release controlling membrane material over a pharmaceutical composition that swells upon hydration. After swallowing, the tablet hydrates and expands such that the membrane ruptures to directly expose some surfaces of the core tablet to hydrating and eroding liquids, thus generating in situ a tablet that releases active ingredient in approximately zero order fashion. Similarly, U.S. Pat. No. 4,252,786 provides a rupturable relatively water-insoluble water-permeable film which is formed of a combination of hydrophobic and hydrophilic polymers over an insoluble swelling type delayed release matrix or core containing the medicament which core includes a blend of polyvinyl pyrrolidone and a carboxyvinyl hydrophilic polymer.

Yet other gastric-retained formulations include concertina-folded films containing drug that are contained in a gelatin capsule then released as the capsule dissolves in the stomach, and swell and unfold to a size that is retained in the stomach until it breaks down into smaller pieces.

Depending upon a number of factors, including the size of the hydrated tablet and its ability to withstand the mechanical forces within the stomach, the hydrated form may or may not be retained in the stomach or upper intestine for an extended period of time.

Other aspects of this disclosure are directed to cognition-enhancing pharmaceutical compositions and combinations of pharmaceutical compositions for administration to a subject in an oral dosage form that is retained in the upper gastrointestinal tract (e.g., the stomach or the stomach and upper part of the small intestine).

In one embodiment the compositions that are retained in the upper gastrointestinal tract are a pharmaceutical composition prepared in a dosage form that swells or unfolds to a size such that the dosage form is retained in the stomach for at least 1 hour, at least 2 hours, at least 3 hours, at least 4 hours, at least 5 hours, at least 6 hours or for a period of longer than 6 hours.

In another embodiment the compositions that are retained in the upper gastrointestinal tract are in the form of a tablet comprising a pharmaceutical composition that expands or changes shape upon hydration so as to prevent its passage out of the stomach. Such compositions, which are adapted for retention in the stomach and are useful for the prolonged delivery of an active agent, typically comprise a polymer matrix that swells upon hydration when contacted with the fluids of the stomach resulting in a form that will not easily pass out of the stomach.

One type of pharmaceutical composition which undergoes a shape change upon hydration so that it will not readily pass out of the stomach that can be adapted for delivery is described in U.S. Pat. No. 6,488,962. In one embodiment the composition for delivering a composition described herein is a controlled-release oral drug dosage form for releasing a drug into at least a portion of a region defined by the stomach and the upper gastrointestinal tract, where the dosage form is a solid monolithic matrix containing compositions described herein. In such an embodiment the matrix is non-circular in shape and has first and second orthogonal axes of unequal length, the matrix being one that swells in an unrestricted manner along both such axes upon exposure to water, the longer such axis having a maximum length of 3.0 cm when said matrix is unswollen, and the shorter such axis achieving a minimum length of 1.2 cm within one hour of immersion of said dosage form in water and wherein the matrix has a shape which when projected onto a plane, is either an oval or a parallelogram.

Another pharmaceutical composition that in certain embodiments undergoes a shape change so that it will not readily pass out of the stomach and that can be adapted for delivery is described in U.S. Pat. No. 6,682,759. Formulations described in that patent comprise both immediate-release and prolonged-release component.

In certain embodiments, pharmaceutical compositions described herein comprise a multiple granular composition, each granular composition comprises at least one pharmaceutically acceptable, water swellable polymer or hydrogel. Preferably, the controlled release dosage form comprises a bi-granular composition comprising a first granulation and a second granulation wherein the first granulation comprises at least one polymer and a drug (compositions described herein) and the second granulation comprises at least one polymer which may be the same polymer as the polymer of the first granulation, or a different polymer than the polymer of the first granulation. In addition, the second granulation contains a drug which may be the same drug or a different drug than the first granulation. In certain preferred embodiments the first granulation has a faster dissolution rate than the dissolution rate of the second granulation, and the release rate of the drug from the dosage form can be modified by adjusting the ratio of two types of granulations. Such formulations are described for example in U.S. Pat. No. 7,476,403.

In addition to the above-described compositions that undergo a shape change upon hydration, a variety of other pharmaceutical compositions recognized in the art may be adapted for the sustained release with substantially no noticeable cholinergic side effects, or at most only mild or moderate cholinergic side effects. Such compositions include: the prolonged release dosage form adapted for gastric retention employing a swellable/erodible polymer, such as poly(ethylene oxide) described in U.S. Pat. No. 6,120,803, which may additionally include liposomes, nanoparticles or enteric-coated drug particles; the layered formulations comprising at least one layer that can swell described in U.S. Pat. No. 5,780,057; the tablets described in U.S. Pat. No. 5,464,633; the tablets having a core of controlled geometric form providing zero order release of active drug substances described in U.S. Pat. No. 5,422,123; and the hydrogel containing envelopes described in U.S. Pat. No. 5,147,646.

Other disclosures of oral dosage forms that swell to sizes that will prolong the residence time in the stomach that may be used to formulate sustained release compositions are found in: U.S. Pat. No. 5,007,790 "Sustained-Release Oral Drug Dosage Form"; U.S. Pat. No. 5,582,837 Alkyl-Substituted Cellulose-Based Sustained-Release Oral Drug Dosage Forms"; U.S. Pat. No. 5,972,389 "Gastric-Retentive Oral Drug Dosage Forms for the Controlled Release of Sparingly Soluble Drugs and Insoluble Matter"; WO 98/55107 "Gastric-Retentive Oral Drug Dosage Forms for Controlled Release of Highly Soluble Drugs"; U.S. Patent Appln. No. US 2001/0018707 "Extending the Duration of Drug Release Within the Stomach During the Fed Mode"; WO 96/26718 "Controlled Release Tablet"; and the formulations found in U.S. Pat. No. 5,007,790.

Numerous patents and patent applications, some of which are mentioned above, describe sustained release compositions that may be employed to provide sustained release. Exemplary patents and applications that describe sustained release compositions include U.S. Pat. No. 7,438,927 Methods of treatment using a gastric retained gabapentin dosage, U.S. Pat. No. 7,413,751 Methods of treatment using a gastric retained losartan dosage, U.S. Pat. No. 7,405,238 Pharmacological inducement of the fed mode for enhanced drug administration to the stomach, U.S. Pat. No. 6,723,340 Optimal polymer mixtures for gastric retentive tablets. U.S. Pat. No. 6,682,759 Manufacture of oral dosage forms delivering both immediate-release and sustained-release drugs, U.S. Pat. No. 6,635,280 Extending the duration of drug release within the stomach during the fed mode, U.S. Pat. No. 6,488,962 Tablet shapes to enhance gastric retention of swellable controlled-release oral dosage forms, U.S. Pat. No. 6,451,808 Inhibition of emetic effect of metformin with 5-HT3 receptor antagonists, U.S. Pat. No. 6,340,475 Extending the duration of drug release within the stomach during the fed mode, U.S. Pat. No. 5,972,389 Gastric-retentive, oral drug dosage forms for the controlled-release of sparingly soluble drugs and insoluble matter, U.S. Pat. No. 5,582,837 Alkyl-substituted cellulose-based sustained-release oral drug dosage forms, U.S. Pat. No. 5,007,790 Sustained-release oral drug dosage form (mentioned above), and published application Nos. 20090028941 Pulsatile gastric retentive dosage forms, 20070184104 Gastric retentive gabapentin dosage forms and methods for using same, 20060159743 Methods of treating non-nociceptive pain states with gastric retentive gabapentin, 20050013863 Dual drug dosage forms with improved separation of drugs, 20030147952 Manufacture of oral dosage forms delivering both immediate-release and sustained-release drugs, 20030104062 Shell-and-core dosage form approaching zero-order drug release, 20030104053 Optimal polymer mixtures for gastric retentive tablets, 20030044466 Pharmacological inducement of the fed mode for enhanced drug administration to the stomach, 20030039688 Extending the duration of drug release within the stomach during the fed mode, and 20020051820 Extending the duration of drug release within the stomach during the fed mode Water-swellable polymers useful in the preparation of a sustained release dosage forms include polymers that are non-toxic and that swell in a dimensionally unrestricted manner upon contact with water and hence of gastric fluid. Examples of polymers meeting this description include, without limitation: cellulose polymers and their derivatives including, but not limited to, hydroxymethyl cellulose, hydroxyethyl cellulose, hydroxypropyl cellulose, hydroxypropylmethyl cellulose, carboxymethylcellulose, and microcrystalline cellulose polysaccharides and their derivatives polyalkylene oxides polyethylene glycols chitosan poly (vinyl alcohol) xanthan gum maleic anhydride copolymers poly(vinyl pyrrolidone) starch and starch-based polymers maltodextrins poly (2-ethyl-2-oxazoline) poly(ethyleneimine) polyurethane hydrogels crosslinked polyacrylic acids and their derivatives. In addition, copolymers of the polymers listed above, including block copolymers and graft polymers. Specific examples of copolymers are PLURONIC® and TECTONICS®, which are polyethylene oxide-polypropylene oxide block copolymers available from BASF Corporation, Chemicals Div., Wyandotte, Mich. USA. Further examples are hydrolyzed starch polyacrylonitrile graft copolymers, commonly known as "Super Slurper." which are available from Illinois Corn Growers Association, Bloomington. Ill., USA.

The term "cellulose" is used herein to denote a linear polymer of anhydroglucose. Examples of cellulosic polymers are alkyl-substituted cellulosic polymers that ultimately dissolve in the GI tract in a predictably delayed manner. Types of alkyl-substituted cellulose derivatives include those substituted with alkyl groups of 1 to 3 carbon atoms each. In terms of their viscosities, one class of alkyl-substituted celluloses includes those whose viscosities are within the range of about 3 to about 110,000 centipoise as a 2% aqueous solution at 25° C. Another class is those whose viscosities are within the range of about 1,000 to about 5,000 centipoise as a 1% aqueous solution at 25° C. Types of alkyl-substituted celluloses include hydroxyethyl cellulose and hydroxypropyl methylcellulose. Specific examples of hydroxyethyl celluloses include NATRASOL® 250HX and 250HHX NF (National Formulary), available from Aqualon Company, Wilmington. Del., USA., the hydroxypropylmethylcelluloses comprising the "Methocel" range from Dow Chemical Company (http://www.dow.com/dowexcipients/products/index.htm), including the Methocel K range, and the Eudragit series of poly (meth)acrylates from Degussa.

Some examples of polyalkylene oxides that can be used in the dosage forms disclosed herein include poly(ethylene oxide) and poly(propylene oxide). Poly(ethylene oxide) is a linear polymer of unsubstituted ethylene oxide. Poly(ethylene oxide) polymers having viscosity-average molecular weights of about 200,000 and higher can be used. Examples of poly(ethylene oxide)s that are commercially available are: POLYOX® NF, grade WSR Coagulant, molecular weight 5 million POLYOX® grade WSR 301, molecular weight 4 million POLYOX® grade WSR 303, molecular weight 7 million POLYOX® grade WSR N-60K, molecular weight 2 million; each of which are products of Union Carbide Chemicals and Plastics Company Inc. of Danbury, Conn. USA.

Depending upon the particular requirements of the pharmaceutical composition involved, coatings may be selected from those known in the art. Coatings that are permeable, partly (semi-permeable), or impermeable may be employed. Such coatings may be complete coatings or coatings provided with openings (drilled). Coatings may also be selected on properties other than their permeability, including their solubility in various environments and their permeability to water.

Examples of coatings insoluble in an acidic medium, such as stomach acid, include without limitation, polymers such as cellulose acetate phthalate, cellulose acetate mellitate, cellulose acetate succinate, hydroxypropylmethylcellulose phthalate, hydroxypropylmethylcellulose acetate succinate, carboxymethylcellulose ether, polyvinylacetate phthalate, polyester of styrene and maleic acid copolymer, polyester of vinylether and maleic acid copolymer, vinylacetate and crotonic acid copolymer, copolymers of methacrylic acid and ethylacrylate, copolymer of methacrylic acid and methacrylate, e.g., EUDRAGIT® L100, EUDRAGIT® L100-55, EUDRAGIT® L30D-55, EUDRAGIT® S100, or their combinations.

Examples of coatings which are insoluble (insoluble polymers), irrespective of pH, include without limitation, coatings that may comprise ethylcellulose, copolymers of methacrylate/trimethyl-amonioethylethacrylate (e.g., EUDRAGIT® RL PO, EUDRAGIT® RL 100, EUDRAGIT® RL30D, EUDRAGIT® RS PO, EUDRAGIT® RS100, EUDRAGRIT® RS30D or their combinations), neutral polymer of methacrylate (e.g., EUDRAGIT® NE 30 D, EUDRAGRIT® NE 40 D) or their combinations.

Examples of coatings that have limited solubility (poorly soluble coatings) include coatings formed from combinations of the above-listed insoluble polymers with soluble polymers such as, for example, combinations of ethylcellulose and hydroxypropylmethylcellulose, hydroxypropylcellulose, hydroxyethylcellulose, methylcellulose or polyvinylpyrolidone, a combination of methacrylate/trimethylammonio ethylmethacrylate copolymers (e.g., EUDRAGIT® RL PO, EUDRAGIT® RL 100, EUDRAGIT® RL30D, EUDRAGRIT® RS PO, EUDRAGIT® RS100, EUDRAGRIT® RS30D or their combinations) and hydroxypropylmethylcellulose, hydroxypropylcellulose, hydroxyethylcellulose or methylcellulose, a combination of neutral methacrylate polymer (e.g., EUDRAGIT® NE 30 D, EUDRAGIT® NE 40 D) and hydroxypropylmethylcellulose, hydroxypropylcellulose, hydroxyethylcellulose, methylcellulose or polyvinylpyrrolidone.

Coatings may optionally comprise other excipients conventionally used in coatings, including, but not limited to, fillers, e.g., talc, lactose, polysaccharides and others, plasticizers, e.g., dibutyl sebacate, triethyl citrate, polyethylene glycol, adipic acid, coconut oil, oleic acid and the like, colorants, e.g. titanium dioxide, lakes, pigments and the like, antioxidants and other excipients. The release rates may be modified by including additional polymers ("modifiers"). These may also strengthen the tablet to reduce the rate of erosion. They may also prevent unwanted initial release of drug in a "burst" when the tablet first hydrates. For example, Formulation #2 below in Example 12 contains Ethocel as a modifier, and formulation #3 in Example 12 contains partially pre-gelatinized starch as a modifier. The starch may actively interact with the Methocel to improve the properties of the tablets. Numerous modifier polymers are known to those skilled in the art and may replace a proportion of the filler. Further, various fillers and/or binders may be used. For example, formulation #1 in Example 12 below contains finely milled microcrystalline cellulose (MCC), which has excellent properties for dry compression. The compressibility indexes of selected grades of MCC are quite similar to that of Methocel K4M. Formulations #2 and 14 in Example 12 below also contain lactose, which is soluble, and leaches out of the tablet along with drug and may help water penetrate into the tablet, but may cause drug to be release more quickly than desired. Those skilled in the art will understand that many other types of filler may be used, including insoluble fillers, such as calcium phosphate dehydrate or calcium sulfate. Insoluble fillers will generally slow down release of drug.

The oral dosage forms described herein can find utility when administered to subjects who are either in the fed mode or the fasting mode. The fed more is also referred to as post-prandial. In the fed mode a contrasted with the unfed mode, particulate matter is retained in the stomach longer, as a result of the different modes of contractions in the stomach. The narrowing of the pyloric opening that occurs in the fed mode serves as a further means of promoting gastric retention by retaining a broader range of smaller dosage form sizes.

The fed mode is normally induced by food ingestion, but can also be induced pharmacologically by the administration of pharmacological agents that have an effect that is the same or similar to that of a meal. These fed-mode inducing agents may be administered separately or they may be included in the dosage form as an ingredient dispersed in the dosage form or in an outer immediate release coating or as a separate dosage form. Examples of pharmacological fed-mode inducing agents are disclosed in U.S. Pat. No. 7,405,238, entitled "Pharmacological Inducement of the Fed Mode for Enhanced Drug Administration to the Stomach," mentioned above.

The amount of a compound or composition described herein that can be present in an immediate or sustained release oral pharmaceutical composition may very from about 0.1 to 99% of the dosage by weight depending on the dosage form. Thus, in some embodiments the composition may comprise a percentage by weight of from less than 0.001%, from 0.001 to 0.01%, from 0.01 to 0.1%, from 0.1 to 1%, from 1% to 3%, from 3% to 5%, from 5% to 10%, from 10% to 15%, from 15% to 25%, from 25% to 50%, from 50% to 75%, and in some embodiments greater than 75%. For example, some embodiments of a tablet comprising MCD-396 can contain 0.01 to 20 mg of MCD-386 in 750-1000 mg of excipients.

In addition to the excipients and carriers described above, pharmaceutically acceptable excipients and carriers known to those skilled in the art may be used to prepare compositions according to this disclosure. Such excipients and carriers are described, for example, in "Remington's Pharmaceutical Sciences" Mack Pub. Co., New Jersey (1991) and other related such texts.

2. Transdermal and Transmucosal Dosage Forms

As discussed herein, the compositions disclosed herein may be metabolized in subjects such a human patients and thus the transdermal or transmucosal route for delivery of drugs may provide an advantageous ability to provide any of the compositions described herein to a human patient in an immediate or sustained release fashion. Indeed, as discussed in Example 10 below, it was found in one instance in rats that approximately ⅓ of the oral dosage could be delivered via iontophoretic patch to achieve approximately the same blood level of MCD-386 as delivered orally.

A variety of dosage forms are suitable to provide transdermal deliver in immediate and sustained release fashions, including but not limited to lotions, creams, salves, transdermal patches and iontophoretic transdermal patches. Where the dosage form is intended to deliver a composition described herein via a transmucosal route (e.g., nasal, oral, rectal, vaginal etc.) the dosage form may be lotion, gel, cream, salve, suppository, pessary, or a mist for nasal administration. A variety of transdermal or transmucosal systems for delivery of drugs that may be adaptable to the delivery of the compositions described herein are described, for example, in U.S. Pat. Nos. 5,785,991; 4,764,381; 4,956,171; 4,363,970; 5,453, 279; 4,883,660; 5,719,197 and EP Patent Appln. Nos.: 0 271 983; 0 267 617; 0 261 429; and 0 526 561.

Lotions, gels, salves, and creams suitable for the delivery of the compositions described herein may be formulated from a variety of components. Some examples of lotions and gels may be found in U.S. Pat. Nos. 5,939,427; 5,670,547; and 5,721,275. U.S. Pat. No. 7,404,965 describes cream, lotion, spray, ointment, gel, aerosol, tablet, suppository or patch device for transdermal or transmucosal administration of medicaments Where the lotion or gel is water based the composition providing sustained release, it will typically comprise a gelling agent and water, the compositions may optionally contain polyols (such as glycerin or propylene glycol), chelating or sequestering agent such as EDTA, antioxidants, preservatives, surfactants and proteinaceous materials.

Suitable water soluble gelling/viscosity enhancing agents include, without limitation, acidic carboxy polymers such as polyacrylate polymers. In some embodiments the polyacrylate polymers are CARBOPOL® polymers such as CARBOPOL® 940 CARBOPOL® 934 and CARBOPOL® 941 (available from B.F. Goodrich Chemical Co., Cleveland, Ohio). Gelling agents such as CARBOPOL® 940 are typically employed in an amount of about 0.2 to 0.5 weight percent of the formulation or vehicle, although other percentages may be suitable.

Polyols (polyhydroxy compounds such as glycerin or propylene glycol) may be incorporated into the compositions to provide a variety of desirable properties. Polyols can stabilize the formulation, and act as a humectant so as to avoid irritation of the skin, especially where repeated applications of the composition may be necessary.

Suitable antioxidants include BHT and related compounds.

Preservatives to retard the growth of microorganisms suitable for use in the compositions and dosage forms described herein include, for example, sorbic acid and imidazolidinyl urea, although numerous others are available.

Suitable surfactants can be selected from pharmaceutically acceptable non-ionic, anionic and cationic compounds. Suitable surfactants include, without limitation, octoxynol-9 (polyethylene glycol mono[p-(1,1,3,3-tetramethylbutyl)phenyl]ether), lecithin; sorbitan monoesters, such as sorbitan monoleate, sorbitan monolaurate, sorbitan monopalmitate, sorbitan monostearate; polysorbates, such as those prepared from lauric, palmitic, stearic and oleic acids; polysorbate 20, mononylphenyl ethers of polyethylene glycols, such as the monoxynols; polyoxyethylene monoesters, such as polyoxeethylene monostearate, polyoxyethylene monolaurate, polyoxyethylene monoleate; dioctyl sodium sulfosuccinate; sodium lauryl sulfate.

Where it is desirable to employ proteinaceous materials in the composition, suitable proteins may include collagen, elastin and the like.

a. Transdermal Patches

Transdermal patches, discussed in more detail below, have the added advantage of providing controlled delivery of compounds and compositions described herein. Because of the ability of transdermal patches to release drugs over long and short periods of time such patches provide a suitable means for the delivery of compounds and compositions described herein. Patches also can be especially desirable since the subject may have cognitive impairment and so there may be a real risk that the subject may forget to take other forms of medication discussed above such as pills, or may take too much or too little of his/her medication. Currently there are two prevalent types of transdermal patch designs, both of which may be employed for immediate and sustained release. The first design is the reservoir type where the drug is contained within a reservoir having a basal surface that is permeable to the drug. The second is a matrix type, where the drug is dispersed in a polymer layer affixed to the skin. Both designs typically include a backing layer and an inner release liner layer that is removed prior to use. If desired, the control of delivery by means of a patch may allow for the ability to control/modify the cholinergic side effects discussed herein, whether by controlled delivery of the muscarinic agonist and/or controlled co-delivery of a muscarinic antagonist that can reduce or eliminate the cholinergic side effects that otherwise would be experienced in the absence of the antagonist.

Transdermal patches that may be adapted for delivery of the compositions described herein include but are not limited to those described in previous patents and patent applications. Such transdermal patches include, without limitation: patches with reservoir layer comprising water-swellable matrixes described in U.S. Pat. No. 4,668,232; transdermal patches comprised of water-insoluble material that contains particles of medicament in a water-soluble/swellable polymer and an underlayer that controls the amount of water vapor passing from the skin to the matrix described in U.S. Pat. No. 5,230,898; transdermal patches comprising two-phase drug-containing matrix for sustained release of medicament described in U.S. Pat. No. 5,989,586; and patches with an adhesive layer comprising specific alkylacrylates and hydrophilic monomers and a matrix containing an alcohol, a penetration enhancer, water, and medicament described in WO 00/4720. Other transdermal patches that may be adapted for the delivery include: the three layer patches employing a pressure-sensitive adhesive which controls release of the active agent described in WO 9825592; and the acrylate polymer/polysiloxane patches that act as solubility based drug delivery systems described in U.S. Pat. No. 5,958,446.

Transdermal patches typically employ one or more skin-penetration enhancers to assist medicaments in passing through the skin. A variety of skin penetration enhancers have been described in the field. See, for example, U.S. Pat. Nos. 7,425,340, 5,411,740, 5,500,222, 5,614,211, 5,736,577, 5,834,010, 6,555,129 and 5,747,065. Examples of skin-penetration enhancers include, but are not limited to, polyhydric alcohols such as dipropylene glycol, propylene glycol, and polyethylene glycol which may enhance drug solubility; oils such as olive oil squalene, and lanolin; fatty ethers such as cetyl ether and oleyl ether, fatty acid eaters such as isopropyl myristate which enhance drug diffusibility; men and urea derivatives such as allantoin which affect the ability of keratin to retain moisture; polar solvents such as dimethyldecyl-phosphoxide, methyloctyl-sulfoxide, dimethyllaurylamine, dodecylpyrrolidone, isosorbitol, dimethyl-acetonide, dimethylsulfoxide, decy)methyl-sulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate To avoid the use of skin-penetration enhancers, transdermal delivery formulations such as patches may be applied in conjunction with the use of an apparatus that generates hydrophilic micro-channels in skin of a subject using the patch or composition. See, for example, U.S. Pat. Nos. 7,415,306 and 6,148,232. Where such an apparatus is employed, the transdermal patch and other formulations may avoid or limit the need to use skin penetration enhancing agents. In addition, apparatuses that generate hydrophilic micro-channels in skin are compatible with the use of iontophoretic patches that are described below. See, e.g., U.S. Pat. No. 7,415,306.

b. Transdermal Iontophoretic Devices

The use of iontophoresis, also referred to as electrotransport, in drug delivery is well known. Iontophoresis is the process of delivering an ionized substance (such as a drug) through intact skin by the application of an electrical field to generate an electrical current. Generally, the iontophoretic drug delivery device described herein comprises a power source for generation of an electrical current and two electrode compartments that when in contact with the skin or adhering to the skin of a subject will pass a generated electrical current through the skin. In the presence of the electrical current, drug passage through the skin is enhanced. In iontophoretic drug delivery, the rate of transdermal delivery can be controlled by selection of the patch design, including the selection of the contents of the electrode compartments, the surface area of the patch, and by the strength of the generated electrical current. The rate of delivery of drug is proportional to the current and therefore the quantity of drug delivered will be determined by the current and duration of current, thereby enabling convenient control of drug delivery by adjustment of the current.

Controlled and/or continuous delivery at constant rates is thus a useful method of delivering the compounds and compositions described herein. And as with the patches discussed above, iontophoretic devices also can be desirable since the subject may have cognitive impairment and so there may be a real risk that the subject may forget to take other forms of medication discussed above such as pills, or may take too much or too little of his/her medication. Iontophoretic delivery can ensure relatively constant plasma concentrations and, more importantly, proper control of pharmacologic and toxic effects. If desired, the control of delivery through iontophoresis allows for the ability to modify the cholinergic side effects discussed herein, whether by controlled delivery of the muscarinic agonist and/or controlled co-delivery of a muscarinic antagonist that can reduce or eliminate the cholinergic side effects that otherwise would be experienced in the absence of the antagonist.

Iontophoretic devices are described in numerous U.S. patents, including for example, the following U.S. Pat. Nos. 3,991,755, 4,141,359, 4,250,878, 4,395,545, 4,744,787, 4,747,819, 4,927,408, 5,080,646, 5,084,006, 5,125,894, 5,135,477, 5,135,480, 5,147,296, 5,147,297, 5,158,537, 5,162,042, 5,162,043, 5,167,616, 5,169,382, 5,169,383, and 5,415,628.

Generally, at least two electrodes are used in an iontophoretic device. Both of these electrodes are disposed so as to be in intimate electrical contact with some portion of the skin of the subject. One electrode, called the active or donor electrode, is the electrode from which a drug, drug precursor or other substance is delivered into the body of the subject by iontophoresis and/or by bulk flow of drug solution induced by the current. For a positive ionic form of a drug, the active electrode is the anode ad for a negative ionic form, the cathode. The other electrode, called the counter or return or indifferent electrode, serves to close the electrical circuit through the subject's body. In conjunction with the patient's skin contacted by the electrodes, the circuit is completed by connection of the electrodes to a source of electrical energy, for example, a battery.

Electrodes may be constructed of any of a large variety of electrically conductive materials, including both inert and sacrificial materials.

Inert conductive materials are those electrically conductive materials which, when employed in the iontophoretic devices, do not themselves undergo or participate in electrochemical reactions. Thus, an inert material distributes without being eroded or depleted due to the distribution of current and conducts current through the generating hydronium or hydroxyl ions by, respectively, either reduction or oxidation of water. Inert conductive materials typically include, for example, stainless steel, platinum, gold, and carbon or graphite.

Althernatively, the electrode may comprise a sacrificial conductive material. A material may be considered sacrificial if when employed as an electrode in an iontophoretic device described herein, material is eroded or depleted due to its oxidation or reduction. Such erosion or depletion occurs when the materials and formulations used in the iontophoretic device enable a specific electrochemical reaction, such as when a silver electrode is used with a formulation containing chloride ions. In this situation, the current distributing member would not came electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes may also be employed. In such cases, the metal would oxidize to metal ions, which would then be precipitated as an insoluble salt.

For cathodes, the current distributing member may be constructed from any electrically conductive material provided an appropriate electrolyte formulation is provided. For example, the cathodic current distributing member may be constructed from a metal/metal salt material. A preferred cathodic material is a silver/silver halide material. In such embodiments, a metal halide salt is preferably employed as the electrolyte. In this case, the device would electrochemically generate halide ions from the electrode as the metal is reduced. Also, accompanying silver ions in a formulation would be reduced to silver metal and would deposit (plate) onto the electrode. In other embodiments, the cathode material may be an intercalation material, an amalgam, or other material which can take electrolyte cations such as sodium out of solution, below the reduction potential of water. In addition, other materials may be used which permit the plating out of a metal from the appropriate electrolyte solution. Thus, metals such as silver, copper, zinc, and nickel, and other materials, such as carbon, may be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context. Nonetheless, the term sacrificial encompasses such materials and is intended to include materials that undergo physical and/or chemical changes during iontophoresis.

The current distributing member may take any form known in the art, such as the form of a plate, foil layer, screen, wire, or dispersion of conductive particles embedded in a conductive matrix.

Iontophoresis device includes a drug or agent reservoir or source to be iontophoretically delivered or introduced into the subject. Such drug reservoir is electrically connected to the anode or the cathode of the iontophoretic device to provide a fixed or renewable source of one or more drugs. In the case of MCD-386 and the other oxadiazoles and thiadiazoles described above which are positively charged at physiological pH, the drug reservoir will be connected to the anode.

A variety of iontophoretic patch designs can be employed to deliver the compositions described herein. For example, iontophoretic delivery devices have been developed in which the donor and counter electrode assemblies have a multi-laminate construction. In these devices, the donor and counter electrode assemblies are each formed by multiple layers of usually polymeric matrices. For example, U.S. Pat. No. 4,731,049 discloses a donor electrode assembly having a hydrophilic polymer based electrolyte reservoir and drug reservoir layers, a skin-contacting hydrogel layer, and optionally one or more semipermeable membrane layers. U.S. Pat. No. 4,474,570 discloses an iontophoretic device wherein the electrode assemblies include a conductive resin film electrode layer, a hydrophilic gel reservoir layer, and aluminum foil conductor layer and an insulating backing layer. U.S. Pat. No. 7,031,768 discloses a planar disposable transdermal iontophoretic delivery system with a galvanic battery, serving as the sole source of power and control for the system, and in which the galvanic battery is provided with a lot-tested coulombic capacity rating to predict dosage.

The drug and electrolyte reservoir layers of the iontophoretic delivery device may be, for example, formed of hydrophilic polymers, as described, for example, in U.S. Pat. Nos. 4,474,570, 4,383,529 and 4,764,164. Hydrophilic polymers may be desired since water is the preferred solvent for ionizing many drug salts, and hydrophilic polymer components of the drug reservoir in the donor electrode and the electrolyte reservoir in the counter electrode can be hydrated in situ while attached to the body by absorbing water from the skin through transepidermal water loss or sweat or from a mucosal membrane by absorbing saliva in the case of oral mucosal membranes. Once hydrated, the device begins to deliver ionized agent to the body. This enables the drug reservoir to be manufactured in a dry state, giving the device a longer shelf life. Hydrogels have been used as the drug reservoir matrix and electrolyte reservoir matrix in iontophoretic delivery devices, in part due to their high equilibrium water content and their ability to quickly absorb water. In addition, hydrogels tend to have good biocompatibility with the skin and with mucosal membranes.

An electrolyte reservoir can be arranged in electrical communication with a current distributing member. Typically, electrical communication requires that electrons from the current distributing member are exchanged with ions in the electrolyte reservoir upon the application of electrical current. Such electrical communication is preferably not impeded to any excessive degree by any intervening material(s) used in the construction of the iontophoretic device. In other words, the resistivity of the interface is preferably low.

The electrolyte reservoir comprises at least one electrolyte. i.e., an ionic or ionizable component which can act to conduct current toward or away from the current distributing member. Typically, the electrolyte comprises one or more mobile ions, the selection of which is dependent upon the desired application. Examples of suitable electrolytes include aqueous solutions of salts. One electrolyte is an aqueous solution of NaCl, having a concentration of less than 1 mole/liter (<1 M) or at about physiological concentration. Other electrolytes include salts of physiological ions including, but not limited to, potassium, chloride, and phosphate. The salt and its concentration may be selected as desired for particular applications.

Other chemical species may be selected by the skilled artisan for inclusion in the electrolyte reservoir. Such other reservoir species include, without limitation, chelation agents (e.g., citrate ions, EDTA) surfactants (e.g. non-ionic, cationic, or anionic), buffers, ionic excipients, osmolarity adjusters (e.g., polyethylene glycols, sugars), ionic antibiotics, penetration enhancers (e.g., alkanols), stabilizers, enzyme inhibitors, preservatives, thickening agents (e.g., acrylic acids, cellulosic resins, clays), and the like.

The iontophoretic patch may contain chemical substances to prevent the build up of hydrogen ions and hydroxyl ions produced by the electrolysis of water, which may interfere with drug delivery, cause breakdown of drugs, or cause skin irritation. U.S. Pat. No. 4,973,303 discloses an iontophoretic electrode containing a non-mobile, insoluble ion-exchange resin to buffer pH.

Alternatively, the electrolyte may have a material which is itself relatively immobile in the absence of an electric field, but which acts to deliver mobile ions in the presence of an electric field. In the latter case, the electrolyte may more properly be termed an ion source. Examples of ion sources can include polyelectrolytes, ion exchange membranes and reins, non-ionic buffers which become ionic upon pH change, and other known ion sources.

Alternatively, the electrolyte reservoir may contain counter-ions that form a soluble salt with an electrochemically generated ion. For example, in an apparatus employing a silver anodal current distributing member, a suitable counter-ion might be acetate or nitrate. Such counter-ions can be used when other means are provided for sequestering electrochemically generated ions.

Thus, the electrolyte reservoir can provide at least one ion of the same charge as the electrochemically generated ion, to permit current to be conducted, and at least one oppositely charged ion.

Additionally, the flux profile of a composition described herein that is being delivered by iontophoresis can be controlled by adding to or having other ions present in the reservoir containing the drug. These ions which would compete with the drug ions for current (competing ions). To achieve various flux profiles for the drug being iontophoretically delivered, constant current can be applied but with varying concentrations of the competing ions.

Embodiments of the iontophoretic apparatus described herein can include a suitable backing film positioned on top of the electrolyte reservoir. The backing film provides protection against contamination and damage to the current distributing member, if present, and the electrolyte reservoir of the apparatus.

Embodiments of the iontophoretic devices described herein can include a release liner which may be fixed to the underside of the ionized substance reservoir by an adhesive. The release liner protects the surface of the ionized substance reservoir which contacts the epithelial surface from contamination and damage when the device is not in use. When the device is ready for use, the release liner may be peeled off to expose the epithelial contacting surface of the ionized substance reservoir for application of the device to a subject.

Figure 6:
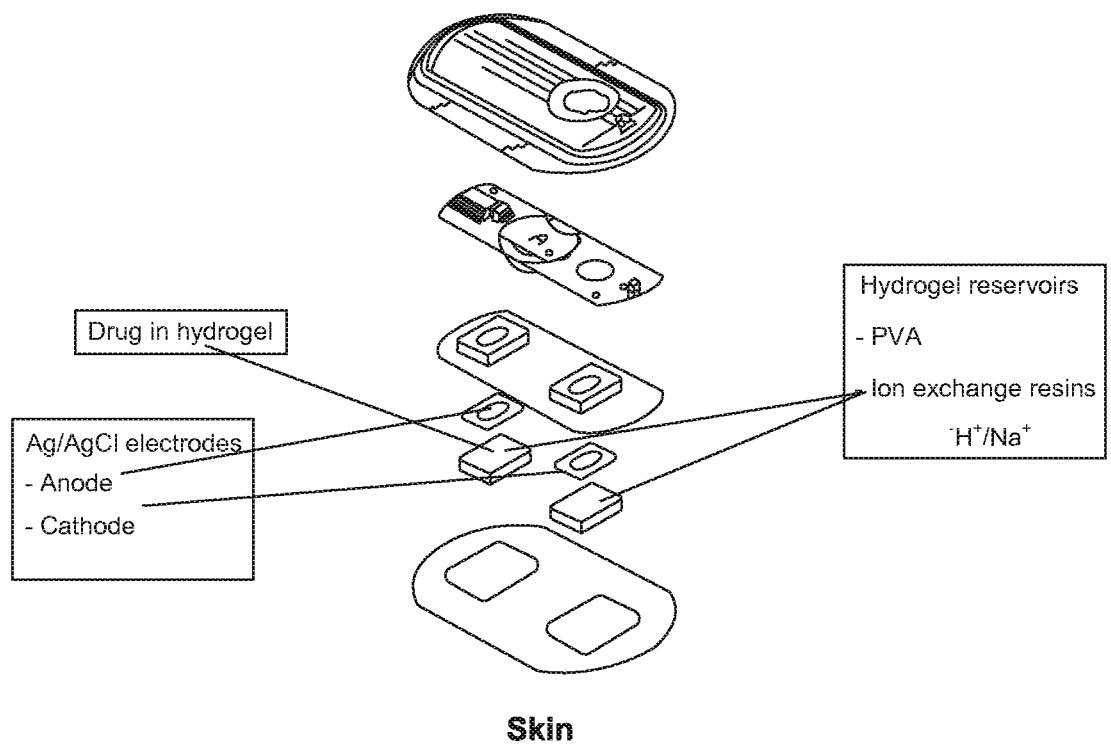
FIG. 6 is a plan view of a representative iontophoretic patch in accordance with this disclosure.

One embodiment of iontophoretic delivery, which may provide acceptable or even advantageous results, is described in U.S. Pat. Nos. 6,425,892 and 7,302,293. This device describes a patch system that is able to deliver multiple, identical doses from transdermal electrotransport delivery devices. These devices are also can provide patient management to a wider patient population in which different patients require different amounts of a drug or pharmaceutical composition in repeated multiple dosages. Briefly, these patents generally describe a component of the Ionsys™ system. This system comprises a plastic top housing that contains the battery and electronics, and a red plastic bottom housing containing two hydrogel reservoirs and a polyisobutylene skin adhesive. Only one of the hydrogels (the anode, located under the dosing button) contains active ingredient (which in the case of the Ionsys™ system is fentanyl), along with inactive ingredients. The other hydrogel (the cathode) contains only pharmacologically inactive ingredients. The bottom housing has a red tab that is used only for system removal from the skin and during disposal. A siliconized clear, plastic release liner covers the hydrogels and must be removed and discarded prior to placement on the skin. The system is powered by a 3-volt lithium battery. An adaptation of the system described in these patents that can be employed to provide iontophoretic delivery of compositions according this disclosure is provided as FIG. 6.

One additional advantage of patches and iontophoretic devices is that the active ingredient is passed through the skin instead of through the patient's digestive tract, and thus the active ingredient(s) avoid "first-pass metabolism" that can cause a loss or degradation of the active ingredient(s).

Where iontophoretic devices or patches are used to deliver both an agonist and an antagonist, then the agonist and antagonist may be in a mixture in one device or patch, may be provided separately within the same device or patch, or may be provided in two separate devices and/or patches that would both be applied to the patient 3. Infusion and Implantable Dosage Form In addition to the use of pharmacological compositions or dosage forms that control the release of compounds by virtue of their structure or composition, controlled administration of the compounds and compositions described herein may be achieved using an infusion pump to administer the drug. Infusion pumps may be electro/mechanical infusion pumps that may be external (not implanted) or implantable. Infusion pumps may also be osmotic pumps that can be implanted rather than electro/mechanical pumps. Like patches and iontophoretic devices, infusion pumps and implantable devices may provide an advantage in that the patient, who may have cognitive impairment, is not required to remember to take his/her medication, or how much to take.

One advantage of employing an electro/mechanical or osmotic pump to infuse a composition described herein is that the compound may be administered in a more local fashion, that is achievable by oral delivery (e.g., the drug may be delivered to cerebrospinal environment).

Regardless of the type of infusion pumping system employed, administration of suitable amounts of a composition described herein to maintain appropriate circulating levels of the drug may be achieved by altering the infusion parameters. The concentration can be controlled by limiting the quantity (volume) of the pharmaceutical composition that the infusion pump administers, the concentration present in the infused pharmaceutical composition, the rate of infusion, or any combination thereof. Where the infusion pump is an electro/mechanical pumping systems it may contain a programmable pumping mechanism (and any necessary memory or computer implemented functions) that permit control of delivery. Programmable pumps also permit both the duration and rate of pump action to be regulated and provide any desired delivery profile.

A variety of pumping systems suitable or adaptable for the administration of the compounds and compositions disclosed herein have been described in the art. Implantable pumps, some of which are refillable with out being removed, are described for example in U.S. Pat. Nos. 7,351,239, 7,347,854, 7,341,577, 7,044,932, 7,043,295, 4,013,074, and 4,692,147. Implantable delivery devices that are controlled by an external control device such as the system described in U.S. Pat. No. 6,873,268 may also be employed. External pumps are described for example in U.S. Pat. Nos. 7,347,836 and 6,475,180.

Implantable osmotic delivery devices referred to as "osmotic pumps" or "osmotic infusion pumps" may also be employed for the delivery of any of the compounds or compositions decried herein. Although a variety of different pumps have been designed, such devices typically include a reservoir, an expendable osmotic material, a drug formulation which in this case comprises a compound or composition, and at least one delivery orifice. Where the expandable osmotic material and the drug formulation are formed of separate materials, the expandable osmotic material and the drug formulation may be separated by a member, such as a piston, which is movable within the reservoir. At least a portion of the reservoir included in an osmotic pump is generally semipermeable, allowing water to be taken into the system while preventing or minimizing the undesired escape of materials forming the expandable osmotic material or the drug formulation from the reservoir. The osmotic material draws water from the environment into the osmotic pump through the semipermeable portion of the reservoir which expands as it imbibes water and the compound/composition is discharged through the delivery orifice of the osmotic pump.

Various different implantable osmotic delivery devices that may be adapted for the immediate or sustained release delivery and include, but are not limited to, those described in: U.S. Pat. Nos. 5,234,693, 5,279,608, 5,336,057, 5,728396, 5,985,305, 5,997,527, 5,997,902, 6,113,938, 6,132,420, 6,217,906, 6,261,584, 6,270,787, and 6,287,295.

In some embodiments, the implantable delivery devices operate by diffusion and may also operate osmotically. Such devices employ one or more semipermeable membranes surrounding or separating a composition comprising a compound or composition described herein (that may have additional coatings or layers internal or external to one or more semipermeable membrane(s)) from the surrounding environment into which the composition is to be released. Implantable diffusional delivery devices that may be adapted for the sustained release delivery at levels that enhance cognitive function include, but are not limited to those described in U.S. Pat. Nos. 6,375,978 and 6,004,582.

Implantable delivery devices (e.g., implantable infusion pumps, osmotic pumps, and diffusional devices) may be implanted in a variety of locations, but are generally implanted subcutaneously. Such devices, particularly osmotic pumps and devices that operate by diffusion devices, may be adapted for use as rectal suppositories, vaginal pessaries for delivery of compositions described herein. (See for example U.S. Pat. No. 4,576,604.) Such devices may be implanted in other environments. For example U.S. Pat. No. 6,004,582 describes the use of a device in environments including "oral, ocular, nasal, vaginal, glands, gastrointestinal tract, rectum, cervical, intrauterine, arterial, venous, otic, sublingual, dermal, epidermal, subdermal, implant, buccal bioadhesive, mucosal and other similar environments."U.S. Pat. No. 4,576,604 describes the use of osmotic delivery devices orally and also as vaginal pessaries and ano-rectal suppositories. U.S. Pat. No. 6,740,333 describes controlled release suppositories.

In other embodiments, compounds and compositions described herein can be incorporated into implantable biodegradable or resorbable compositions and matrices adaptable for delivery. Included in such compositions are the biodegradable polymer compositions described in U.S. Pat. No. 6,455,526, the resorbable matrices described in U.S. Pat. No. 6,497,901, the injectable biodegradable matrices described in U.S. Pat. No. 5,384,333, the poly(phosphoesters) compositions described in U.S. Pat. No. 5,194,193, and the calcium sulfate controlled release matrices described in U.S. Pat. No. 6,030,636.

Each of the documents cited herein is incorporated herein by reference in its entirety, and in particular for their disclosures of the compositions and dosage forms that may be employed or adapted for use in administration to subjects as described herein.

VI. Patient Testing

As discussed above, the foregoing compositions and dosage forms are useful for providing cognitive enhancement to a subject especially humans. Due to patient-to-patient variability observed with MCD-386, which may be due at least in part to the effect of the patient's ability to metabolize the drug, in practice it may be advantageous to initially test a patient to determine his/her response to a drug comprising one of the above-described compounds, e.g., one or more of a compound of Formulas I, IA, IB, II, IIA, IIB, III, IIIA, IIIB, IV, IVA, IVB, XI, XIA and XIB (described above in sections C and D). Thus, before prescribing the dosage of a composition described herein, the subject may be given an initial dose and then tested at a pre-determined time interval following administration to determine serum or plasma concentration. In addition to testing the concentration, or in the alternative, the subject may observe or be observed for the onset of substantially no, mild, moderate or severe cholinergic side effects to determine the patient's response to the drug and tolerance to the side effects, if any. In this way, a more accurate determination of the appropriate dose to prescribe can be made. Accordingly, embodiments of the disclosure herein provide testing a subject to determine the concentration of a composition described herein in the subject's serum or plasma at a predetermined time following administration of a pre-determined dose of that composition, and/or testing a patient to determine the amount of cholinergic side effects, if any, following administration of a pre-determined dose. Either or both of these tests may be conducted prior to prescribing the dosage for a subject in order to prescribe the appropriate dosage for that subject. Alternatively, or in addition, subjects may be tested again over time to determine whether their concentration of following administration has changed, thereby warranting a change in their prescription.

EXAMPLES

The following non-limiting examples are provided merely to illustrate various aspects or embodiments of this disclosure.

The following abbreviations are used throughout the present disclosure with respect to chemical terminology:

Boc: N-tert-Butoxycarbonyl
Bn: Benzyl
Bu: Butyl

Cbz or Z: Benzoyloxycarbonyl
DCC: Dicyclohexylcarbodiimide
DCM Dichloromethane
D.I. Deionized
DEAD Diethyl azodicarboxylate
DIAD Diisopropyl azodicarboxylate
DIEA Diisopropylethylamine
DIPEA Diisopropyl ethylamine
DMAP: N,N-dimethyl-4-aminopyridine
DMF: N,N-Dimethylformamide
DMSO: Dimethylsulfoxide
Et: Ethyl
Et3N: Triethylamine
FtOAc: Ethyl acetate
EtOH: Ethanol
Fmoc: Fluorenyl-methoxy-carbonyl
HPLC: High Pressure Liquid Chromatography
IPA: iso-propyl alcohol
K2CO3 Potassium carbonate
KH Potassium hydride
LiOH Lithium hydroxide
Me: Methyl
MeOH: Methanol
mL Milliliters(s)
Mmt: p-Methoxyphenyldiphenylmethyl
MS (ESI): Electrospray ionization mass spectrometry
MTBE: Methyl-tert-butyl ether
Na2CO3 Sodium carbonate
NaHCO3 Sodium bicarbonate
NaH Sodium hydride
NMM: N-Methylmorpholine
NMR: Nuclear Magnetic Resonance
PBS Phosphate buffer solution
Ph: Phenyl
r.t. Room temperature
tBu: tert-butyl
TFA: trifluoroacetic acid
THF: Tetrahydrofuran
THP: Tetrahydropyrimidine
TLC Thin layer chromatography Example 1

Synthesis of 3-(1,1-d$_2$-ethyl)-5-(1,4,5,6-tetrahydro-pyrimidin-5-yl)-1,2,4-oxadiazole hydrochloride

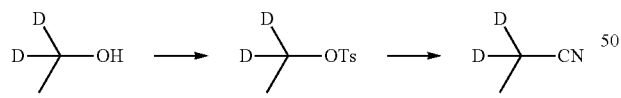

Step 1A: 1,1-d$_2$-Ethyl tosylate

A mixture of anhydrous pyridine (80 mol) mid p-toluenesulfonyl chloride (22.0 g, 115 mmol) was cooled to −11 C and treated slowly with ethyl-1,1-d$_2$-alcohol (CDN Isotopes, Pointe-Clair, Quebec, Canada. Product No. D-60) over 4 minutes. The temperature increased to −1 C then slowly decreased to −8 C. The mixture was stirred below 0 C for an additional 40 minutes. The mixture was cooled to −5 C and treated with a chilled (0 C) solution of 10% H$_2$SO$_4$ (250 mL). The mixture warmed (exotherm) to 35 C and was cooled 5 C and stirred for 30 minutes. The mixture was further cooled to 0 C and the solids collected by filtration, washed with 40 mL of chilled D.I. water and suction-dried for 5 minutes. The solids were further dried overnight under high vacuum at room temperature to afford 16.1 g of white solid (74.3%).

Step 1B: 2,2-d$_2$-Propionitrile

A mixture of KCN (13.4 g, 206 mmol) in anhydrous DMSO (88 mL) was treated with the d$_2$-ethyl tosylate (16.1 g, 79.6 mmol) and heated to 90-100° C. for 4 hours. The reaction apparatus was set up for distillation and the oil bath heated to 150° C. Product distilled at 90-100° C. providing 2.9 g of clear, colorless liquid.

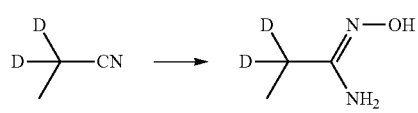

Step 2: 2,2-d-Propionamidoxime

To a chilled solution of hydroxylamine HCl (2.69 g, 38.67 mmol) in methanol (30 mL) was added sodium methoxide (2.14 g, 39.68 mmol). The temperature of the mixture was maintained at 0° C. for an hour before propionitrile-d$_2$ (2.9 g, 50.88 mmol) was added. The mixture was warmed to room temperature and then warmed at 50° C. for 4 hours. The cooled mixture was filtered and evaporated to a residue that was triturated with EtOAc (3×25 mL) and filtered. The combined filtrates were reduced in vacuo, affording 1.6 g of residue. MS (ESI) m/z 91.1 (M+1)$^+$.

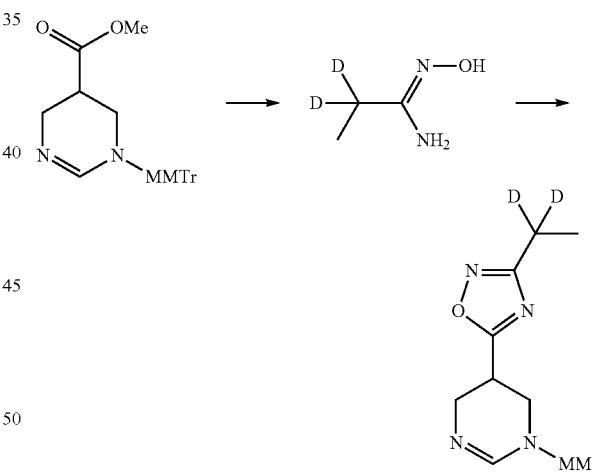

Step 3: 3-(1,1-d$_2$-Ethyl)-5-(1-((4-methoxyphenyl)diphenylmethyl)-4,4,5,6-tetrahydropyrimidin-5-yl)-1,2,4-oxadiazole A mixture of 60% NaH (0.66 g, 16.6 mmol) in THF (20 mL) was stirred under nitrogen and treated with a solution of d$_2$ propionamidoxime (1.5 g, 16.6 mmol) in THF (4 mL). The mixture was stirred rapidly at room temperature for 20 minutes. The Mmt-THP methyl ester (methyl 1-((4-methoxyphenyl)diphenylmethyl)-1,4,5,6-tetrahydropyrimidine-5-carboxylate, 2.75 g, 6.6 mmol, prepared according to U.S. Pat. No. 5,403,845) was added, followed by a rise with THF (10 mL). The reaction mixture was heated to 50° C. for 1.5 hours then stirred overnight at room temperature. Most of the THF was removed under vacuum and the residue extracted with EtOAc (40 mL) and D.I. water (30 mL). The aqueous layer was extracted with EtOAc (25 mL) and the combined organic layers washed with saturated brine (20 mL) and condensed. The residue was chromatographed over 20 g of silica gel using EtOAc (0.1% Et$_3$N) followed by EtOAc:McOH:Et$_3$N (gradient up to 90:9:1). The product was dried overnight under high vacuum to 1.46 g of white foam (48.6%). MS (ESI) m/z 455 (M+1)$^+$. $^1$H NMR (CDCl$_3$, 400 MHz): δ 1.27 (s, 3H), 2.80-2.90 (m, 1H), 3.20-3.26 (t, 1H), 3.40-3.55 (m, 2H), 3.69-3.75 (m, 1H), 3.79 (s, 3H), 6.83-6.85 (d, 2H), 7.23-7.40 (m, 12H), 7.65 (s, 1H).

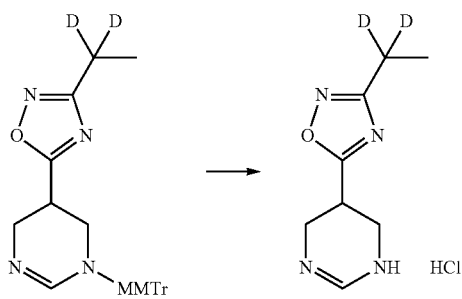

Step 4: 3-(2,2-d$_2$-Ethyl)-5-(1,4,5,6-tetrahydropyrimidin-5-yl)-1,2,4-oxadiazole hydrochloride The Mmt-protected intermediate (1.4 g, 3.08 mmol) was stirred in 14 mL, of dichloromethane at room temperature and treated with a solution of 2M HCl in EtOH (7.3 ml, 15.4 mmol). The resulting orange solution was stirred overnight at room temperature. An additional 2 mL of 2M HCl-EtOH was added and solution warmed to 45° C. for 1 hour. The mixture was cooled to room temperature and condensed under vacuum to about 5 mL final volume. The mixture was warmed to about 35-40° C. and treated slowly with 11 mL of MTBE, at which time a precipitate formed. The slurry was cooled to 10° C. filtered, and the solids washed with 4 mL of EtOH: MTBE (1:3). The solid was recrystallized from EtOH and MTBE, and dried overnight under high vacuum to 0.427 g of white to off-white solid (63.3%). MS (ESI) m/z 183 (M+1)$^+$. $^1$H NMR (DMSO-d$_6$, 400 MHz): δ 1.21 (s, 3H), 3.67-3.75 (m, 4H), 3.76 (m, 1H), 8.23 (s, 1H), 10.0 (bs, 2H).

Example 2

Synthesis of 3-(2,2,3,3,3-d$_5$-ethyl)-5-(1,4,5,6-tetrahydropyridin-5-yl)-1,2,4-oxadiazole hydrochloride

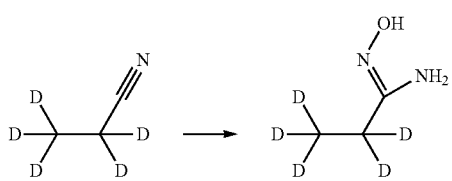 [SMILES: [2H]C([2H])([2H])C([2H])([2H])C#N ; [2H]C([2H])([2H])C([2H])([2H])/C(N)=N/O]

Step 1: 2,3,3,3-d$_5$-Propionamideoxime

Sodium methoxide (0.84 g, 15.60 mmol) was added to a stirred mixture of hydroxylamine HCl (1.08 g, 15.60 mmol) in anhydrous methanol (20 mL) at room temperature. The mixture was stirred for 0.5 hours before propionitrile-3,3,3-d$_3$ (1.0 g, 16.60 mmol; CDN Isotopes, Pointe-Clair, Quebec, Canada. Product No. D-531) was added. The mixture was stirred room temperature overnight before it was warmed at 45-50° C. for 6 hours. The cooled mixture was filtered and evaporated to a residue that was triturated with ethyl acetate (3×25 mL). The combined filtrates were concentrated in vacuo, to afford 0.7 g of an amber oil. MS (ES) m/z 94 [M+1]$^+$.

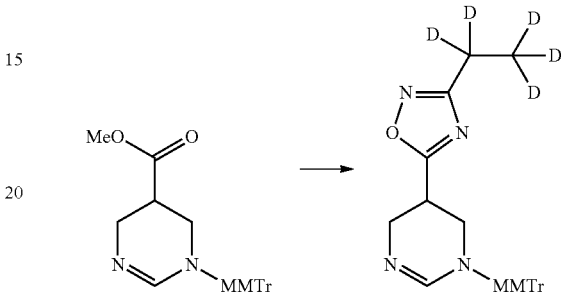

Step 2: 3-(1,1,2,2,2-d$_2$-ethyl)-5-(1-((4-methoxyphenyl)diphenylethyl-1,4,5,6-tetrahydropyrimidine-5-yl)-1,2,4-oxadiazole Sodium hydride (60% in mineral oil, 0.24 g, 6.03 mmol) was stirred in anhydrous THF (10 mL) and treated with a solution of d$_5$-propionitrile in 5 mL of THF. The mixture was stirred for 15 minutes and treated with a solution of Mmt-THP protected methyl ester (1.0 g, 2.41 mmol) in 5 mL of THF. The mixture was stirred at 60° C. for 2 hours then further heated to 75° C. for an additional 1.5 hours. The mixture was concentrated under vacuum and extracted with EtOAc and water. The organic layer was washed with brine, dried (Na$_2$SO$_4$), and filtered. The solution was condensed and the residue chromatographed over silica gel with EtOAc (0.1% Et$_3$N), followed by EtOAc:MeOH:Et$_3$N (90:9:1) to afford 0.55 g of white solid after drying under vacuum. MS (ESI) m/z 458 (M+1)$^+$. $^1$H NMR (CDCl$_3$, 400 MHz): δ 2.8-2.9 (m, 1H), 3.23 (t, 1H), 3.4-3.6 (m, 2H), 3.70-3.75 (m, 1H), 3.79 (s, 3H), 6.83-6.85 (d, 2H), 7.20-7.45 (m, 12H), 7.65 (s, 1H).

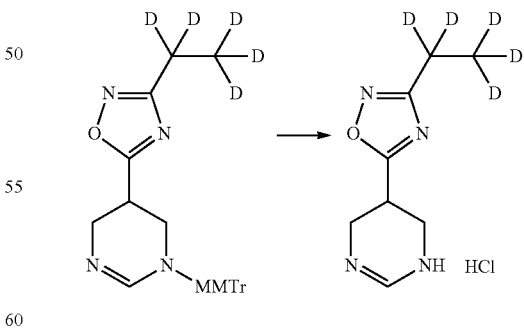

Step 3: 3-(1,1,2,2,2-d$_5$-ethyl)-5-(1,4,5,6-tetrahydropyrimidine-5-yl)-1,2,4-oxadiazole hydrochloride The Mmt-protected intermediate (0.53 g, 1.15 mmol) was stirred in 20 mL of dichloromethane and treated with 10 mL of a 2M HCl solution in diethyl ether. The mixture was stirred overnight at room temperature at which time TLC analysis revealed a trace amount of starting material. The mixture was condensed under vacuum and the residue dissolved in 2 mL of MeOH. The solution was treated with 1 mL of 1.25 M HCl-MeOH for 15 minutes and condensed under vacuum. The residue was dissolved in 1 mL of MeOH and treated with 4 mL of EtOAc, followed by 1 mL of hexane. The mixture was stirred under a stream of nitrogen until it concentrated to about ½ volume. The resulting solids were collected by filtration and washed with EtOAc. The wet solid was recrystallized using the same procedure (MeOH:EtOAc:Hexane). The product was dissolved in MeOH, treated with charcoal and warmed for 5 minutes. Filtration through Celite, followed by crystallization with EtOAc and hexane, produced 109 mg (42.8%) of an off-white solid after drying under high vacuum. MS (ESI) m/z 186 (M+1)+. $^1$H NMR (DMSO-$d_6$. 400 MHz): δ 3.6-3.8 (m, 4H), 3.9 (m, 1H), 8.24 (s, 1H), 10.1 (b, 2H).

Example 3

Synthesis of 3-($d_3$-methyl)-5-(1,4,5,6-tetrahydropyrimidin-5-yl)-1,2,4-oxadiazole hydrochloride

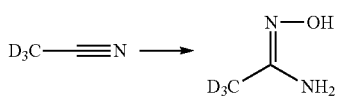

Step 1: $d_3$-Acetamidoxime

To a chilled solution of hydroxylamine HCl (7.16 g, 103 mmol) in methanol (60 mL) was added sodium methoxide (5.73 g, 106 mmol). The ice-chilled temperature of the mixture was maintained for an hour before acetonitrile-$d_3$ (6.0 g, 136 mmol) was added. The mixture was warmed to room temperature and was allowed to stir overnight before it was warmed to 40-43° C. for 4 hours. The cooled mixture was filtered and evaporated to a residue that was triturated with ethyl acetate (3×50 mL). The combined extracts were concentrated in vacuo, affording 1.5 g of a brown residue. MS (ESI) m/z 77.9 (M+1)+.

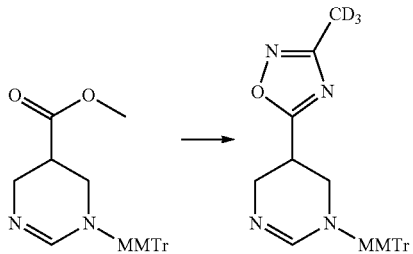

Step 2: 3-($d_3$-Methyl)-5-((4-methoxyphenyl)diphenylethyl)-1,4,5,6-tetrahydropyrimidin-5-yl)-1,2,4-oxadiazole To a chilled slurry of NaH (60% in mineral oil, 382 mg, 7.95 mmol) and dry THF (10 mL) was added acetamidoxime-$d_3$ (558 mg, 7.24 mmol). Molecular sieves (500 mg) wee added as the mixture was warmed to 50° C. for 40 minutes. Mmt-protected THP-methyl ester (1.0 g, 2.41 mmol) in 8 mL of THF was added and the mixture was warmed to 50° C. for 30 minutes, after which it was allowed to stir overnight at room temperature. The mixture was quenched with water (150 mL) and extracted with EtOAc (4×60 mL). The combined organics were washed with brine and dried over 50/50 ($K_2CO_3$/$Na_2SO_4$). The residue resulting from evaporation was loaded onto 20 g of silica gel in dichloromethane (DCM). The compound was eluted with DCM and DCM:MeOH:Et$_3$N (95:4:1) to afford 680 mg of a tan solid. MS (ESI) m/z 442.3 (M+1)+. $^1$H NMR (CDCl$_3$) δ2.78 (m, 1H), 3.20 (m, 1H), 3.47 (m, 2H), 3.75 (m, 1H), 3.80 (s, 3H), 6.83-7.39 (m, 14H), 7.55 (s, 1H).

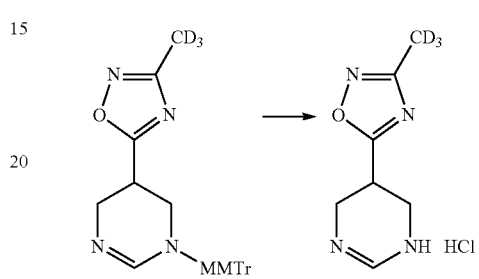

Step 3: 3-($d_3$-methyl)-5-(1,4,5,6-tetrahydropyrimidin-5-yl)-1,2,4-oxadiazole hydrochloride To a solution of Mmt-THP-methyl oxadiazole-$d_3$ (650 mg, 1.47 mmol) in MeOH (5 mL) was added 12 mL of 1.25 M HCl in MeOH. The solution was warmed for 4 hours at 35-43° C. before most of the Mmt protecting group was removed as determined by TLC (DCM:MeOH:Et$_3$N, 90:9:1). MeOH was removed in vacuo and the residue was triturated with MTBE (2×15 mL). Crystallization from EtOH and MTBE (2×) afforded 160 mg of a white solid. MS (ESI) m/z 170.2 (M+1)+, $^1$H NMR (DMSO-$d_6$) δ3.65 (dd, 2H), 3.76 (dd, 2H), 3.90 (m, 1H), 8.24 (s, 1H), 10.1 (bs, 2H).

Example 4

Synthesis of 3-(2,2,2-$d_3$-Ethyl)-5-(1,4,5,6-tetrahydropyrimidin-5-yl)-1,2,4-oxadiazole hydrochloride

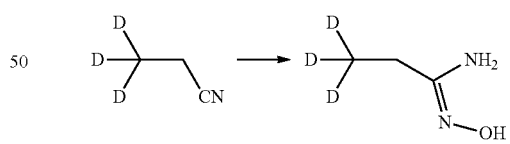

Step 1: 3,3,3-$d_3$-Propionamidoxime

Sodium methoxide (0.9 g, 16.67 mmol) was added to a stirred mixture of hydroxylamine HCl (1.16 g, 16.67 mmol) in anhydrous methanol (20 mL) at room temperature. The mixture was stirred for 0.5 hours before propionitrile-3,3,3-$d_3$ (1.03 g, 17.74 mmol) was added. The mixture was stirred mom temperature overnight before it was warmed at 45-50° C. for 6 hours. The cooled mixture was filtered and evaporated to a residue that was triturated with ethyl acetate (3×20 mL). The combined filtrates were concentrated in vacuo, to afford 0.6 g of amber oil. MS (ESI) m/z 92 [M+1]+.

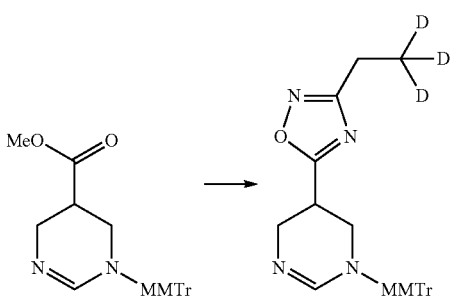

Step 2: 3-(2,2,2-d₃-Ethyl)-5-(1-((4-methoxyphenyl)
diphenylmethyl)-1,4,6-tetrahydropyrimidin-5-yl)-1,
2,4-oxadiazole NaH (60% in mineral oil, 310 mg, 7.75 mmol) was suspended in anhydrous THF (10 mL) at room temperature. Propionamidoxime-3,3,3-d₃ (590 mg, 6.47 mmol) was dissolved in 5 mL of THF and added to the NaH suspension and the mixture was warmed to 45-50° C. for 30 min. Mint protected THP-methyl ester (1.34 g, 3.23 mmol) in 10 mL of THF was added and the reaction mixture was heated at 45-50° C. for 1.5 hrs. The mixture was quenched with water (50 mL) and extracted with ethyl acetate (1×100 mL, 1×50 mL). After solvent removal, the crude product was chromatographed (silica gel 60; 1% TEA-ethyl acetate to 95:4:1 EtOAc:MeOH:TEA). The product fractions were concentrated in vacuo to afford 490 mg off-white foam. MS (ESI) m/z 456 [M+1]⁺. ¹H NMR (CDCl₃) δ2.68 (m, 2H), 2.80 (m, 1H), 3.22 (m, 1H), 3.49 (m, 2H), 3.69-3.75 (m, 1H), 3.79 (m, 3H), 6.83-6.86 (d, 2H), 7.23-7.39 (m, 12H), 7.65 (s, 1H).

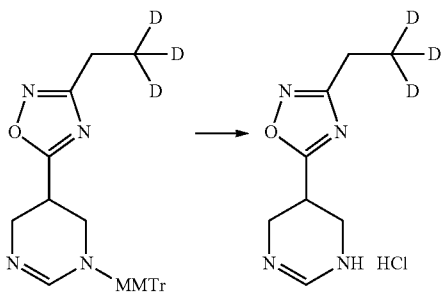

Step 3: 3-(2,2,2-d₃-Ethyl)-5-(1,4,5,6-tetrahydropyrimidin-5-yl)-1,2,4-oxadiazole hydrochloride To a solution of Mmt-THP-methyl oxadiazole-d₃ (480 mg, 1.05 mmol) in 5 mL DCM, 15 mL of 1.25 M HCl in MeOH was added. The solution was stirred overnight at ambient temperature followed by warming for 3 hours at 45-50° C. The MeOH was removed in vacuo and the residue was triturated with MTBE (2×5 mL). Treatment with activated carbon (50 mg) in ethanol (5 mL) followed by crystallization from EtOH/MTBE afforded 180 mg of a white solid. MS (ESI) m/z 184 [M+1]⁺, ¹H NMR (DMSO-d₆) 2.50 (s, 4H), 3.33 (s, 1H), 3.63-3.90 (m, 4H), 8.24 (s, 1H).

Example 5

Functional Activity at Muscarinic Type M1 and M3 Receptor

The functional activities of compounds at the muscarinic M1 and M3 receptors were evaluated by measuring the production of inositol phosphate from radio-labeled inositol following incubation of the compounds with Chinese Hamster Ovary cells expressing rat M1 receptors (M1-CHO: ATCC #CRL-1984) or rat M3 receptors (M3-CHO: ATCC #CRL-1981), using a modification of the method of Buck et al (BBRC 173: 666-672 (1990)). M1-CHO cells and M3-CHO cells were grown in 10 cm plates (Fisherbrand 08-717-53) in DMEM medium containing 10.24% fetal bovine serum (FBS), 1.9 mM glutamine, 511 units/ml of penicillin/streptomycin, and 973 micrograms/ml of G418 sulfate, and after trypsinization replated at 30,000 cells/well in 96 well microplates in DMEM with serum containing 50% reduced inositol and incubated for 24 hours at 36.5° C. in 95% air/5% $CO_2$. The medium was changed to 70 L/well of inositol-free DMEM containing 2 mM glutamine, 10% FBS and 10 μCi/ml of [3H]-inositol (PE:cat #NET114A250UC), incubated overnight as above, then 100 μL of a solution of the test compound in HBSS containing 10 mM LiCl and 20 mM HEPES, pH 7.4 was added, incubation was continued for 60 min under the above conditions, and the test was stopped by removing the test compound and replacing with 100 μL of 50 mM formic acid in water at 4° C. After 20 min at room temperature, after confirming complete lysis using a microscope, 20 μL of cell extract was transferred to a microplate with white walls and clear bottoms (Greiner T-3026-19) preloaded with 80 μL of YSi-SPA beads (GE: cat #RPNQ0013, 12.5 mg/mL in water), shaken on an orbital shaker at 100 rpm for 60 min, allowed to settle for a minimum of 120 min, then counted in a scintillation counter to measure the amount of [3H]-inositol converted to [3H]-inositol phosphate. The counts for each concentration of each compound were expressed as a percentage of the counts for maximal stimulation with the reference compound carbachol, and $S_{max}$ (maximum stimulation of inositol phosphate production from inositol) was calculated using a curve-fitting algorithm. Table 1 shows the mean $S_{max}$ of each compound relative to the mean $S_{max}$ for carbachol. The compounds in Table 1 are all dihydropyrimidine-oxadiazoles which vary only at the oxadiazole side chain.

TABLE 1

| Compound No. | Oxadiazole Sidechain | M1/CHO PI turnover Relative Mean $S_{max}$ | M3/CHO PI turnover Relative Mean $S_{max}$ |
|---|---|---|---|
| Carbachol | | 100.0 | 100.0 |
| 1c | Et | 70.0 | 46.4 |
| 2c | D5-Et | 67.7 | 16.5 |
| 3c | Me | 91.6 | 93.9 |
| 4c | D3-Me | 98.6 | 92.6 |
| 5c | D3-Et | 48.9 | 28.8 |
| 6c | D2-Et | 84.0 | 15.1 |
| 7c | CycloPropyl | 2.7 | 0 |
| 8c | Propenyl | 27.3 | 33.3 |

Example 6

Blood and Brain Concentrations (Rats)

Long-Evans Hooded rats (Charles River: male, 250-350 g) were dosed with solutions of test compounds in PBS by oral gavage. At the desired time after dosing, the animals were anesthetized with isoflurane, and then euthanized by cervical dislocation. Blood was obtained by cardiac puncture, transferred to a 1.5 mL microcentrifuge tube containing 15 U Heparin, and the plasma recovered after centrifugation. Brains were dissected, weighed, immediately chilled to 4° C., and homogenized using a PowerGen 125 homogenizer in five volumes of ice-cold 2% formic acid. Proteins were precipitated from plasma and brain homogenate with two and five volumes respectively of ice-cold 2% formic acid and clarified by centrifugation. The supernatant was ultra-filtered by centrifugation through a 3K MWCO spin column (Pall Life Sciences), following the manufacturer's instructions. The concentration of compound in the ultra-filtrate was subjected to reverse phase liquid chromatography using a 150×2.1 mm Agilent C8 reverse-phase column on a Shimadzu Prominence LC, eluting the compounds with a gradient of 2% to 50% of acetonitrile+0.1% formic acid for compound M1-50,382, or an isocratic flow of 2% acetonitrile+0.1% formic acid for the rest of the compounds listed. The concentration of the compound in the column effluent was measured using an Applied Biosystems API-3200 triple quadrupole mass spectrometer equipped with an electrospray sample injection system. The counts of the characteristic parent and product ions of each test compound were converted to concentration units by comparison with a standard calibration curve. Results are shown in Tables 2 and 3 below.

TABLE 2

| Compound No. | Oxadiazole Sidechain | Relative plasma $C_{max}$ (10 mg/kg po) 1 hr MCD-386 = 1.00 | Terminal $T_{1/2}$ (10 mg/kg po) MCD-386 = 1.00 |
|---|---|---|---|
| 1c | Et | 1.00 | 1.00 |
| 2c | D5-Et | 2.64 | 0.92 |
| 3c | Me | — | — |
| 4c | D3-Me | — | — |
| 5c | D3-Et | — | — |
| 6c | D2-Et | 2.49 | — |
| 7c | CycloPropyl | 2.43 | 0.84 |
| 8c | Propenyl | 0.51 | — |

TABLE 3

| Compound No. | Oxadiazole Sidechain | Brain $C_{max}$ (10 mg/kg po) 1 hr MCD-386 = 1.00 |
|---|---|---|
| 1c | Et | 1.00 |
| 2c | D5-Et | 0.61 |
| 3c | Me | — |
| 4c | D3-Me | — |
| 5c | D3-Et | — |
| 6c | D2-Et | 0.82 |
| 7c | CycloPropyl | 2.16 |
| 8c | Propenyl | 0.53 |

Example 7

Metabolites

Oxadiazoles disclosed herein as well as other oxadiazoles were investigated to determine the formation of metabolites. Animals were dosed, blood taken, serum prepared, serum proteins precipitated and ultrafiltrates prepared as described in Example 6. In separate experiments, urine was collected from rats for 16-24 hours after dosing, using standard metabolic cages. The urine container and collected urine were maintained at 4° C. Urine was lyophilized, taken back into water. The ultrafiltrate was prepared by adding formic acid to a final concentration of 1% to the urine samples, then filtered through a 0.2 um nylon membrane. The ultrafiltrate was subjected to LC-MS analysis. Instead of measuring the product ions in Q3, manual Q1 scans of the liquid chromatograph were undertaken, seeking parent ions of potential metabolites of the compounds. The criteria for identifying metabolites were as follows: (1) the ion should be present in the sera or urines of dosed rats, but not in sera or mines from non-dosed rats (2) the ion should be identifiable as a metabolic derivative of the dosed compound (e.g. loss of a functional chemical moiety, addition of a hydroxyl group or a glucuronic acid moiety, etc). Metabolites were determined not to be present if no compound meeting the above criteria could be detected in serum or urine. Results are shown in Table 4, below.

TABLE 4

| Compound No. | Oxadiazole Sidechain | Presence of metabolites (10 mg/kg po) |
|---|---|---|
| 1c | Et | Yes |
| 2c | D5-Et | No |
| 3c | Me | — |
| 4c | D3-Me | — |
| 5c | D3-Et | — |
| 6c | D2-Et | No |
| 7c | cyPr | No |
| 8c | propenyl | — |

Example 8

Synthesis of 3-(1,1-d$_2$-ethyl)-5-(1,4,5,6-tetrahydro-pyrimidin-5-yl)-1,2,4-oxadiazole hydrochloride

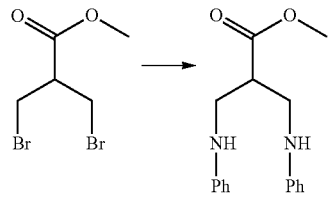

Step 1: Methyl 3-(benzylamine)-2-(benzylamino)methyl)propanoate dihydrochloride

Methyl 3-bromo-2-(bromomethyl)propenoate (20 g, 0.077 mol) was stirred in chloroform (200 mL) at 0-5° C. Benzylamine (21 mL, 0.193 mol) was added dropwise and the mixture was stirred at 0-5° C. for 15 min. Diisopropylethylamine (26 mL, 0.154 mol) was added dropwise and the mixture was warmed to room temperature and was refluxed for 2.0 hours. The mixture was cooled to room temperature and the organics were washed with 4×100 mL water, 1×100 mL saturated sodium chloride, and dried over Na$_2$SO$_4$. The dried organics were evaporated to a residue. The residue was dissolved in 50 mL methanol and cooled over ice water. To the chilled solution anhydrous HCl in ethanol 2.55 M (91 mL, 0.231 mol) was added. The mixture was concentrated to obtain an off-white solid. The solids were recrystallized from 60 mL 2-propanol and 180 mL ethyl acetate to obtain 23.71 g of dihydrochloride salt in 79.9% yield. The product was shown by Mass Spectroscopy to be a mixture of bis-benzyl diamine and mono-benzyl diamine, HPLC indicates 90% bis-benzyl diamine and 10% mono-benzyl diamine. An analytical sample of the bis-benzyl diamine was obtained from normal-phase silica gel chromatography (5% MeOH/EtOAc). MS (ESI) m/z 313 [M+1]$^+$. $^1$H NMR (CDCl$_3$) 2.80-2.91 (m, 5H), 3.69 (s, 3H), 3.76 (s, 4H), 7.23-7.30 (m, 10H).

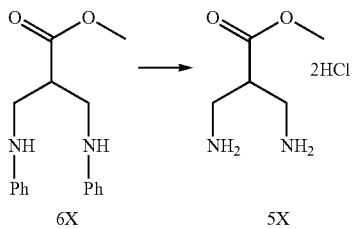

Step 2: Methyl 3-amino-2-(aminomethyl)propanoate dihydrochloride

Methyl 3-(benzylamino)-2-(benzylamino)methyl)propenoate dihydrochloride (6x) (22 g, 0.057 mol) was added to a Paar flask containing 198 mL acetic acid, 88 mL methanol and 7.0 g 10% Pd/C. The mixture was hydrogenated overnight in a Pair shaker at 34° C., upon which the reaction was still incomplete. So 1.8 g of 10% Pd/C was added and hydrogenation was continued overnight at 40-45° C. The reaction was complete and the mixture was filtered though a celite pad and washed with 2×100 mL methanol. The filtrate was concentrated, and the resulting residue was further concentrated from 100 mL of 1:1 methanol:toluene to remove residual acetic acid. The residue was dissolved in anhydrous HCl in ethanol 2.55 M (67 mL, 0.171 mol) and concentrated. The mixture was finally concentrated from 100 mL of 1:1 methanol:toluene to obtain an off white solid. The solids were recrystallized from 115 mL methanol and 115 mL ethyl acetate to obtain 10.19 g of dihydrochloride salt in 2 crops, 87% yield. MS (ESI) m/z 133 [M+1]$^+$. $^1$H NMR (CD$_3$OD) 3.26-3.31 (m, 5H), 3.86 (m, 3H).

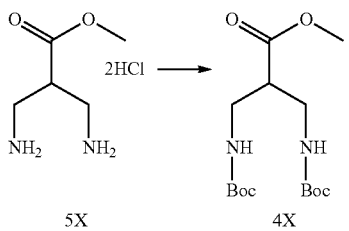

Step 3: Methyl 3-(tert-butoxycarbonylamino)-2-((tertbutoxycarbonylamino)methyl) propionate Methyl 3-amino-2-(aminomethyl)propionate dihydrochloride (5x) (11 g, 0.0536 mol) was added to a stirred mixture of di-tert-butyldicarbonate (23.4 g, 0.107 mol) and sodium hydrogen carbonate (18 g, 0.214 mol) in ethanol (165 mL) at room temperature. The mixture was heated to 40-45° C. for 2.5 hours upon which mass spectroscopy indicated the reaction was complete. The mixture was cooled to room temperature and concentrated. The residue was dissolved in 300 mL ethyl acetate and the organics were washed with 3×100 mL water, 1×100 mL saturated sodium chloride, and dried over Na$_2$SO$_4$. The dried organics were evaporated to an oil. The oil was dried under vacuum in a water bath at 40-45° C. for 2 hours to obtain 18.13 g of a clear colorless oil 101.8% yield. The material was used without purification. MS (ESI) m/z 333 [M+1]$^+$. $^1$H NMR (CDCl$_3$) 1.43 (s, 18H), 2.71-2.77 (m, 1H), 3.17-3.26 (m, 2H), 3.50-3.58 (m, 2H), 3.71 (m, 3H), 5.22 (s, 2H).

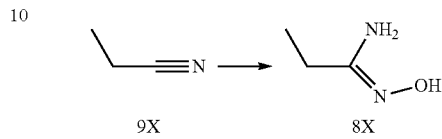

Step 4: Propionamidoxime

A solution consisting of propionitrile (5 g, 90.78 mmol) and methanol (40 mL) was heated to 64° C. prior to adding hydroxylamine (50% hydroxylamine by wt. in water, 4.28 ml, 69.83 mmol) in portions over a 25 min period. The mixture was refluxed for 4 hours at 67° C. and then allowed to stir overnight at room temperature. Evaporation of the solvent at 40° C. under vacuum followed by a 30 mL methanol azeotrope and drying under high vacuum for 6 hours provided the title compound, as a low melting off-white substance, in almost quantitative yield (6.0 g, 68.10 mmol). MS (ESI) m/z 89 [M+1]$^+$. $^1$H NMR (DMSO-d6) 1.01 (t 3H), 1.96 (q, 2H), 5.29 (s, 2H), 8.68 (s, 1H).

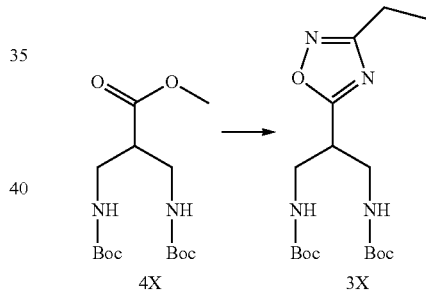

Step 5: tert-Butyl 2-(3-ethyl-1,2,4-oxadiazole-1-yl)propane-1,3-diyldicarbamate

NaH (60% in mineral oil, 1.19 g, 0.0322 mol) was suspended in anhydrous THF (38 mL) at room temperature. Propionamidoxime (2.53 g, 0.0287 mol) was dissolved in 15 mL of THF and added to the NaH suspension and the mixture was warmed to 45-50° C. for 30 min. Methyl 3-(tert-butoxycarbonylamino)-2-((tertbutoxycarbonylamino)methyl) propionate (3) (3.82 g, 0.0115 mol) in 15 mL of THF was added to the mixture and the reaction mixture was heated at 45-50° C. for 2.0 hrs. The mixture was concentrated and partitioned between water (50 mL) and ethyl acetate (1×150 mL). The organics were washed with 2×50 mL water, 1×50 mL saturated sodium chloride, and dried over Na$_2$SO$_4$. The dried organics were evaporated to a semisolid. The residue was crystallized from 3 mL 2-propanol and 18 mL hexanes to obtain 1.5 g of white solid, 35% yield. MS (ESI) m/z 371 [M+1]$^+$. $^1$H NMR (CDCl$_3$) 1.30-1.34 (m, 3H), 1.44 (s, 18H), 2.72-2.78 (m, 2H), 3.33 (m, 4H), 3.74-3.78 (m, 1H), 7.26 (s, 2H).

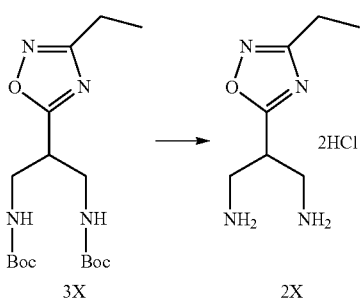 [SMILES: CCc1noc(C(CNC(=O)OC(C)(C)C)CNC(=O)OC(C)(C)C)n1 ; CCc1noc(C(CN)CN)n1]

Step 6: 2-(3-ethyl-1,2,4-oxadiazole-5-yl)propane-1,
3-diamine dihydrochloride

To a stirred mixture of ter-butyl 2-(3-ethyl-1,2,4-oxadiazol-5-yl)propene-1,3-diyldicarbamate (3×) (1.4 g, 0.0038 mol) in 3 mL ethanol, 2.3 M HCl in ethanol (13 mL, 0.0303 mol) was added at room temperature. The mixture was heated to 40-45° C. for 1 hour upon which mass spectroscopy indicated the reaction was complete. The resulting slurry was cooled to room temperature and 16 mL ethyl acetate was added. The solids were filtered and washed with 5 mL 10% ethanol/ethyl acetate and 2×5 mL ethyl acetate to obtain 0.78 g of dihydrochloride salt, 84.7% yield. MS (ESI) m/z 171 [M+1]+. 1H NMR (CD$_3$OD) 1.32-1.36 (m, 3H), 2.81-2.83 (m, 2H), 3.49-3.51 (m, 4H), 3.90-3.96 (m, 1H).

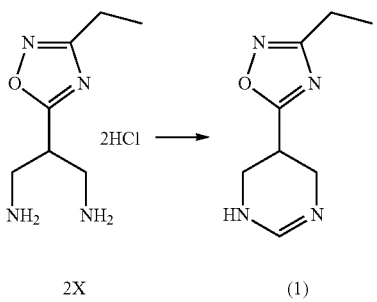

Step 7: 3-ethyl-5-(1,4,5,6-tetrahydropyrimidin-5-yl)-
1,2,4-oxadiazole (1)

To a stirred mixture of 2-(3-ethyl-1,2,4-oxadiazol-5-yl)propene-1,3-diamine dihydrochloride (2×) (5.0 g, 0.0206 mol) in 60 mL ethanol, triethylorthoformate (24 mL, 0.144 mol) was added at room temperature. The mixture was heated to reflux for 1 hour upon which mass spectroscopy indicated the reaction was complete. The mixture was evaporated and concentrated from 50 mL ethanol to remove excess triethylorthoformate. The residue was crystallized twice from 2-propanol/MTBE followed by ethanol/MTBE to obtain 2.6 g of white solid, 58% yield, HPLC purity 99.8%. MS (ESI) m/z 181 [M+1]+. 1H NMR (DMSO d6) 1H NMR (DMSO d6) 1.20-1.24 (m, 3H), 2.71-2.75 (s, 2H), 3.63-3.91 (m, 5H), 8.24 (s, 1H).

Biological Results for Compounds Prepared it this Example

Compounds 2 and 6 were M1-subtype functionally selective muscarinic agonists, as evaluated by PI turnover in cell lines expressing individual subtypes of muscarinic receptors, with a similar efficacy and selectivity to compound 1. Compound 7 demonstrated muscarinic agonist activity in vivo, even though its activity in vitro (Table 4) was relatively low.

The plasma concentrations of compound 7 was approximately 2.4 times and compounds 2 and 6 were approximately 2.5 to 2.6 times higher than those of compound 1 after oral dosing to rats. No metabolites were identified in plasma or urine of rats dosed orally with compounds 2, 6 and 7. It is concluded that the higher plasma concentrations of compounds 2, 6, and 7 are due to reduced or no metabolism of these compounds. Compounds 2, 6, and 7 penetrated into the brain of rats after oral dosing.

Compound 4 was a near full-agonist at both M1- and M3-subtype muscarinic receptors as evaluated by PI turnover. However, it was not selective for the M1 subtype. In these respects it was essentially the same as compound 3. In rats, compounds 3 and 4, dosed orally, produced copious salivary flow, which was relatively short-lived, underscoring the lack of M1- versus M3-subtype selectivity. The duration of action was short, suggesting a very short plasma half-life.

These results suggest that compounds 2 and 6 will have utility for stimulating M1 muscarinic activity in humans, while avoiding the side effects due to stimulation of M3 muscarinic receptors. These compounds will have utility for improving cognition and memory, with low potential for causing side effects at therapeutic doses.

The properties of compounds 2 and 6 were unexpected and surprising. Adding 5 or 2 deuterium atoms respectively, despite their different chemical properties relative to hydrogen, did not significantly alter the intrinsic efficacy at the M1-subtype muscarinic receptor, nor their functional selectivity for the M1- versus the M3-subtype muscarinic receptors. It is notable that practically all other small changes made to the ethyl side chain, such as converting it to longer chain alkyl reduced the efficacy at the M1-subtype muscarinic receptor. Replacing the ethyl side chain with methyl or D3-methyl, dramatically increased the intrinsic efficacy at muscarinic receptors. However replacing the ethyl with methyl or D3-methyl also dramatically reduced the functional selectivity for the M1-subtype over the M3-subtype, which was demonstrated not only in cell lines, but also by side effects in vivo. These small changes also dramatically reduced the duration of action. Thus, compounds 2 and 6 are unique in their beneficial combinations of properties as potential drugs.

Example 9

Immediate Release Formulation

The hydrochloride salt of MCD-386 ("MCD-386HCl") was formulated with the following excipients and loaded into #3 hard gelatin capsules (5 mg dose) or #2 hard gelatin capsules (0.2 mg dose).

TABLE 5

| Component | 5 mg Capsule | 0.2 mg Capsule |
|---|---|---|
| MCD386 HCl | 5.0 mg | 0.2 mg |
| Lactose, Anhydrous, NF | 168.0 mg | 113.8 mg |
| Citric Acid Anhydrous, USP | 3.5 mg | 2.5 mg |
| Stearic Acid, NF | 3.5 mg | 2.5 mg |
| Sodium Chloride, USP[a] | 1 unit | 0.2 mg |

[a]Not present in the drug product, used as a polishing agent only

A single 5 mg capsule or 5×0.2 mg capsules (1 mg total dose) were administered orally to healthy male volunteer human subjects with 125 ml of water. Six such subjects receiving the 5 mg dose, and a different 6 subjects received the 1 mg dose.

Subjects were monitored, among other things, for typical signs of muscarinic cholinergic action, such as increased salivation, lachrimation and diaphoresis.

Venous blood samples were drawn at various intervals after dosing from each subject into standard tubes for bioanalytical and pharmacokinetic analysis. The blood was allowed to clot, and the serum separated, using common clinical laboratory techniques. Serum samples were stored at −20 deg C. until used for analysis.

MCD-386 HCt, which exists in serum principally as the protonated form of MCD-386, was assayed in clinical serum samples as follows. 200 μL aliquots of serum samples were spiked with 50.0 μL of diluent for subject samples and QC samples and 50 μL of the appropriate intermediate standard solution for standards. Twenty five microliters (25.0 μL) of working internal standard stock solution and 40.0 μL of 10 N sodium hydroxide was then added and the samples were vortex mixed. Three milliliters (3.00 mL) of ethyl acetate was added followed by 5 minuses of vigorous vortexing and centrifugation. The top organic layer was transferred to a clean tube, evaporated to dryness, and the sample was reconstituted with 100 μL of diluent (0.1% formic acid). A 10 μL aliquot of this reconstituted sample was injected into Phenomenex Synergy 4μ POLAR-RP, 75×2.0 mm (P/N 00C-4336-B0) on a Waters Acuity UPLC LC system, and eluted using a gradient of from 12% to 90% acetonitrile containing 0.1% formic acid 10.1% formic acid in water. The eluant flow of the LC was injected by Turbo Ion Spray (positive ion) into a Sciex API 4000 (Applied Biosystems). The MS/MS transitions monitored were 181.1 m/z to 111.0 m/z for MCD-386 HCl and 186.1 m/z to 111.1 m/z for the internal standard, D5-MCD-386 HCl. The calibration curve was linear between 0.100 ng/mL and 50.0 ng/mL for MCD-386 HCl. The lower limit of quantitation (LLOQ) was 0.100 ng MCD-386 HCl per mL of serum. MCD-386 HCl concentrations are expressed as free base.

The bioanalytical method for the extraction of metabolites from serum samples entailed adding 450 uL of a 90% acetonitrile+0.1% formic acid solution to 50 uL of the serum samples. The samples were vortexed and centrifuged at 16,000×g at 4° C. for 10 minutes. The supernatants were transferred to 3K molecular weight cut-off (MWCO) spin filters (Pall, Nanosep, #82031-346). Samples were filtered by centrifugation at 13,000×g at 4° C. for 20 minutes. The filtrates were transferred to a 96-well plate and sealed for LC/MS/MS analysis. The system used for this analysis was a Shimadzu Prominence HPLC system. Sample separation and desalting was achieved with a HPLC column (Phenomenex Luna, 3 um, 150×2.0 mm) maintained at 35° C., using a gradient of 100% to 50% of 90% acetonitrile+30 mM ammonium formate, pH 3.5/H2O+30 mM ammonium formate, pH 3.5 at a flowrate of 0.3 mL/min. The autosampler was maintained at 4° C. Injection volumes for all samples and standards were 40 uL. MRM methods for two possible metabolites were made. An API 3200 triple-quadrupole mass spectrometer with a Turbo V source (Applied Biosystems) was used, following commonly used procedures which would be readily set up by a person skilled in the art of LC-MS/MS. The counts of the characteristic parent and product ions of the free base metabolites were converted to concentration units by comparison with a standard calibration curve.

The bioanalytical results are analyzed using Win Nonlin software and common pharmacokinetic methods known to those skilled in the art.

Figure 5:
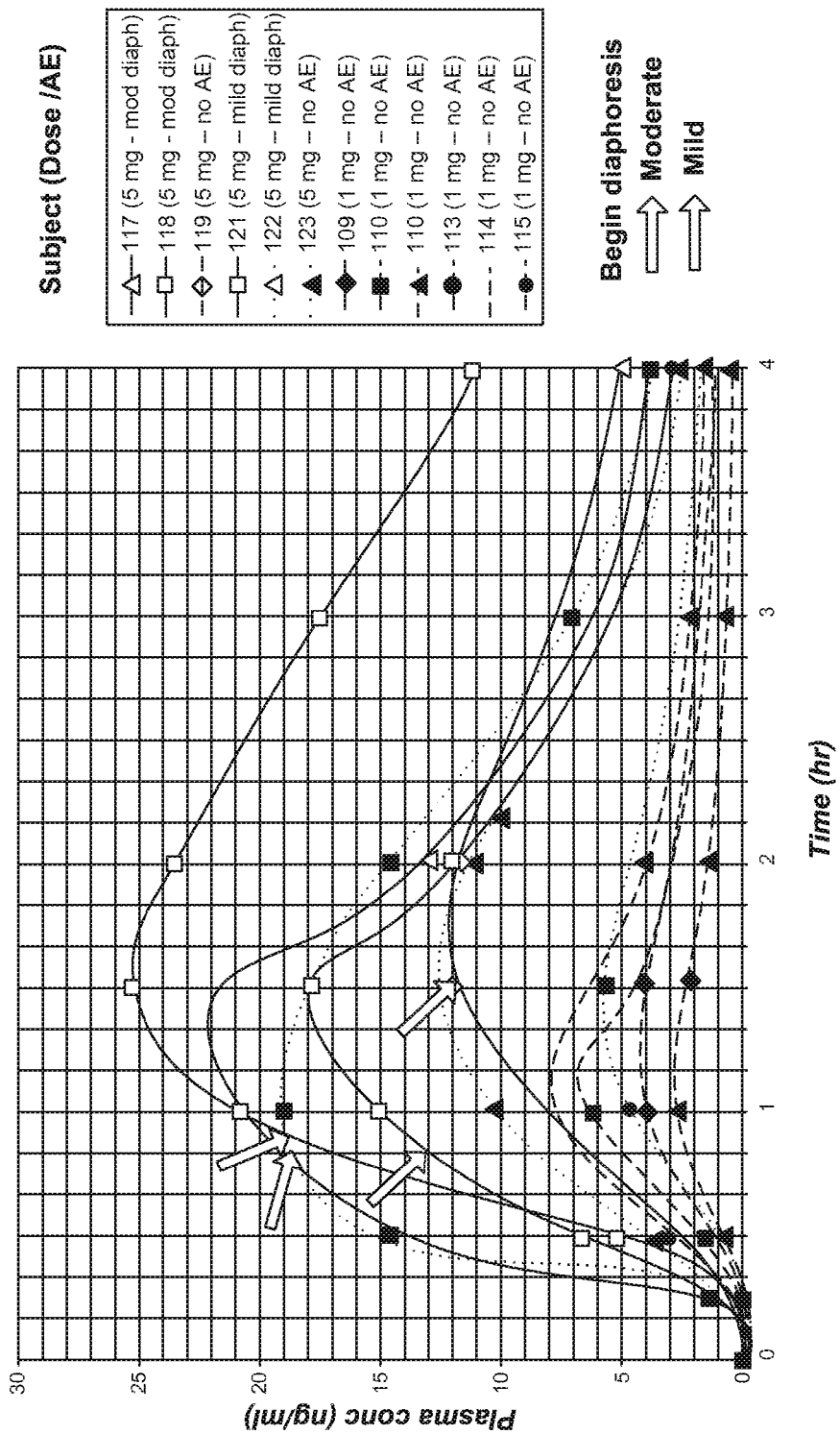
FIG. 5 shows the Cmax and diaphoresis results for two cohorts of patients described in Example 1 who were given 1 mg and 5 mg of immediate release formulations of the hydrochloride salt of 5-(3-ethyl-1,2,4-oxadiazol-5-yl)-1,4,5,6-tetrahydropyrimidine.

The results of the testing are provided in FIG. 5. As seen therein, none of the subjects in the 1 mg total dose cohort experienced any observable cholinergic side effects of the MCD-386 HCl. In the cohort receiving 5 mg of MCD-386 HCl, two subjects experienced no observable side effects, and four subjects showed signs of muscarinic cholinergic activity. Two of these latter subjects experienced mild, transient diaphoresis that resolved within a short period, and two subjects experienced moderate diaphoresis that resolved within a short period. One of the latter subjects also experienced mild hypersalivation.

The pharmacokinetic analysis showed that the free base of MCD-386 was rapidly released from the formulation and rapidly absorbed. The Tmax was between 1 and 1.5 hours. The serum Cmax in the 6 subjects receiving 1 mg of MCD-386 HCl did not exceed 8 ng/ml. The serum Cmax in the 6 subjects receiving 5 mg of MCD-386 HCl ranged from 7.9 ng/m to 25.2 ng/ml, demonstrating a degree of subject-to-subject variability.

The two subjects with moderate diaphoresis had higher Cmax than the subjects with mild diaphoresis. The subject experiencing mild hypersalivation had the highest Cmax. The side effects appeared to be related to the serum concentration of the free base However the Cmax in two subjects experiencing no side effects was within the range of the four subjects that experienced side effects, demonstrating that there is person-to-person variability in the relationship between side effects and serum concentration.

The pharmacokinetic analysis also revealed a short half-life of the free base. In the 1 mg cohort, the half-life was 1.44+/−0.28 (SD) hours. In the 5 mg cohort, the half-life was 1.71+/−0.62 (SD) hours. The half-life in one subject was longer than any of the other 5 subjects, and was 2.93 hours. Excluding this subject, the mean half-life for the other 5 subjects in the 5 mg cohort was 1.44+/−0.19 hours. The mean half-life in a third cohort of 6 subjects receiving 0.2 mg of MCD-386 HCl was 1.2+/−0.28 (SD) hours.

Significantly, abundant amounts of a main metabolite of the free base were identified in the serum samples of five out of six subjects in the 5 mg dose cohort. As discussed previously, the main metabolite was found to have the structure 5-(3-((1-hydroxyethyl)-1,2,4-oxadiazol-5-yl)-1,4,5,6-tetrahydropyrimidine. The one subject with no metabolites bad the highest Cmax and the longest serum half-life (discussed above), suggesting that metabolism might be contributing to the surprisingly short half-life of the free base, and further that if metabolism can be reduced, the serum concentration of the free base could be maintained for longer. In view of these results, the transdermal delivery method described herein should provide an advantageous approach to not only reduce the deleterious effects of metabolism by avoiding first-pass metabolism by bypassing the intestinal walls and liver, thereby improving bioavailability, but also means to control blood levels of the drug, thereby avoiding side effects, maintaining therapeutic effects, and reducing the dosage frequency.

Example 10

Delivery of MCD-386 in Rats Using an Iontophoresis Patch

The transdermal delivery method described in this application provides a practical way to not only reduce metabolism (since transdermal delivery the drug avoids first-pass metabolism by bypassing the intestinal walls and liver), improving bioavailability, but also to provide a means to control blood levels of the drug, thereby avoiding side effects.

Two patches were made up, consisting (in order from the outer layer to the skin contacting surface, respectively): adhesive tape (Transpore, 27 mm wide, 3M), circular stainless steel electrodes (22 mm dia) with a central hole for a stainless steel machine screw to which the electrode wire was attached, and 2 layers of 3 MM CHR filter paper (Cat #3030-861, Whatman international, Ltd).

The mid-dorsal area of a Long Evans Hooded rat (approximate weight, 320 grams), surgically prepared with a jugular vein catheter (Charles River), was shaved and the skin was then cleaned using an Electrode Prep Pad (Professional Disposables, Inc, Cat #B59800).

100 µl of a solution of MCD-386 HCl (10 mg/ml) was applied to the filter paper pd of one electrode patch assembly, to become the anode, and 100 µl of 0.9% saline was applied to the filter paper pad of another electrode patch assembly, to become the cathode.

The electrode patch assemblies were place one on each side of the spine in the mid-dorsal region, previously prepared as above. The electrodes were connected with the indicated polarity to a simple electrical circuit comprising a 9 volt alkaline battery, a variable resistance potentiometer (10 k ohms) and a digital multimeter. The current was manually adjusted to and maintained at 380 microamps, using the potentiometer.

A second similar catheterized rat was dosed orally by gavage with MCD-386 HCl (10 mg/kg).

Blood (400 µl) was withdrawn from the catheters in each rat every 30 minutes, transferred to 1.5 ml centrifuge tubes containing heparin (15 units/tube), and the plasma was separated by centrifugation from the cellular components. The plasma samples were maintained at 4 deg C. until analyzed.

Proteins were precipitated from plasma samples with two volumes of ice-cold 2% formic acid and clarified by centrifugation. The supernatants were ultra-filtered by centrifugation through a 3K MWCO spin column (Pall Life Sciences), following the manufacturer's instructions.

The ultra-filtrates were subjected to reverse-phase liquid chromatography using a 150×2.1 mm Agilent C8 reverse-phase column on a Shimadzu Prominence LC, eluting the MCD-386 with an isocratic flow of 2% acetonitrile+0.1% formic acid. The concentration of MCD-386 in the column effluent was measured using an Applied Biosystems API-3200 triple quadrupole mass spectrometer equipped with a Turbo V source (electrospray sample injection) system. The counts of the characteristic parent ions of the protonated MCD-386 (m/z=181.2) and product (m/z=111.1) ions were converted to concentration units by comparison with a standard calibration curve.

The experiment demonstrates that MCD-386 may be delivered efficiently by iontophoresis. Notably, the plasma concentration of MCD-386 reached almost 850 nM 30 minutes after turning on the current. The plasma concentration at 30 minutes of a rat administered 3.1 mg/kg by iontophoresis was almost identical to that of the rat administered MCD-386 by oral gavage (Table 6), suggesting that the bioavailability by transdermal delivery is up to three times higher than by oral administration. The results indicate that transdermal delivery may avoid first pass metabolism of MCD-386 in the intestinal wall and/or liver, as appears to occur with oral dosing of MCD-386. The patch delivered drug at a rate sufficiently high to exceed the threshold plasma concentration to cause increased salivation. Skilled artisans, however, will appreciate that the current may be adjusted to deliver drug at a lower rate to maintain a steady plasma concentration above the therapeutic level and below the level at which side effects such as diaphoresis or salivation are triggered.

TABLE 6

| Route of Administration | Dose (mg/kg) | Plasma Concentration (nM) |
| --- | --- | --- |
| Iontophoresis patch | 3.2 | 848 |
| Oral gavage | 10.0 | 911 |

A person skilled in the art will also appreciate that an iontophoresis patch designed for human use may have several additional features, e.g., to assure the safety and comfort of patients, the quality, cost and reproducibility of manufacture, the shelf-life, and to improve the convenience to patients and the like. The adhesive tape would be medical grade, so as not to irritate the skin. The patch may be distributed preassembled in an impermeable pouch, such as a peel-apart foil pouch, and may have the appropriate amount of drug already loaded, and may be pre-wetted, so that the patient need only open the packaging and apply the patch to the skin. The drug-containing anodic compartment and the cathodic compartment may be part of a unitary device, with the optimum spacing, to simplify the accurate placement of the electrodes on the skin. To increase the delivery capacity and reduce the frequency of replacing the patches, the electrode compartments may contain immobilized buffers to absorb the ions produced by electrolysis of the water, thereby stabilizing the pH and preventing skin irritation or chemical burns. The electrodes may be any inert, electrically conducting material (such as carbon), and may be fabricated economically by many different processes such as deposition by spraying or printing. Alternatively, the electrodes may be consumed (even provide the current by acting as a battery), providing a means to control the amount of electrical power provided by controlling the amount of electrode material. The electronic circuit preferably contains current controlling components, since current determines the rate of delivery of the drug, and most preferably will provide constant current against varying electrical resistance. The electronic circuit may usefully provide indicators that the unit is functional, that it is within specifications that it has been activated, and may also provide safety interlocks and warnings for patient safety.

Example 11

Prophetic Example of Delivery of MCD-386 to Humans Using an Iontophoretic Patch

The drug is delivered from a reservoir compartment, in intimate contact with the skin, containing an anodic electrode A second compartment, also in intimate contact with the skin, contains a cathodic electrode. Both compartments contain absorbent layers which contain dissolved buffers and electrolytes wetted with an aqueous solution providing electrical contact between the electrodes and the skin. The reservoir compartment additionally contains a measured amount of drug dissolved in the aqueous phase. The electrodes are connected with the appropriate polarity to a direct current source with a means to control the current. Since the drug is positively charged at the pH of the drug solution and at the pH of the epidermis and dermis, it is transported out of the reservoir, through the epidermis and dermis, taken up by the microvasculature, and distributed around the vascular system. The rate of delivery of drug is proportional to the current, so the dosing rate may be controlled by controlling the current by varying the voltage, preferably using a constant current control device.

DuPel BLUE electrodes (EMPI, St Paul, Minn.) are used for iontophoretic delivery of MCD-386. These ready-made devices contain (in order of distance from the skin) an adhesive patch, carbon electrodes with a snap connector for electrical connection, a layer of pH buffering resin, a foam drug reservoir, and wicking paper layer that contacts the skin. Depending on the dose required, small (cat #199332-1.5 ml capacity), medium (cat #199335-2.5 ml capacity) or large (Cat#199336-4.0 ml capacity) patches are used. A solution of MCD-386 HCl (3.1 mg/ml) in sterile water for injection USP is applied to the device that is to be the anode (in the small sized device, assuming three times a day dosing in an average patient), and a few drops of sterile water for injection USP is applied to the part of the device that is to be the cathode, following the manufacturer's instructions contained in the product insert. The amount of MCD-386 HCl applied to the device may be tailored for each patient, either by adjusting the concentration of MCD-386, or using the medium or large devices. The devices are pressed onto the skin, following the instructions in the product insert, and are attached by the adhesive on the outer circumference of the patch. The positive (red) wire of a constant current DC power source (EMPI DuPel device) is applied to the drug containing (anodic) device and the black wire is attached to the non-drug containing (cathodic) device. The current is tailored for each patient, starting at 250 microamps, using increasing current until the appearance of diaphoresis signals the maximum tolerated dose has been reached. The current is then reduced until no diaphoresis occurs, and maintained until a maximum current dose of 80 mA•min has been administered. Alternatively, the current may be set using the serum concentration of MCD-386.

Example 12

Prophetic Examples of Gastric Retained Tablet Formulations of MCD-386

Drug, polymer(s) and fillers) are provided in fine particulate form, about 90% passing through a 100-mesh screen. Preferably, CR grades and direct compression grades of polymer(s) and fillers are used. All excipients age produced under GMP for Finished Pharmaceuticals and meet the compendial requirements of the United States and Europe.

A pre-selected amount of MCD-386 is added to the blender to provide a dose of 5.0 mg (expressed as the free base) per finished tablet—in this case approximately 5.0 grams for each 750 grams of formulation mix to make about 1,000 tablets, without allowance for waste. Drug, polymer and filler are blended for 10 minutes in a V-blender. Powder flow aid and lubricant are added and blending is continued for a further 5 minutes. These processes are well-known in the art, and a wide range of equipment is available for batches ranging from laboratory scale to commercial scale.

In the compositions of this example, drug release is principally controlled by the rapid formation of a dense gel layer on the outside layers of the tablet when it contacts fluid in the stomach of the patient. The gel is formed by rapid hydration of the Methocel polymer. Preferably the Methocel polymer is in fine particle form to ensure rapid hydration and uniform dense gel formation. The drug release rate is controlled by the concentration of polymer and its viscosity. For faster release, the lower viscosity Methocel K4M grade is used. For slower release, the higher viscosity K15M or K100M grades are used. These may be mixed to achieve intermediate levels of viscosity, and the properties of the mixes may be predicted using the Furchgott equation. Mixes of two Methocel polymers may give better results than single grades, independent of viscosity. Formulation mix #4 (Table 10) below contains a high molecular weight polyoxyethylene diffusion control polymer (Polyox WSR-303 NF from Dow Chemical Company). Other suppliers provide hydrophilic gel matrices with similar properties and these may be substituted for Methocel by one skilled in the art. The Eudragit RS and RL grades of (meth)acrylate polymers from Degussa/Evonik (Rohm GMBH & Co KG. Germany) are two examples of suitable polymers. An extended discussion of suitable polymers is provided in Tiwari, S B and Rajabi-Siahboomi, A R., "Extended-Release Oral Drug Delivery Technologies: Monolithic Matrix Systems". Chapter 11 in Methods on Molecular Biology, Vol 437: Drug Delivery Systems (Humana Press).

Tablet erosion is also controlled by the polymer concentration and viscosity, higher concentrations and higher viscosity reducing the disintegration rate of the tablets.

The release rates may be modified by including additional polymers ("modifiers"). These may also strengthen the tablet to reduce t rate of erosion. They may also prevent unwanted initial release of drug in a "burst" when the tablet first hydrates. Formulation #2 (Table 8) contains Ethocel as a modifier, and formulation #3 (Table 9) contains partially pro-gelatinized starch as a modifier. The starch may actively interact with the Methocel to improve the properties of the tablets. Numerous modifier polymers are known to those skilled in the art and may replace a proportion of the filler.

Different fillers/binders may be used. For example, formulation #1 (Table 7) contains finely milled microcrystalline cellulose (MCC), which has excellent properties for dry compression—the compressibility indexes of selected grades of MCC are quite similar to that of Methocel K4M. Formulation #2 and #4 contain lactose, which is soluble, and leaches out of the tablet along with drug and may help water penetrate into the tablet, but may cause drug to be release more quickly than desired. Those skilled in the art will understand that many other types of filler may be used, including insoluble fillers, such as calcium phosphate dehydrate or calcium sulfate. Insoluble fillers will generally slow down release of drug.

Alternatively, wet granulation techniques well know in the art are used to provide uniform distribution of the relatively low dose of drug and thereby achieve adequate dose reproducibility. The drug, polymer and filler are mixed and wetted with water using a cone spray nozzle, wet milled, dried in a 110 deg F. oven, dry milled, blended with lubricant for 1 minute in a suitably-sized V-blender, and then compressed into tablets.

The blended mix is compressed into tablets using a tablet press (e.g. Manesty F3 single station press, or fully instrumented Piccolla rotary 10-station) using 12.8 mm concave tooling. The compression force and rate is controlled to provide well-compressed non-friable tablets without layering flaws and with suitable hardness.

The tablets made with formulation mix #2 are also coated with ethylcellulose to further modify the release rate, using an aqueous suspension of ethylcellulose (Surelease, Coloreon) and methods that are well-known in the art. The tablets are tumbled in a coating machine, Surelease is sprayed onto the tablets at a suitable rate and they are quickly and continuously air-dried. Coating is complete when the weight has increased by about 4%. The coating machine may be the pan type (O'Hara Lab Coat-I) or may use a fluidized bed process (Glatt). The coatings may contain plasticizers to avoid crazing and cracking, and glidants such as talc or silica may be added, to improve processability and handling. Coating substances are available from many manufacturers that may be substituted for ethylcellulose by a person skilled in the art, such as the Eudragit NE or NM grades of (meth)acrylate polymers from Degussa/Evonik (Rohm GMBH & Co KG, Germany)

Any of the tablets manufactured using any these formulation mixes may be additionally coated with an active layer such as ethyl cellulose, or a coating to make it easier to swallow the tablets, or simply for esthetics. Such costing substances and methods are well-known in the art.

Tablets are tested for physical properties (e.g. hardness—Key International Hardness Tester, Model HT500), dissolution (standard USP protocols, using a USP Type 2 apparatus (Distek Model 2100) with a peddle speed of 50 rpm and artificial gastric fluid, and disintegration. It will be appreciated that the compositions exemplified in this example may be modified to achieve the desired release rate and duration of release.

TABEL 7

| Formulation mix #1 | | Source | Amount |
|---|---|---|---|
| Polymer | Methocel K4M Premium CR or DC Grades | Dow Chemical Company | 35.0% |
| Filler | Microcrystalline cellulose- Avicel PH102 | FMC, Brussels, Belgium | 64.0% |
| Powder flow aid | Aerosil 200 | Degussa (Evonik), Dusseldorf, Germany | 0.5% |
| Lubricant | Magnesium stearate | Malinckrodt | 0.5% |
| | Total | | 100.0% |

TABLE 8

| Formulation mix #2 (final tablet coating 4% by weight of ethylcellulose (Surelease-Colorcon) | | Source | Amount |
|---|---|---|---|
| Polymer | Methocel K15M Premium CR or DC Grades | Dow Chemical Company | 35.0% |
| Modifier polymer | Ethocel 100FP Premium | Dow Chemical Company | 25.0% |
| Filler | Lactose Fast-Flo #316 | Foremost Farms, WI | 39.0% |
| Powder flow aid | Aerosil 200 | Degussa (Evonik), Dusseldorf, Germany | 0.5% |
| Lubricant | Magnesium stearate | Malinckrodt | 0.5% |
| | Total | | 100.0% |

TABLE 9

| Formulation mix #3 | | Source | Amount |
|---|---|---|---|
| Polymer | Methocel K4M Premium CR or DC Grades | Dow Chemical Company | 35.0% |
| Filler | Partially pregelatinized starch-Starch 1500 | Colorcon | 64.0% |
| Powder flow aid | Aerosil 200 | Degussa (Evonik), Dusseldorf, Germany | 0.5% |
| Lubricant | Magnesium stearate | Malinckrodt | 0.5% |
| Total | | | 100.0% |

TABLE 10

| Formulation mix #4 | | Source | Amount |
|---|---|---|---|
| Polymer | Polyox WSR-303 NF | Dow Chemical Company | 39.0% |
| Filler | Lactose Fast-Flo #316 | Foremost Farms, WI | 60.0% |
| Powder flow aid | Aerosil 200 | Degussa (Evonik), Dusseldorf, Germany | 0.5% |
| Lubricant | Magnesium stearate | Malinckrodt | 0.5% |
| Total | | | 100.0% |

Example 13

Metabolism of MCD-386

As discussed above in Example 9, it has been discovered that MCD-386 is metabolized in the body, that the ability of the body to metabolize MCD-386 HCl may vary from person to person, and that persons with no or decreased ability to metabolize Compound I will have increased bloodstream concentrations of MCD-386. Accordingly, before prescribing the dosage of MCD-386, physicians may want to test that patient for his/her ability to metabolize the drug. The main metabolite of MCD-386, which is 5-(3-((1-hydroxyethyl)-1, 2,4-oxadiazol-5-yl)-1,4,5,6-tetrahydropyrimidine, can be screened for directly by preparing a test to detect the presence and quantity of the metabolite following administration of the drug. Such a test can be accomplished any number of ways. For example, following a predetermined time after administration, a blood sample can be taken and used to determine the concentration of Compound I in the patient's bloodstream. That concentration then can be compared against known values (as determined from patients who are able to metabolize the drug) to determine the patient's ability to metabolize the drug. Alternatively, the blood can be tested to determine the presence and quantity of the metabolite, which is then compared to known values. Any number of methods for determining the presence and quantity of the Compound I or its metabolite can be employed. For example, an antibody to MCD-386 or its metabolite can be generated using known methods of immunization and selection, and used to detect and quantify the metabolite, e.g. in a antibody-antigen binding reaction. Other quantification tests such as HPLC can be used. Alternatively, the enzymes (or variant alleles of the respective genes) responsible for metabolism can be identified and the patient then could be screened for the presence of the enzyme or gene variant. The test for determining the patient's ability to metabolize MCD-386 may be performed instead of or in addition to either or both of the tests described above, i.e., to determine the patient's concentration of MCD-386 or observed cholinergic side effects, following administration of MCD-386.

Accordingly, embodiments of the disclosure herein provide testing patients to determine their ability to metabolize MCD-386. This test may be conducted prior to prescribing the dosage for a patient in order to prescribe the appropriate dosage for the patient. Alternatively, or in addition, patients may be tested over time to determine whether their ability to metabolize the drug has changed, thereby warranting a change in their prescription.

Example 14

Coated Matrix Controlled Release Tables of MCD-386 Composition

The tablets have a core containing drug, hydrogel polymer, release modifiers and inactive excipients, with the composition shown in Table 11. Cores have an ethyl cellulose/hypromellose coating as shown in Table 11. These tablets release MCD-386 less than 15% in 30 minutes, between 45 and 70% in 240 minutes and >90% in 720 minutes, to provide for twice-a-day dosing.

TABLE 11

| Component | Reference to Quality Std | Function | mg per tablet |
| --- | --- | --- | --- |
| Core Tablet: | | | |
| Drug substance | NF | Active ingredient | 5 |
| Hydroxypropyl methylcellulose | USP | Drug release control | 60 |
| Sodium carboxy methylcellulose | USP | Drug release control | 60 |
| Avicel PH102 (microcrystalline cellulose) | USP | Insoluble filler | 71 |
| Emcompress (dicalcium phosphate) | USP | Insoluble filler | 200 |
| Aerosil 200 (colloidal silicon dioxide) | USP | Glidant | 2 |
| Magnesium stearate | USP | Lubricant | 2 |
| Core tablet weight | | | 400 mg |
| Film Coat Solution: | | | |
| Purified water | ? | Solvent | |
| Surelease E-7-19040 (ethyl cellulose aqueous solution) | USP | Drug release control | 12 |
| Hydroxypropyl methylcellulose | USP | Pore-forming agent | 4 |
| Total Tablet Weight | | | 416 mg |

Manufacture

MCD-386 and all excipients in powder form are passed separately through 710 micron sieves, and the material passing through the sieves is used in manufacturing the tablets, as follows.

Sieved HPMC, MCC and dicalcium phosphate are added to a stainless steel mixer and tumble blended for 10 minutes. Half the blend is removed and set aside. Sieved MCD-386 is added to the remaining blend in the blender and tumble blended for 10 minutes. The set-aside blend is added back into the blender containing the MCD-386 blend and tumble blended for 10 minutes. Successively, the sieved silica, and then the sieved magnesium stearate are added and tumble blended for 5 minutes and 3 minutes respectively. The powder blend is compressed to tablets using 10 mm diameter, normal concave tooling in a Manesty F3 or Picollo tablet press using conditions well known to those skilled in the art.

The coating material is made by dissolving an appropriate amount of Pharmacoat 600 in water, then adding an appropriate amount of Surelease E-7-19040, and mixing for 30 minutes in a mixer.

The tablets are coated to 4% weight gain in a perforated pan tablet coater with an aqueous suspension of Surelease E-7-19040 (ethylcellulose) and Pharmacoat 600 (hydroxypropylmethylcellulose). The coating is allowed to dry. The tablets are allowed to cure for 48 hours before dissolution testing.

Example 15

Controlled Release Oral Formulation of MCD-36 and Muscarinic Antagonist—MCD-366CR Forte Protocol: see Example 29

Figure 7:
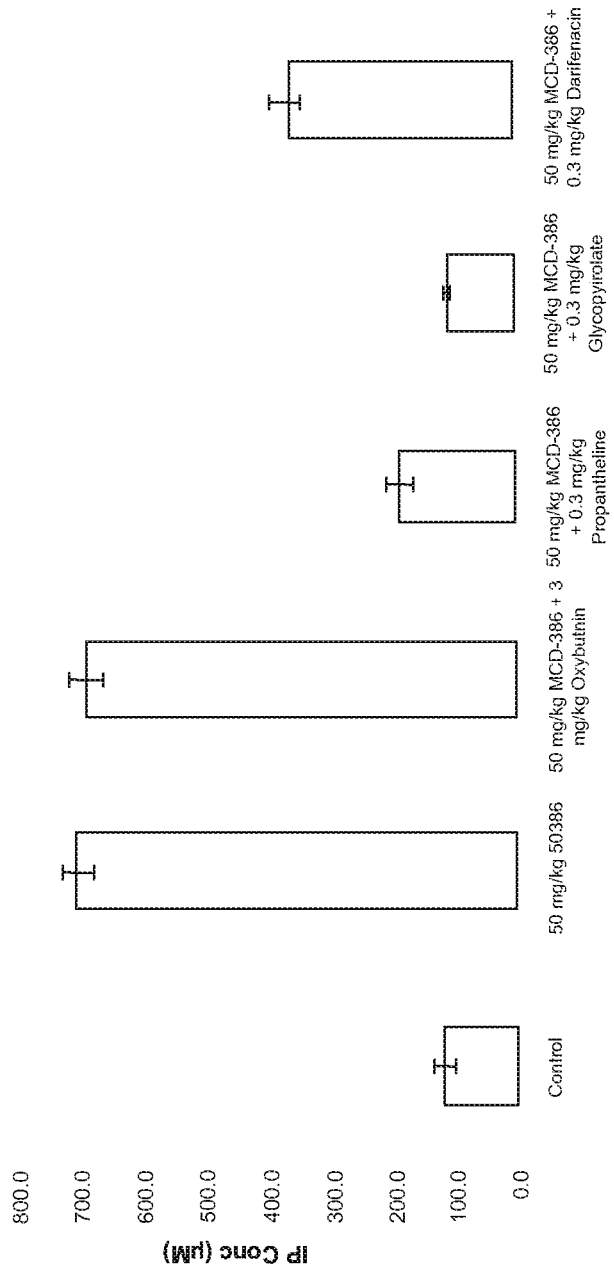
FIG. 7. shows that the salivary gland inositol phosphate response to a dose of 50 mg/kg of MCD-386.

Results:

This shows that the salivary gland inositol phosphate response to a dose of 50 mg/kg of MCD-386 is virtually completed inhibited by a dose of 0.3 mg·kg of glycopyrrolate or propantheline. These a quaternary amino-type muscarinic agonists with poor brain penetration. Darifenacin and oxybutini, both tertiary amines, are less effective. In addition, these drugs are known to penetrate the blood-brain barrier and may therefore inhibit the therapeutic effects of the agonist in the brain. This demonstrates the utility of combinations of agonist and peripherally selective antagonist to block the peripheral stimulation of the inositol phosphate pathway and thereby avoid peripheral side-effects while enabling higher doses of MCD-396 to be administered in order to achieve a greater disease-modifying effect. See FIG. 7

Example 16

Controlled Release Oral Formulation of Compound 3 (a Racemic Mixture of 3-methyl-5-(piperidin-3-yl)-1,2,4-oxadiazole) Series Drug and Muscarinic Antagonist Protocol see Example 29

Figure 8A:
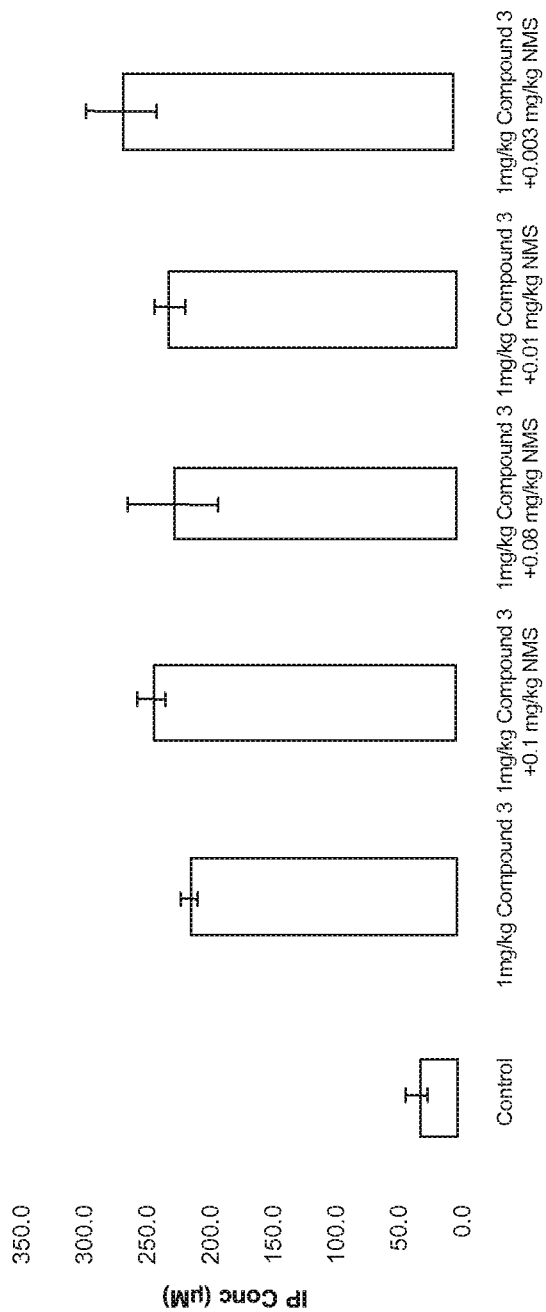
FIGS. 8A & 8B show the blockade by NMS of salivary inositol phosphate signaling pathway activation by Compound 3 (a racemic mixture of 3-methyl-5-(piperidin-3-yl)-1,2,4-oxadiazole) in normal rats (delivered by sc injection).
Figure 8B:
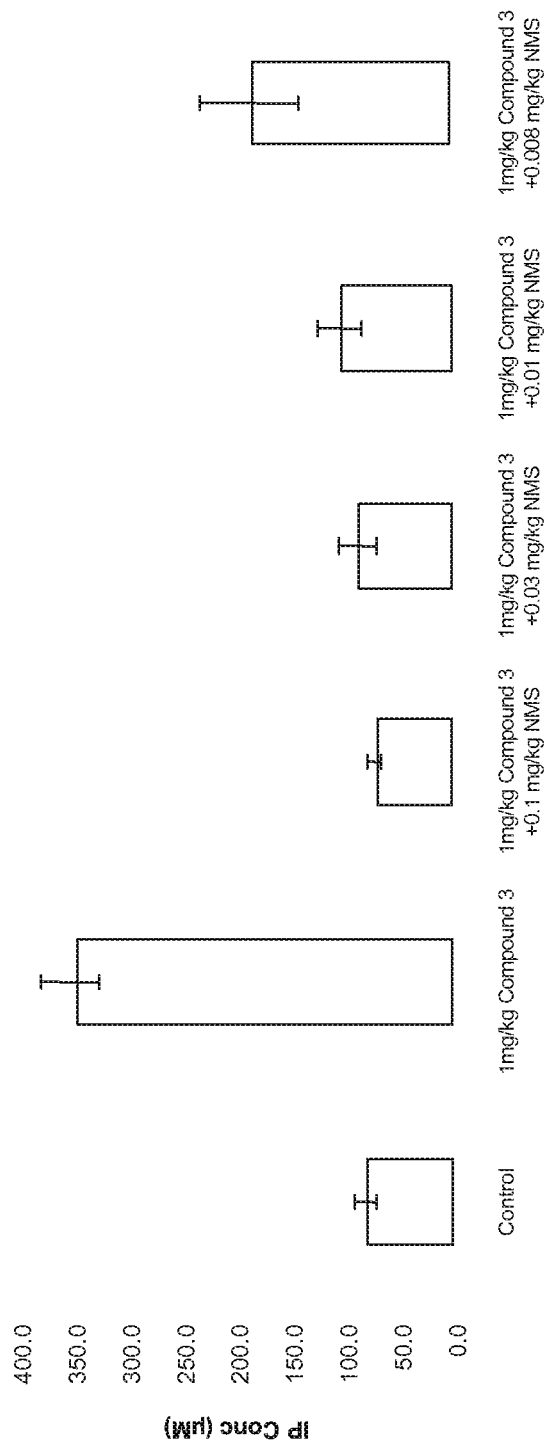
Figure 8C:
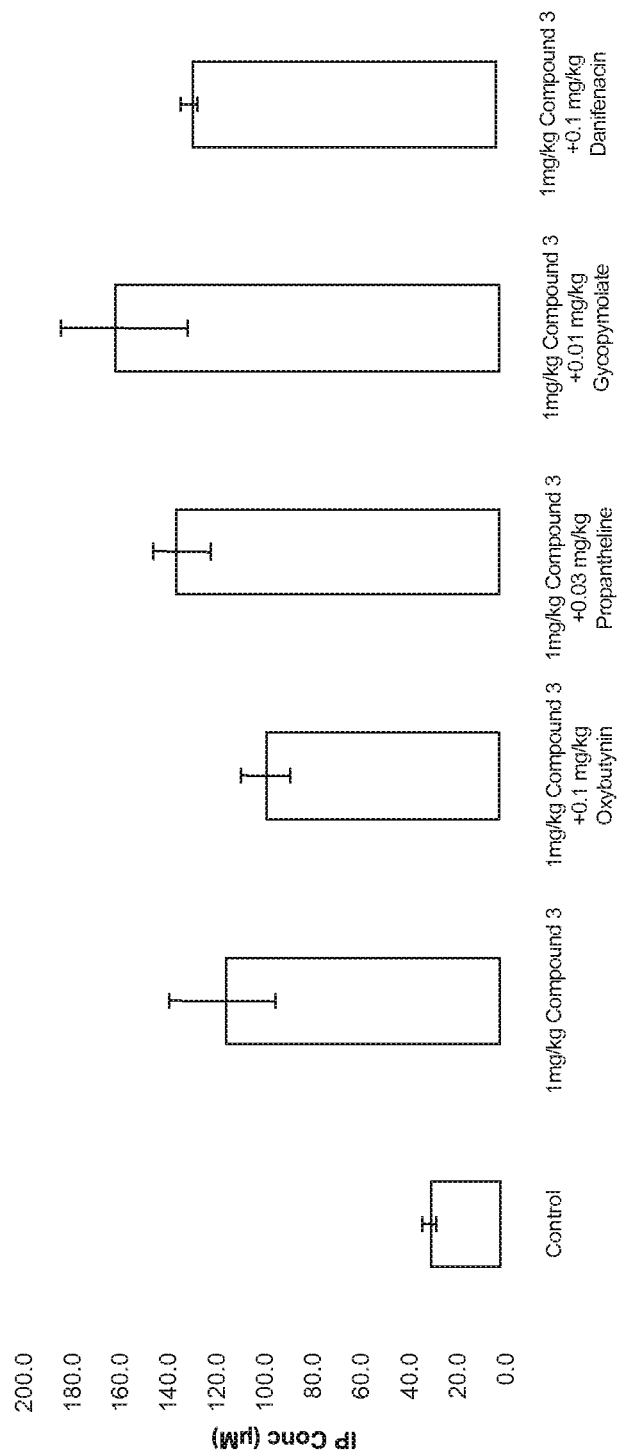
FIGS. 8C & 8D show the effects of various muscarinic antagonists on the activation of the hippocampal (FIG. 8C) and salivary gland (FIG. 8D) inositol phosphate signaling pathway activation by Compound 3 in normal rats (delivered by sc injection).
Figure 8D:
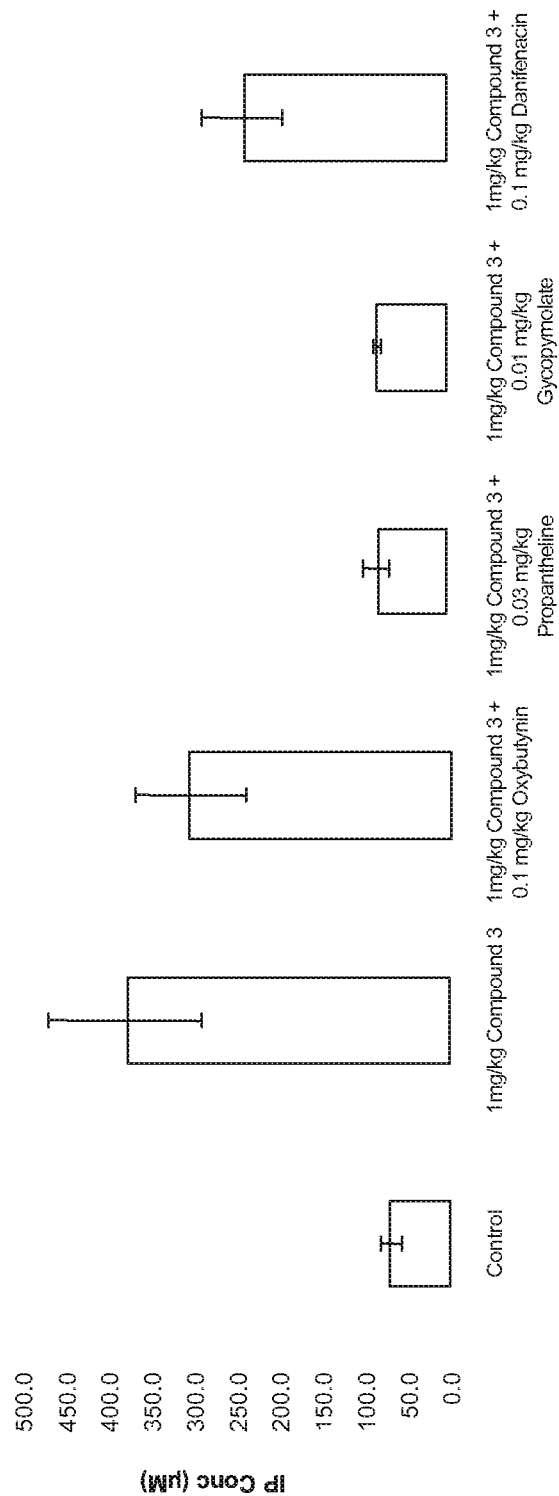

Results:

FIGS. 8A & 8B show that a dose of 0.1 mg/kg of NMS will completely block the increase in salivary gland inositol phosphate caused by a dose of 1 mg/kg of Compound 3 (a racemic mixture of 3-methyl-5-(piperidin-3-yl)-1,2,4-oxadiazole). This dose of NMS does not inhibit the increase in inositol phosphate in the hippocampus. Thus, NMS may be used to block the effects of Compound 3 (a racemic mixture of 3-methyl-5-(piperidin-3-yl)>1,2,4-oxadiazole) in the periphery without blocking the potential disease-modifying effects in the brain. Lower doses of NMS in the range 0.03 mg/kg to 0.01 mg/kg are nearly as effective as 0.1 mg/kg, but there is some breakthrough activation of inositol phosphate in the salivary glands at a dose of 0.003 mg/kg. This demonstrates the potential of NMS, a peripherally selective muscarinic antagonist to block potential peripheral side effects of Compound 3 (a racemic mixture of 3-methyl-5-(piperidin-3-yl)-1,2,4-oxadiazole), without blocking its therapeutic effects. FIGS. 8C & 8D show that 0.03 mg/kg of glycopyrrolate or propantheline can block increase in the salivary gland inositol phosphate caused by 1 mg/kg of Compound 3 (a racemic mixture of 3-methyl-5-(piperidin-3-yl)-1,2,4-oxadiazole), without blocking the increase in hippocampal inositol phosphate. These are quaternary amine-type muscarinic antagonists with poor brain penetration. Doses of 0.1 mg/kg of oxybutinin or darifenacin were less effective. Darifenacin and oxybutinin, both tertiary amines, are less effective. In addition, these drugs are known to penetrate the blood-brain barrier and may therefore inhibit the therapeutic effects of the agonist in the brain. See FIGS. 8A, 8B, 8C & 8D.

Example 17

Transdermal Delivery of Compound 3 (a Racemic Mixture of 3-methyl-5-(piperidin-3-yl)-1,2,4-oxadiazole) Series Drug and Muscarinic Antagonist From One Skim Patch (by Ontophoresis)

Protocol
Iontophoretic Transdermal Delivery of Experimental Compounds and Drug Substances
Experimental compounds and drug substances were delivered transdermally in rats using iontophoresis as follows. The fur was shaved from the backs of Long Evans Hooded rats weighing 225 to 325 grams, using electric clippers. Experimental compounds and drug substances were formulated at suitable concentrations an aqueous mixture of the following composition:

| | |
|---|---|
| Polyvinyl alcohol (Sigma Aldrich/P1763-250G) in de-ionized water | 15% |
| Ion exchange resin Amberlite IRP88 Polacrilin (Rohm and Haas/IRP88)-K | 0.1 |
| Ion exchange resin Amberlite IRP64 Polacrilex (Rohm and Haas/IRP641)-H | 0.3 |
| Ion exchange resin Cholestyramine (Sigma Aldrich/C4650-25G)-Cl | 5 |
| Glycerine (Sigma/G5516-100 mL) | 5 |

The polyvinyl alcohol/water was heated to 95 deg C. until it became clear, then the other constituents were added and mixed well. The mixture was introduced into suitable molds containing a disc-shaped cavity 2.2 cm diameter and 2.2 mm deep. Molds may be fabricated using two glass sheets separated by a silicone rubber sheet with suitable sized cavities and filling ports cut-outs. The molds were subject to 3 freeze-thaw cycles at −80 deg C. and 20 deg C. until a firm cryogel was obtained. The gels were separated from the molds and trimmed into a circular shape. The gel was placed in a silicone rubber casing with one face in contact with a circular silver foil anodic electrode (22 mm dial 250 microns thick), and the assembly was placed on the shaved skin of the that such that the other face was in contact with the skin on one side of the back of the rat. The rubber casing formed a seal over and around the gel/electrode assembly. A similar assembly was constructed incorporating a gel containing 0.9% sodium chloride and no drug, and a silver chloride-coated silver foil cathodic electrode. This was placed on the other side of the shaved back of the rat, the edges of the gel discs being about 20 mm apart at their nearest point. A DC voltage was applied across the two patches from a constant-current DC power supply and the voltage adjusted to obtain the desired current such that the skin of the animal completed the electrical circuit.

Figure 9A:
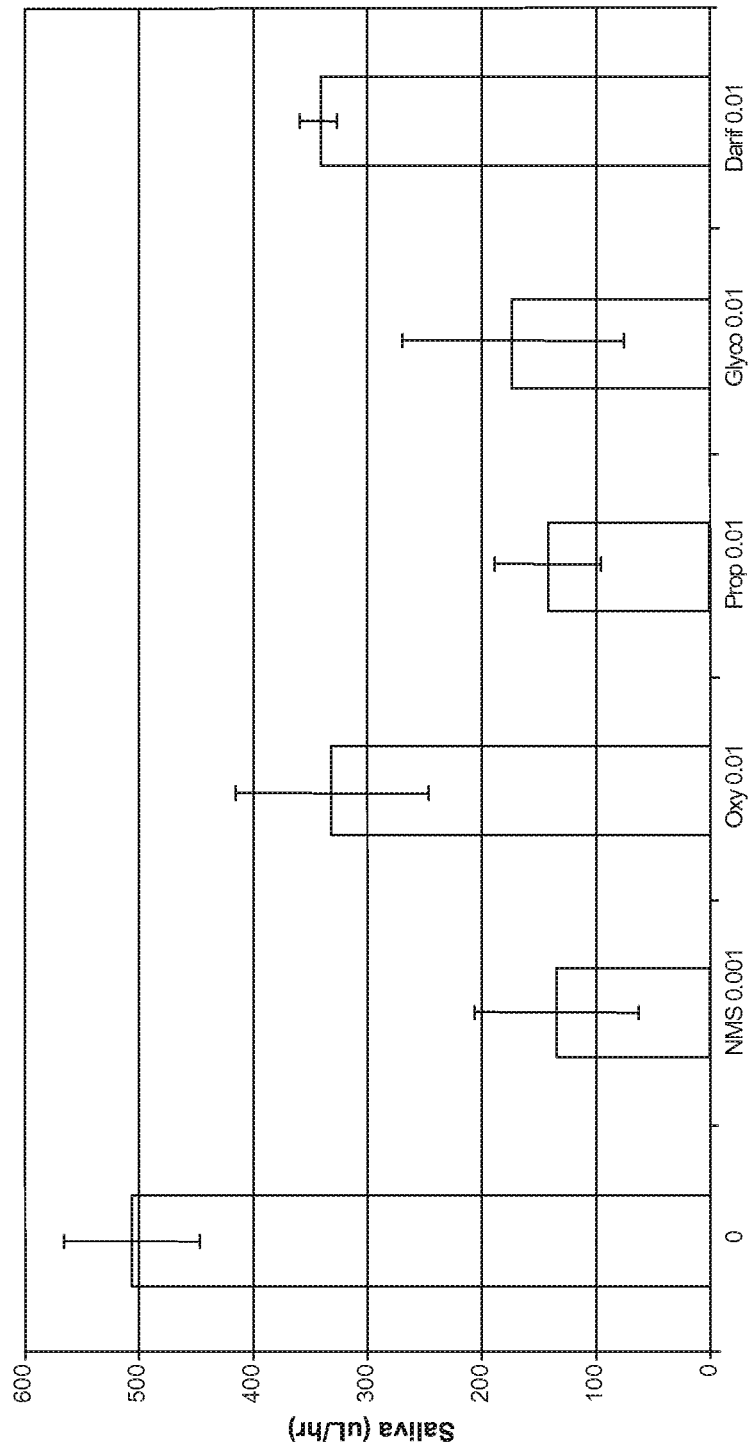
FIG. 9A shows the reduction or blockade of salivation caused by Compound 3 by peripherally selective muscarinic antagonists delivered with Compound 3 by transdermal iontophoresis.
Figure 9B:
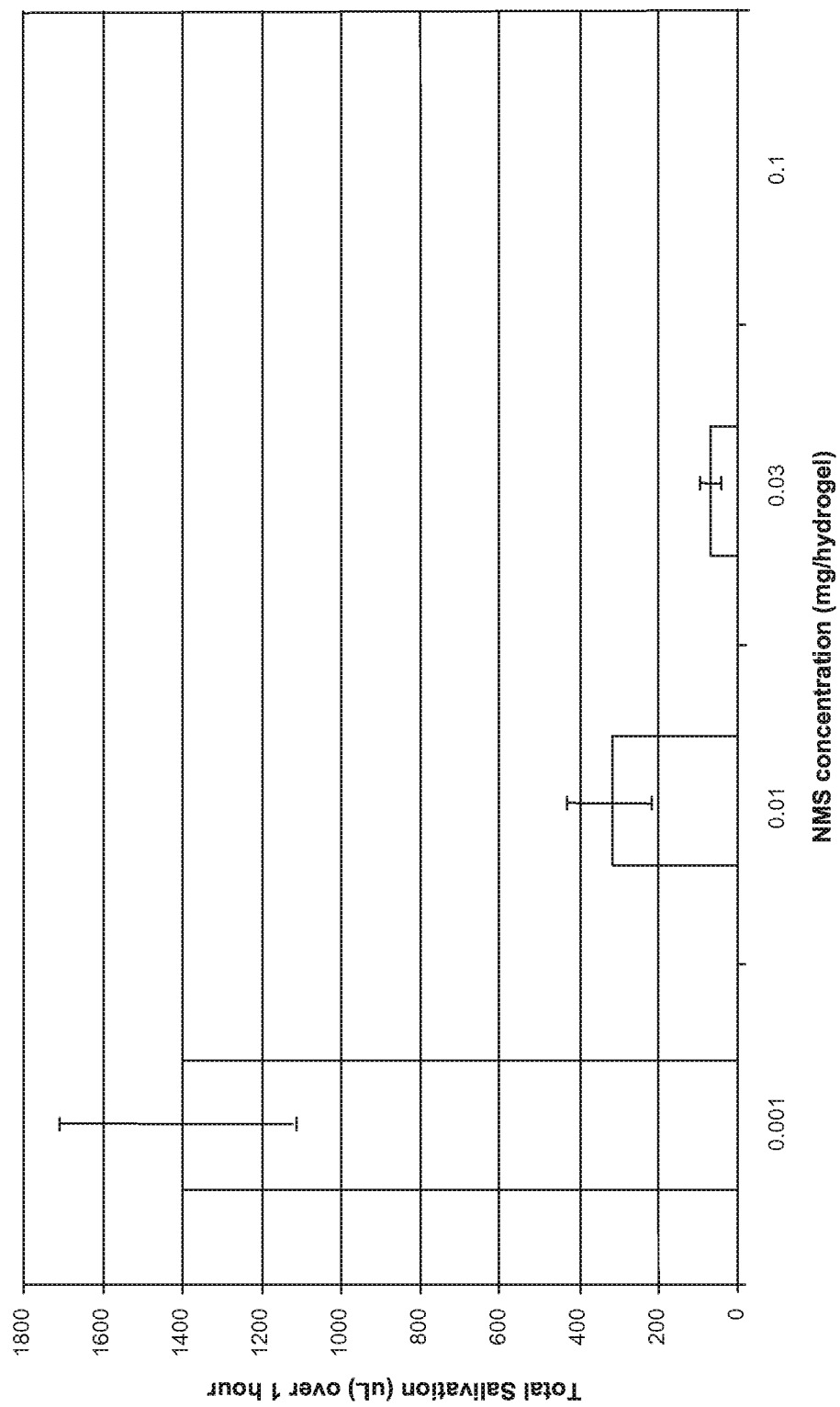
FIG. 9B shows the reduction or blockade of salivation caused by MCD-386 by the peripherally-selective muscarinic antagonist N-methylscopolamine (NMS) delivered with MCD-386 by transdermal iontophoresis.

Results
Iontophoretic devices were manufactured that contained 1 mg of compound 3 or 1 mg of Compound 3 (a racemic mixture of 3-methyl-5-(piperidin-3-yl)-1,2,4-oxadiazole) plus 0.01 mg of NMS, oxybutynin, propantheline, glycopyrrolate, or darifenacin. The devices were placed on shaved backs of anesthetized rats and salivation was measured. This shows that the salivation caused by transdermal iontophoretic delivery in the rat of Compound 3 (a racemic mixture of 3-methyl-5-(piperidin-3-yl)-1,2,4-oxadiazole) can be greatly reduced by simultaneously delivering, from the same patch, NMS, propantheline or glycopyrrolate. Oxybutinin and darifenacin reduced salivation, but were less effective. This demonstrates that combinations of a subtype selective muscarinic agonist and a peripherally selective muscarinic antagonist can be delivered efficiently and simultaneously from a single iontophoretic device, and that the combination can reduce or prevent unwanted side effects. See FIGS. 9A & 9B.

Example 18

Synthesis of 3-Methyl-5-(piperidin-3-yl)-1,2,4-oxadiazole

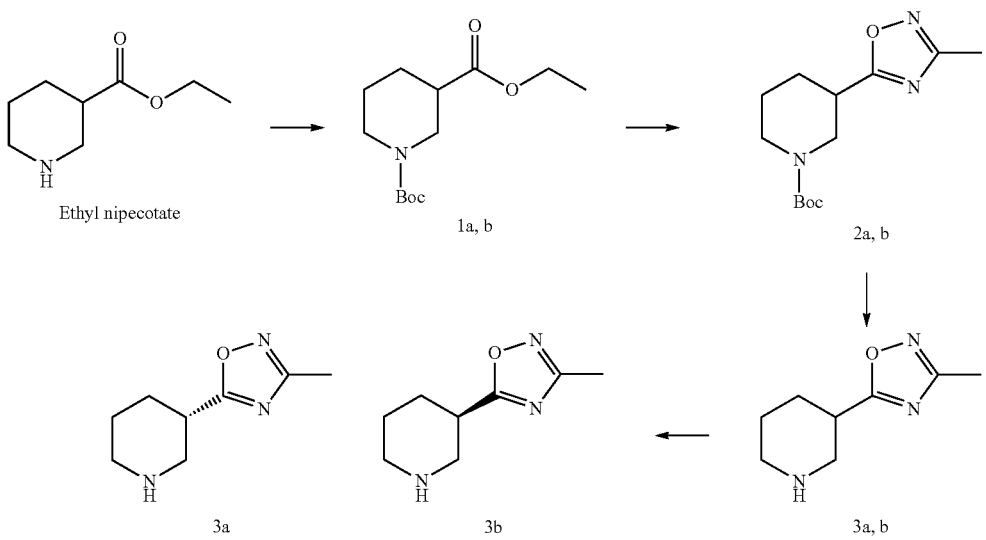

1-N-Boc-Ethyl nipecotate (1)

Ethyl nipecotate (1.5 g, 0.0095 mol) was added dropwise to a solution of di-tert-butyl dicarbonate (2.17 g, 0.0099 mol) and triethylamine (1.4 mL, 0.0099 mol) in methylene chloride (25 mL) at 0-5° C. A catalytic amount of dimethylaminopyridine was added and the mixture was stirred at 0-5° C. for 15 min. The solution was allowed to warm to room temperature and stirred for 18 hrs. The reaction mixture was concentrated and the oil was dried under vacuum for 2 hours. The material was used without purification. MS (ESI) m/z 296 [M+K]+.

tert-Butyl 3-(3-methyl-1,2,4-oxadiazol-5-yl)piperidine-1-carboxylate (2a,b)

1-N-Boc-ethyl nipecotate (1) (1.2 g, 0.0047 mol) and acetamide oxime (0.87 g, 0.0118 mol) were dissolved in 30 mL tetrahydrofuran. Sodium methoxide (1.27 g, 0.0235 mol) was added and the mixture was heated at reflux for 1.75 hours. The mixture was concentrated and partitioned between water (50 mL) and ethyl acetate (1×100 mL). The aqueous layer was extracted with an additional 50 mL ethyl acetate. The combined organics were washed with 1×50 mL water, 1×50 mL saturated sodium chloride, and dried over $Na_2SO_4$. The dried organics were evaporated to an oil. The residue was chromatographed with 5 g silica gel, 15% ethyl acetate/hexanes, to obtain 0.81 g of clear colorless oil. MS (ESI) m/z 306 [M+K]+. $^1$H NMR (CDCl$_3$) δ 1.45 (s, 9H), 1.55-62 (m, 1H), 1.78-1.81 (d, 2H), 2.18-2.20 (m, 1H), 2.38 (s, 3H), 2.90-2.96 (t, 1H), 3.03-3.08 (m, 2H), 3.94-3.97 (m, 2H).

3-Methyl-4-(piperidin-3-yl)-1,2,4-oxadiazole (3a,b)

tert-Butyl 3-(3-methyl-1,2,4-oxadiazol-5-yl)piperidine-1-carboxylate 2a,b (0.81 g, 0.0030 mol) was dissolved in 5 mL dichloromethane. Hydrochloric acid in ethanol (2.5 M) (2.43 mL, 0.0060 mol) was added and the mixture was heated to 40° C. for 3 hours. 20 mL of MTBE was added and the product precipitated from solution. The solids were filtered and washed with 3×5 mL MTBE and dried under vacuum overnight to obtain 574 mg of a white solid in 94% yield. MS (ESI) m/z 168 [M+1]+. $^1$H NMR (DMSO-d6) δ 1.74-1.82 (m, 3H), 2.11-2.14 (d, 1H), 2.31 (s, 3H), 2.87 (t, 1H), 3.10-3.30 (m, 2H), 3.49-3.56 (m, 3H).

Chiral resolution of 3-methyl-5-(piperidin-3-yl)-1,2,4-oxadiazole (3a and 3b)

Methyl-5-(piperidin-3-yl)-1,2,4-oxadiazole (0.83 g, 0.0050 mol) and D-tartaric acid (0.74 g, 0.0050 mol) were dissolved in hot methanol (10 mL) and the solution was refluxed for 15 minutes. 30 mL of acetonitrile was added and the resulting solution was allowed to cool to room temperature. The crystals were filtered, washed with 10 mL of 1:3 methanol:acetonitrile, and recrystallized 3 times from methanol:acetonitrile (10 mL 20 mL) as before to give the D-tartrate salt of S-(+)-3-methyl-5-piperidin-3-yl)-1,2,4-oxadiazole (3a), 193 mg white solid. The optical purity 100% ee, as determined by HPLC analysis (Chiral Technologies Chiral-AGP, 4.0 mm×150 mm, 0.5% methanol 20 mM sodium phosphate pH=7). MS (ESI) m/z 168 [M+1]+. $^1$H NMR (DMSO-d6) δ 1.67-1.79 (m, 3H), 2.10-2.13 (m, 1H), 2.33 (s, 3H), 2.76-2.82 (t, 1H), 3.01-3.14 (m, 2H), 3.31-3.36 (m, 1H), 3.44-3.47 (m, 1H), 3.95 (s, 1H).

The liquors were concentrated and free based with saturated sodium bicarbonate and extracted with 4×50 mL dichloromethane. The organics were dried over sodium sulfate and concentrated. In a similar manner, 3-methyl-5-(piperidin-3-yl)-1,2,4-oxadiazole (0.54 g, 0.0032 mol) and L-tartaric acid (0.49 g, 0.0032 mol) were dissolved in hot methanol (10 mL) and the solution was refluxed for 15 minutes. 25 mL of acetonitrile was added and the resulting solution was allowed to cool to room temperature. The crystals were filtered, washed with 10 mL of 1:3 methanol:acetonitrile, and recrystallized 4 times from methanol:acetonitrile (10 mL:25 mL) as before to give the L-tartrate salt of R-(−)-3-methyl-5-(piperidin-3-yl)-1,2,4-oxadiazole (3b), 199 mg white solid. The optical purity was 100% ee, as determined by HPLC analysis (Chiral Technologies Chiral-AGP, 4.0 mm×150 mm, 0.5% methanol, 20 mM sodium phosphate pH=7). MS (ESI) m/z 168 [M+1]+. $^1$H NMR (DMSO-d6) δ 1.64-1.79 (m, 3H), 2.10-2.13 (m, 1H), 2.33 (s, 3H), 2.75-2.81 (t, 1H), 3.01-3.14 (m, 2H), 3.29-3.37 (m, 1H), 3.43-3.47 (m, 1H), 3.95 (s, 1H).

Example 19

Synthesis of 3-Methyl-5-(1-methylpiperidin-3-yl)-1,2,4-oxadiazole

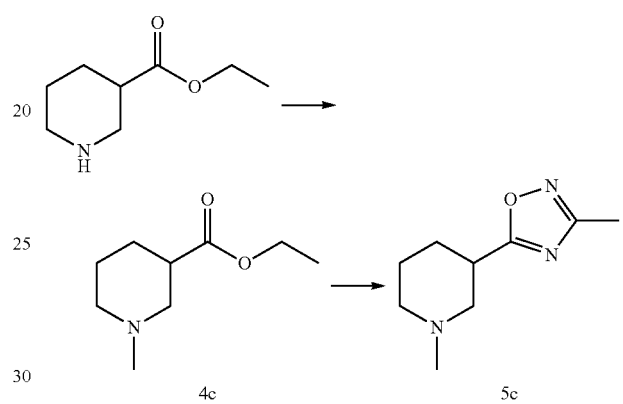

N-Methyl-ethyl nipecotate (4c)

Ethyl nipecotate (5.0 g, 0.032 mol) was dissolved in acetone (50 mL), Methyl iodide (3 mL, 0.048 mol) was added dropwise over 1 hour and the mixture was stirred at room temperature for 1 hour. The mixture was concentrated to remove acetone and partitioned between saturated sodium bicarbonate (50 mL) and ethyl acetate (1×50 mL). The aqueous layer was extracted with an additional 2×50 mL ethyl acetate. The combined organics were washed with 2×50 mL water, 150 mL saturated sodium chloride, and dried over $Na_2SO_4$. The dried organics were evaporated to an oil to obtain 1.43 g. The material was used without further purification. MS (ESI) m/z 172 [M+H]+.

3-Methyl-5-(1-methylpiperidin-3-yl)-1,2,4-oxadiazole (5c)

1-N-Boc-ethyl nipecotate (1) (0.7 g, 0.0041 mol) and acetamide oxime (0.75 g, 0.0102 mol) were dissolved in 30 mL tetrahydrofuran. Sodium methoxide (1.1 g, 0.0205 mol) was added and the mixture was heated at reflux for 2 hours. The mixture was concentrated to remove THF and partitioned between water (25 mL) and dichloromethane (1×25 mL). The aqueous layer was extracted with an additional 2×25 mL dichloromethane. The combined organics were washed with 1×50 mL saturated sodium chloride, and dried over $Na_2SO_4$. The dried organics were evaporated to an oil. The residue was chromatographed with 5 g silica gel, 5% methanol/ethyl acetate, to obtain 0.51 g of the free base. Hydrochloric acid in ethanol (2.5 M) (1.6 mL, 0.011 mol) was added and the mixture was concentrated to dryness. Crystallization from ethanol/MTBE afforded 436 mg white solid. MS (ESI) m/z 182 [M+H]+. $^1$H NMR (DMSO-d6) δ 1.59-1.66 (m, 1H), 1.88-1.98 (s, 2H), 2.17-2.20 (d, 1H), 2.34 (s, 3H), 2.77 (s, 3H), 2.92-2.95 (m, 1H), 3.18-3.21 (m, 1H), 3.37-3.47, (d, 1H), 3.60-3.78, (m, 2H).

Example 20

Synthesis of 7a and 7b

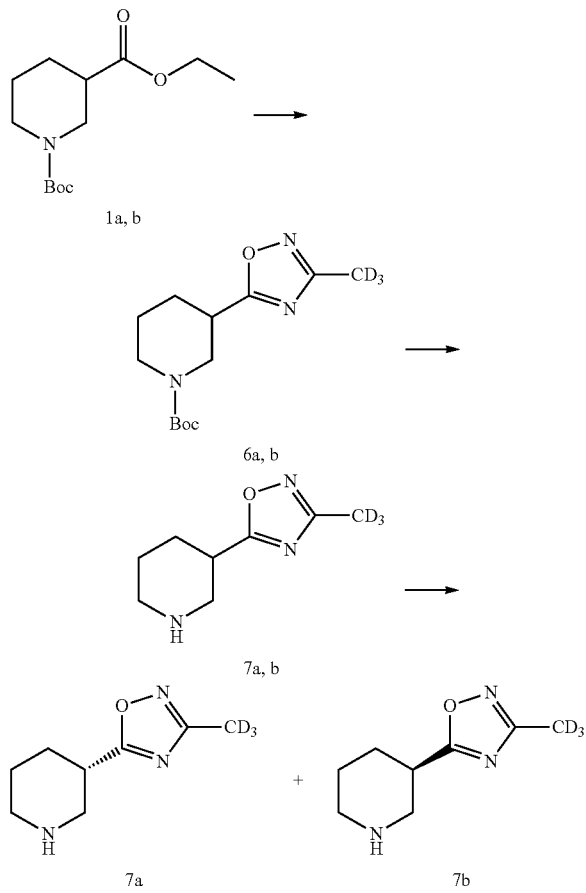

tert-Butyl 3-(3-D3-methyl-1,2,4-oxadiazol-5-yl)piperidine-1-carboxylate (6a,b)

1-N-Boc-ethyl nipecotate (1) (1.0 g, 0.0039 mol) and D3-acetamide oxime (0.75 g, 0.0098 mol) were dissolved in 50 ml tetrahydrofuran. Sodium methoxide (1.05 g, 0.0195 mol) was added and the mixture was heated at reflux for 30 minutes. The mixture was concentrated and partitioned between water (50 mL) and ethyl acetate (1×100 mL). The aqueous layer was extracted with man additional 50 mL ethyl acetate. The combined organics were washed with 1×50 mL water, 150 mL saturated sodium chloride, and dried over Na$_2$SO$_4$. The dried organics were evaporated to an oil. The residue was chromatographed with 5 g silica gel, 20% ethyl acetate/hexanes, to obtain 0.78 g of clear colorless oil. MS (ESI) m/z 309 [M+K]+. $^1$H NMR (CDCl$_3$) δ 1.46 (s, 9H), 1.57-1.61 (m, 1H), 1.79-1.82 (d, 2H), 2.18-2.20 (m, 1H), 2.91-2.96 (t, 1H), 3.03-3.08 (m, 2H), 3.94-3.97 (m, 2H).

3-D3-Methyl-5-(piperidin-3-yl)-1,2,4-oxadiazole (7a,b)

tert-Butyl 3-(3-methyl-1,2,4-oxadiazol-5-yl)piperidine-1-carboxylate 6a,b (0.81 g, 0.0030 mol) was dissolved in 1 mL ethanol. Hydrochloric acid in ethanol (2.5 M) (2.0 mL, 0.0050 mol) was added and the mixture was heated to 40° C. for 3 hours. 9 mL of MTBE was added and the product precipitated from solution. The solids were filtered and washed with 2×5 mL MTBE and dried under vacuum overnight to obtain 574 mg of a white solid in 94% yield. MS (ESI) m/z 170 [M+1]+. $^1$H NMR (DMSO-d6) δ 1.74-1.83 (m, 3H), 2.14-2.17 (d, 1H) 2.89-2.92 (m, 1H), 3.12-3.32 (m, 2H), 3.50-3.57 (m, 3H).

Chiral resolution of 3-D3-methyl-5-(piperidin-3-yl)-1,2,4-oxadiazole (7a and 7b)

3-methyl-5-(piperidin-3-yl)-1,2,4-oxadiazole (0.86 g, 0.0050 mol) and D-tartaric acid (0.76 g, 0.0050 mol) were dissolved in hot methanol (10 mL) and the solution was refluxed for 30 minutes. 45 mL of acetonitrile was added and the resulting solution was allowed to cool to room temperature. The crystals were filtered, washed with 10 mL of 1:3 methanol:acetonitrile, and recrystallized 3 times from methanol:acetonitrile (10 mL: 20 mL) as before to give the D-tartrate salt of S-(+)-3-D3-methyl-5-(piperidin-3-yl)-1,2,4-oxadiazole (7a), 331 mg white solid. The optical purity 100% ee, as determined by HPLC analysis (Chiral Technologies Chiral-AGP, 4.0 mm×150 mm, 0.5% methanol, 20 mM sodium phosphate pH=7). MS (ESI) m/z 170 [M+1]+. $^1$H NMR (DMSO-d6) δ 1.64-1.79 (m, 3H), 2.10-2.13 (m, 1H), 2.75-2.81 (m, 1H), 3.01-3.06 (dd, 1H), 3.11-3.14 (d, 1H), 3.30-3.36 (m, 1H), 3.43-3.47 (m, 1H).

The liquors were concentrated and free based with saturated sodium bicarbonate and extracted with 3×50 mL dichloromethane. The organics were dried over sodium sulfate and concentrated. In a similar manner, 3-D3-methyl-5-(piperidin-3-yl)-1,2,4-oxadiazole (0.56 g, 0.0033 mol) and L-tartaric acid (0.49 g, 0.0033 mol) were dissolved in hot methanol (10 mL) and the solution was refluxed for 30 minutes. 30 mL of acetonitrile was added and the resulting solution was allowed to cool to room temperature. The crystals were filtered, washed with 10 mL of 1:3 methanol:acetonitrile, and recrystallized 2 times from methanol:acetonitrile (10 mL:25 mL) as before to give the L-tartrate salt of R-(−)-3-D3-methyl-5-(piperidin-3-yl)-1,2,4-oxadiazole (7b), 310 mg white solid. The optical purity was 100% ee, as determined by HPLC analysis (Chiral Technologies Chiral-AGP, 4.0 mm×150 mm, 0.5% methanol, 20 mM sodium phosphate pH=7). MS (ESI) m/z 170 [M+1]+. $^1$H NMR (DMSO-d6) δ 1.64-1.79 (m, 3H), 2.10-2.13 (m, 1H), 2.75-2.81 (m, 1H), 3.01-3.06 (dd, 1H), 3.11-3.16 (d, 1H), 3.29-3.36 (m, 1H), 3.43-3.47 (m, 1H).

Example 21

Synthesis of 12a and 12b

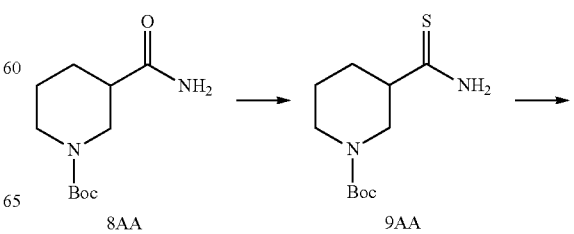

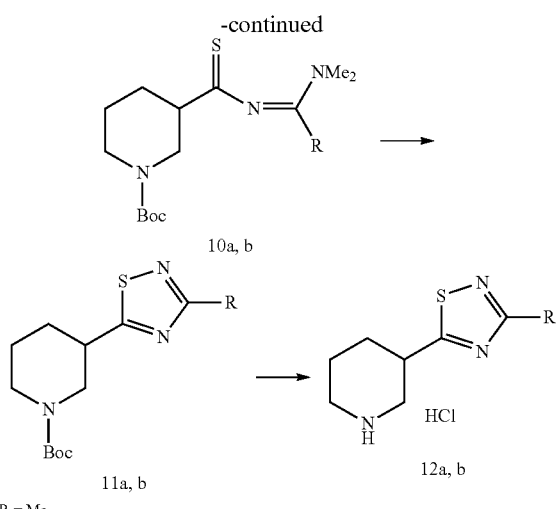

a: R = Me
b: R = H tert-Butyl 3-carbamothioylpiperidine-1-carboxylate (9AA)

Amide 8AA (2.0 g, 8.76 mmol) and Lawesson's reagent (1.79 g, 4.42 mmol) ware stirred in toluene (45 mL) and the mixture heated to 62° C. for 4 hours. The mixture was treated with 5 g of silica gel and 15 mL of methanol, and evaporated to dryness. The solid residue was chromatographed over 30 g of silica gel, eluting with $CH_2Cl_2$:MeOH (96:4). The product was chromatographed again, eluting with $CH_2Cl_2$:MeOH (97:3) and dried to 1.338 g of 2 as white foam. MS (ESI) m/z 283 [M+K]+. $^1$H NMR (CDCl$_3$) δ 1.30-1.50 (m, 1H), 1.55-1.65 (bs, 1H), 1.9-2.0 (m, 1H), 2.0-2.2 (m, 1H), 2.60-2.75 (bs, 1H), 3.0-3.2 (bs, 1H), 3.3-3.45 (bs, 1H), 3.6-3.95 (m, 2H), 7.43 (bs, 2H).

tert-Butyl 3-(1-(dimethylamino)ethylidenecarbamothioyl)piperidin-1-carboxylate (10a)

Thioamide 9AA (1.25 g, 5.11 mmol) was stirred in 25 mL of dichloromethane and treated with dimethylacetamide dimethylacetal (1.63 g, 12.2 mmol). The mixture was stirred for 4 5 days then concentrated under reduced pressure. The product was chromatographed over silica gel (15 g) with $CH_2Cl_2$: MeOH (91:2) to afford 1.55 g of yellow oil. MS (ESI) m/z 352 [M+K]+. $^1$H NMR (CDCl$_3$) δ 1.45 (s, 9H), 1.45-1.60 (m, 2H), 1.65-1.75 (m, 1H), 2.10-220 (m, 1H), 2.40 (s, 3H), 2.60-2.80 (m, 2H), 2.85-2.95 (m, 1H), 3.12 (s, 3H), 3.19 (s, 3H), 4.0-4.15 (m, 1H), 4.20-4.30 (m, 1H).

tert-butyl 3-(3-methyl-1,2,4-thiadiazol-5-yl)piperidine-carboxylate (11a)

Compound 10a (1.5 g, 4.78 mmol) was stirred in ethanol (20 mL) and treated with pyridine (0.76 g, 9.6 mmol). A solution of hydroxylamine-O-sulfonic acid (0.65 g, 5.74 mmol), in methanol (4 mL) was added and stirring continued for 2.5 hours. The mixture was allowed to stand overnight at 4° C. The mixture was condensed under vacuum and extracted with dichloromethane and deionized water. The organic layer was dried (Na$_2$SO$_4$) and condensed under vacuum. The product was filtered through a plug of silica gel, with hexane:EtOAc (8:2) to remove low R$_f$ impurities, and dried to 0.92 g of clear oil. MS (ESI) m/z 322 [M+K]+. $^1$H NMR (CDCl$_3$) δ 1.47 (s, 9H), 1.59-1.68 (m, 1H) 1.71-1.88 (m, 2H) 2.12-2.22 (m, 1H), 3.02-3.12 (t, 1H) 3.15-335 (m, 2H), 3.81-3.90 (dt, 1H), 4.14 (bs, 1H).

3-methyl-5-(piperidin-3-yl)-1,2,4-thiadiazole hydrochloride (12a)

The Boc-protected intermediate 11 (0.87 g, 3.07 mmol) was stirred in dichloromethane (10 mL) and treated with 10 mL of a 2.53 M solution of HCl in EtOH. After warming to 35° C. for 2 hours, the mixture was concentrated under vacuum. The product was precipitated from IPA:MTBE (1:10). The product was recrystallized from IPA:MTBE three times to afford a high purity sample (42 mg) of white solid. MS (ESI) m/z 184 [M+1]+. $^1$H NMR (CDCl$_3$) δ 1.68-1.91 (m, 3H), 2.13-2.20 (d, 1H), 2.58 (s, 3H), 2.87-2.95 (dt, 1H), 3.14 (t, 1H), 3.25-3.28 (d, 1H), 3.54-3.59 (d, 1H), 3.65-3.73 (m, 1H), 9.10 (s, 2H).

5-piperidin-3-yl)-1,2,4-thiadiazole (12b)

The methods described above for 12a were used for the preparation of 12b (dimethylformamide dimethylacetal was employed for 10b). MS (ESI) m/z 170 [M+1]+. $^1$H NMR (CDCl$_3$) δ 1.74-1.82 (m, 1H), 1.84-1.94 (m, 2H), 2.20-2.22 (d, 1H), 2.89-2.95 (m, 1H), 3.14-3.19 (t, 1H), 3.26-3.28 (d, 1H), 3.58-3.61 (dd, 1H), 3.77-3.83 (m, 1H), 9.32 (bs, 2H).

Example 22

Synthesis of 13

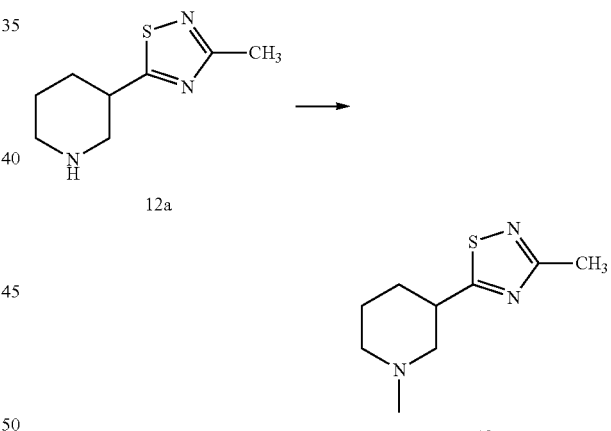

3-methyl-5-(t-methylpiperidin-3-yl)-1,2,4-thiadiazole (13)

A solution of 12a (400 mg, 1.82 mmol) in formic acid (3 mL) and 37% formaldehyde (3 mL) was heated to 85° C. for 30 minutes. The cooled mixture was slowly added to a rapidly stirred mixture of saturated potassium carbonate (15 mL) and dichloromethane (20 mL). The aqueous layer was extracted again (3×20 mL) with dichloromethane. The organic layer was concentrated and the residue chromatographed over silica gel (6 g) with 8% methanol in dichloromethane to provide 190 mg of clear, pale amber oil. The free base was converted to the HCl salt in isopropanol by the addition of excess HCl-EtOH. The resulting solution was concentrated and the residue was crystallized from isopropanol-ethyl acetate (1:3) to afford 13 (100 mg) as a white solid. An analytical sample was obtained by recrystallization twice more from isopropanol-ethyl acetate. MS (ESI) m/z 198 [M+1]+. ¹H NMR (CDCl₃) δ 1.55-1.70 (m, 1H), 1.90-2.05 (m, 2H), (bd, 1H), 2.58 (s, 3H), 2.77 (s, 3H), 2.95 (bs, 1H), 3.15-326 (m, 1H), 3.41-3.44 (d, 1H), 3.71-3.74 (d, 1H), 3.83 (t, 1H), 10.87 (bs, 1H).

Example 23

Comparative Example: Methyl Scan

Scheme 12 immediately below shows the synthesis for the 6-methyl analogs. The same route was used for all the methyl-piperidine analogs.

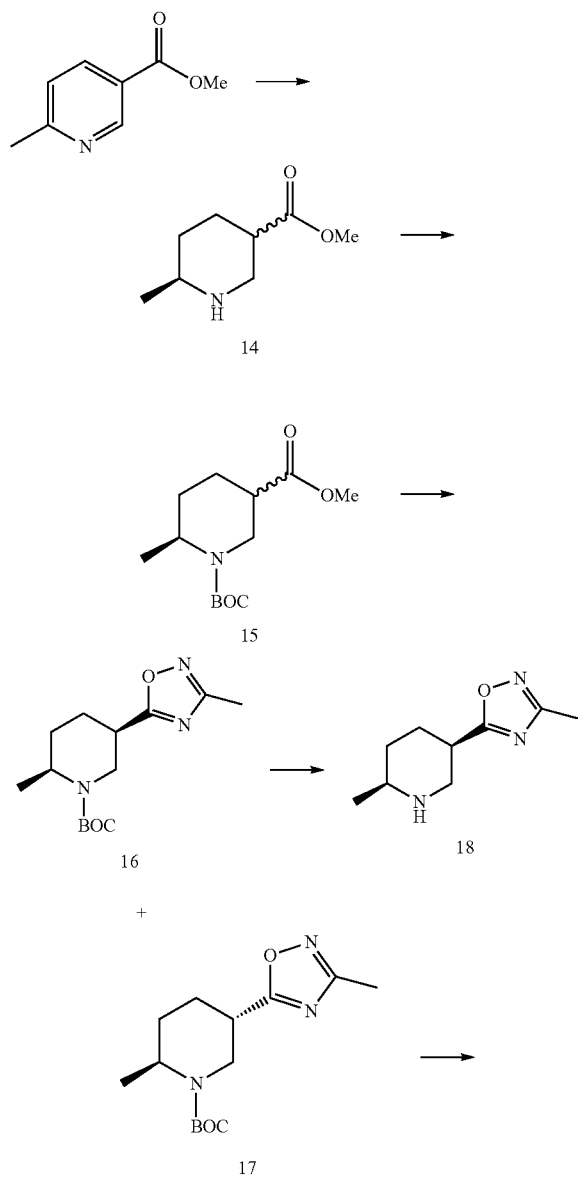

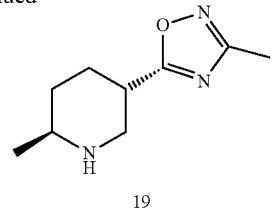

19

Methyl 6-methylpiperidin-3-carboxylate (14)

Methyl 6-methylnicotinate (4.9 g, 32.4 mmol) was combined with 10% Pd/C (wet, 2.5 g), methanol (40 mL) and acetic acid (50 mL) and hydrogenated at 40° C., (50 psi) for 15 hours. The mixture was filtered through a pad of Celite, washed with methanol and concentrated under reduced pressure. The residue was co-evaporated with 80 mL of toluene and then with 50 mL of methanol. The residue was partitioned between 40 mL of dichloromethane and 20 mL of saturated K₂CO₃. The aqueous layer was extracted with dichloromethane and the combined organics dried with anhydrous K₂CO₃. The solution was concentrated and dried under vacuum to 5.0 g of pale yellow oil. The cis/trans product mixture was not well separated by TLC (R$_f$=0.55 and 0.57. CH₂Cl₂:MeOH:NH₄OH, 90:9:1). The crude product mixture was taken directly to the next step.

1-tert-butyl 3-methyl 6-methylpiperidine-1,3-dicarboxylate (15)

Methyl 6-methylpiperidine-3-carboxylate 14 (4.9 g, 31.1 mmol) was stirred in 50 mL of dichloromethane and treated with di-t-butyl dicarbonate (7.13 g, 32.6 mmol) (mild exotherm), followed by triethylamine (3.29 g, 32.6 mmol). The mixture was stirred overnight and extracted with 20 mL of 10% NH₄Cl. The aqueous layer was extracted with dichloromethane and the combined organic layers dried (Na₂SO₄) and concentrated. Chromatography over silica gel (75 g) with 10% EtOAc in hexane provided first the cis-isomer (0.62 g), followed by mixed fractions (6.88 g). Continued elution with 20% EtOAc provided some trans-isomer (0.29 g).

cis-isomer MS (ESI) m/z 296 [M+K]+. ¹H NMR (CDCl₃) δ 1.12-1.14 (d, 3H), 1.46 (s, 9H, Boc), 1.53 (s 9H, Boc rotamer), 1.56-1.59 (m, 1H), 1.65-1.79 (m, 2H), 1.86-1.92 (m, 1H), 2.30-2.45 (m, 1H), 2.90 (bt, 1H), 3.69 (s, 3H), 4.17 (bs, 1H), 4.40 (bs, 1H).

trans-isomer: MS (ESI) m/z 296 [M+K]+. ¹H NMR (CDCl₃) δ 1.13-1.14 (d, 3H), 132-1.39 (m, 1H), 1.45 (s, 9H, Boc), 1.73-1.95 (m, 2H), 1.97-2.05 (bd, 1H), 2.57 (bs, 1H), 3.04-3.09 (dd, 1H), 3.69 (s, 3H), 4.30-4.41 (m, 2H).

tert-Butyl 2-methyl-5-(3-methyl-1,2,4-oxadiazole-5-yl)piperidin-1-carboxylate (16+17)

Acetamideoxime (1.43 g, 19.4 mmol) was stirred in 40 mL of tetrahydrofuran and treated with sodium methoxide (1.68 g, 31.1 mmol). The mixture was heated for several minutes and a solution of cis- and trans-15 (2.0 g, 7.77 mmol) in 10 mL of tetrahydrofuran, was added. The mixture was heated to 55-60° C. for 40 minutes, cooled and extracted with 2% citric acid solution (30 mL) and ethyl acetate (40 mL). The aqueous layer was extracted with additional ethyl acetate (25 mL) and the combined organic layers washed with brine. The solution was dried with sodium sulfate and condensed to an oil. Chromatography over silica gel (40 g) with 10% EtOAc in hexane eluted first the cis-isomer (1.12 g oil). Continued elution with 20% EtOAc provided the trans-isomer (0.35 g oil).

cis-isomer (16): MS (ESI) m/z 320 [M+K]+. ¹H NMR (CDCl₃) δ 1.17-1.19 (d, 3H), 1.47 (s, 9H), 1.61-1.67 (d, 1H), 1.74-1.84 (in 1H), 1.84-1.96 (m, 1H), 1.97-2.06 (m, 1H), 2.39 (s, 3H), 2.94-3.12 (m, 2H), 4.17-4.37 (m, 1H), 4.37-4.60 (m, 1H).

trans-isomer (17): MS (ESI) m/z 320 [M+K]+. ¹H NMR (CDCl₃) 1.18-1.20 (d, 3H), 1.41 (s, 9H), 1.95-2.20 (m, 3H), 2.37 (s, 3H), 3.14-3.19 (m, 1H), 3.27-3.31 (dd, 1H), 4.35-4.49 (m, 2H).

3-Methyl-6-(6-methylpiperidin-3-yl)-1,2,4-oxadiazole (18)

A solution of 16 (1.05 g, 3.73 mmol) in 12 mL of dichloromethane was treated with 5.9 mL (14.9 mmol) of a 2.53 M solution of HCl-EtOH. After stirring 15 hours, the solution was concentrated in vacuo. The residue was crystallized from isopropanol-methyl-t-butyl ether (1:6) to afford 0.46 g of 18 as a white solid. MS (ESI) m/z 182 [M+1]+. ¹H NMR (DMSO-Q) δ 1.21-1.23 (d, 3H), 1.50-1.60 (m, 1H), 1.80-1.90 (m, 1H), 1.95-2.05 (m, 1H), 2.10-2.20 (m, 1H), 2.35 (s, 3H), 3.27-3.35 (bs, 3H, H₂O), 3.35-3.42 (dd, 1H), 3.50-3.57 (dd, 1H), 3.57-3.64 (m, 1H), 8.44 (bs, 1H), 9.68 (bs, 1H).

Additional methyl piperidine analogs were made, as HCl salts, using the methods described above.

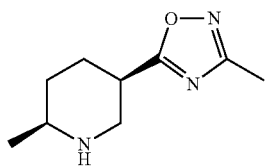

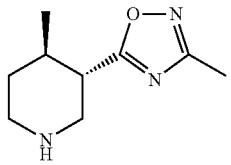

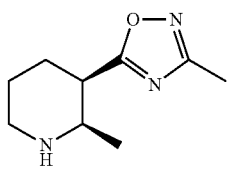

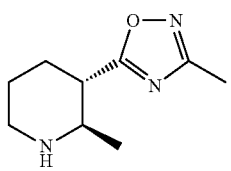

19: MS (ESI) m/z 182 [M+1]+. ¹H NMR (DMSO-d₆) δ 1.25-1.27 (d, 3H), 1.55-1.68 (dq, 1H), 1.69-1.81 (dq, 1H), 1.87-1.95 (dd, 1H), 2.14-2.22 (bd, 1H), 2.34 (s, 3H), 3.10-3.22 (m, 2H), 3.41-3.51 (tt, 1H), 3.56-3.64 (bd, 1H), 9.24 (bs, 2H).

20: MS (ESI) m/z 182 [M+1]+. ¹H NMR (DMSO-d) δ 0.92-0.94 (d, 3H), 1.35-1.46 (q, 1H), 1.95-2.10 (m, 1H), 2.13-2.22 (d, 1H), 2.33 (s, 3H) 2.52-2.60 (t, 1H), 2.97-3.07 (t, 1H), 3.18-3.26 (bd, 1H), 3.49-3.63 (m, 2H 9.30 (bs, 2H).

21: MS (ESI) m/z 182 [M+1]+. ¹H NMR (DMSO-d₆) δ 0.96-0.98 (d, 3H), 1.66-1.76 (m, 1H), 1.84-1.98 (m, 1H), 2.10-2.20 (bd, 1H), 2.36 (s, 3H), 2.65-2.72 (t, 1H), 3.04-3.10 (dd, 1H), 3.29-3.30 (d, 1H), 3.52-3.58 (dd, 1H), 3.66-3.72 (m, 1H), 8.91 (bs, 2H).

22: MS (ESI) m/z 182 [M+1]+. ¹H NMR (DMSO-d₆) δ 0.84 (d, 3H, —CH₃), 1.55 (m, 1H) 1.85-1.99 (m, 2H), 2.35 (s, 3H, oxadiazole-CH₃), 2.97-3.05 (m, 1H) 3.08-3.15 (m, 1H), 3.17-3.24 (m, 1H), 3.28-3.33 [shadowed by a much larger water peak](d, 1H) 3.48-3.52 (m, 1H), 9.34 (bs, 2H).

23: MS (ESI) m/z 182 [M+1]+. ¹H NMR (DMSO-d₆) δ 0.83 (d, 3H, —CH₃), 1.64 (m, 1H), 1.99 (m, 1H), 2.36 (s, 3H, oxadiazole-CH₃), 2.43 (m, 1H), 3.06-3.13 (m, 2H), 3.38 (d, 2H), 3.72 (q, 1H), 9.25 (bs, 2H).

24: ¹MS (ESI) m/z 182 [M+1]+. ¹H NMR (DMSO-d₆) δ 1.18 (d, 3H, —CH), 1.74-1.88 (m, 2H), 2.00 (m, 2H), 2.36 (s, 3H, oxadiazole-CH₃), 3.02-3.16 (m, 2H), 3.69 (m, 1H), 3.85 (m, 1H), 9.15 (bs, 2H).

25: MS (ESI) m/z 182 [M+1]+. $^1$H NMR (DMSO-d$_6$) δ 1.20 (d, 3H, —CH$_3$), 1.82 (m, 3H), 2.06 (m, 1H), 235 (s, 3H, oxadiazole-CH$_3$), 2.99 (m, 1H), 3.27-3.45 (m, 3H), 9.47 (s, 2H).

Example 24

Synthesis of 27

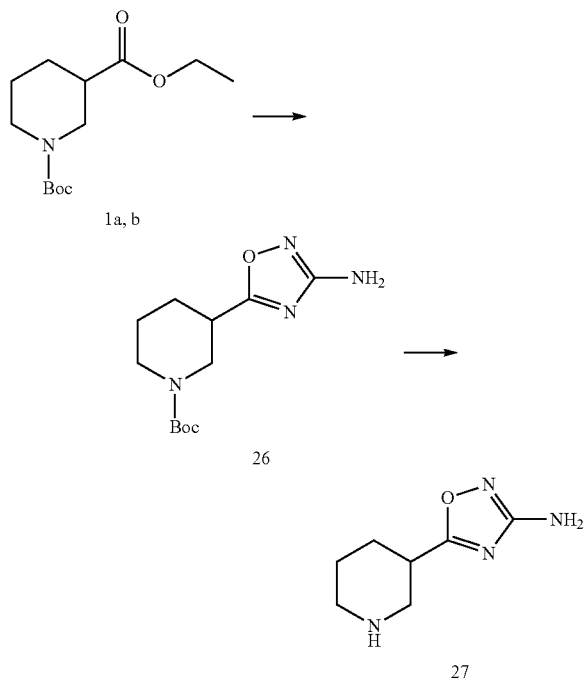

tert-Butyl 3-(3-amino-1,2,4-oxadiazole-5-yl)piperidine-1-carboxylate (26)

Hydroxylamine (50%) in water (3.6 mL 0.059 mol) was added to cyanamide (50%) in water (3.24 g 0.077 mol) in methanol (100 mL) and the mixture was refluxed for 4.5 hours. The mixture was concentrated to remove methanol/water, followed by concentration from 2×25 mL methanol to remove residual water to obtain 5.32 g of hydroxyguanidine as an amber oil which was used without further purification MS (ESI) m/z 76 [M+H]. 1-N-Boc-ethyl nipecotate 1a,b (1.0 g, 0.0039 mol) and hydroxyguanidine (0.73 g, 0.0097 mol) were dissolved in 50 mL tetrahydrofuran. Sodium methoxide (1.05 g, 0.0195 mol) was added and the mixture was heated at reflux for 1.0 hours. Additional hydroxyguanidine (0.73 g, 0.0097 mol) and Sodium methoxide (1.05 g, 0.0195 mol) were added and the mixture was heated at reflux for an additional hour. The mixture was concentrated and partitioned between water (25 mL) and ethyl acetate (1×100 mL). The aqueous layer was extracted with an additional 50 mL ethyl acetate. The combined organics were washed with 2×50 mL saturated sodium bicarbonate, 1×50 mL saturated sodium chloride, and dried over Na$_2$SO$_4$. The dried organics were evaporated to an oil. The residue was chromatographed with 5 g silica gel, 25%-50% ethyl acetate/hexanes, to obtain 0.35 g of clear colorless oil. MS (ESI) m/z 307 [M+K]+. $^1$H NMR (CDCl$_3$) δ 1.46 (s, 9H), 1.57 (m, 1H), 1.72-1.80 (d, 2H), 2.16-2.18 (m, 1H), 2.88-2.97 (m, 2H), 3.10-3.26 (m, 1H), 3.93-3.97 (m, 2H), 4.31 (s, 2H).

3-Amine-5-(piperidin-3-yl)-1,2,4-oxadiazole (27)

tert-Butyl 3-(3-amino-1,2,4-oxadiazol-5-yl)piperidine-1-carboxylate 26 (0.33 g, 0.00123 mol) was dissolved in 2 mL ethanol. Hydrochloric acid in ethanol (2.5 M) (2.00 mL, 0.00493 mol) was added and the mixture was heated to 40° C. for 1 hour. 12 mL of MTBE was added and the product precipitated from solution. The solids were filtered and washed with 2×5 mL MTBE, and recrystallized 3 times from methanol:isopropanol to give 127 mg white solid. MS (ESI) m/z 168 [M+1]+. $^1$H NMR (DMSO-d6) δ 1.67-1.82 (m, 3H), 2.08-2.12 (d, 1H), 2.86-2.90 (t, 1H), 3.06-3.12 (t, 1H), 3.21-3.24 (d, 1H), 3.33 (s, 2H), 3.49-3.52 (d, 1H), 6.32 (s, 2H).

Example 25

Synthesis of 31

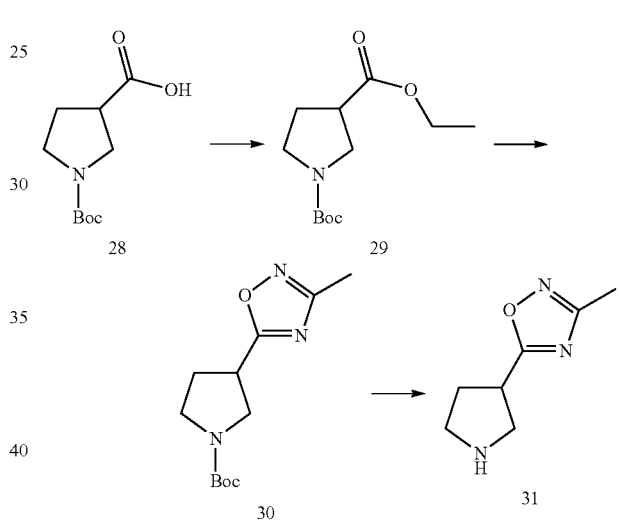

1-tert-Butyl 3-ethyl pyrrolidine-1,3-dicarboxylate (29)

1-(tert-butoxycarbonyl)pyrrolidine-3-carboxylic acid (28) (1.0 g, 0.0046 mol) and triethylamine (0.78 mL, 0.0056 mol) were dissolved in 20 mL tetrahydrofuran and cooled over ice water. Ethyl chloroformate (0.48 mL, 0.0051 mol) was added dropwise at 0-5° C. and the reaction was stirred for 30 minutes. A catalytic amount of dimethylaminopyridine was added followed by 5 mL ethanol and the mixture was warmed to room temperature and stirred for 1 hour. The mixture was concentrated and partitioned between water (50 mL) and ethyl acetate (1×100 mL). The aqueous layer was extracted with an additional 50 mL ethyl acetate. The combined organics were washed with 1×50 mL water, 1×25 mL saturated sodium chloride, and dried over Na$_2$SO$_4$. The dried organics were evaporated to an oil. The residue was chromatographed with 10 g silica gel, 20% ethyl acetate/hexanes to obtain 0.92 g of clear colorless oil. MS (ESI) m/z 282 [M+K]+. $^1$H NMR (CDCl$_3$) δ 1.25-1.31 (t, 3H), 1.49 (s, 9H), 1.57 (s, 2H), 3.01-3.07 (m, 1H), 3.30-3.36 (m, 1H), 3.47-3.65 (m, 3H), 4.13-4.20 (m, 2H).

tert-butyl 3-(3-methyl-1,2,4-oxadiazol-5-yl)pyrrolidine-1-carboxylate (30)

The methods described above for 2a,b were used for the preparation of 30. MS (ESI) m/z 292 [M+K]+. $^1$H NMR (CDCl$_3$) δ 1.49 (s, 9H), 2.12-2.21 (m, 1H), 2.33 (s, 3H), 2.36-2.45 (m, 1H), 2.87 (t, 1H), 3.23-3.30 (m, 2H), 3.41-3.46 (m, 1H), 3.61-3.66 (dd, 1H), 3.88-3.96 (m, 1H).

3-methyl-5-(pyrrolidin-3-yl)-1,2,4-oxadiazole (31)

The methods described above for 3a,b were used for the preparation of 31. MS (ESI) m/z 154 [M+1]+. $^1$H NMR (DMSO-d6) δ 2.12-2.21 (m, 1H), 2.33 (s, 3H), 2.36-2.45 (m, 1H), 2.87 (t, 1H), 3.23-3.30 (m, 2H), 3.41-3.46 (m, 1H), 3.61-3.66 (dd, 1H), 3.88-3.96 (m, 1H).

Example 26

Synthesis of 35

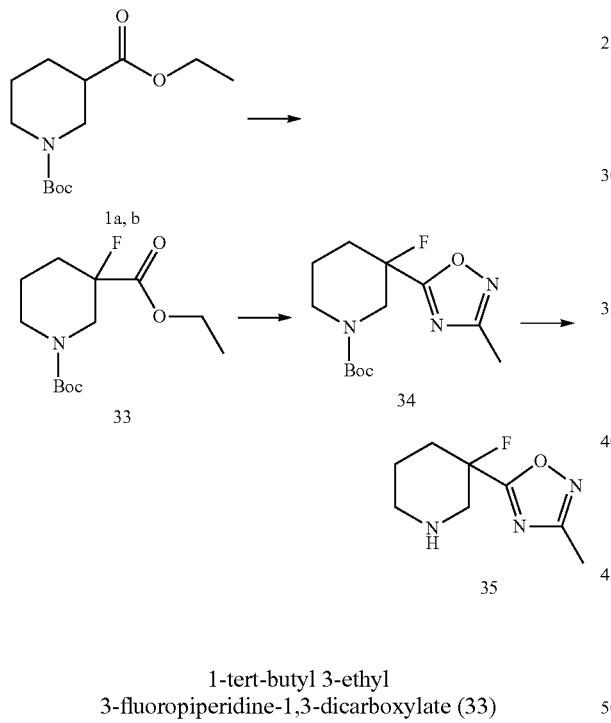

1-tert-butyl 3-ethyl 3-fluoropiperidine-1,3-dicarboxylate (33)

1-N-Boc-ethyl nipecotate 1a,b (1.6 g, 0.0062 mol) in 20 mL of tetrahydrofuran, was cooled over dry ice/acetone to −783° C. and lithium diisopropylamide (3.7 mL, 0.0075 mol) was added over 5 minutes. The mixture was stirred for 15 minutes at −78±3° C. Selectfluor (2.64 g, 0.0075 mol) was added as a slurry in 5 mL tetrahydrofuran. The reaction was stirred for an additional 15 minutes at −78±3° C. and warmed to room temperature. After stirring for 2 hours the reaction mixture was partitioned between saturated sodium bicarbonate (50 mL) and ethyl acetate (1×100 mL). The aqueous layer was extracted with an additional 2×50 mL ethyl acetate. The combined organics were washed with 1×50 mL 5% citric acid, 1×50 mL water, 1×50 mL saturated sodium chloride, and dried over Na$_2$SO$_4$. The dried organics were evaporated to an oil. The residue was chromatographed with 25 g silica gel, 5-10% ethyl acetate/hexanes, to obtain 0.80 g of clear colorless oil as a 1:1 mixture of 1a,b and 33. MS (ESI) m/z 314 [M+K]+ (33) and MS (ESI) m/z 296 [M+K]+ (1). The material was used in the next step without further purification.

tert-Butyl 3-fluoro-3-(3-methyl-1,2,4-oxadiazol-5-yl)piperidine-1-carboxylate (34)

The mixture of 1-tert-butyl 3-ethyl 3-fluoropiperidine-1,3-dicarboxylate 33 and 1a,b (0.8 g, 0.0029 mol) and acetamide oxime (0.54 g, 0.0073 mol) were dissolved in 30 mL tetrahydrofuran. Sodium methoxide (0.79 g, 0.0146 mol) was added and the mixture was heated at reflux for 1.75 hours. The mixture was concentrated and partitioned between water (25 mL) and ethyl acetate (1×100 mL). The aqueous layer was extracted with an additional 50 mL ethyl acetate. The combined organics were washed with 1×25 mL water, 1×40 mL saturated sodium chloride, and dried over Na$_2$SO$_4$. The dried organics were evaporated to an oil. The residue was chromatographed to remove 1a,b with 15 g silica gel, 100% dichloromethane to 5% ethyl acetate/dichloromethane, to obtain 0.18 g of clear colorless oil. MS (ESI) m/z 324 [M+K]+. $^1$H NMR (CDCl$_3$) δ 1.45 (s, 9H), 1.55-62 (m, 1H), 1.70-1.74 (d, 1H), 1.92-1.95 (m, 1H), 2.17 (m, 1H), 2.29-2.32 (m, 1H), 2.43 (s, 3H), 3.06-3.12 (m, 1H), 3.89-3.92 (m, 2H).

5-(3-fluoropiperidin-3-yl)-3-methyl-1,2,4-oxadiazole (35)

The methods described above for 3a,b were used for the preparation of 35 hydrochloride salt. MS (ESI) m/z 286 [M+1]+. $^1$H NMR (DMSO-d6) δ 1.90-1.96 (m, 2H), 2.13-2.33 (m, 1H), 2.42 (s, 3H), 2.98-3.05 (m, 1H), 3.23-3.28 (d, 1H), 3.58-3.71 (dd, 2H), 3.86-3.92 (t, 2H).

Example 27

Synthesis of 46

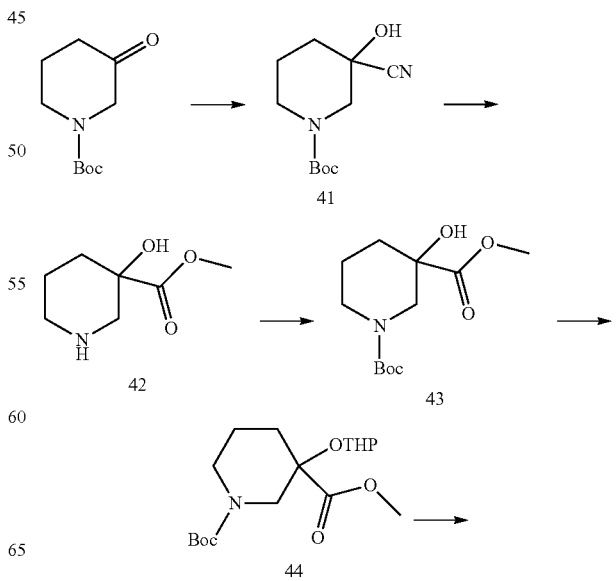

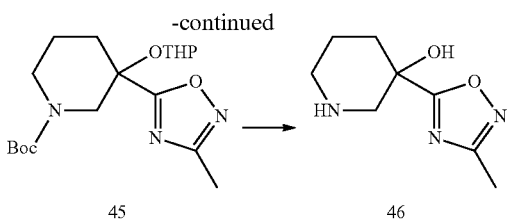

tert-Butyl
3-cyano-3-hydroxypiperidine-1-carboxylate (41)

1-Boc-3-piperidinone (5.0 g, 0.0251 mol) in THF (15 mL) was added dropwise to a solution of potassium cyanide (1.8 g 0.0276 mol) in water (15 mL) at 0-5° C. Acetic acid (1.6 mL, 0.0276 mol) was added and the solution was allowed to warm to room temperature and stir for 1 hr. The mixture was partitioned between water (50 mL) and ethyl acetate (1×150 mL). The organics were washed with 2×50 mL water, 1×50 mL saturated sodium chloride, and dried over $Na_2SO_4$. The dried organics were evaporated to obtain 5.5 g of yellow solid. The material was used without purification. MS (ESI) m/z 265 [M+K]+.

methyl 3-hydroxypiperidine-3-carboxylate (42)

tert-Butyl 3-cyano-3-hydroxypiperidine-1-carboxylate (41) (5.5 g, 0.0243 mol) was dissolved in 50 mL methanol and 25 mL concentrated hydrochloric acid. The mixture was heated at reflux for 5 hours. The mixture was concentrated to remove water. The resulting semi-solids were concentrated from 3×100 mL methanol:toluene (1:1) to remove residual water. The mixture was dissolved in 60 mL methanol and 2 mL acetyl chloride and stirred for 18 hrs. The solution was concentrated from 2×50 mL methanol and 50 mL methanol:ethylacetate (1:1) to obtain 5.8 g of amber oil. The material was used without further purification. MS (ESI) m/z 160 [M+H]+.

1-tert-butyl 3-methyl
3-hydroxypiperidine-1-dicarboxylate (43)

Methyl 3-hydroxypiperidine-3-carboxylate (42) (5.8 g, 0.0296 mol) was stirred in 100 mL dichloromethane. Triethylamine (8.7 mL, 0.0622 mol) and a catalytic amount of dimethylaminopyridine was added and the mixture was stirred at 0-5° C. for 30 min. Di-tert-butyl dicarbonate (6.79 g, 0.0311 mol) was added portion-wise to the solution and the mixture was stirred at 0-5° C. for 15 min. The solution was allowed to warm to room temperature and stirred for 18 hrs. The mixture was partitioned between water (50 mL) and ethyl acetate (200 mL). The organics were washed with 3×50 mL water, 1×50 mL saturated sodium chloride, and dried over $Na_2SO_4$. The dried organics were evaporated to an oil. The residue was chromatographed with 70 g silica gel, 20-25% ethyl acetate/hexanes, to obtain 6.14 g of clear colorless oil. MS (ESI) m/z 298 [M+K]+.

Example 28

Evaluation of Muscarine Agonist Activity

Muscarinic M1 and M3 agonist activity was evaluated by measuring the stimulation of inositol phosphate (IP) production in the presence of lithium chloride from A9L cells transfected with expression plasmids containing human muscarinic M1 and M3 receptors, respectively. The cell lines were a gift from Professor W Messer, and the methods were as described in Tejada F R et al. J. Med. Chem. 2006:49:7518-31 except that the assay was scaled down to run in 384 well plates, and IP was measured in the cell lysates using the non-isotopic IPOne TR-FRET assay (CIS-BIO, Inc).

Cells were grown to 90% confluence in 384 well hi-base plates (Greiner Bio-One), compounds were added at suitable concentrations in growth medium containing 10 mM LiCl, buffered with an extra 10 mM HEPES (pH7.4), and incubated for 60 minutes at 37° C. Cells were lysed and assayed for IP following the manufacturer's instructions. Each plate contained a standard set of concentrations of carbachol, enabling the $EC_{50}$ and maximum stimulation by a full agonist to be determined for comparative purposes.

The intrinsic efficacy of a compound was calculated as the stimulation of IP production expressed as a percentage of the maximal stimulation caused by treatment with carbachol. The value for a full agonist is 100%, while partial agonists give values below 100%. The potency of each compound was obtained from replicate multi-point dose-response curves, and the results were expressed semi-quantitatively relative to the potency of carbachol at its $EC_{50}$, thereby correcting for the experiment-to-experiment variability of the sensitivity of the assay.

TABLE 12

| | huM1/A9L | | huM3/A9L | |
|---|---|---|---|---|
| Compound | $ED_{50}$ relative to CCh* | Smax | $ED_{50}$ relative to CCh | Smax |
| Carbachol (CCh) | 1 | 100% | 1 | 100% |
| 3 | + | 108% | +/− | 54% |
| 3a | + | 129% | +/− | 66% |
| 3b | +/− | 147% | − | 47% |
| 7 | + | 116% | +/− | 60% |
| 7a | +/− | 81% | −− | 76% |
| 7b | + | 90% | +/− | 86% |
| 12a | + | 101% | + | 58% |
| 12b | − | 100% | − − | 60% |
| 27 | + | 97% | +/− | 20% |
| 31 | + | 113% | − | 60% |
| 35 | − | 81% | −− | 70% |
| Comparative Examples | | | | |
| 5 | inactive | 20% | inactive | 20% |
| 18 | inactive | 14% | inactive | 18 |
| 19 | inactive | 15% | inactive | 34 |
| 20 | inactive | 9% | inactive | 20% |
| 21 | inactive | 18% | inactive | 14% |
| 22 | inactive | 23% | inactive | 15% |
| 23 | inactive | 23% | inactive | 19% |
| 24 | −− | 41% | inactive | 32% |
| 25 | inactive | 3% | inactive | 20% |
| 36** | + | 72% | + | 39% |
| 37*** | ++ | 50-100 | ++ | 50-100 |
| 38 | inactive | 15% | inactive | <14% |
| 39 | inactive | 40% | inactive | 20% |
| 40 | inactive | 0% | inactive | 0% |

*Key: ++ potency >10x CCh; + potency 2-10x CCh; +/− potency 0.5-2x CCh; − potency <0.5-0.1x CCh; − − potency <0.1x CCh; inactive, potency too low to determine.
**3-methyl-5-(1-methyl-1,2,5,6-tetrahydropyridin-3-yl)-1,2,4-oxadiazole; J. Chem. Soc., Chem. Commun. 1988, 1618.
***3-methyl-5-(quinuclidin-3-yl)-1,2,4-oxadiazole; J. Med. Chem. 1990, 33(4), 1128.

As shown in Table 12, compounds described herein exhibited excellent potency at M1 muscarinic receptors, generally exceeding that of carbachol, a well known muscarinic agonist. In addition, the compounds exhibited good intrinsic efficacy as measured by Smax, and in some cases significantly exceeded the intrinsic efficacy of carbachol. Surprisingly, unlike carbachol, compounds described herein are selective for M1 receptors as demonstrated by greater potency, greater efficacy or both at the M1 receptors versus M3 receptors. Thus, such compounds would be expected to exhibit fewer of the side effects that result from stimulation of M3 receptors in the peripheral nervous system (e.g. salivation, lacrimation or tearing, diaphoresis or sweating, vomiting and diahorrea). Many of the compounds described herein also display advantages over certain known muscarinic agonists such as compounds 36 and 37. Thus, while compound 37 is highly potent, it is essentially non-selective between M1 and M3 receptors. Compound 36 shows some selectivity for M1 versus M3 receptors but has lower intrinsic efficacy than many of the compounds described herein. Also, as discussed below, both compounds 36 and 37 are far less metabolically stable than compounds described herein.

Surprisingly, as shown in Table 12, embodiments described herein show superior potency and efficacy compared to compounds of closely related structure. Thus, compound 5, the N-methyl analog of Compound 3 (a racemic mixture of 3-methyl-5-(piperidin-3-yl)-1,2,4-oxadiazole), is essentially inactive. By contrast, the N-methyltetrahydropyridine compound 36 displayed reasonable potency and efficacy at M1 muscarinic receptors. In addition, the 2-methyl, 4-methyl, 5-methyl and 6-methyl analogs of compound 3 (compounds 18-25) were essentially inactive at the M1 receptors. Likewise compound 38, 3-ethyl-5-(piperidin-3-yl)-1,2,4-oxadiazole, was also essentially inactive.

Example 29

In Vivo Measurement of Tissue Inositol Phosphate Signaling Pathway Activation

Figure 10A:
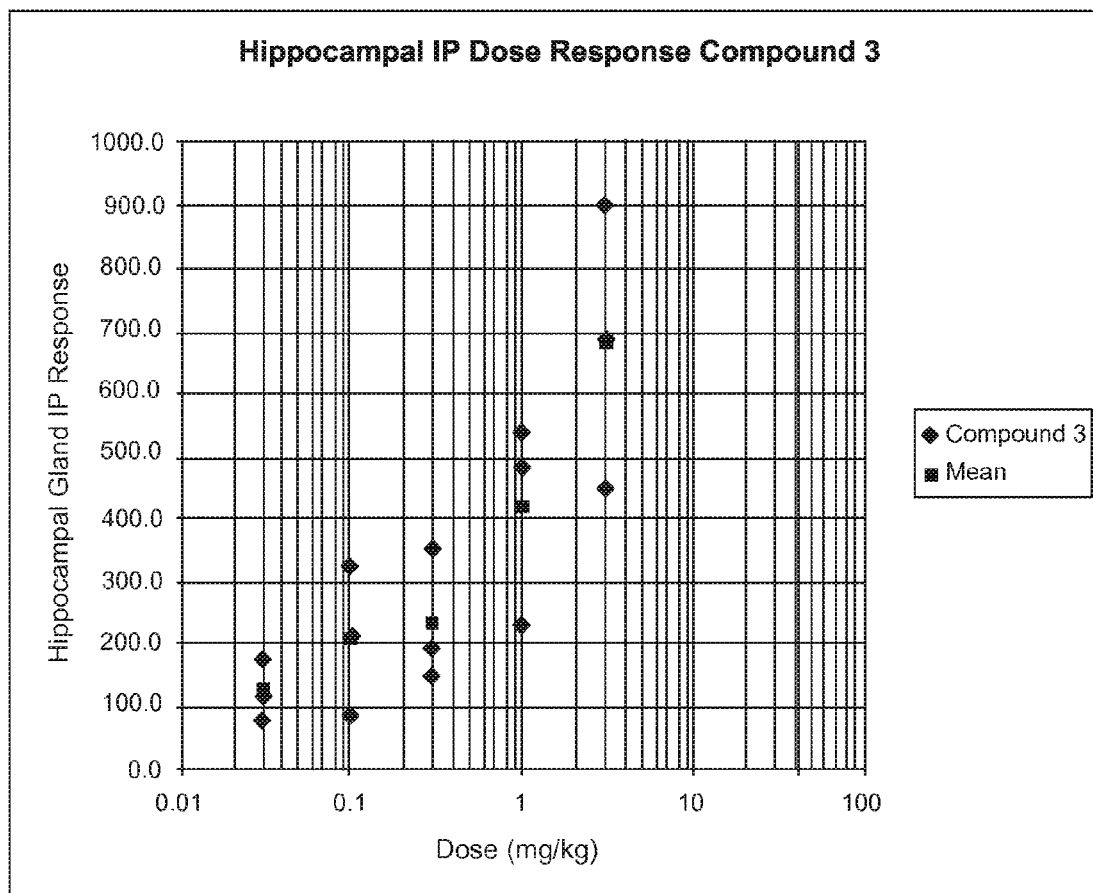
FIG. 10A shows activation of the hippocampal inositol phosphate signaling pathway involved in disease-modification by Compound 3 (a racemic mixture of 3-methyl-5-(piperidin-3-yl)-1,2,4-oxadiazole) in normal rats.

Experimental compounds or drug substances were administered using standard techniques to Long Evans Hooded rats weighing 225 to 350 grams, and which had been pretreated with a subcutaneous injection of lithium chloride at a suitable dose between 3 and 10 mmoles per kg. At suitable times the animals were briefly anesthetized using 5% isoflurane and euthanized by decapitation. The brains and submaxillary salivary glands were rapidly dissected out, and the hippocampuses were dissected from the brains. The dissected tissues were homogenized in a suitable volume of ice-cold phosphate-buffered saline containing 10 mM lithium chloride, pH7.4, using a tissue homogenizer, and used immediately or frozen in aliquots at −80 deg C. for future use. The concentration of inositol-1-phosphate was determined in the homogenates using the IPOne TR-FRET assay (CisBio cat no 621PAPEB), following the manufacturer's instruction Results are shown in FIGS. 10A & 10B. FIG. 10A shows that Compound 3 (a racemic mixture of 3-methyl-5-(piperidin-3-yl)-1,2,4-oxadiazol) cases an increase in the hippocampal IP response in normal rats and that this was dose-dependent in the dose range 0.03 mg/kg to at least 3 mg/kg. At the latter dose, it appears that the maximum level of stimulation had not been reached. FIG. 10B shows that a dose of 30 mg/kg sc of MCD-386 caused a 71% increase in the concentration of IP in the hippocampus of rats. Inositol phosphate is a key signaling pathway, which can activate several potentially disease-modifying mechanisms. These results strongly suggest that subtype-selective muscarinic agonists may have disease-modifying activity for Alzheimer's disease.

Example 30

In Vivo Measurement of Salivation

Suitable doses of test compounds or drug substances were administered using standard techniques to Long Evans Hooded rats weighing 225 to 350 grams, or CD-1 mice weighing 30 to 50 grams, which had been anesthetized using 2-3.5%% of isoflurane in oxygen. The animals were placed slightly head-down on an inclined, heated ramp. Rectal temperature was monitored using a thermocouple and the temperature of the heating pad was adjusted manually to maintain normal body temperature. Saliva was collected from the mouth by absorption onto pre-weighed slips of filter paper. The filter paper was changed periodically and the amount of saliva was measured by weighing the filter paper slips Results.

Figure 11:
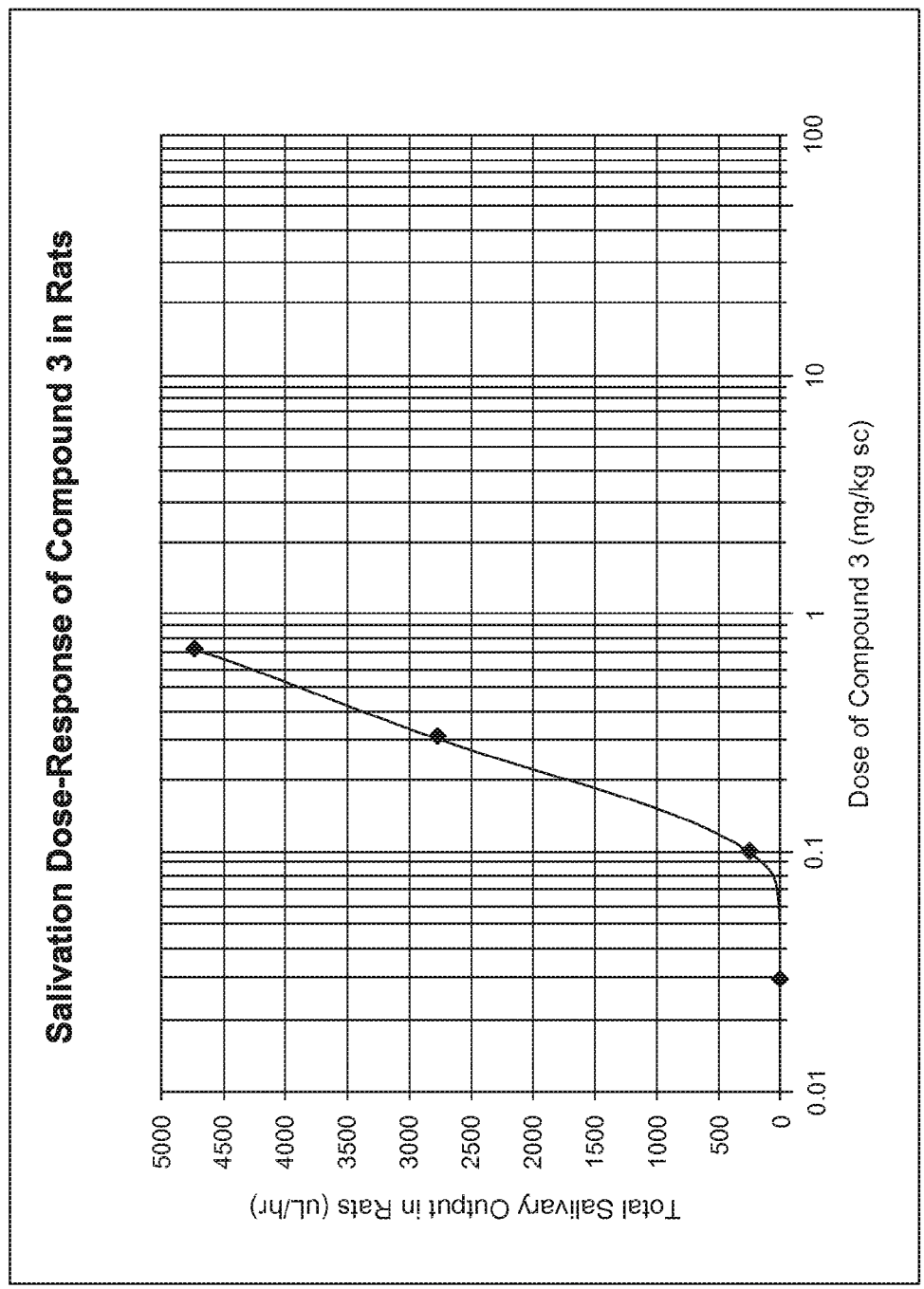
FIG. 11 shows the salivation side-effect dose-response by Compound 3 (a racemic mixture of 3-methyl-5-(piperidin-3-yl-1,2,4-oxadiazole) in anesthetized normal rats.
Figure 12:
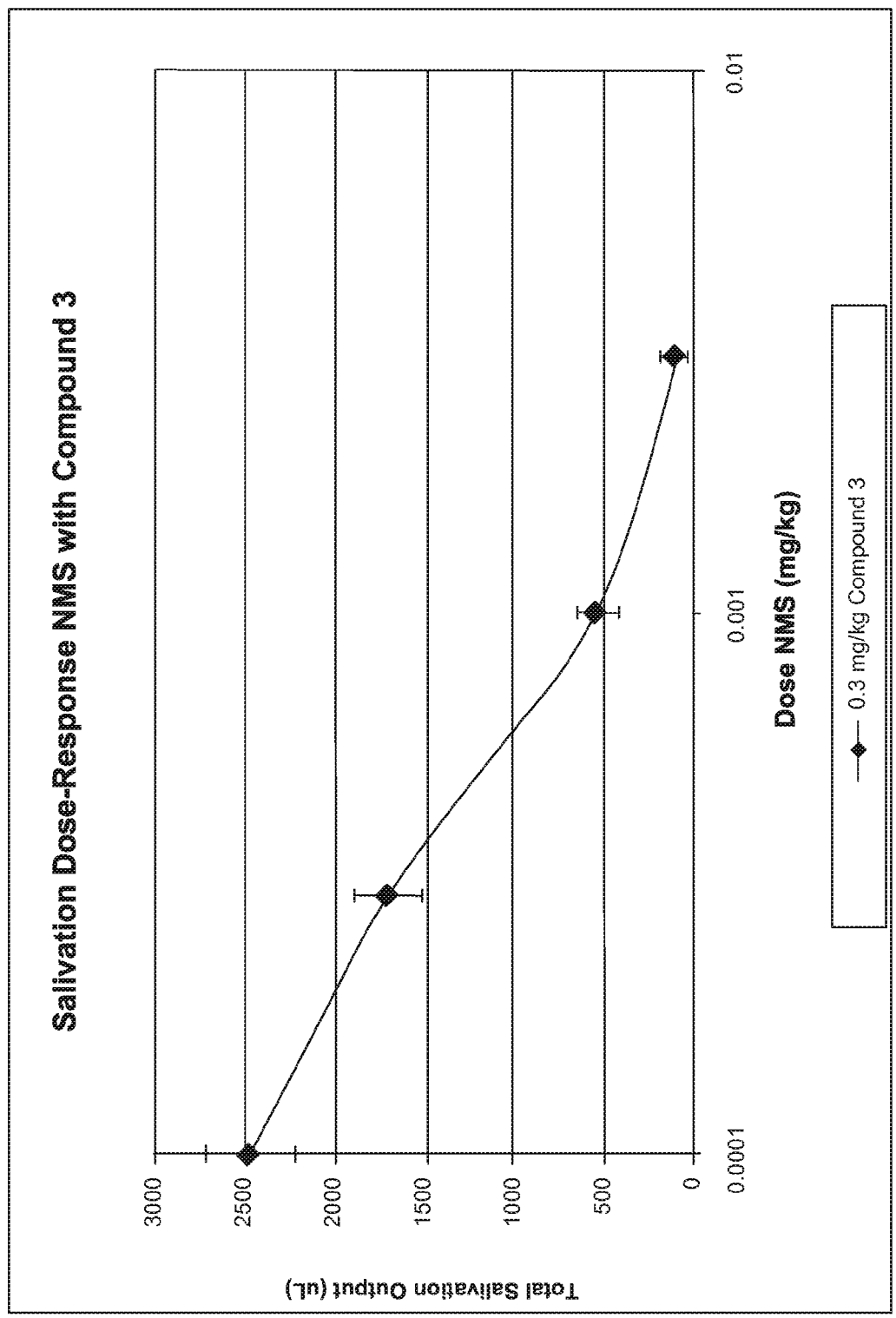
FIG. 12 shows the inhibition of Compound 3 (a racemic mixture of 3-methyl-5-(piperidin-3-yl)-1,2,4-oxadiazole) induced salivation by muscarinic antagonist NMS.
Figure 13:
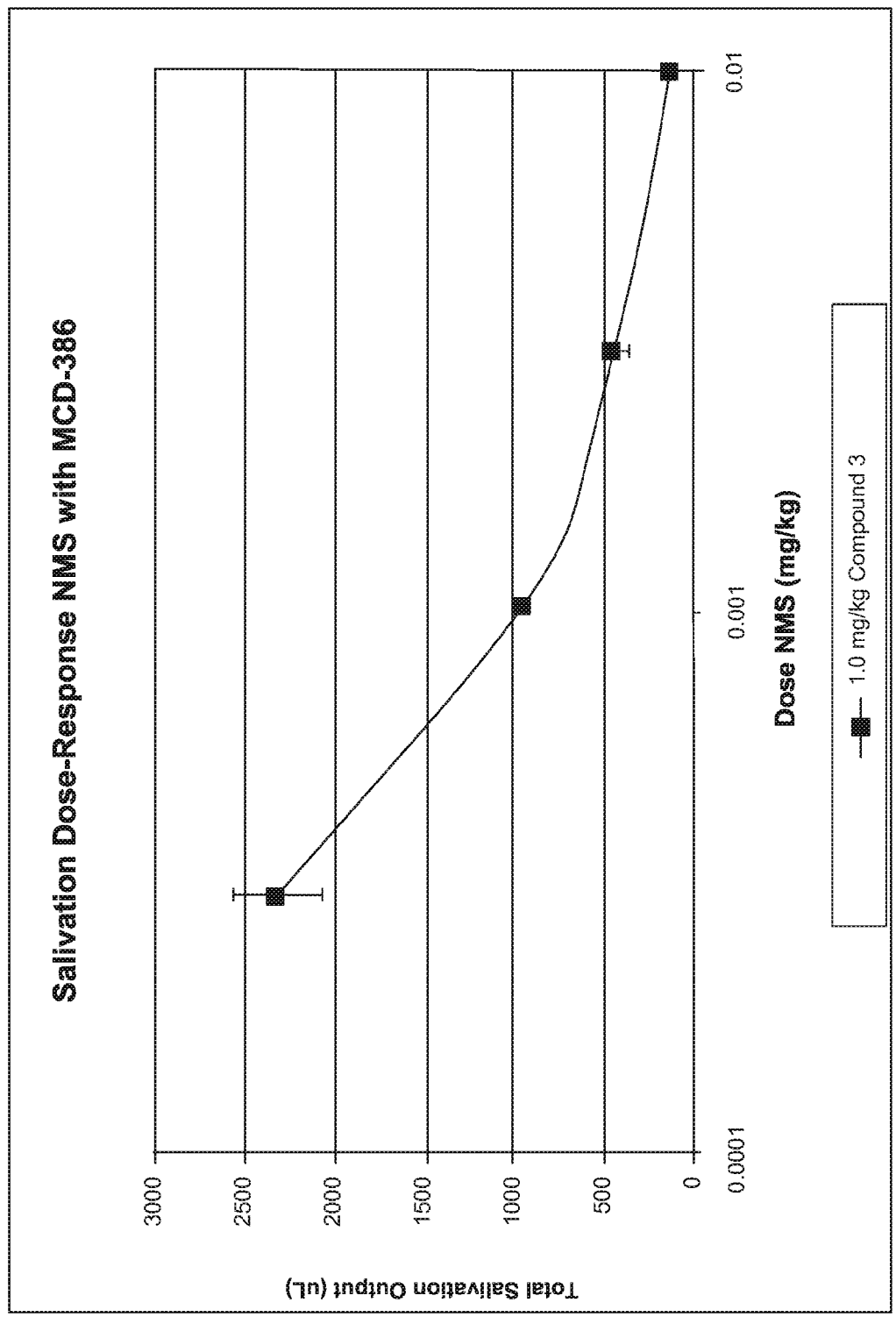
FIG. 13 shows the inhibition of MCD-386 induced salivation by NMS.

FIG. 11 shows that Compound 3 (a racemic mixture of 3-methyl-5-(piperidin-3-yl)-1,2,4-oxadiazole) causes salivation in anesthetized normal rats, and the effect is dose-dependent between about 0.1 mg/kg and 1 mg/kg. Salivation is an undesirable side effect of muscarinic agonists and is likely the result of incomplete selectivity of Compound 3 (a racemic mixture of 3-methyl-5-(piperidin-3-yl)-1,2,4-oxadiazole). FIG. 12 shows that N-methylscopolamine (NMS) causes a dose-dependent decrease in salivation caused by a dose of 0.3 mg/kg of Compound 3 (a racemic mixture of 3-methyl-5-(piperidin-3-yl)-1,2,4-oxadiazole). The combination of an antagonist with Compound 3 (a racemic mixture of 3-methyl-5-(piperidin-3-yl)-1,2,4-oxadiazole) avoids the side effects associated with residual muscarinic M3 activity of Compound 3 (a racemic mixture of 3-methyl-5-(piperidin-3-yl)-1,2,4-oxadiazole). FIG. 13 shows a similar dose-dependent reduction in unwanted salivation side-effect by NMS caused by a 1 mg/kg dose of MCD-386.

Example 31

Apomorphine Induced Climbing

Compound 3 (a racemic mixture of 3-methyl-5-(piperidin-3-yl)-1,2,4-oxadiazole) was tested for activity in the apomorphine induced climbing model of psychosis in comparison to standard antipsychotic agents as well as a known muscarinic agonist, xanomeline. As described in Costall et. al. European Journal of Pharmacology 1978, 50, 39, individual CD-1 mice, 1-2 months old, were placed in a cylindrical wire mesh cage (13.2 an high×13.2 cm diameter) constructed of steel wire 1 mm thick spaced at 1.2 cm$^2$. Cylinders were placed in a standard OptiMICE mouse cage (29×32×9×29 cm and 14 cm high) with adequate wood chip bedding provided. Observations of climbing (defined as 3 or more paws off the ground) were carried out every 5 minutes at a duration of 1 minute for 30 minutes. Animals were injected subcutaneously under isoflurane anesthesia with test compounds, reference compounds, which included clozapine, haloperidol, olanzapine and xanomeline, or PBS as a control. This was followed 5 minutes later by 2 mg/1 g apomorphine hydrochloride. All drugs were dissolved in PBS or a mixture of (by volume) 96% PBS and 4% hydroxypropyl-beta-cyclodextrin, and dosed at a rate of 5 ml per kilogram of body weight. Following injections, animals were replaced in the mesh cages and observed for climbing (defined as 3 or more paws off the ground) every 5 minutes for 1 minute for 60 minutes after dosing.

Results are shown in FIG. 1. In the apomorphine induced climbing model, Compound 3 (a racemic mixture of 3-methyl-5-(piperidin-3-yl)-1,2,4-oxadiazole) was unexpectedly highly active and highly potent. This suggests that Compound 3 (a racemic mixture of 3-methyl-5-(piperidin-3-yl)-1,2,4-oxadiazole) has a novel first-in-class antipsychotic activity. By comparison, the M1 muscarinic agonist 5-(3-ethyl-1,2,4-oxadiazole-5-yl)-1,4,5,6-tetrahydro-pyrimidine.HCl (U.S. Pat. No. 5,175,166), Compound 48 was inactive in this model, demonstrating that M1 muscarinic agonist activity is not predictive of activity in the present assay. More surprisingly, Compound 3 (a racemic mixture of 3-methyl-5-(piperidin-3-yl)-1,2,4-oxadiazole) was equipotent to haloperidol, one of the most potent antipsychotic agents available, in inhibiting climbing. Compound 3 (a racemic mixture of 3-methyl-5-(piperidin-3-yl)-1,2,4-oxadiazole) also exhibited orders of magnitude better activity than another muscarinic agonist that was tested, xanomeline, as well as the standard antipsychotic agents, olanzapine and clozapine. These results suggest potential utility for treating the positive symptoms of schizophrenia.

Compound 3 (a racemic mixture of 3-methyl-5-(piperidin-3-yl)-1,2,4-oxadiazole) was also tested in the apomorphine induced climbing model by administering it (0.1 mg/kg) as above in combination with the muscarinic antagonist scopolamine (0.3 mg/kg), which acts both peripherally and centrally, and N-methylscopolamine, which acts only peripherally and does not enter the brain. Results are shown in Table 13 below and demonstrate that the efficacy of Compound 3 (a racemic mixture of 3-methyl-5-(piperidin-3-yl)-1,2,4-oxadiazole) was inhibited by scopolamine, but not N-methylscopolamine. These results show that the potential anti-psychotic action of 3 is mediated by activation of central muscarinic receptor and not by direct antagonism of dopamine action, distinguishing its action from that of the so-called typical antipsychotic drugs (such as haloperidol) or the atypical antipsychotic drugs (olanzapine and clozapine). Furthermore, the putative anti-psychotic activity of compound was unaffected by N-methylscopolamine, demonstrating that the use of this drug to combat potential peripheral adverse effects of Compound 3 (a racemic mixture of 3-methyl-5-(piperidin-3-yl)-1,2,4-oxadiazole) would not block its anti-psychotic action.

TABLE 13

| Compound | Climbing Mean (secs) | SEMS |
| --- | --- | --- |
| Control | 4.3 | 1.6 |
| APO (2 mg/kg) | 51.7 | 3.5 |
| Cmpd 3 (0.1 mg/kg) + APO | 8.9 | 6.7 |
| cmpd 3 + APO + scopolamine (0.3 mg/kg) | 47.0 | 4.6 |
| Cmpd 3 + APO + N-Methyl Scopolamine (0.3 mg/kg) | 12.3 | 4.7 |

Example 32

Aβ Levels

Figure 14:
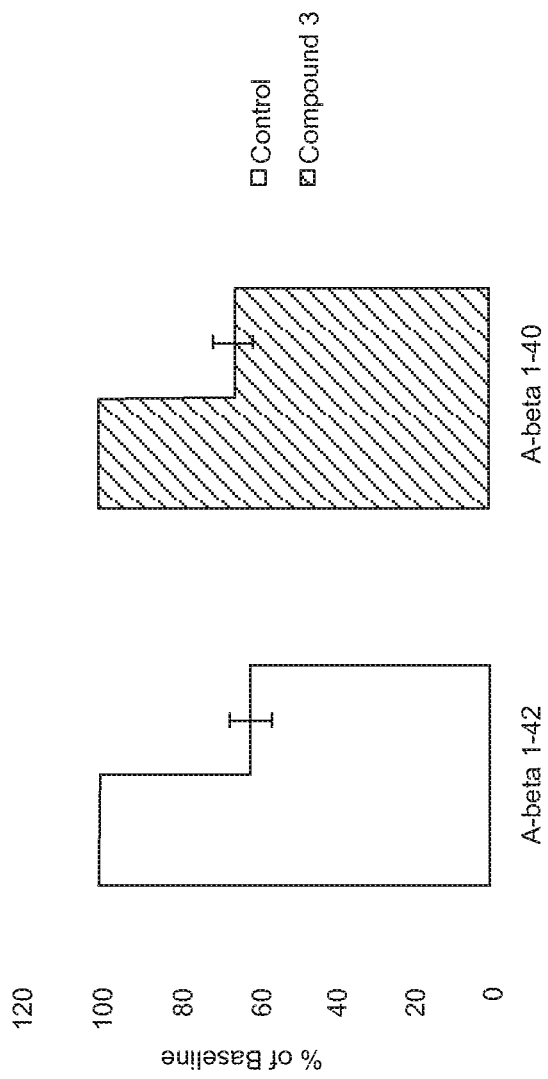
FIG. 14 shows the inhibition of A-beta production in a transgenic Alzheimer's mouse model by a single dose of Compound 3 (a racemic mixture of 3-methyl-5-(piperidin-3-yl)-1,2,4-oxadiazole), a more direct measure of disease-modifying activity.

Compound 3 (a racemic mixture of 3-methyl-5-(piperidin-3-yl)-1,2,4-oxadiazole) was found to reduce by approximately 40% the concentration of A-beta 1-40 and A-beta 1-42 in the hippocampal microdialysate (Cirrito J et al, J Neurosci 2003; 23: 8844-53) of Tg-2576 transgenic mice, engineered to overproduce human APP containing the Swedish mutation that sensitizes it to the action of gamma-secretase. These mice have high concentrations of A-beta in their brain tissue, thought to be the cause of neuron death in Alzheimer's disease, and accumulate amyloid plaques, recapitulating one of the hallmark pathological features of Alzheimer's disease. This suggests that Compound 3 (a racemic mixture of 3-methyl-5-(piperidin-3-yl)-1,2,4-oxadiazole) will have disease-modifying activity for Alzheimer's disease. See FIG. 14.

Example 33

Metabolic Studies

Susceptibly/Resistance to Metabolism by Flavin Monoxygenase 1 (FMO1)

Compounds were incubated with human FMO1 Supersomes (BD Biosciences, #456241) and an NADP-regenerating system in a glycine buffer (pH 9.5) for a total of 60 minutes. Aliquots were removed every 10 minutes, and 1% formic acid was added to halt the reaction. Samples were centrifuged, filtered through 0.2 micron spinfilter and the amount of each compound in the supernatants was quantitated using LC/MS/MS.

Figure 2:
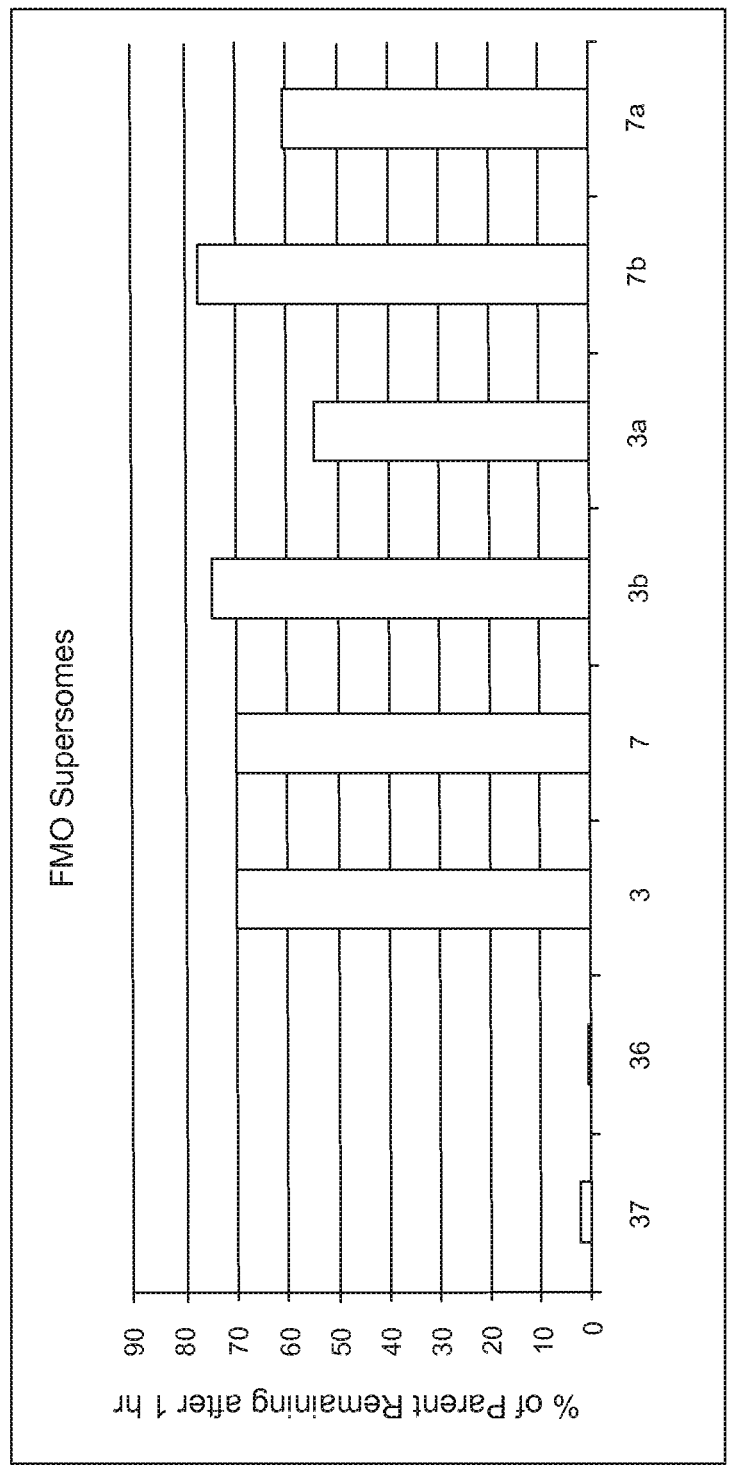
FIG. 2 illustrates the resistance of compounds of this disclosure and prior art compounds to metabolism by FMO1 Supersomes.

Results are shown in FIG. 2 for compounds 3, 3a, 3b, 7, 7a, 7b, 36 and 37. After 6 hours, compounds 36 and 37 were almost completely metabolized in FMO Supersomes. By contrast, the compounds 3, 7 and their enantiomers were less than half metabolized. Surprisingly, compounds 3b and 7b the R-enantiomers of 3 and 7, were less than 30% metabolized.

Susceptibility/Resistance to Metabolism by Rat Liver Microsomes

Compounds were incubated with pooled male Sprague-Dawley rat liver microsomes (BD Biosciences. #452501) and an NADP-regenerating system in a phosphate buffer (pH 7.4) for a total of 6 hours. Aliquots were removed every 2 hours, and 1% formic acid was added to halt the reaction. Samples were centrifuged, filtered through 0.2 micron spinfilter and the amount of each compound in the supernatants was quantitated using LC/MS/MS.

Figure 3:
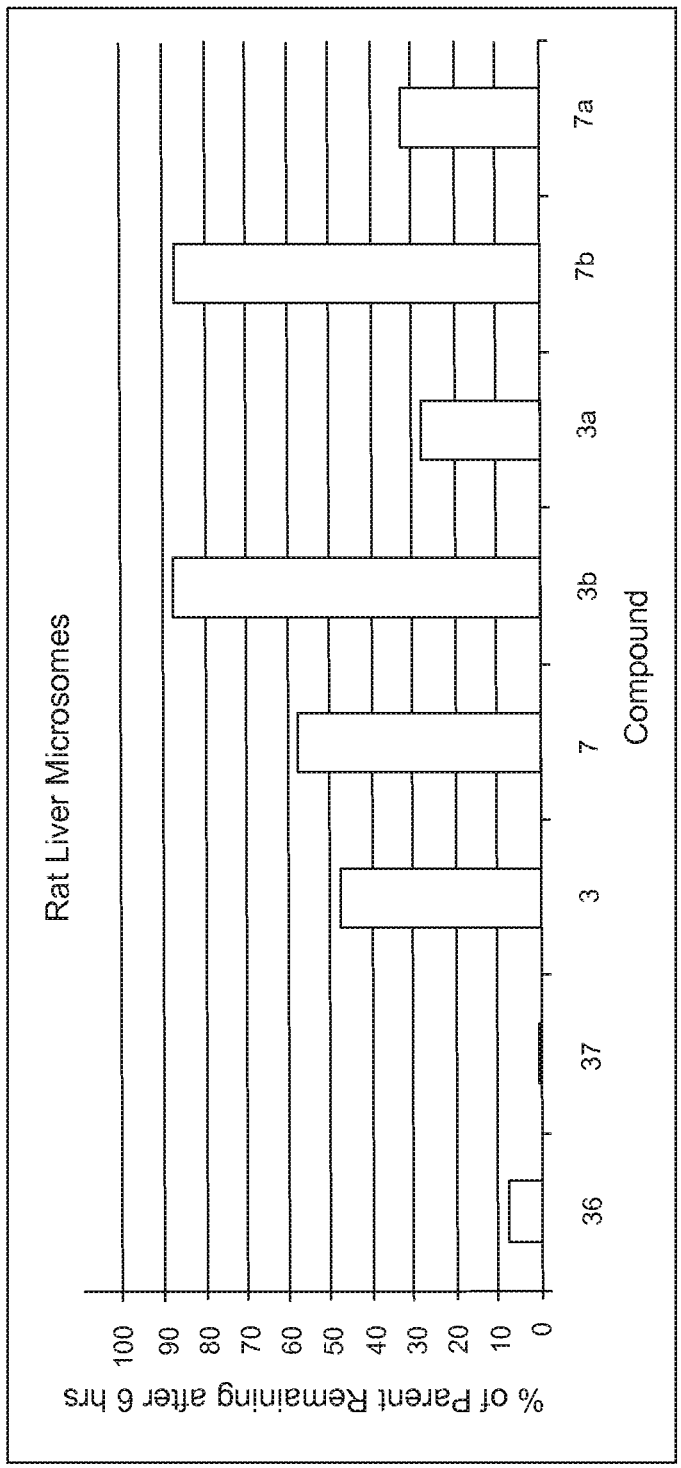
FIG. 3 illustrates the resistance of compounds of this disclosure and prior art compounds to metabolism by rat liver microsomes.

Results are shown in FIG. 3 for compounds 3, 3a, 3b, 7, 7a, 7b, 36 and 37. While these compounds were more extensively metabolized in rat liver microsomes than human liver microsomes or FMO Supersomes, they were still far more stable than compounds 36 and 37.

Susceptibility/Resistance to Metabolism by Human Liver Microsomes

Compounds were incubated with pooled male human liver microsomes (BD Biosciences. #452172) and an NADP-regenerating system in a phosphate buffer (pH 7.4) for a total of 6 hours. Aliquots were removed every 2 hours, and 1% formic acid was added to halt the reaction. Samples were centrifuged, filtered through 0.2 micron spinfilter and the amount of each compound in the supernatants was quantitated using LC/MS/MS.

Figure 4A:
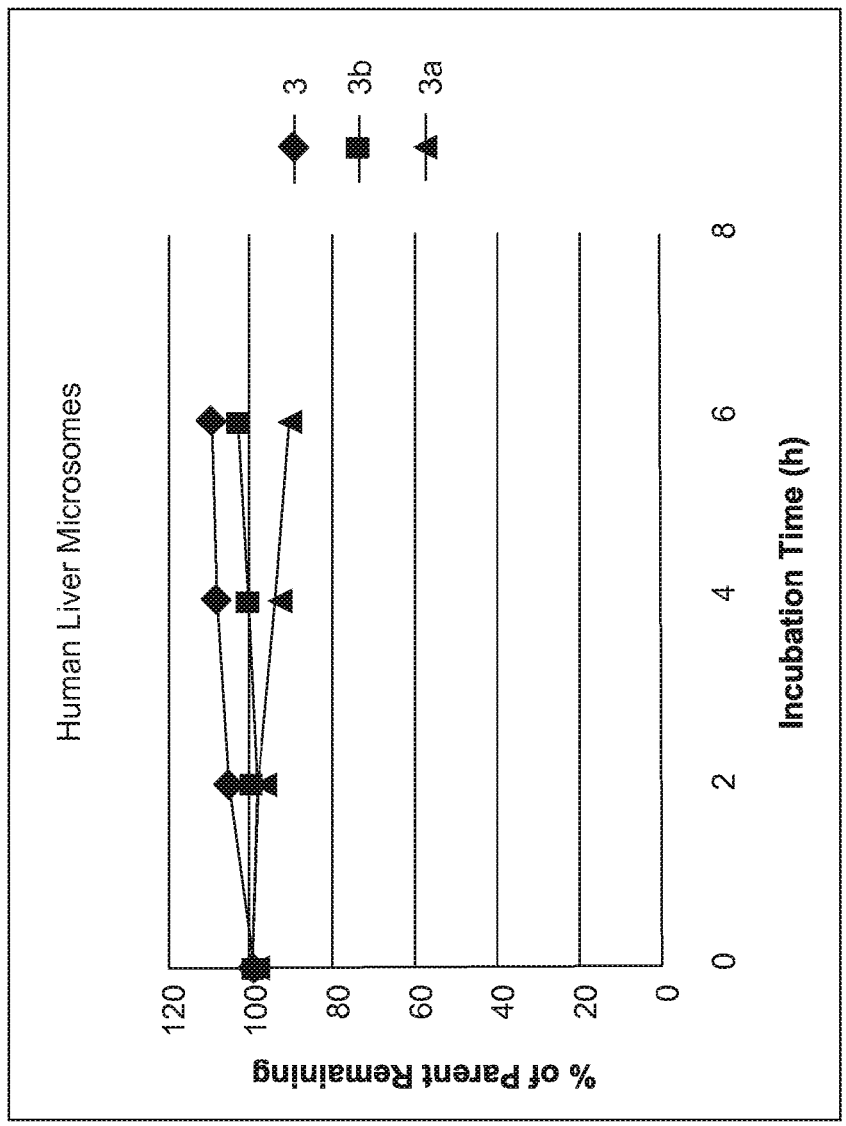
FIGS. 4A and 4B compare the resistance of compounds of this disclosure to metabolism by human liver microsomes.
Figure 4B:
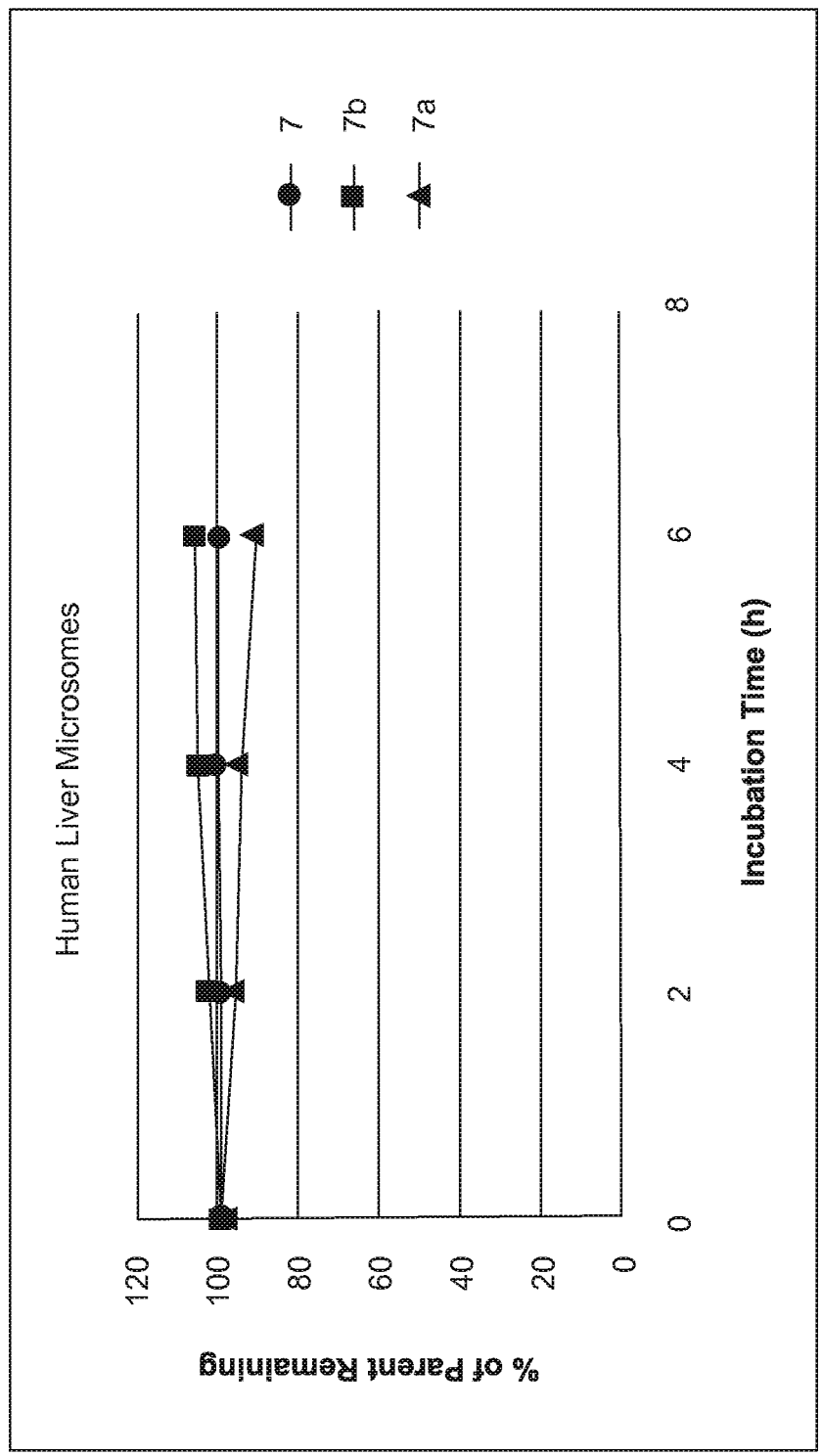

Results are shown in FIGS. 4A and 4B. Compounds 3, 3a, 3b, 7, 7a and 7b were metabolized significantly less in human liver microsomes than in rat liver microsomes. The S-enantiomers 3a and 7a were metabolized faster than the R-enantiomers, 3b and 7b respectively, as was found in rat liver microsomes and FMO Supersomes. The different rates of metabolism may reflect the different activities of the FMO enzyme in the rat liver and human liver microsomes.

Notably, compound 36 was nearly completely metabolized in the above assays. It shares a major structural element with the well-known agonist, xanomeline. One of the most serious problems of xanomeline (U.S. Pat. No. 5,043,345), and one of the reasons that xanomeline was abandoned even after showing therapeutic benefits in both Alzheimer's disease and schizophrenia, is that it was heavily metabolized in the N-methyltetrahydropyridine ring, the same moiety contained in compound 36. By contrast, the compounds in accordance with this disclosure were much more stable to metabolism in the above assays.

Example 34

Compound 3 (a racemic mixture of 3-methyl-5-(piperidin-3-yl)-1,2,4-oxadiazole) crossed the lipid membrane at a much higher rate than the known muscarinic agonist 3-ethyl-5-(1,4,5,6-tetrahydropyrimidin-5-yl-1,2,4-oxadiazole, compound 48 (CDD-0102), in the PAMPA test, suggesting a much greater ability of compound 3 (a racemic mixture of 3-methyl-5-piperidin-3-yl)-1,2,4-oxadiazole) to cross the blood-brain barrier (Table 14). This was confirmed by dosing the compound orally to rats. The concentration of compound 3 (a racemic mixture of 3-methyl-5-(piperidin-3-yl)-1,2,4-oxadiazole) in the brain one hour after dosing was 238 times the concentration in the plasma. By comparison, the ratio of brain/plasma concentration of Compound 48 was 0.07 to 0.13. Compounds 36 and 37 with quinuclidine and N-methyltetrahydropyridine rings, respectively, crossed the lipid layer in the PAMPA test slightly better and significantly better, respectively, than compound 3. The highest rate of penetration was seen with compound 35, a fluorine containing piperidine compound similar to compound 3a.

TABLE 14

| Compound | PAMPA Permeability Coefficient (×10⁶) | Brain/plasma ratio |
| --- | --- | --- |
| Compound 48 | 0.05 | 0.07-0.13 |
| Compound 3 | 2.56 | 2.38 |
| Compound 36 | 12.75 | — |
| Compound 37 | 3.02 | — |
| Compound 35 | 16.3 | = |
| Ranitidine (low brain penetration) | 0.26 | Very low |
| Clonidine (mid-hi brain penetration) | 7.95 | = |

The invention(s) as defined by the appended claims is/are not to be limited in scope by the embodiments disclosed herein. Indeed, various modifications of the embodiments shown and described herein will become apparent to those skilled in the art from the foregoing description and thus should be deemed to fall within the scope of the appended claims. All publications, patent applications, issued patents, and other documents referred to in this specification are herein incorporated by reference as if each individual publication, paten application, issued patent, or other document was specifically and individually indicated to be incorporated by reference in its entirety. Definitions that are contained in text incorporated by reference are excluded to the extent that they contradict definitions in this disclosure.

Example 35

A schema for the preparation of an azabicyclo-substituted oxadiazole, 5-(3-azabicyclo[4.1.0]heptan-1-yl)-3-methyl-1,2,4-oxadiazole, is illustrated below:

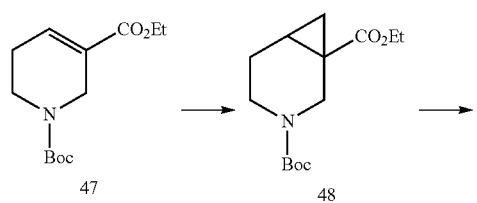

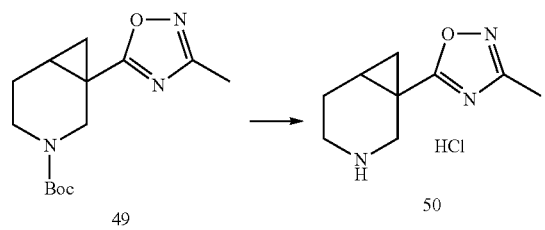

The N-Boc protected conjugated ester was prepared as previously described (Org. Let. 2000, 2(25), 4037). The cyclopropyl group was installed by reaction with Corey's reagent (TMSO1, NaH, DMSO), at 50-60° C., followed by aqueous work up and silica gel chromatography, in 18% yield. It was found that at higher temperatures the reaction failed and starting material was recovered. At lower temperatures, the yield dropped below 5%. The oxadiazole ring was prepared as described above, by reaction with acetamide oxime and sodium methoxide, in 66.9% yield. Standard deblocking with HCl-EtOH provided the desired product, as the HCl salt, in 91% yield.

Preparation of 5-(3-azabicyclo[3.1.0]hexan-1-yl)-3-methyl-1,2,4-oxadiazole

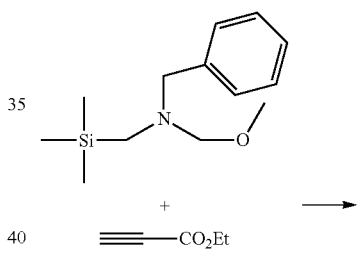

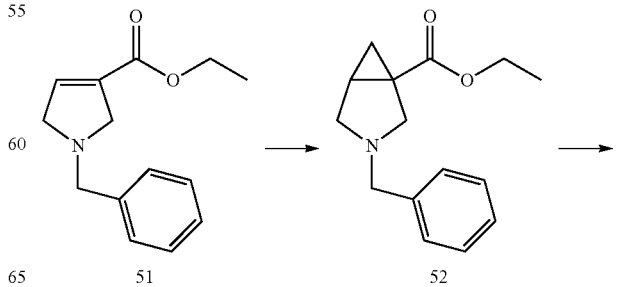

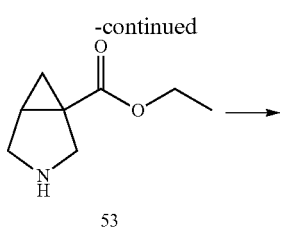

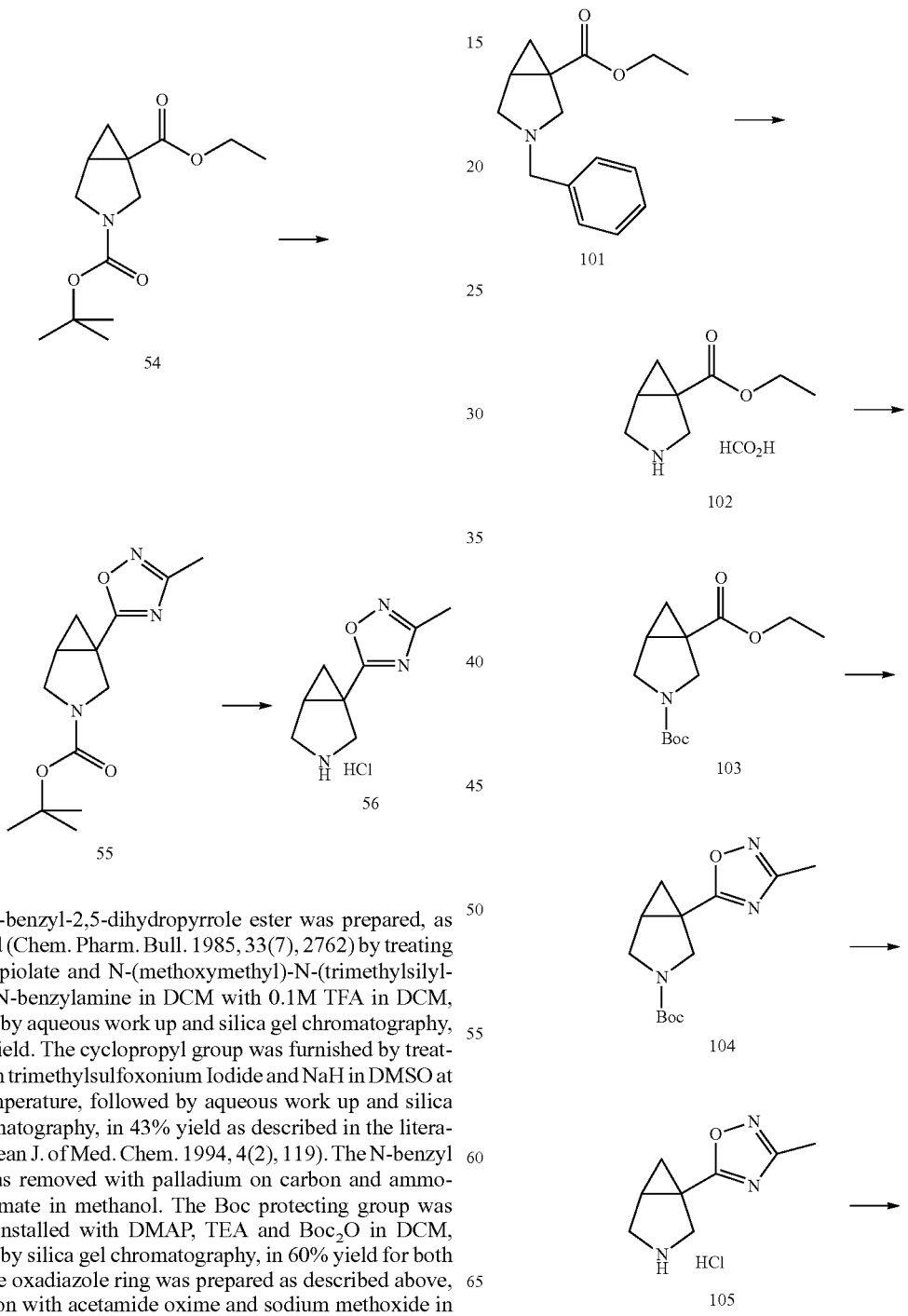

provided the intermediate in 54% yield. Standard deblocking with HCl-EtOH provided the desired product, as the HCl salt, in 82% yield.

Example 36

Synthesis of 106a and 106b

Scheme 101:

The N-benzyl-2,5-dihydropyrrole ester was prepared, as described (Chem. Pharm. Bull. 1985, 33(7), 2762) by treating ethyl propiolate and N-(methoxymethyl)-N-(trimethylsilylmethyl)-N-benzylamine in DCM with 0.1M TFA in DCM, followed by aqueous work up and silica gel chromatography, in 44% yield. The cyclopropyl group was furnished by treatment with trimethylsulfoxonium Iodide and NaH in DMSO at room temperature, followed by aqueous work up and silica gel chromatography, in 43% yield as described in the literature (Korean J. of Med. Chem. 1994, 4(2), 119). The N-benzyl group was removed with palladium on carbon and ammonium formate in methanol. The Boc protecting group was directly installed with DMAP, TEA and Boc₂O in DCM, followed by silica gel chromatography, in 60% yield for both steps. The oxadiazole ring was prepared as described above, by reaction with acetamide oxime and sodium methoxide in methyl THF. Aqueous work up and silica gel chromatography

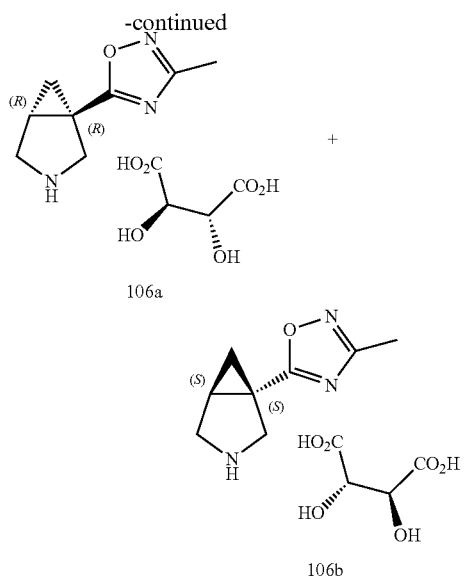

106a

106b

3-tert-butyl 1-ethyl 3-azabicyclo[3.1.0]hexan-1,3-dicarboxylate (103)

The preparation of compound 101 has been carried out previously (Korean J. Med. Chem., 1994, 4(2), 119). To a solution of ethyl 3-benzyl-3-azabicyclo[3.1.0]hexane-1-carboxylate (101) (3.96 g, 16.14 mmol) and ammonium formate (5.09 g, 80.71 mmol) in 80 mL of methanol was suspended 2.5 g of 10% palladium on carbon (Degussa type E101 NE/W). The mixture was refluxed for 15 minutes filtered through Celite and condensed to clear, colorless oil (102). MS (ESI) m/z 172.1 [M+H]$^+$. Dichloromethane (50 mL), triethylamine (2.45 g, 24.24 mmol) and 4-dimethylaminopyridine (20 mg) were then added to the oil. The mixture was chilled in an ice bath before the addition of di-tert-butyl dicarbonate (3.70 g, 16.95 mmol) in 10 mL of dichloromethane and was allowed to warm to mom temperature for 45 minutes. Evaporation of the mixture followed by chromatography over 30 g of silica gel with hexanes/ethyl acetate, afforded 3.5 g of 103 as clear, colorless oil. MS (ESI) m/z 294.0 [M+K]$^+$. $^1$H NMR (CDCl$_3$) δ: 0.84 (m, 1H), 1.26 (1, 3H), 1.44 (s, 9H), 1.57 (m, 2H), 2.02 (m, 1H), 3.41 (m, 1H), 3.64 (m, 2H), 4.15 (q, 2H).

tert-Butyl 1-(3-methyl-1,2,4-oxadiazole-yl)-3-azabicyclo[3.1.0]hexane-3-carboxylate (104)

2-Methyltetrahydrofuran (15 mL), acetamide oxime (2.54 g, 34.3 mmol) and sodium methoxide (3.70 g, 68.6 mmol) were added to 3-tert-butyl 1-ethyl 3-azabicyclo[3.1.0]hexane-1,3-dicarboxylate (103) (3.5 g, 13.72 mmol) and the mixture was heated to reflux for 20 minutes. Upon cooling the suspension was treated with 60 mL, of water and extracted with ethyl acetate (2×50 mL). The combined organics were washed with saturated sodium chloride and dried over magnesium sulfate. The mixture was concentrated and the residue was chromatographed over 20 g of silica gel with hexanes/ethyl acetate; obtained 1.95 g of 104 as a white solid. MS (ESI) m/z 304.0[M+K]$^+$. $^1$H NMR (CDCl$_3$) δ: 1.17 (m, 1H), 1.46 (s, 9H), 1.74 (m, 1H), 2.18 (s, 2H), 2.22 (m, 1H), 2.36 (s, 3H), 3.50 (m, 1H), 3.70 (m, 1H).

5-(3-Azabicyclo[3.1.0]hexan-1-yl)-3-methyl-1,2,4-oxadiazole (105)

HCl/EtOH (8.49 mL of 2.53 M solution) was added to tert-butyl 1-(3-methyl-1,2,4-oxadiazol-5-yl)-3-azabicyclo[3.1.0]hexane-3-carboxylate (104) (1.9 g, 7.16 mmol) in 5 mL of ethanol. The solution was refluxed for 5 minutes, cooled and condensed to a white solid. The crude solid was crystallized from ethanol and diethyl ether, obtained 1.18 g of white solid hydrochloride salt MS (ESI) m/z 165.8[M+H]$^+$. $^1$H NMR (CDCl$_3$) δ: 1.18 (m, 2H), 1.50 (s, 3H), 3.42 (m, 3H), 3.74 (m, 2H), 9.64 (s, 2H).

5-((1R,5R)-3-Azabicyclo[3.1.0]hexan-1-yl)-3-methyl-1,2,4-oxadiazole (106a) and 5-((1S,5S)-3-Azabicyclo[3.1.0]hexan-1-yl)-3-methyl-1,2,4-oxadiazole (106b)

5-(3-Azabicyclo[3.1.0]hexan-1-yl)-3-methyl-1,2,4-oxadiazole (105) (923 mg, 4.58 mmol) was dissolved in water (20 mL) and treated with saturated sodium bicarbonate (40 mL), and 5 g of sodium chloride (pH8). The aqueous layer was extracted with dichloromethane (6×100 mL), the organic layers combined, dried over magnesium sulfate and filtered through a fritted glass filter. The filtrate was treated with D-tartaric acid (655 g, 4.36 mmol) in 60 mL of methanol and evaporated to dryness. The solid residue was dissolved in 6 mL of methanol and then 23 mL of acetonitrile were added. An oily residue that formed was decanted away from and dried under vacuum. The crude solid was dissolved into a minimal amount of boiling methanol (40 mL) and then acetonitrile (100 mL, 2.5:1, acetonitrile to methanol ratio) was added. The mixture was allowed to stir at room temperature for 20 minutes prior to isolation. The process was repeated until the crystalline substance exceeded an enantiomeric purity of 99.5°; obtained 440 mg of 5-((1S,5S)-3-azabicyclo[3.1.0]hexan-1-yl)-3-methyl-1,2,4-oxadiazole (106b). The optical purity was determined by HPLC analysis (Chiral Technologies Chiral-AGP, 4.0 mm×150 mm, 0.5% methanol 20 mM sodium phosphate pH=7). (106b) MS (ESI) m/z 165.8 [M+H]$^+$. $^1$H NMR (DMSO-d6) δ: 1.44 (m, 2H), 2.23 (m, 1H), 2.28 (s, 3H), 3.06 (s, 2H), 3.35 (m, 2H), 4.13 (s, 2H).

The combined mother liquors were evaporated and the salt was free-based in dichloromethane as described above for 16b prior to adding L-tartaric acid (400 mg, 2.66 mmol) in 20 mL of methanol. The exact recrystallization procedure was repeated as described above; obtained 168 mg of 5-((1R,5R)-3-azabicyclo[3.1.0]hexan-1-yl)-3-methyl-1,2,4-oxadiazole (106). The optical purity (99.5%) was determined by HPLC analysis (Chiral Technologies Chiral-AGP, 4.0 mm×150 mm, 0.5% methanol, 20 mM sodium phosphate pH=7). (106) MS (ESI) m/z 165.8 [M+H]$^+$. $^1$H NMR (DMSO-d6) δ: 1.44 (m, 2H), 2.23 (m, 1H), 2.28 (s, 3H), 3.06 (s, 2H), 3.35 (m, 2H), 4.13 (s, 2H).

Example 37

Absolute Configuration of 106a by X-Ray Crystallography

A colorless crystal of 106a with approximate dimensions 0.14×0.07×0.07 mm$^3$ was selected under oil under ambient conditions and attached to the tip of a MiTeGen MicroMount®. The crystal was mounted in a stream of cold nitrogen at 100(1) K and centered in the X-ray beam by using a video camera. The crystal evaluation and data collection were performed on a Bruker SMART APEXII diffractometer with Cu K$_\alpha$ (λ=1.54178 Å) radiation and the diffractometer to crystal distance of 4.03 cm.

Figure 15:
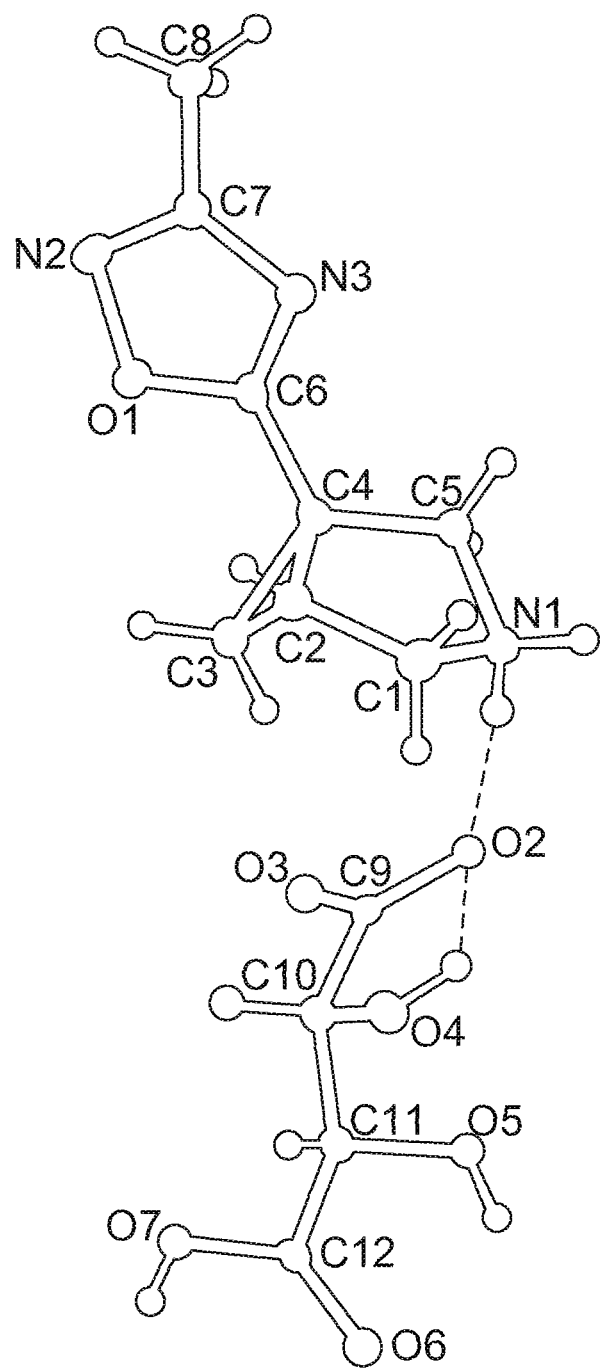

The resulting X-ray structure, as represented in an ORTEP drawing is shown in FIG. 15. The absolute configuration of compound 106a was confirmed to be (1R,5R).

Example 38

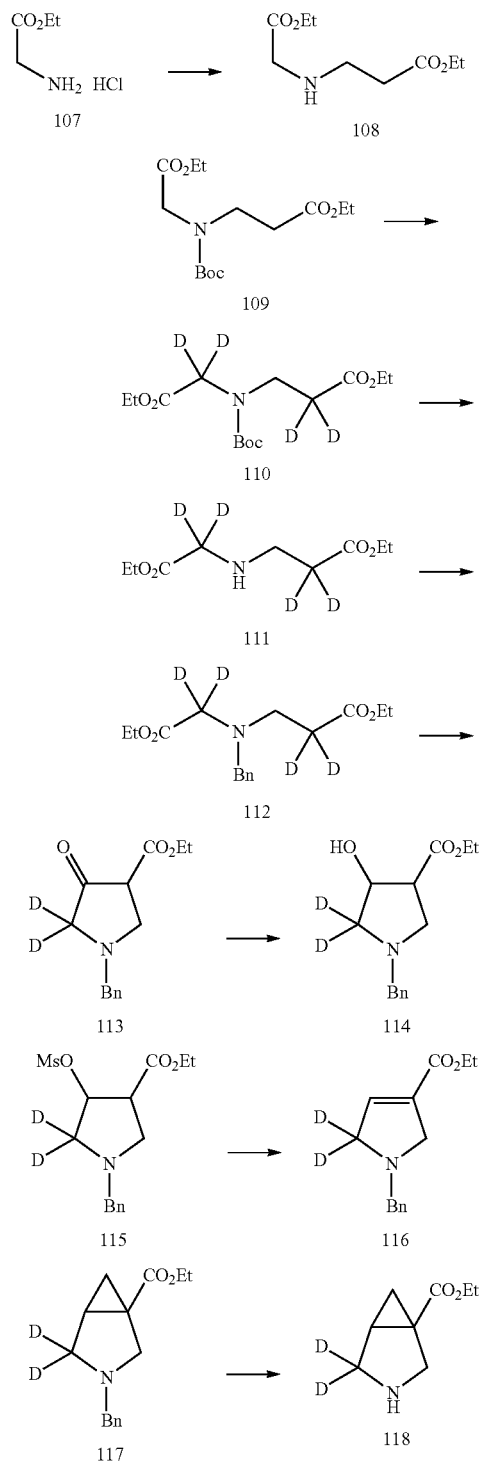

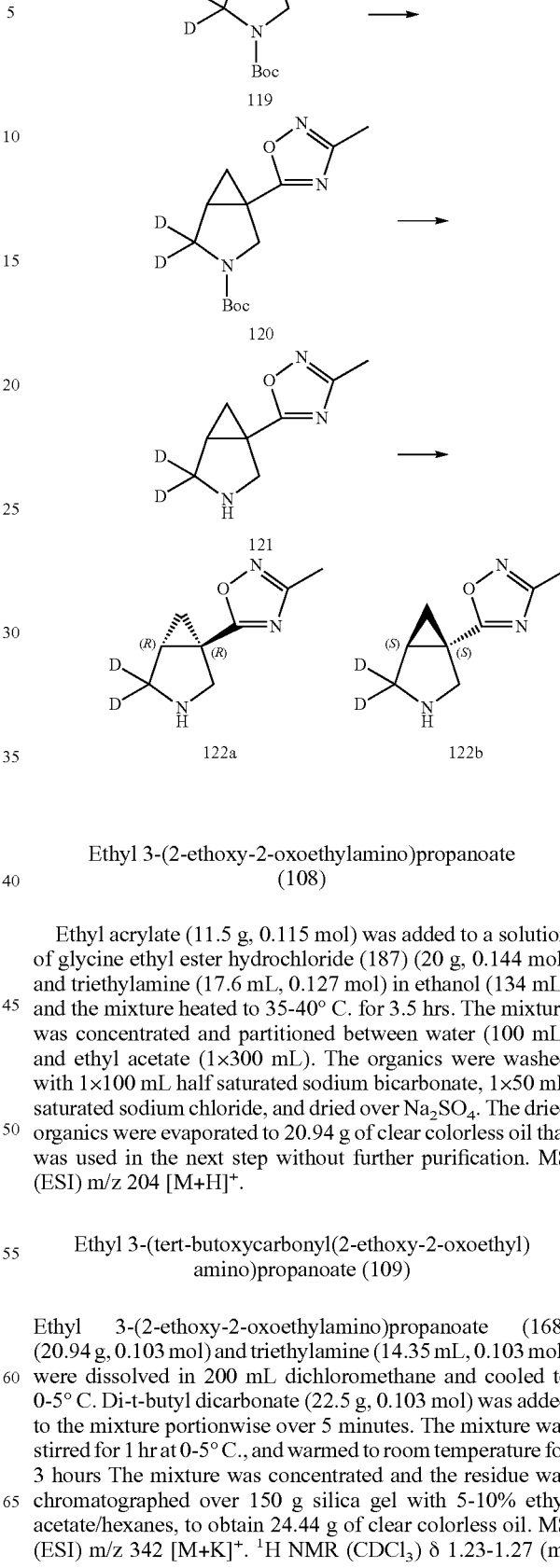

Ethyl 3-(2-ethoxy-2-oxoethylamino)propanoate (108)

Ethyl acrylate (11.5 g, 0.115 mol) was added to a solution of glycine ethyl ester hydrochloride (187) (20 g, 0.144 mol) and triethylamine (17.6 mL, 0.127 mol) in ethanol (134 mL) and the mixture heated to 35-40° C. for 3.5 hrs. The mixture was concentrated and partitioned between water (100 mL) and ethyl acetate (1×300 mL). The organics were washed with 1×100 mL half saturated sodium bicarbonate, 1×50 mL saturated sodium chloride, and dried over $Na_2SO_4$. The dried organics were evaporated to 20.94 g of clear colorless oil that was used in the next step without further purification. MS (ESI) m/z 204 $[M+H]^+$.

Ethyl 3-(tert-butoxycarbonyl(2-ethoxy-2-oxoethyl) amino)propanoate (109)

Ethyl 3-(2-ethoxy-2-oxoethylamino)propanoate (168) (20.94 g, 0.103 mol) and triethylamine (14.35 mL, 0.103 mol) were dissolved in 200 mL dichloromethane and cooled to 0-5° C. Di-t-butyl dicarbonate (22.5 g, 0.103 mol) was added to the mixture portionwise over 5 minutes. The mixture was stirred for 1 hr at 0-5° C., and warmed to room temperature for 3 hours The mixture was concentrated and the residue was chromatographed over 150 g silica gel with 5-10% ethyl acetate/hexanes, to obtain 24.44 g of clear colorless oil. MS (ESI) m/z 342 $[M+K]^+$. $^1H$ NMR ($CDCl_3$) δ 1.23-1.27 (m, 6H), 1.39 (s, 4.5H), 1.46 (s, 4.5H)-Boc rotamers, 2.58-2.63 (dt, 2H), 3.49-3.56 (dt, 2H), 3.94 (s, 1H), 4.00 (s, 1H), 4.08-4.17 (m, 4H).

Ethyl 3-(tert-butoxycarbonyl(2 ethoxy-2-oxoethyl) amino)propanoate-d4 (110)

Ethyl 3-(tert-butoxycarbonyl(2-ethoxy-2-oxoethyl) amino)propanoate (109) (31 g, 0.102 mol) was dissolved in 200 mL ethanol-d. DBU (26 mL, 0.174 mol) was added and the mixture was heated to reflux for 1.5 hours. The mixture was stirred at 35-40° C. for 16.5 hrs. The deuterium exchange was 50% complete by mass spectroscopy and the mixture was concentrated. The resulting oil was dissolved in 100 mL of ethanol-d and heated to 60° C. for 4 hrs. The deuterium exchange was 80% complete by mass spectroscopy and the mixture was concentrated. The resulting oil was dissolved in 100 mL of ethanol-d and stirred for 3 days at room temperature The mixture was concentrated and partitioned between 10% citric acid in water (200 mL) and ethyl acetate (1×300 mL). The aqueous layer was back extracted with ethyl acetate (1×200 mL). The combined organics were washed with 1×50 mL 5% citric acid in water, 1×100 mL saturated sodium bicarbonate, and dried over $Na_2SO_4$. The dried organics were evaporated to an oil to obtain 31.5 g of clear, pale yellow oil that was used in the next step without further purification. MS (ESI) m/z 346 [M+K]$^+$.

Ethyl 3-(2-ethoxy-2-oxoethylamino)propanoate-d4 (111)

Ethyl 3-(tert-butoxycarbonyl(2-ethoxy-2-oxoethyl) amino)propenoate-d4 (110) (20 g, 0.0.065 mol) was dissolved in 200 mL $CH_2Cl_2$ and the solution was cooled to 0-5° C. Trifloroacetic acid (30 mL) was added and the mixture was heated to 35° C. for 3.5 hours. The mixture was concentrated from 100 mL ethyl acetate and partitioned between ethyl acetate (100 mL) and 100 mL saturated sodium bicarbonate. The pH was adjusted with solid sodium bicarbonate to pH=8. Water (50 mL) and ethyl acetate (100 mL) were added. The organics were washed with water (50 mL) and the aqueous layer was back extracted with ethyl acetate (1×100 mL). The combined organics were washed 1×50 mL saturated sodium chloride, and dried over $Na_2SO_4$. The dried organics were evaporated to 11.33 g of clear, pale yellow oil that was used in the next step without further purification. MS (ESI) m/z 208 [M+H]$^+$.

Ethyl 3-(benzyl(2-ethoxy-2-oxoethyl)amino)propanoate-d4 (112)

Ethyl 3-(2-ethoxy-2-oxoethylamino)propanoate-d4 (111) (11.3 g, 0.055 mol) was dissolved in 120 mL acetonitrile. Potassium carbonate (9.12 mL, 0.066 mol) and benzyl bromide (7.14 ml, 0.060 mol) were added and the mixture was stirred for 1 hour at mom temperature and stored at 5° C. for 16 hrs. The mixture was heated to 40° C. for 1.5 hours. The reaction mixture was concentrated and partitioned between water (200 mL) and $CH_2Cl_2$ (1×100 mL). The aqueous layer was back extracted with $CH_2Cl_2$ (2×50 mL) and the combined organics were dried over $Na_2SO_4$. The dried organics were evaporated to an oil and chromatographed over 100 g silica gel with 5-10% ethyl acetate/hexanes, to obtain 14.03 g of clear, colorless oil. MS (ESI) m/z 298 [M+H]$^+$. $^1$H NMR (CDCl$_3$) δ 1.23-1.28 (m, 6H), 3.04 (s, 2H), 3.82 (s, 2H), 4.11-4.17 (m, 4H), 7.23-7.30 (m, 5H).

Ethyl 1-benzyl-4-hydroxypyrrolidine-3-carboxylate-5,5-d2 (114)

Ethyl 3-(benzyl(2-ethoxy-2-oxoethyl)amino)propanoate-d4 (112) (14 g, 0.0471 mol) and ethanol-d (5.5 mL, 0.0942 mol) were dissolved in 200 mL tetrahydrofuran and cooled to 0-5° C. Potassium tert-butoxide (5.81 g, 0.0518 mol) was added to the mixture portionwise over 2 minutes. The mixture was stirred for 45 minutes, acetic acid-d4 (3.24 mL, 0.0565 mol) was added followed by sodium borohydride (3.56 g, 0.0942 mol) and 4 mL 1:1 ethanol water. The mixture was stirred at 0-5° C. for 2.25 hrs, and quenched with 50 mL saturated ammonium chloride. Water (50 mL) and ethyl acetate (100 mL) were added. The aqueous layer was back extracted with ethyl acetate (100 mL). The combined organics were washed 1×50 mL water, 1×50 mL saturated sodium chloride, and dried over $Na_2SO_4$. The dried organics were evaporated to an oil to obtain 10.34 g of clear off-white oil that was used in the next step without further purification. MS (ESI) m/z 252 [M+H]$^+$.

Ethyl 1-benzyl-2,5-dihydro-1H-pyrrole-3-carboxylate-5,5-d2 (116)

Ethyl 1-benzyl-4-hydroxypyrrolidine-3-carboxylate-5,5-d2 (114) (10.34 g, 0.0411 mol) and triethylamine (6.9 mL, 0.0493 mol) were dissolved in 200 mL anhydrous $CH_2Cl_2$ and cooled to 0-5° C. Methane sulfonyl chloride (3.5 mL, 0.0453 mol) was added to the mixture dropwise over 2 minutes. The mixture was stirred for 30 minutes, saturated sodium chloride (50 mL) was added and the aqueous layer was extracted with $CH_2Cl_2$ (2×50 mL). The combined organics were dried over $Na_2SO_4$ and concentrated to a yellow oil. The residue was dissolved in $CH_2Cl_2$ (50 mL) followed by DBU (8 mL, 0.0534 mol). The mixture was stirred at room temperature for 15 minutes, diluted with ethyl acetate (150 mL) and water (50 mL). The aqueous layer was beck extracted with ethyl acetate (50 mL). The combined organics were washed 1×50 mL water, 2×50 mL saturated sodium chloride, and dried over $Na_2SO_4$. The dried organics were evaporated to an oil and chromatographed over 100 g silica gel with 5-20% ethyl acetate/hexanes, to obtain 7.08 g of clear light yellow oil. MS (ESI) m/z 234 [M+H]$^+$. $^1$H NMR (CDCl$_3$) δ 1.25-1.28 (m, 3H), 3.69 (s, 2H), 3.82 (s, 2H), 4.13-4.21 (m, 2H), 7.25 (s, 1H), 7.31-738 (m, 5H).

Ethyl 3-hexyl-3-azabicyclo[3.1.0]hexane-1-carboxylate-4,4-d2 (117)

Sodium hydride (1.34 g, 0.0333 mol) was suspended in anhydrous DMSO. TMSOI (6.67 g, 0.0303 mol) was added portionwise over 10 minutes. Ethyl 1-benzyl-2,5-dihydro-1H-pyrol-3-carboxylate-5,5-d2 (116) (7.08 g, 0.0303 mol) was dissolved in 25 mL anhydrous DMSO and added to the mixture dropwise over 15 minutes. The mixture was stirred for 30 minutes, quenched with water (10 mL) and was partitioned between ethyl acetate (200 mL) and water (70 mL). The organics were washed with water (2×50 mL) and saturated sodium chloride (50 mL). The aqueous layer was back extracted with ethyl acetate (100 mL). The combined organics were dried over $Na_2SO_4$. The dried organics were evaporated to an oil and chromatographed over 60 g silica gel with 5-10% ethyl acetate/hexanes, to obtain 2.44 g of clear light yellow oil. MS (ESI) m/z 248 [M+H]$^+$. $^1$H NMR (CDCl$_3$) δ 1.21-1.24 (m, 3H), 1.26-1.30 (dd, 1H), 1.47-1.49 (dd, 1H), 1.88-1.91 (q, 1H), 2.71-2.73 (d, 1H), 3.05-3.07 (d, 1H), 3.61-3.62 (m, 2H), 4.09-4.14 (q, 2H), 7.23-731 (m, 5H).

3-tert-Butyl 1-ethyl-3-azabicyclo[3.1.0]hexane-1,3-dicarboxylate-4,4-d2 (119)

10% Pd/C (1.2 g), methanol (35 mL), and ammonium formate (2.75 g, 0.0437 mol) were added to Ethyl 3-benzyl-3-azabicyclo[3.1.0]hexane-1-carboxylate-4,4-d2 (117) (2.44 g, 0.0097 mol) and the mixture was heated to reflux for 1 hr. Upon cooling the suspension was filtered though Celite and concentrated to dryness. Dichloromethane (40 mL) and triethylamine (2.02 mL, 0.0146 mol) were added and the solution was cooled to 0-5° C. Di-t-butyl dicarbonate (22.5 g, 0.103 mol) was added and the mixture was stirred and warmed to room temperature for 1.5 hours The mixture was concentrated and the residue was chromatographed over 25 g silica gel with 5-15% ethyl acetate/hexanes, to obtain 2.21 g of clear, colorless oil. MS (ESI) m/z 296 [M+K]$^+$. $^1$H NMR (CDCl$_3$) δ0.83-0.85 (t, 2H), 1.25-1.28 (m, 3H), 1.44 (s, 9H), 1.56-1.60 (m, 1H), 3.61-3.79 (m, 2H), 4.13-4.19 (m, 2H).

tert-Butyl-1-(3-methyl-1,2,4-oxadiazole-5-yl)-3-azabicyclo[3.1.0]hexane-3-carboxylate-4,4-d2 (120)

2-methyl-tetrahydrofuran (42 mL), acetamide oxime (1.59 g, 0.0215 mol) and sodium methoxide (2.75 g, 0.0437 mol) were added to 3-tert-Butyl 1-ethyl-3-azabicyclo[3.1.0]hexane-1,3-dicarboxylate-4,4-d2 (119) (2.44 g, 0.0097 mol) and the mixture was heated to reflux for 2 hrs. Upon cooling the suspension was partitioned between ethyl acetate (150 mL) and water (50 mL). The organic layer was washed with water (50 mL), saturated sodium chloride (50 mL) and dried over Na$_2$SO$_4$. The mixture was concentrated and the residue was chromatographed over 25 g silica gel with 10-20% ethyl acetate/hexanes, to obtain 1.27 g of clear, colorless oil. MS (ESI) m/z 306 [M+K]$^+$. $^1$H NMR (CDCl$_3$) δ 1.17-1.19 (m, 1H), 1.46 (s, 9H), 1.60 (m, 1H), 1.72-1.78 (m, 1H), 2.36 (s, 3H), 3.91-4.00 (d, 2H).

5-(4,4-d2-3-Azabicyclo[3.1.0]hexan-1-yl)-3-methyl-1,2,4-oxadiazole (121)

11.5 ml of 2.53 N HCl was added to tert-butyl 4,4-d2-(3-methyl-1,2,4-oxadiazol-5-yl)-3-azabicyclo[3.1.0]hexane-3-carboxylate (120) (3.107 g, 11.62 mmol) in 15 mL of ethanol. The solution was warmed to boiling for 5 minutes, cooled and condensed to a white solid (2.22 g). The material was used in the next step without further purification. MS (ESI) m/z 168.0 [M+H]$^+$.

Chiral Resolution of 5-((1R,5R)-4,4-d2-3-azabicyclo[3.1.0]hexan-1-yl)-3-methyl-1,2,4-oxadiazole and 5-(1S,5S)-4,4-d2-3-azabicyclo[3.1.0]hexan-1-yl)-3-methyl-1,2,4-oxadiazole (122a and 122b)

5-(4,4-d2-3-Azabicyclo[3.1.0]hexan-1-yl)-3-methyl-1,2,4-oxadiazole (121) was dissolved in water (10 mL) saturate sodium bicarbonate (25 mL), and 5 g of sodium chloride (pH=8). The aqueous layer was extracted with dichloromethane (3×100 mL) and the organic layers dried over sodium sulfate and filtered through a fitted glass fiber. The filtrate was treated with L-tartaric acid (1.74 g, 11.62 mmol) in 7 mL of methanol and evaporated to dryness. The solid residue was dissolved in 40 mL of methanol and then 160 mL of acetonitrile were added. The mixture was allowed to stir at room temperature for 20 minutes before collecting the precipitate by suction filtration. The isolated solid was dissolved into a minimal amount of boiling methanol (60 mL) and then acetonitrile (160 mL, 2.5:1, acetonitrile to methanol ratio) were added. The mixture was allowed to stir at room temperature for 20 minutes prior to isolation. The process was repeated until the crystalline substance exceeded an enantiomeric purity of 99.5%; obtained 476 mg of 5-((1R,5R)-4,4-d2-3-azabicyclo[3.1.0]hexan-1-yl)-3-methyl-1,2,4-oxadiazole (122a) The optical purity was determined by HPLC analysis (Chiral Technologies Chiral-AGP, 4.0 mm a 150 mm, 0.5% methanol, 20 mM sodium phosphate pH=7). MS (ESI) m/z 168 [M+H]$^+$. $^1$H NMR (DMSO-d6) δ 1.39-1.42 (m, 1H), 1.49-1.50 (m, 1H), 2.28 (s, 3H), 3.35-3.41 (m, 2H), 4.13 (s, 1H).

The combined mother liquors were evaporated and provided as a free base in dichloromethane prior to adding D-tartaric acid (1.52 g, 10.11 mmol) in 7 mL of methanol. The exact procedure was repeated as described above; obtained 815 mg of 99.5% of 5-((1S,5S)-4,4-d2-3-4-azabicyclo[3.1.0]hexan-1-yl)-3-methyl-1,2,4-oxadiazole (122b). The optical purity was determined by HPLC analysis (Chiral Technologies Chiral-AGP, 4.0 mm×150 mm, 0.5% methanol, 20 mM sodium phosphate pH=7). MS (ESI) m/z 168 [M+H]$^+$. $^1$H NMR (DMSO-d6) δ 1.39-1.42 (m, 1H), 1.49-1.50 (m, 1H), 2.28 (s, 3H), 3.35-3.41 (m, 2H), 4.13 (s, 1H).

Example 39

Scheme 103:

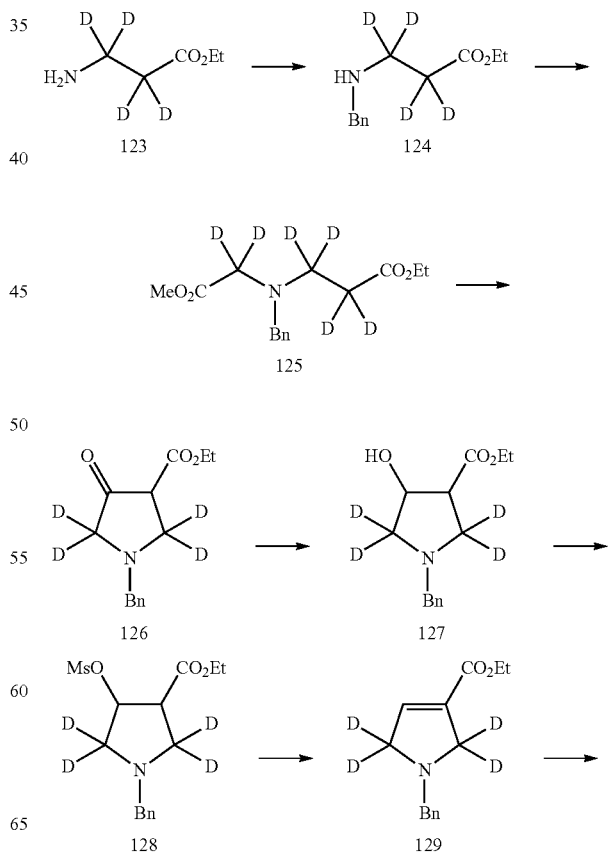

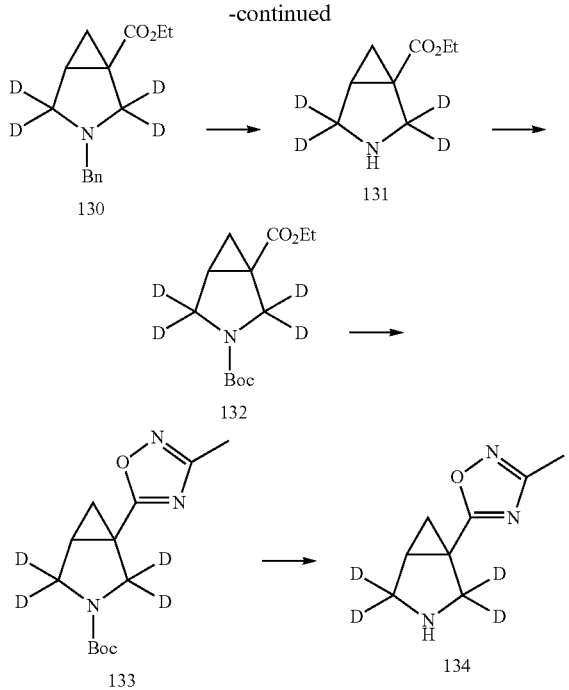

Beta-anlanine-2,2,3,3-d4 ethyl ester deuterium chloride (123)

Beta alanine-2,2,33-d4 (2.56 g, 0.0275 mol) was dissolved in 1.0M DCl/ether (41.3 ml, 0.0413 mol) and ethanol-d (25 mL) and stirred for 17 hours at room temperature. The mixture was heated to 35-40° C. for 1 hr. and evaporated to dryness to obtain 4.34 g of white semi-solid that was used in the next step without further purification. MS (ESI) m/z 159 [M+H]$^+$.

N-Benzyl beta alanine-2,2,3,3-d4 ethyl ester (124)

Beta-alanine-2,2,33-d4 ethyl ester (123) (4.33 g, 0.0273 mol), triethylamine (4.18 mL, 0.0300 mol) and benzaldehyde (2.62 mL, 0.0259 mol) were dissolved in 120 mL CH$_2$Cl$_2$ and stirred at room temperature for 30 minutes. Sodium triacetoxyborohydride (6.35 g, 0.0300) was added in 3 portions and the mixture was stirred at room temperature for 2.75 hours. The reaction was quenched with 50 mL water and extracted with CH$_2$Cl$_2$ (2×50 mL). The combined organics were washed with saturated sodium chloride (50 mL), dried over sodium sulfate and concentrated. The residue was chromatographed over 40 g silica gel with 60-100% ethyl acetate/hexanes and 10% methanol/ethyl acetate, to obtain 4.61 g of 124 as clear colorless oil MS (ESI) m/z 212 [M+H]$^+$.

Ethyl 3-(benzyl(2-ethoxy-2-oxoethyl)amino)propanoate-d6 (125)

Methyl bromoacetate-2,2-d2 (2.1 mL, 0.022 mol) was added to a suspension of N-Benzyl beta alanine-2,2,3,3-d4 ethyl ester (124) (4.61 g, 0.022 mol) and sodium carbonate (2.5 g, 0.024 mol) in tetrahydrofuran (50 mL) and D$_2$O (2.5 mL). The mixture was heated to 35-40° C. for 7 hrs. The mixture was concentrated and partitioned between water (25 mL) and ethyl acetate (×150 mL). The organics were washed with water (25 mL) and saturated sodium chloride (25 mL) The aqueous layer was extracted with ethyl acetate (50 mL) and the combined organics were dried over Na$_2$SO$_4$, and concentrated to an oil. The residue was chromatographed over 50 g silica gel with 10-15% ethyl acetate/hexanes to obtain 4.46 g of 125 as clear colorless oil. MS (ESI) m/z 286 [M+H]$^+$. $^1$H NMR (CDCl$_3$) δ 123-1.26 (t, 3H), 3.68 (s, 3H), 3.81 (s, 2H) 4.12-4.14 (q, 2H), 7.23-7.30 (m, 5H).

Ethyl 1-benzyl-4-hydroxypyrolidine-3-carboxylate-2,2,3,5,5-d5 (127)

The methods described above for 114 were used for the preparation of 127. The material was used in the next step without further purification as a mixture of ethyl and methyl esters. Compound 125 (4.46 g) was used to produce 2.94 g of compound 127 as yellow oil. MS (ESI) m/z 255 [M+H]$^+$.

Ethyl 1-benzyl-4-hydroxypyrolidine-3-carboxylate-2,2,5,5-d4 (129)

The methods described above for 116 were used for the preparation of 129. The material was chromatographed over 30 g silica gel with 10-15% ethyl acetate that failed to purify the compound. All fractions were concentrated and the material was used in the next step as a mixture of ethyl and methyl esters without further purification. Compound 127 (2.94 g) was used to produce 1.78 g of compound 129 as yellow oil. MS (ESI) m/z 236 [M+H]$^+$.

Ethyl 1-benzyl-4-hydroxypyrolidine-3-carboxylate-2,2,5,5-d4 (130)

The methods described above for 117 were used for the preparation of 130. The material was chromatographed with 50 g silica gel 5-10% ethyl acetate that failed to separate the methyl and ethyl esters. All fractious were concentrated and the material was used in the next step as a mixture of ethyl and methyl esters. Compound 129 (1.78 g) was used to produce 660 mg of compound 130 as light yellow oil. MS (ESI) m/z 250 [M+H]$^+$.

3-tert-Butyl 1-ethyl-3-azabicyclo[3.1.0]hexane-1,3-dicarboxylate-2,2,4,4-d4 (132)

The methods described above for 119 were used for the preparation of 132, starting from 660 mg of compound 130. The product was chromatographed over 4.5 g silica gel with 5% ethyl acetate/hexane, which failed to separate the ethyl and methyl esters. All product-containing fractions were concentrated and the material was used in the next step as a mixture of ethyl and methyl esters; obtained 450 mg of yellow oil. MS (ESI) m/z 298 [M+K]$^+$. $^1$H NMR (CDCl$_3$) δ 0.83-0.85 (t, 2H), 1.24-1.28 (m, 3H), 1.44 (s, 9H), 1.53-1.56 (s, 1H), 4.13-4.19 (m, 2H).

tert-Butyl-1-(3-methyl-1,2,4-oxadiazole-5-yl)-3-azabicyclo[3.1.0]hexane-3-carboxylate-2,2,4,4-d4 (133)

The methods described above for 120 were used for the preparation of 133, starting from 450 mg of compound 132. The product was chromatographed over 4.5 g of silica gel with 15% ethyl acetate/hexane to obtain 330 mg of clear colorless oil. MS (ESI) m/z 308 [M+K]$^+$. $^1$H NMR (CDCl$_3$) δ 1.16-1.17 (m, 1H), 1.46 (s, 9H), 1.72-1.78 (m, 1H), 2.20-2.22 (m, 1H), 2.36 (s, 3H).

5-(2,2,4,4-d4-3-Azabicyclo[3.1.0]hexane-1-yl)-3-methyl-1,2,4-oxadiazole (134)

The methods described above for 121 were used for the preparation of 134, starting from 330 mg of compound 133. The product was crystallized from ethanol (2 mL) and tert-butyl methyl ether (12 mL). The solids were collected and washed with tert-butyl methyl ether (2×5 mL) and dried under vacuum to obtain 22 mg of white crystalline solid. MS (ESI) m/z 169 [M+H]+. ¹H NMR (DMSO-d6) δ 1.65-1.74 (m, 2H), 2.31 (s, 3H), 2.44-2.46 (m, 1H).

Example 40

Chart 101: Deuterium-Labeled Analogs

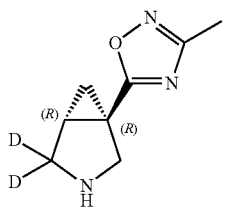

122a

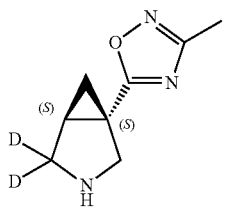

122b

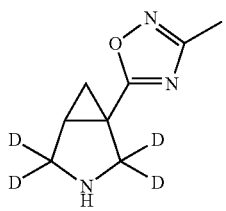

134

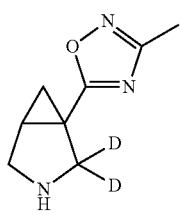

135

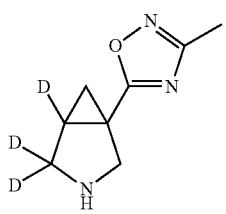

136

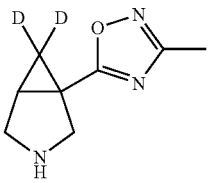

137

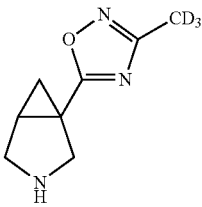

138

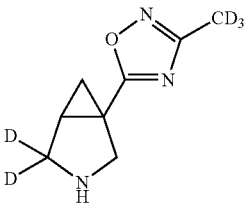

139

Using the chemistry described above, additional analogs (Chart 101) were synthesized by employing the appropriate deuterated starting materials. For example, compound 135 was prepared using beta-alanine-d4. Compound 13 was prepared after employing sodium borodeuteride reduction of compound 113. Compound 137 was obtained by using a deuterated analog of the TMSOI reagent and compounds 138 and 139 were prepared by utilizing a duterated analog of acetamide oxime for construction of the oxadiazole ring (see Table 101). ¹H NMR spectra of each compound listed in Table 101 was consistent with the expected structure.

TABLE 101

Reagents used to prepare deuterated analogs.

| Compound | Deuterated Reagent Used | MS (ESI) [M + H]+. |
|---|---|---|
| 135 | beta-alanine-d4 | 168 |
| 136 | NaBD₄ cyclic ketone reduction | 169 |
| 137 | TMSOI-d9 | 168 |
| 138 | acetamideoxime-d3 | 169 |
| 139 | acetamideoxime-d3 | 171 |

Example 41

Scheme 104: Enantiospecific synthesis of azabicyclo compounds.

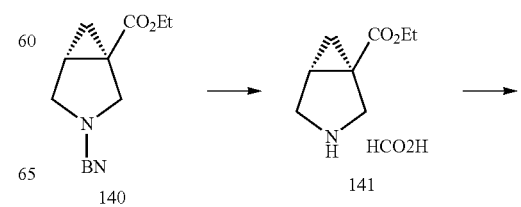

140     141

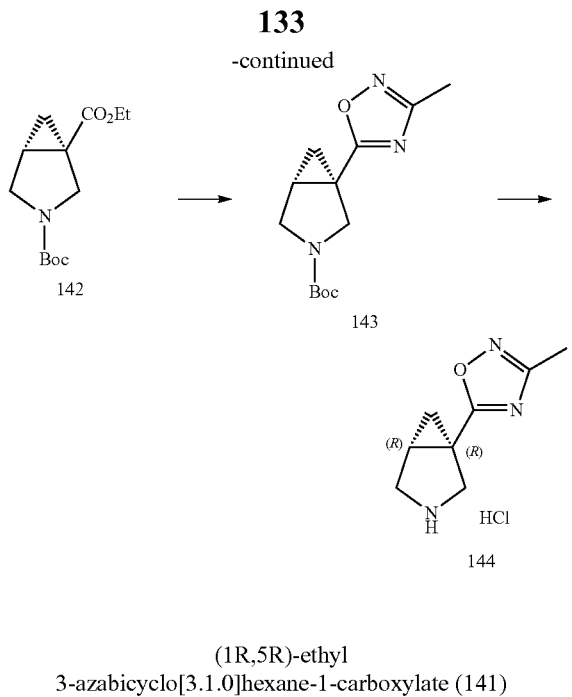

(1R,5R)-ethyl 3-azabicyclo[3.1.0]hexane-1-carboxylate (141)

(1R,5R)-ethyl 3-benzyl-3-azabicyclo[3.1.0]hexane-1-carboxylate hydrochloride (140) was prepared as previously reported (WO2010007032A1 and Korean J. Med. Chem. 1994, 4(2), 119), starting from enantiomerically pure epichlorohydrin. Compound 140 (1.53 g, 0.0062 mol) was dissolved in methanol (30 mL). Ammonium formate (1.77 g, 0.0280 mol) and 1.53 g of 10% palladium on carbon was added and the mixture was heated to reflux for 4.5 hours. The mixture was filtered and concentrated and carried on to the next step without further purification. MS (ESI) m/z 156 [M+H]$^+$.

(1R,5R)-3-tert-Butyl-ethyl 3-azabicyclo[3.1.0]hexane-1,3-dicarboxylate (142)

(1R,5R)-Ethyl 3-azabicyclo[3.1.0]hexane-1-carboxylate (141-formate) was dissolved in CH$_2$Cl$_2$ (30 mL) and triethylamine (1.08 mL, 0.0078 mol). Di-t-butyl dicarbonate (1.49 g, 0.0078 mol) was added and the mixture was stirred at room temperature for 1 hour. The reaction was concentrated and the residue was chromatographed over 25 g of silica gel with 15% ethyl acetate/hexanes, to obtain 1.27 g of clear colorless oil. MS (ESI) m/z 294 [M+K]$^+$. $^1$H NMR (CDCl$_3$) δ 0.82-0.85 (t, 1H), 1.24-1.28 (m, 3H), 1.44 (s, 9H), 1.56-1.59 (m, 2H), 3.40-3.79 (m, 4H), 4.13-4.19 (m, 2H).

(1R,5R)-tert-Butyl 1-(3-methyl-1,2,4-oxadiazol-5-yl)-3-azabicyclo[3.1.0]hexane-3-carboxylate (143)

2-Methyl-tetrahydrofuran (40 mL), acetamide oxime (0.93 g, 0.0125 mol) and sodium methoxide (1.1 g, 0.020 mol) were added to (1R,5R)-3-tert-butyl 1-ethyl 3-azabicyclo[3.1.0]hexane-1,3-dicarboxylate (142) (1.27 g, 0.0050 mol) and the mixture was heated to reflux for 3 hours. Upon cooling the suspension was partitioned between ethyl acetate (100 mL) and water (25 mL). The organic layer was washed with water (25 mL), saturated sodium chloride (25 mL) and dried over Na$_2$SO$_4$. The mixture was concentrated and the residue was chromatographed over 25 g of silica gel with 15-25% ethyl acetate/hexanes, to obtain 0.75 g of clear colorless oil. MS (ESI) m/z 304 [M+K]$^+$. $^1$H NMR (CDCl$_3$) δ 1.16-1.17 (m, 1H), 1.46 (s, 9H), 1.60 (s, 1H), 1.72-1.75 (m, 1H), 2.36 (s, 3H), 3.49-3.51 (m, 1H), 3.65-3.79 (dd, 1H), 3.91-4.00 (m, 2H).

5-((1R,5R)-3-azabicyclo[3.1.0]hexan-1-yl)-3-methyl-1,2,4-oxadiazole (144)

2.5 M HCl (4.5 mL, 0.0113 mol) was added to (1R,5R)-tert-butyl 1-(3-methyl-1,2,4-oxadiazol-5-yl)-3-azabicyclo[3.1.0]hexane-3-carboxylate (143) (0.75 g, 0.0028 mmol) in 4 mL of ethanol. The solution was heated to 50° C. for 2.5 hours, cooled and condensed to a white solid. The material crystallized from 5 mL hot ethanol and 20 mL t-butyl methyl ether. The solids were isolated by filtration and washed with t-butyl methyl ether (2×5 mL) and dried under vacuum over night to 0.48 g white crystalline solid. The optical purity (99.68%) was determined by HPLC analysis (Chiral Technologies Chiral-AGP, 4.0 mm×150 mm, 0.5% methanol, 20 mM sodium phosphate pH=7). MS (ESI) m/z 166 [M+H]$^+$. $^1$H NMR (DMSO-d6) δ 1.66-1.69 (m, 1H), 1.73-1.76 (m, 1H), 2.31 (s, 3H), 2.47-2.49 (m, 1H), 3.37-3.41 (m, 2H), 3.70-3.74 (m, 2H).

Example 42

Scheme 105: Direct formation of N-H azabicyclo compound with ammonia.

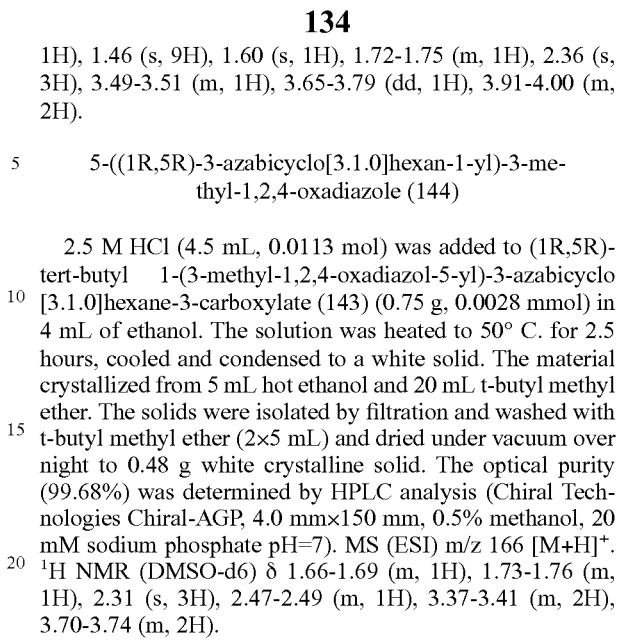

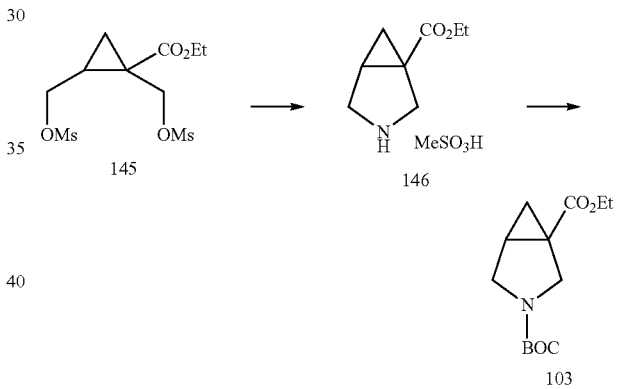

Ethyl 3-azabicyclo[3.1.0]hexane-1-carboxylate (146)

Ethyl 1,2-bis((methylsulfonyloxy)methyl)cyclopropenecarboxylate (145) was prepared as described previously (WO2010007032A1). Compound 145 (7.5 g, 0.0227 mol) was dissolved in methanol (10 mL). Ammonia in methanol (7 N) (37.5 mL, 0.262 mol) was added and the mixture was heated to 60° C. for 4.5 hours. The mixture was concentrated and carried on to the next step without further purification. MS (ESI) m/z 156 [M+H]$^+$.

3-tert-Butyl 1-ethyl 3-azabicyclo[3.1.0]hexane-1,3-dicarboxylate (103)

Ethyl 3-azabicyclo[3.1.0]hexane-1-carboxylate (146-mesylate) was dissolved in ethanol (75 mL). Sodium hydrogen carbonate (2.29 g, 0.0272 mol) and di-t-butyl dicarbonate (5.45 g, 0.0249 mol) were added and the mixture was stirred at room temperature for 1 hour. The mixture was concentrated and partitioned between ethyl acetate (150 mL) and water (50 mL). The organics were washed with 5% citric acid (50 mL), water (50 mL), and brine (50 mL). The solution was dried over sodium sulfate and concentrated. The residue was dissolved in 15 mL of 10% water/ACN and extracted with 4×50 mL hexane. The hexane layer was washed with water (25 mL), dried over sodium sulfate and concentrated to obtain 3.6 g of clear light yellow oil. MS (ESI) m/z 294 [M+K]$^+$.

Example 43

Evaluation of Muscarinic Agonist Activity In Vitro

Muscarinic M1 and M3 agonist activity was evaluated by measuring the stimulation of inositol phosphate (IP) production in the presence of lithium chloride from A9L cells transfected with expression plasmids containing human muscarinic M1 and M3 receptors, respectively. The cell lines were a gift from Professor William Messer, and the methods were as described in Tejada et al. (J. Med. Chem. 2006; 49: 7518-31) except that the assay was scaled down to run in 384-well plates and the concentration of inositol-1-phosphate in the lysates was determined using the non-isotopic IP-One Terbium TR-FRET assay kit (Cisbio Bioassays, cat. #621PAPEJ) according to the manufacturer's instructions.

Cells were grown to 90% confluence in 384-well high-base, small-volume plates (Greiner Bio-One) compounds were added at suitable concentrations in growth medium containing 10 mM LiCl, buffered with an extra 10 mM HEPES (pH=7.4), and incubated for 60 minutes at 37° C. Cells were lysed and assayed for IP following the manufacturer's instructions. Each plate contained a standard set of concentrations of carbachol, enabling the EC$_{50}$ and maximum stimulation (S$_{max}$) by a full agonist to be determined for comparative purposes.

The intrinsic efficacy of a compound was calculated as the stimulation of IP production expressed as a percentage of the maximal stimulation caused by treatment with carbachol. The value for a full agonist is 100%, while partial agonists give values below 100%. The potency of each compound was obtained from the replicate multi-point dose-response curves, and the results were expressed relative to the potency of carbachol at its EC$_{50}$, thereby correcting for the experiment-to-experiment variability of the sensitivity of the assay.

Table 111 shows that the compounds were potent, efficacious and selective agonists at muscarinic M1 receptors, with reduced efficacy and potency at muscarinic M3 receptors.

TABLE 111

| | huM1/A9L | | huM3/A9L | |
|---|---|---|---|---|
| Compound | Potency relative to carbachol | S$_{max}$ | Potency relative to carbachol | S$_{max}$ |
| Carbachol | 1 | 100% | 1 | 100% |
| 105 | 0.78 | 58% | 0.17 | 33% |
| 106b | 0.51 | 40% | 0.27 | 42% |
| 106a | 1.72 | 80% | 0.46 | 45% |
| 136 | 0.89 | 41% | 0.45 | 36% |
| 121 | 1.10 | 73% | 0.45 | 37% |
| 122a | 1.09 | 77% | 0.38 | 44% |
| 122b | 0.54 | 47% | 0.50 | 28% |
| 134 | 1.17 | 61% | 0.35 | 41% |
| 135 | 1.39 | 70% | 0.49 | 46% |
| 138 | 1.34 | 93% | 0.37 | 43% |
| 137 | 1.26 | 97% | 0.19 | 62% |

Example 44

Evaluation of Muscarinic Agonist Activity In Vivo

In lithium chloride-treated laboratory rodents engagement of muscarinic M1 receptors in the hippocampus may usefully be evaluated in vivo by measuring the increase in the tissue of inositol phosphate (Bymaster F P et al Brain Res 795 (1998) 179-190). This may also be extended to measure engagement of muscaric M3 receptors in the salivary glands.

Experimental compounds were administered subcutaneously at 3 mg/kg using standard techniques to Long Evans Hooded rats weighing 225 to 350 g. and which had been pretreated with a subcutaneous injection of lithium chloride at a suitable dose between 3 and 5 mmole/kg. At suitable times the animals were briefly anesthetized using 5% isoflurane and euthanized by decapitation. The brains and submaxillary salivary glands were rapidly dissected out, and the hippocampuses were dissected from the brains. The dissected tissues were homogenized in a suitable volume of ice-cold phosphate-buffered saline containing 10 mM lithium chloride (pH=7.4) using a tissue homogenizer, and used immediately or frozen in aliquots at −80° C. for future use. The concentration of inositol-1-phosphate was determined in the homogenates using the non-isotopic IP-One Terbium TR-FRET assay kit (Cisbio Bioassays, cat. #621PAPEJ) according to the manufacturer's instructions.

Table 112 shows that the compounds cause a robust increase in inositol phosphate in the hippocampus, expressed as Increase (%)=100*(concentration of IP in hippocampus in treated rats)

(concentration of IP in hippocampus of control rats)

with a smaller increase in the salivary glands. This demonstrates that they potently and efficaciously engaged the muscarinic M1 receptors in the hippocampus and were selective for the muscarinic M1 receptors in the hippocampus over the muscarinic M3 receptors in the salivary glands.

TABLE 112

| Compound | Increase in Inositol Phosphate in Hippocampus/Control | Increase in Inositol Phosphate in Salivary Gland/Control |
|---|---|---|
| 105 (3 mg/kg) | 563% | 219% |
| 106b (3 mg/kg) | 141% | 104% |
| 106a (3 mg/kg) | 376% | 191% |
| 136 (3 mg/kg) | 694% | 231% |
| 121 (3 mg/kg) | 795% | 239% |
| 122a (3 mg/kg)* | 487% | 182% |
| 122b (3 mg/kg)* | 150% | 163% |
| 134 (3 mg/kg) | 574% | 214% |
| 135 (3 mg/kg) | 614% | 194% |
| 138 (3 mg/kg) | 357% | 217% |
| 137 (3 mg/kg) | 503% | 198% |

*Tested with 3 mmole/kg LiCl (all others with 5 mmole/kg LiCl)

Example 45

Metabolism of Compounds In Human Liver Microsomes

Compounds were incubated with pooled male human liver microsomes (BD Biosciences, #452172) and an NADP-regenerating system in a phosphate buffer (pH 7.4), following a method similar to the manufacturer's suggested protocol, for a total of 6 hours. Aliquots were removed every 2 hours, and 1% formic acid was added to halt the reaction. Samples were centrifuged, filtered through 0.2 micron spinfilter, and the amount of each compound in the supernatants was quantitated using LC/MS/MS as follows. The ultra-filtrates were subjected to reverse-phase liquid chromatography using a 150×2.1 mm Agilent C8-reverse phase column on a Shimadzu Prominence LC, eluting the compound with a gradient of 2%-50% acetonitrile+0.1% formic acid over 5 minutes. The concentration of the compound in the column effluent was measured using an Applied Biosystems API-3200 triple quadrupole mass spectrometer equipped with a Turbo V source (electrospray sample injection) system. The counts of the characteristic parent ions of the protonated compound and product ions were converted to concentration by comparison with a standard calibration curve. The parent/daughter ion pairs that were monitored for each compound were: 166.0/82.0 (105), 166.0/82.0 (106b), 166.0/82.0 (106a), 169.0/83.0 (136), 168.2/83.0 (121) 168.1/83.0 (122a), 168.1/83.0 (122b), 170.2/83.0 (134), 168.2/84.1 (135), 168.1/84.1 (137) and 169.2/82.1 (138).

Table 113 shows that only 10-26% of the compounds was metabolized in the human liver microsomal preparation over 6 hours, while by comparison, 100% of xanomeline was lost. The compounds were relatively highly resistant to metabolism.

TABLE 113

| Compound | Loss at 6 hrs (%) |
| --- | --- |
| Xanomeline | 100 |
| 105 | 27 |
| 106b | 29 |
| 106a | 50 |
| 136 | 11 |
| 121 | 13 |
| 122a | 20 |
| 122b | 13 |
| 134 | 10 |
| 135 | 26 |
| 138 | 29 |
| 137 | 24 |

Example 46

Evaluation in an In Vitro Model of Blood-Brain Barrier Penetration

PAMPA is a useful in vitro model for predicting the passive diffusion of drugs across the blood-brain barrier (Li, D et al Eur Jour of Med Chem 38 (2003) 223-232).

Compounds were diluted in a 100 mM phosphate buffer (pH 7.4) to a concentration of 400 µM and the stock solutions were placed into a 96-well filter plate (Millipore, #MAIPN4510) pre-wetted with 20 mg/mL porcine brain polar lipid extract in 100% dodecane (Avanti, #131022) and placed into a 96-well acceptor plate (Millipore, #MSSACCEPTOR) whose wells were filled with the same phosphate buffer as in the filter plate. This assembly was incubated at room temperature for 24 hours. The experiment was halted by separating the filter plate from the acceptor plate. Aliquots were removed from the filter plate wells, acceptor plate wells, and stock solutions, and 1% trifluoroacetic acid was added to each. All solutions were measured by LC/UV, and passive diffusion rates were calculated using the peak area values (Avdeef, Alex, 2003, Page 147 in Absorption and Drug Development. Hoboken, N.J.: John Wiley & Sons).

In Table 114 the permeability coefficients of the compounds are shown and compared with ranitidine (which does not penetrate the BBB) and clonidine, which does penetrate the BBB, indicating good potential BBB penetration of the compounds.

TABLE 114

| Compound | PMPA Permeability Coefficient ($\times 10^6$) | Brain/Plasma Ratio |
| --- | --- | --- |
| 105 | 4.49 | 0.38 |
| 106b | 4.37 | 0.6 |
| 106a | 4.25 | 0.39 |
| 136 | 3.71 | 0.56 |
| 121 | 3.78 | 0.51 |
| 122a | 3.93 | 0.59 |
| 122b | 3.70 | 0.58 |
| 134 | 3.46 | 0.65 |
| 135 | 5.40 | 0.61 |
| 138 | 4.10 | |
| 137 | 4.00 | |
| Ranitidine | 0.18 | |
| Clonidine | 7.66 | |

Example 47

Blood and Brain Concentrations (Rats)

Long-Evans Hooded rats (Charles River male, 230-300 g) were dosed with solutions of test compounds in PBS by tail vein injection. The dome for all compounds was 3 mg/kg. At one hour, the animals were anesthetized with isoflurane, and then euthanized by decapitation. Trunk blood was collected into a 1.5 mL microcentrifuge tube containing 15 U Heparin, and the plasma recovered after centrifugation. Brains were dissected, weighed, immediately chilled to 4° C., and homogenized using a PowerGen 125 homogenizer in five volumes of ice-cold 2% formic acid. Proteins were precipitated from plasma and brain homogenate with nine and five volumes respectively of ice-cold 2% formic acid and clarified by centrifugation. The supernatant was ultra-filtered by centrifugation through a 3K MWCO spin column (Pall Life Sciences), following the manufacturer's instructions. The concentration of compound in the ultra-filtrate was subjected to reverse-phase liquid chromatography using a 150×2.1 mm Agilent C8 reverse-phase column on a Shimadzu Prominence LC, eluting the compounds with a gradient of 2% to 50% of acetonitrile+0.1% formic acid for all compounds. The concentration of the compound in the column effluent was measured using an Applied Biosystems API-3200 triple quadrupole mass spectrometer equipped with an electrospray sample injection system. The counts of the characteristic parent and product ions of each test compound were converted to concentration units by comparison with a standard curve.

Pharmacokinetic parameters for plasma are shown in Table 115.

TABLE 115

| Compound No. | Plasma Concentration at 1 hr (µM) | Plasma Terminal Half-life (Hr) |
|---|---|---|
| 105 | 15.0 | 1.1 |
| 106b | 9.5 | 1.1 |
| 106a | 5.6 | 0.7 |
| 136 | 13.6 | 1.15 |
| 121 | 16.8 | 1.26 |
| 122a | 12.2 | 0.97 |
| 122b | 8.8 | 1.3 |
| 134 | 13.5 | 1.4 |
| 135 | 13.8 | 1.0 |

Table 116 demonstrates that the compounds penetrate into the brain and achieve high concentrations.

TABLE 116

| Compound No. | Brain Concentration at 1 hr (µM) |
|---|---|
| 105 | 4.4 |
| 106b | 5.5 |
| 106a | 3.5 |
| 138 | 5.5 |
| 137 | 5.5 |
| 136 | 7.4 |
| 121 | 8.6 |
| 122a | 5.0 |
| 122b | 5.1 |
| 134 | 8.4 |
| 135 | 7.7 |

Example 48

Activity of Compounds is the Novel Object Recognition Assay

Object recognition memory—judgment of the prior occurrence of objects—is a key part of human memory, and is commonly impaired in neurodegenerative diseases, such as Alzheimer's disease (Winters B D et al Neursci Behav Rev 32 (2008) 1055-70). This may be modeled in laboratory rodents using delayed spontaneous novel object recognition, which tests the ability of an animal to recognize an object it has previously been exposed to after a delay. Drugs may be evaluated for their ability to improve the animal's ability to remember, recall or recognize objects in this model.

CD-1 Mice (males, 7-8 weeks old) were fasted for 16 hrs and orally dosed with compounds of interest 30 min before experiments began. Throughout those 30 min, animals were left in their home cages except during a 1 min handling habituation session at 10 min post-dosing. All handling and experiments wee carried out under low, indirect light during the hours between 8 am and 3 pm. Compound 122a and donepezil were dissolved in PBS. Xanomeline was dissolved in PBS and 4% hydroxylpropyl-beta-cyclodextrin. All compounds were delivered as a volume of 5 ml/kg. Experiments were divided into a 10 min Introduction Trial (T1) and a 10 min Retention Trial (T2) and were separated by a 1 hr Intertrial Interval (ITI). During T1, mice were allowed to freely investigate two identical objects placed at opposite corners of a black plastic enclosure (12 in wide×15 in long×9 in deep). The objects were pairs of either copper pipe fittings standing on end (1.75 in tall×1.5 in outer diameter) or white plastic caps standing sideways and consisting of a hollow ring (⅝ in long×1.75 in outer diameter) attached to a hollow cube (1 in on a side). Objects were magnetically fixed to the enclosure floor and were wiped down with 10% alcohol between trials. Following T1 animals were returned to their home cages for the 1 hr ITI, after which T2 began. T2 was carried out in the same way as T1, only the previously identical objects were replaced by one novel object paired with a familiar one. Objects and locations were varied to eliminate bias. Mouse activity was recorded using a digital video camera and evaluated after the trial. The time each mouse spent with its nose in contact with either object (investigation) was recorded for each minute of T2, and a Discrimination Score (D Score) was calculated using the following formula once the animal completed a total of 1 min of investigation. The D-score represents the time that the mouse spent exploring the novel object as a percentage of the total time spent exploring both objects.

$D$ Score=100*(novel object investigation time)/
((novel object investigation time)+(familiar object investigation time))

Table 117 demonstrates that control mice receiving an oral dose of saline failed almost completely to recognize the familiar object introduced to them an hour previously (i.e. spent almost an equal amount of time exploring familiar and novel objects for a D score of 51.4%). Compound 122a at an oral dose of 0.3 mg/kg restored the recognition of the familiar object. Similar results were obtained with donepezil and xanomeline at oral doses of 3 mg/kg. These results demonstrate that 122a has the potential to enhance memory and cognition.

TABLE 117

| Compound | Dose | Mean D Score |
|---|---|---|
| Saline | 5 ml/kg | 51.04% |
| 122a | 0.3 mg/kg | 72.09% |
| Xanomeline | 3.0 mg/kg | 72.05% |
| Donepezil | 3.0 mg/kg | 70.35% |

Treatment of Skin Condition

The compounds and compositions of this disclosure may also be used to treat various skin conditions and diseases, including conditions and diseases relating to the regulation of keratinocyte adhesion. For example, the compounds and compositions of this disclosure, including e.g., one or more of a compound of Formulas I, IA, IB, II, IIA, IIB, III, IIIA, IIIB, IV, IVA, IVB, XI, XIA and XIB (described above in sections C and D), may be used to treat diseases such as pemphigus. The compositions may be in any form as described above and may also be formulated for topical administration by means of a cream, ointment, foam, salve, etc.

The invention claimed is:

1. A M1 or M1/M4 selective muscarinic agonist compound of Formula XI, a stercoisomer thereof or a pharmaceutically acceptable salt of said compound or stereoisomer, wherein the compound has the structure:

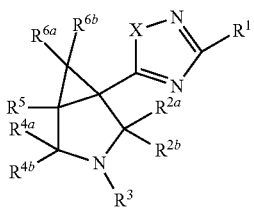

wherein

X is O or S;

R[1] is $NH_2$, a $C_{1-6}$ alkyl group or a $C_{3-6}$ cycloalkyl group, wherein the alkyl or cycloalkyl groups are optionally substituted with 1 or more Deuterium ("D");

R[2], R[2b], R[4a], R[4b], R[5], R[6a] and R[6b] are independently selected from H or D; and R[3] is H, D or an amino-protecting group.

2. The compound of claim 1 wherein the compound has the structure of Formula XIA or XIB:

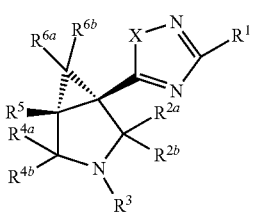

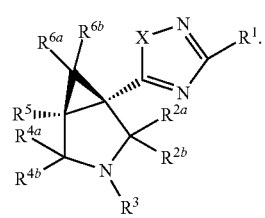

3. The compound of claim 2 selected from the group consisting of 5-((1R,5R)-3-azabicyclo[3.1.0]hexan-1-yl)-3-methyl-d3-1,2,4-oxadiazole, 5-((1R,5R)-2,2-d2-3-azabicyclo[3.1.0]hexan-1-yl)-3-methyl-1,2,4-oxadiazole, 5-((1R,5R)-4,4-d2-3-azabicyclo[3.1.0]hexan-1-yl)-3-methyl-1,2,4-oxadiazole, 5-((1R,5R)-2,2,4,4-d4-3-azabicyclo[3.1.0]hexan-1-yl)-3-methyl-1,2,4-oxadiazole, 5-((1R,5R)-4,4,5-d3-3-azabicyclo[3.1.0]hexan-1-yl)-3-methyl-1,2,4-oxadiazole, 5-((1R,5R)-6,6-d2-3-azabicyclo[3.1.0]hexan-1-yl)-3-methyl-1,2,4-oxadiazole, 5-((1S,5S)-3-azabicyclo[3.1.0]hexan-1-yl)-3-methyl-d3-1,2,4-oxadiazole, 5-((1S,5S)-2,2-d2-3-azabicyclo[3.1.0]hexan-1-yl)-3-methyl-1,2,4-oxadiazole, 5-((1S,5S)-4,4-d2-3-azabicyclo[3.1.0]hexan-1-yl)-3-methyl-1,2,4-oxadiazole, 5-((1S,5S)-2,2,4,4-d4-3-azabicyclo[3.1.0]hexan-1-yl)-3-methyl-1,2,4-oxadiazole, 5-((1S,5S)-4,4,5-d3-3-azabicyclo[3.1.0]hexan-1-yl)-3-methyl-1,2,4-oxadiazole, and 5-((1S,5S)-6,6-d2-3-azabicyclo[3.1.0]hexan-1-yl)-3-methyl-1,2,4-oxadiazole.

4. A pharmaceutically acceptable composition comprising a compound of claim 1 and a pharmaceutically acceptable carrier.

5. A pharmaceutical composition for administration to a subject in need thereof comprising:

(i) an amount of at least one M1 or M1/M4 selective muscarinic agonist compound of claim 1, or a pharmaceutically acceptable form thereof, sufficient to achieve a cognition-enhancing or anti-psychotic or behavior-improving effect in said subject, wherein the amount of said at least one M1 or M1/M4 selective muscarinic agonist is sufficient to cause at least one moderate cholinergic side effect in said subject, said cholinergic side effect being selected from the group consisting of diaphoresis, hypersalivation, flushing, gastro-intestinal tract upsets, increased stomach acid, nausea, vomiting and diarrhea, breathing difficulties, tachycardia, dizziness, syncope, headache, convulsions, somnolence and combinations thereof, and (ii) an amount of at least one muscarinic antagonist, or pharmaceutically acceptable form thereof, sufficient to cause said at least one cholinergic side effect to be at most mild in said subject.

6. A pharmaceutical composition of claim 5, wherein said at least one M1 or M1/M4 selective muscarinic agonist achieves a serum or plasma minimum Cmax sufficient to achieve a cognition-enhancing or anti-psychotic or behavior-improving effect in said subject, wherein the amount of said at least one M1 or M1/M4 selective muscarinic agonists is sufficient to cause at least one moderate cholinergic side effect in said subject, wherein said cholinergic side effect is selected from the group consisting of diaphoresis, hypersalivation, flushing, gastro-intestinal tract upsets, increased stomach acid, nausea, vomiting and diarrhea, breathing difficulties, tachycardia, dizziness, syncope, headache, convulsions, somnolence and combinations thereof, and an amount of at least one muscarinic antagonist, or pharmaceutically acceptable form thereof, sufficient to cause said at least one cholinergic side effect to be at most mild in said subject.

7. A cognition-enhancing pharmaceutical composition for administration to an animal comprising an effective amount of a compound of claim 1 sufficient to achieve a cognition enhancing effect in said animal, wherein the composition provides in an animal that is capable of metabolizing said compound a serum or plasma Cmax of said compound of about 50 ng/ml or less.

8. The pharmaceutical composition of claim 7, wherein said pharmaceutical composition is a dosage form that swells or unfolds to a size such that the dosage form is retained in the stomach for at least 1 hour.

9. The pharmaceutical composition of claim 7, wherein the animal is a human.

10. The pharmaceutical composition of claim 9, wherein the cognition enhancing effect is selected from the group consisting of: improved memory of places; improved memory of people; improved memory of information; improved memory of facts; improved memory of how to operate and use tools; improved ability to analyze information; improved ability to deduce or reason; improved ability to synthesize conclusions; improved ability to think strategically; improved ability to make plans and decisions; improved ability to execute on plans and decisions; improved ability to perform activities of daily living; improved ability to be employed; enhanced activity of neuronal mechanisms responsible for effective memory and cognition comprising muscarinic functions; reduced pathogenetic mechanisms leading to loss of memory and cognitive function; reduced loss of neurons or neuronal activity that lead to loss of cognitive and memory function; improved scores on neuropsychological tests comprising Alzheimer's Disease Assessment Scale—Cognitive Subscale or Mini-Mental State Examination; improved scores on clinical assessments of the activities of daily living comprising Alzheimer's Disease Co-operative Study—Activities of Daily Living increased α-secretase activity as compared to animals having the same cognitive disorder that are not administered the composition; reduced Aβ production as compared to animals having the same cognitive disorder that are not administered the composition increased Secreted Amyloid Precursor Protein Alpha production as compared to animals having the same cognitive disorder that are not administered the composition and/or reduced Tau pathology and/or apoptosis as compared to animals having the same cognitive disorder that are not administered the composition.

* * * * *